(12) United States Patent
Gao et al.

(10) Patent No.: US 9,259,426 B2
(45) Date of Patent: Feb. 16, 2016

(54) 4,6-DI- AND 2,4,6-TRISUBSTITUTED QUINAZOLINE DERIVATIVES USEFUL FOR TREATING VIRAL INFECTIONS

(75) Inventors: Ling-Jie Gao, Heverlee (BE); Piet André Maurits Maria Herdewijn, Wezemaal (BE); Steven Cesar Alfons De Jonghe, Brussels (BE); William John Watkins, Saratoga, CA (US); Lee Shun Chong, Newark, CA (US)

(73) Assignee: Gilead Sciences, Inc., Foster City, CA (US)

(*) Notice: Subject to any disclaimer, the term of this patent is extended or adjusted under 35 U.S.C. 154(b) by 727 days.

(21) Appl. No.: 12/374,433

(22) PCT Filed: Jul. 20, 2007

(86) PCT No.: PCT/BE2007/000091
§ 371 (c)(1),
(2), (4) Date: Jan. 20, 2009

(87) PCT Pub. No.: WO2008/009078
PCT Pub. Date: Jan. 24, 2008

(65) Prior Publication Data
US 2009/0285782 A1 Nov. 19, 2009

Related U.S. Application Data

(60) Provisional application No. 60/807,917, filed on Jul. 20, 2006.

(51) Int. Cl.
| | | |
|---|---|---|
| A61K 31/517 | (2006.01) |
| A61K 31/535 | (2006.01) |
| A61K 31/5375 | (2006.01) |
| A61K 31/5377 | (2006.01) |
| C07D 239/72 | (2006.01) |
| C07D 239/78 | (2006.01) |
| C07D 239/88 | (2006.01) |
| C07D 239/94 | (2006.01) |
| C07D 239/95 | (2006.01) |
| C07D 401/04 | (2006.01) |
| C07D 403/04 | (2006.01) |
| C07D 413/04 | (2006.01) |

(52) U.S. Cl.
CPC ............ *A61K 31/517* (2013.01); *A61K 31/5375* (2013.01); *A61K 31/5377* (2013.01); *C07D 239/72* (2013.01); *C07D 239/78* (2013.01); *C07D 239/88* (2013.01); *C07D 239/94* (2013.01); *C07D 239/95* (2013.01); *C07D 401/04* (2013.01); *C07D 403/04* (2013.01); *C07D 413/04* (2013.01)

(58) Field of Classification Search
CPC ............ A61K 31/517; A61K 31/5375; A61K 31/5377
USPC ................. 514/266.4, 266.1, 266.2
See application file for complete search history.

(56) References Cited

U.S. PATENT DOCUMENTS

| 3,843,791 A | 10/1974 | McFarland |
| 5,281,603 A | 1/1994 | Venkatesan et al. |
| 5,707,998 A | 1/1998 | Takase et al. |
| 5,866,572 A | 2/1999 | Barker et al. |
| 5,955,464 A | 9/1999 | Barker |
| 6,946,465 B2 | 9/2005 | Waer et al. |

(Continued)

FOREIGN PATENT DOCUMENTS

| EP | 0 837 063 | 4/1998 |
| EP | 1 382 603 | 1/2004 |

(Continued)

OTHER PUBLICATIONS

Sielecki et al., "Quinazolines as Cyclin Dependent Kinase Inhibitors,"*Bioorganic & Medicinal Chemistry Letters*, 11: 1157-1160, 2001.
Invitation to pay Additional Fees (PCT/BE2007/000091) mailed Jun. 6, 2008.
International Preliminary Report on Patentability (PCT/BE2007/000091) issued on Jan. 20, 2009.
International Search Report (PCT/BE2007/000091) mailed Nov. 11, 2008.
Written Opinion of the International Searching Authority (PCT/BE2007/000091) mailed Nov. 11, 2008.
U.S. Appl. No. 13/176,627, filed Jul. 5, 2011, Herdewijn et al.
Armarego et al., "Quinazolines. Part IX. Covalent Hydration in the Neutral Species of Substituted Quinazolines," *J. Chem. Soc. B: Phys. Org.* 449-454, 1967.
Dempcy et al., "Regioselective Synthesis of Imidazo[4,5-g]quinazoline Quinone Nucleosides and Quinazoline Amino Nucleosides. Studies of Their Xanthine Oxidase and Purine Nucleoside Phosphorylase Substrate Activity," *J. Org. Chem.* 56:776-785, 1991.

(Continued)

*Primary Examiner* — Shengjun Wang
(74) *Attorney, Agent, or Firm* — Clark & Elbing LLP

(57) ABSTRACT

This invention provides quinazoline derivatives represented by the structural formula: (I); wherein: $R_2$ is hydrogen, NR'R", $C_{1-7}$ alkyl, aryl$C_{1-7}$ alkyl or $C_{3-10}$ cycloalkyl; $R_4$ is amino, $C_{1-7}$ alkyl, $C_{2-7}$ alkenyl, $C_{3-10}$ cycloalkyl, $C_{3-10}$ cycloalkenyl, aryl, heterocyclic, arylalkyl, heterocyclic-substituted $C_{1-7}$ alkyl or $C_{3-10}$ cycloalkyl-$C_{1-7}$ alkyl; $R_5$ is hydrogen or $C_{1-7}$ alkyl, or $R_5$ and $R_4$ together with the nitrogen atom to which they are attached form a heterocyclic ring; Y is a single bond, $C_{1-7}$ alkylene, $C_{2-7}$ alkenylene or $C_{2-7}$ alkynylene; $R_6$ is halogen, heteroaryl or aryl; R' and R" are each independently hydrogen, $C_{1-7}$ alkyl-carbonyl or $C_{1-7}$ alkyl; provided that $R_4$ is not phenyl substituted with morpholino when $R_2$ is H and $R_5$ is H, and provided that when $NR_4R_5$ is piperazinyl, said $NR_4R_5$ is either non-substituted or substituted with methyl or acetyl; a pharmaceutically acceptable addition salt, a stereoisomer, a mono- or a di-N-oxide, a solvate or a pro-drug thereof, for the treatment of viral infections.

8 Claims, 6 Drawing Sheets

(56) References Cited

U.S. PATENT DOCUMENTS

| | | | |
|---|---|---|---|
| 7,074,801 B1 | 7/2006 | Yoshida et al. | |
| 7,276,506 B2 | 10/2007 | Waer et al. | |
| 7,501,513 B2 | 3/2009 | Waer et al. | |
| 2003/0236255 A1 | 12/2003 | Waer et al. | |
| 2004/0038856 A1* | 2/2004 | Chakravarty et al. | 514/1 |
| 2004/0077859 A1 | 4/2004 | Waer et al. | |
| 2004/0167121 A1* | 8/2004 | Aronov et al. | 514/217.07 |
| 2004/0167198 A1 | 8/2004 | Wrasidlo et al. | |
| 2005/0054626 A1 | 3/2005 | Carter et al. | |
| 2005/0191238 A1 | 9/2005 | Casebier et al. | |
| 2005/0282814 A1 | 12/2005 | Wrasidlo et al. | |
| 2006/0189620 A1 | 8/2006 | Waer et al. | |
| 2006/0287314 A1 | 12/2006 | Waer et al. | |
| 2007/0004721 A1 | 1/2007 | Waer et al. | |
| 2007/0032477 A1 | 2/2007 | Waer et al. | |
| 2007/0043000 A1 | 2/2007 | Waer et al. | |
| 2007/0054916 A1 | 3/2007 | Patel et al. | |
| 2008/0004285 A1 | 1/2008 | De Jonghe et al. | |
| 2008/0096883 A1 | 4/2008 | Caravatti et al. | |
| 2008/0112884 A1 | 5/2008 | Casebier et al. | |
| 2008/0182870 A1 | 7/2008 | Bondy et al. | |
| 2008/0312227 A1 | 12/2008 | De Jonghe et al. | |
| 2009/0036430 A1 | 2/2009 | De Jonghe et al. | |
| 2009/0131414 A1 | 5/2009 | De Jonghe et al. | |
| 2009/0253696 A1 | 10/2009 | Herdewijn et al. | |
| 2009/0318456 A1 | 12/2009 | Herdewijn et al. | |
| 2010/0143299 A1 | 6/2010 | Gao et al. | |
| 2010/0305117 A1 | 12/2010 | Herdewijn et al. | |

FOREIGN PATENT DOCUMENTS

| | | |
|---|---|---|
| EP | 1 724 268 A1 | 11/2006 |
| GB | 1 301 319 | 12/1972 |
| JP | 07138238 | 5/1995 |
| JP | 2000-53653 A | 2/2000 |
| JP | 2000-53654 A | 2/2000 |
| WO | WO 94/22855 | 10/1994 |
| WO | WO 96/16960 | 6/1996 |
| WO | WO 97/30034 | 8/1997 |
| WO | WO 99/50264 | 10/1999 |
| WO | WO 03/031406 | 4/2003 |
| WO | WO 2004/026307 | 4/2004 |
| WO | WO 2004/065392 | 8/2004 |
| WO | WO 2004/072033 | 8/2004 |
| WO | WO 2005/020899 | 3/2005 |
| WO | WO 2005/028444 | 3/2005 |
| WO | WO 2005/046698 * | 5/2005 |
| WO | WO 2005/079391 | 9/2005 |
| WO | WO 2005/080377 | 9/2005 |
| WO | WO 2005/105761 | 11/2005 |
| WO | WO 2006/015859 | 2/2006 |
| WO | WO 2006/039718 | 4/2006 |
| WO | WO 2006/069805 * | 7/2006 |
| WO | WO 2008/009077 | 1/2008 |

OTHER PUBLICATIONS

DiMauro et al., Microwave-Assisted Preparation of Fused Bicyclic Heteroaryl Boronates: Application in One-Pot Suzuki Couplings, *J. Org. Chem.* 71:3959-3962, 2006.

Hayakawa et al., "Synthesis and Biological Evaluation of 4-Morpholino-2-phenylquinazolines and Related Derivatives as Novel Pl3 Kinase p110α Inhibitors," *Bioorg. Med. Chem.* 14:6847-6858, 2006.

Homer et al., "Analogs of 3-Amino-7-chloro-1,2,4-benzotriazine 1-oxide as Antimalarial Agents," *J. Med. Chem.* 11:946-949, 1968.

Sasse, "A Simple New Method for Preparation of 2-Substituted Quinazolines," *Synthesis* 379-382, 1978.

Vema et al., "Design of EGFR Kinase Inhibitors: A Ligand-Based Approach and its Confirmation with Structure-Based Studies," *Bioorg. Med. Chem.* 11:4643-4653, 2003.

Urakov et al., "Multiple Reactivity and Tautomerism of Substituted Pyrimidines. IV. Multiple Reactivity of 2- acetamido-4-quinazolinones," *Uzbek J. Chem.* 5-6:37-41, 1995.

Kikelj, "From 2-Aminobenzonitriles and Carbon Dioxide, Carbon Monoxide, Carbon Disulfide, or Potassium O- Ethyl Dithiocarbonate," *Science of Synthesis* 16: 573-749, 2004.

First Inventor Gao, Non-Final Office Action, U.S. Appl. No. 12/374,242, dated Apr. 9, 2012.

* cited by examiner

4,6-DI- AND 2,4,6-TRISUBSTITUTED QUINAZOLINE DERIVATIVES USEFUL FOR TREATING VIRAL INFECTIONS

CROSS-REFERENCE TO RELATED APPLICATIONS

This application is the U.S. National Stage of International Application No. PCT/BE2007/000091, filed Jul. 20, 2007, which, in turn, claims the benefit of U.S. Provisional Application Ser. No. 60/807,917, filed Jul. 20, 2006.

FIELD OF THE INVENTION

The present invention relates to a class of 4,6-di- and 2,4,6-trisubstituted quinazoline derivatives, as well as to pharmaceutical compositions comprising one or more of said 4,6-di- and 2,4,6-trisubstituted quinazoline derivatives and one or more pharmaceutically acceptable excipients. The present invention further relates to the use of said 4,6-di- and 2,4,6-trisubstituted quinazoline derivatives as biologically active ingredients for manufacturing medicaments, more specifically for the prevention or treatment of viral infections and pathologic conditions associated therewith such as, but not limited to, hepatitis C.

BACKGROUND OF THE INVENTION

A large number of quinazoline derivatives is already known in the art. For instance quinazoline derivatives with various substituents on positions 2, 4 and 6 (using the standard atom numbering for the quinazoline moiety) are known with biological activities such as for the treatment or prevention of inflammatory disorders, immune disorders, hyperproliferative disorders such as cancer, and viral infections.

The standard numbering of the positions of the different substituting radicals on the quinazoline core structure is as follows:

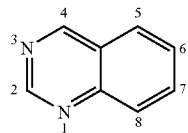

WO 2005/105761 discloses quinazoline derivatives substituted on position 4 with optionally substituted 4-morpholinoanilino for the treatment or prevention of Flaviviridae infections such as but not limited to HCV infection.

WO 98/02434 discloses 2,4,6-substituted quinazoline derivatives, wherein the substituent on position 4 comprises at least a dual ring system, being protein tyrosine kinase inhibitors which are useful for the treatment of cancer and psoriasis.

WO 2006/039718 discloses 2,6-substituted quinazolines and 4-amino-2,6-substituted quinazolines being also protein kinase inhibitors.

However there is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next then years. The 15% to 45% of persons with acute hepatitis C who do recover are not subject to long-term complications and do not need treatment. Since HCV and pestiviruses belong to the same virus family and share many similarities (such as, but not limited to, organisation of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus, others include West Nile virus and Dengue Fever), Genus *Hepacivirus* (type species Hepatitis C virus), and Genus *Pestivirus* (type species Bovine viral diarrhea virus (BVDV), others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and opthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anaemia, which can be treated with erythropoietin. Other side effects include mood swings, irritability, anxiety, insomnia, abdominal pain, nervousness, breathlessness, rash, hair loss, dry skin, nausea, diarrhoea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking the conserved RNA elements employing a nucleic acid based approach including antisense oligonucleotides, ribozymes, RNA aptamers, RNA decoys, and RNA interference. A major drawback for such nucleic acid based approach is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding of a medical utility in a class of 4,6-di- and 2,4,6-trisubstituted quinazoline derivatives represented by the structural formula (I)

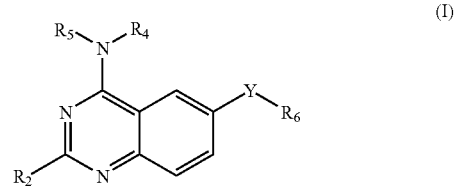

wherein:
- $R_2$ is selected from the group consisting of hydrogen; NR'R"; $C_{1-7}$ alkyl optionally substituted with one or more groups selected from the group consisting of hydroxy, halogen, $C_{1-7}$ alkoxy, $C_{3-10}$ cycloalkyl and heterocyclyl; aryl$C_{1-7}$ alkyl; heterocyclyl; and $C_{3-10}$ cycloalkyl;
- $R_4$ is selected from the group consisting of $C_{1-7}$ alkyl; $C_{2-7}$ alkenyl; $C_{3-10}$ cycloalkyl; $C_{3-10}$ cycloalkenyl; aryl; heterocyclic; arylalkyl; heterocyclic-substituted $C_{1-7}$ alkyl and $C_{3-10}$ cycloalkyl-$C_{1-7}$ alkyl; and wherein said $R_4$ is optionally substituted with one or more $R_7$;
- $R_5$ is hydrogen or $C_{1-7}$ alkyl; or $R_5$ and $R_4$, together with the nitrogen atom to which they are attached, form a 5 to 7-membered heterocyclic ring comprising a nitrogen atom and further optionally comprising at least one heteroatom selected from N, O and S, said ring being optionally substituted with one or more $R_7$;
- Y is selected from the group consisting of a single bond, $C_{1-7}$ alkylene, $C_{2-7}$ alkenylene and $C_{2-7}$ alkynylene;
- $R_6$ is selected from the group consisting of halogen; fused benzo-$C_{5-8}$ cycloalkyl optionally substituted with oxo; heteroaryl and aryl, wherein said heteroaryl or aryl are optionally substituted with one or more $R_8$;
- each $R_7$ and each $R_8$ is independently selected from the group consisting of halogen; nitro; hydroxyl; sulfhydryl; hydroxylamino; cyano; amino; $C_{1-7}$ alkyl; halo $C_{1-7}$ alkyl; $C_{2-7}$ alkenyl; $C_{2-7}$ alkynyl; $C_{1-7}$ alkoxy; halo $C_{1-7}$ alkoxy; $C_{1-7}$ alkylthio; formyl; —CO—NHR$_9$; —CO—NR$_9$R$_9$'; —CS—NHR$_9$; —NR$_{12}$—CO—NHR$_{12}$; —NR$_{12}$—CS—NHR$_{12}$; —SO$_2$NH$_2$; —NR$_{12}$—SO$_2$R$_{11}$; —NR$_{12}$—COR$_{10}$; —NR$_{12}$—CSR$_{10}$; alkoxyamino; mercaptoamino; thioalkylamino; alkylamino; alkenylamino; alkynylamino; alkylsulfoxide; alkylsulfone; hydroxyalkylamino; mercaptoalkylamino; hydrazino; alkylhydrazino; $C_{3-10}$ cycloalkyl; aryl optionally substituted with arylcarbonyl, aryloxy; (O,O-dialkylphosphonyl)-alkyl, alkanoyl, halo-$C_{1-7}$ alkoxy, hydroxy-$C_{1-7}$ alkoxy, hydroxy-$C_{1-7}$ alkyl, di-($C_{1-7}$ alkyl)amino $C_{1-7}$ alkyl, ω-carboxyalkanoylamino, mono-($C_{3-7}$ cycloalkyl)aminocarbonyl, di-($C_{3-7}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy-$C_{1-7}$ alkyl)aminocarbonyl, formylamino, —SO$_2$NH$_2$, arylamino-$C_{1-7}$ alkyl, $C_{1-7}$ alkylsulfonyl, heterocyclylcarbonyl, heterocyclyl-$C_{1-7}$ alkyl and heterocyclyl, wherein said heterocyclyl is optionally substituted with $C_{3-7}$ alkenyloxycarbonyl, $C_{1-7}$ alkyl or $C_{1-7}$ alkyloxycarbonyl; carboxylic acid or esters or thioesters or halides or anhydrides or amides thereof; thiocarboxylic acid or esters or thioesters or halides or anhydrides or amides thereof; heterocyclyl (particularly heteroaryl) optionally substituted with one or more substituents independently selected from the group consisting of hydroxy, oxo, halogen, amino, $C_{1-7}$ alkyl, $C_{1-7}$ alkoxy, acylamino, $C_{1-7}$ alkylsulfonyl, arylsulfonyl, heterocyclyl-$C_{1-7}$ alkyl, heterocyclyl-$C_{1-7}$ alkylamino, aryl and heterocyclyl optionally substituted with $C_{1-7}$ alkyl, arylsulfonyl or (di-$C_{1-7}$ alkylamino)-$C_{1-7}$ alkoxy; and non-aromatic heterocyclyl including a nitrogen atom substituted with heterocyclyl-$C_{1-7}$ alkyl or a carboxylic acid or a $C_{1-7}$ alkyl ester thereof;
- $R_9$ and $R_9$' are each independently selected from the group consisting of hydrogen; $C_{3-10}$ cycloalkyl optionally substituted with one more substituents independently selected from the group consisting of cyano, halogen, hydroxy, amino, $C_{1-7}$ alkyl and $C_{1-7}$ alkoxy; $C_{1-7}$ alkoxy; halo $C_{1-7}$ alkoxy; $C_{1-7}$ alkyl optionally substituted with one or more substituents independently selected from the group consisting of amino, alkylamino, cyano, dialkylamino and heterocyclyl optionally substituted with $C_{1-7}$ alkyl; halo $C_{1-7}$ alkyl; heterocyclyl optionally substituted with $C_{1-7}$ alkyl; aryl and aryl$C_{1-7}$ alkyl wherein the aryl moiety is optionally substituted with one or more halogen; or $R_9$ and $R_9$' together with the nitrogen atom to which they are attached form a nitrogen-containing heterocyclyl group;
- $R_{10}$ and $R_{11}$ are each independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, alkylamino, cyano, dialkylamino, halogen, and heterocyclyl; heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, $C_{1-7}$ alkylamino, cyano, dialkylamino, halogen and heterocyclyl;
- $R_{12}$ is selected from the group consisting of hydrogen and $C_{1-7}$ alkyl, wherein said $C_{1-7}$ alkyl is optionally substituted with one or more substituents independently selected from the group consisting of cyano, halogen and hydroxy;
- R' and R" are each independently selected from the group consisting of hydrogen; $C_{1-7}$ alkyl-carbonyl; and $C_{1-7}$ alkyl optionally substituted with one or more substituents independently selected from the group consisting of hydroxy, halogen, $C_{1-7}$ alkoxy, heterocyclic, aryl$C_{1-7}$ alkyl and $C_{3-10}$ cycloalkyl; or one of R' and R" is hydrogen and the other one of R' and R" is selected from the group consisting of —CHR$_{13}$R$_{14}$ and R$_{15}$, wherein at least one of $R_{13}$ and $R_{14}$ is aryl optionally substituted with one or more $R_{16}$, and the other one of $R_{13}$ and $R_{14}$ is hydrogen or $C_{1-7}$ alkyl optionally substituted with one or more substituents independently selected from the group consisting of halogen and $C_{1-7}$ alkoxy, $C_{3-10}$ cycloalkyl, heterocyclyl and aryl optionally substituted with one or more $R_{16}$;
- $R_{15}$ is selected from the group consisting of $C_{3-10}$ cycloalkyl, heteroaryl and aryl wherein said heteroaryl or aryl is optionally substituted with one or more substituents independently selected from the group consisting of halogen and $C_{1-7}$ alkyl and wherein said $C_{3-10}$ cycloalkyl is optionally substituted, at the carbon position adjacent to the nitrogen atom to which it is attached, with aryl or heteroaryl wherein said aryl is optionally substituted with one or more halogen; and
- each $R_{16}$ is independently selected from the group consisting of halogen, hydroxy, amino, nitro, cyano, trifluoromethyl, trifluoromethoxy, $C_{1-7}$ alkyl, $C_{1-7}$ alkoxy, di-$C_{1-7}$ alkyl)amino, mono-($C_{1-7}$ alkyl)amino, carboxamido, —SO$_2$NH$_2$, carbamoyl, —NR$_{12}$—SO$_2$R$_{11}$ and phenoxy;

provided that when $R_2$ is H and $R_4$ is phenyl, $R_7$ is not morpholino, and provided that when $NR_4R_5$ is piperazinyl, said $NR_4R_5$ is either non-substituted or substituted with methyl or acetyl, and/or a pharmaceutically acceptable addition salt thereof and/or a stereo-isomer thereof and/or a mono- or a di-N-oxide thereof and/or a solvate thereof and/or a pro-drug form thereof.

Based on their biological properties, the present invention relates to the use of these 4,6-di- and 2,4,6-trisubstituted quinazoline derivatives for the manufacture of medicaments, particularly for use in the treatment or prevention of viral infections and pathologic conditions associated therewith such as, but not limited to, especially infections due to Flaviridae. The present invention also relates to individual 4,6-di- and 2,4,6-trisubstituted quinazoline derivatives specifically disclosed herein. The present invention also relates to the use of pharmaceutical compositions comprising said novel 4,6-di- and 2,4,6-trisubstituted quinazoline derivatives, optionally in synergistic combination with other drugs. The present invention also relates to various synthetic methods for making these novel 4,6-di- and 2,4,6-trisubstituted quinazoline derivatives, and salts thereof.

DEFINITIONS

Unless otherwise stated herein, the term "tri-substituted" in relation to the quinazoline structure means that three of the carbon atoms being in positions 2, 4 and 6 of the quinazoline moiety (according to standard atom numbering for the quinazoline moiety) are substituted with an atom or group of atoms other than hydrogen. Unless otherwise stated herein, the term "di-substituted" in relation to the quinazoline structure means that two of the carbon atoms being in positions 4 and 6 of the quinazoline moiety (according to standard atom numbering for the quinazoline moiety) are substituted with an atom or group of atoms other than hydrogen.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methyl-ethyl (isopropyl), 2-methylpropyl (isobutyl), 1,1-dimethylethyl (tert-butyl), 2-methyl-butyl, n-pentyl, dimethylpropyl, n-hexyl, 2-methylpentyl, 3-methylpentyl, n-heptyl and the like. By analogy, the term "$C_{1-4}$ alkyl" refers to such radicals having from 1 to 4 carbon atoms, i.e. up to and including butyl, and "$C_{1-12}$ alkyl" refers to such radicals having from 1 to 12 carbon atoms.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids and aliphatic or cycloaliphatic monosulfonic acids are designated herein as aliphatic or cycloaliphatic acyl and sulfonyl groups and include, but are not limited to, the following:

alkanoyl (for example formyl, acetyl, propionyl, butyryl, isobutyryl, valeryl, isovaleryl, pivaloyl and the like);

cycloalkanoyl (for example cyclobutanecarbonyl, cyclopentanecarbonyl, cyclohexanecarbonyl, 1-adamantanecarbonyl and the like);

cycloalkyl-alkanoyl (for example cyclohexylacetyl, cyclopentylacetyl and the like);

alkenoyl (for example acryloyl, methacryloyl, crotonoyl and the like);

alkylthioalkanoyl (for example methylthioacetyl, ethylthioacetyl and the like);

alkanesulfonyl (for example mesyl, ethanesulfonyl, propanesulfonyl and the like);

alkoxycarbonyl (for example methoxycarbonyl, ethoxycarbonyl, propoxycarbonyl, isopropoxycarbonyl, butoxycarbonyl, isobutoxycarbonyl and the like);

alkylcarbamoyl (for example methylcarbamoyl and the like);

(N-alkyl)-thiocarbamoyl (for example (N-methyl)-thiocarbamoyl and the like);

alkylcarbamidoyl (for example methylcarbamidoyl and the like); and alkoxyalkyl (for example methoxyalkyl, ethoxyalkyl, propoxyalkyl and the like);

Acyl and sulfonyl groups may also originate from aromatic monocarboxylic acids and aromatic monosulfonic acids and include, but are not limited to, the following:

aroyl (for example benzoyl, toluoyl, xyloyl, 1-naphthoyl, 2-naphthoyl and the like);

arylalkanoyl (for example phenylacetyl and the like);

arylalkenoyl (for example cinnamoyl and the like);

aryloxyalkanoyl (for example phenoxyacetyl and the like);

arylthioalkanoyl (for example phenygthioacetyl and the like);

arylaminoalkanoyl (for example N-phenylglycyl, and the like);

arylsulfonyl (for example benzenesulfonyl, toluenesulfonyl, naphthalenesulfonyl and the like);

aryloxycarbonyl (for example phenoxycarbonyl, naphthyloxycarbonyl and the like);

arylalkoxycarbonyl (for example benzyloxycarbonyl and the like);

arylcarbamoyl (for example phenylcarbamoyl, naphthylcarbamoyl and the like);

arylglyoxyloyl (for example phenylglyoxyloyl and the like).

arylthiocarbamoyl (for example phenylthiocarbamoyl and the like); and arylcarbamidoyl (for example phenylcarbamidoyl and the like).

Acyl groups may also originate from an heterocyclic monocarboxylic acids and include, but are not limited to, the following:

heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of the quinazoline ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the quinazoline ring.

As used herein with respect to a substituting radical (including the combination of substituents in certain positions of the quinazoline ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkoxy", "oxyheterocyclic", "heterocyclic-substituted alkoxy", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl, heterocyclic radical or heterocyclic-substituted alkyl (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl and cresoxy, and various isomers of piperidinoxy, 1-methylpiperidinoxy, pyrrolidinoxy, pyridinoxy, tetrahydrofuranyloxy, morpholinoethoxy, piperazinoethoxy, piperidinoethoxy, pyridinoethoxy, pyrrolidinoethoxy, piperidinomethoxy, methylpyridinoxy, methylquinolinoxy, pyridinopropoxy and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the term "halo $C_{1-7}$ alkoxy" means a $C_{1-7}$ alkoxy radical (such as above defined) in which one or more hydrogen atoms are independently replaced by one or more halogens (preferably fluorine, chlorine or bromine) such as, but not limited to, trifluoromethoxy.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{2-7}$ alkenylene" means the divalent hydrocarbon radical corresponding to the above defined $C_{2-7}$ alkenyl, such as vinylidene or allenylidene.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the term "$C_{2-7}$ alkynylene" means the divalent hydrocarbon radical corresponding to the above defined $C_{2-7}$ alkynyl, such as acetylenylidene or propynylidene.

As used herein with respect to a substituting radical, and unless otherwise stated, the terms "arylalkyl", "arylalkenyl" and "heterocyclic-substituted alkyl" or "heterocyclyl alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-tert-butylbenzyl, phenylpropyl, 1-naphthylmethyl, phenylethyl, 1-amino-2-phenylethyl, 1-amino-2-[4-hydroxy-phenyl]-ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluoyl, m-toluoyl, p-toluoyl, 2,3-xylyl, 2,4-xylyl, 3,4-xylyl, o-cumenyl, m-cumenyl, p-cumenyl, o-cymenyl, m-cymenyl, p-cymenyl, mesityl, tert-butylphenyl, lutidinyl (i.e. dimethylpyridyl), 2-methylaziridinyl, methylbenzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphthyl and the like.

As used herein with respect to a substituting radical, and unless otherwise stated, the terms "alkylamino", "cycloalkylamino", "alkenylamino", "cycloalkenylamino", "arylamino", "arylalkylamino", "heterocyclic-substituted alkylamino", "heterocyclic-substituted arylamino", "heterocyclic amino", "hydroxyalkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxy-anilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxyanilino, 4-ethoxyanilino, benzylamino, 2-methoxybenzylamino, 3-methoxybenzylamino, 4-methoxybenzylamino, 2-fluorobenzylamino, 3-fluorobenzylamino, 4-fluorobenzylamino, 2-chlorobenzylamino, 3-chlorobenzylamino, 4-chlorobenzylamino, 2-aminobenzylamino, diphenylmethylamino, α-naphthylamino, methylamino, dimethylamino, ethylamino, diethylamino, diethanolamino, isopropylamino, propenylamino, n-butylamino, tert-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino, dicyclohexylamino and ethynylamino; this definition also includes mixed disubstituted amino radicals wherein the nitrogen atom is attached to two such radicals belonging to two different subsets of radicals, e.g. an alkyl radical and an alkenyl radical, or to two different radicals within the same sub-set of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercapto-alkylamino or alkynylamino (such as above defined, respectively).

As used herein with respect to a substituting radical, and unless otherwise stated, the term "sulfonamido" refers to a radical represented by the formula —$NR_x$—$SO_2R_y$, wherein $R_x$ hydrogen or a cyclic or non-cyclic hydrocarbyl group and $R_y$ is a cyclic or non-cyclic hydrocarbyl group.

As used herein with respect to a substituting radical, and unless otherwise stated, the term "amino-acid" refers to a radical derived from a molecule having the chemical formula $H_2N$—CHR—COOH, wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a quinazoline derivative of this invention with a suitable inorganic solvent (e.g. hydrates) or organic solvent such as, but not limited to, alcohols, ketones, esters, ethers, nitrites and the like.

DETAILED DESCRIPTION OF THE INVENTION

Figure 1:
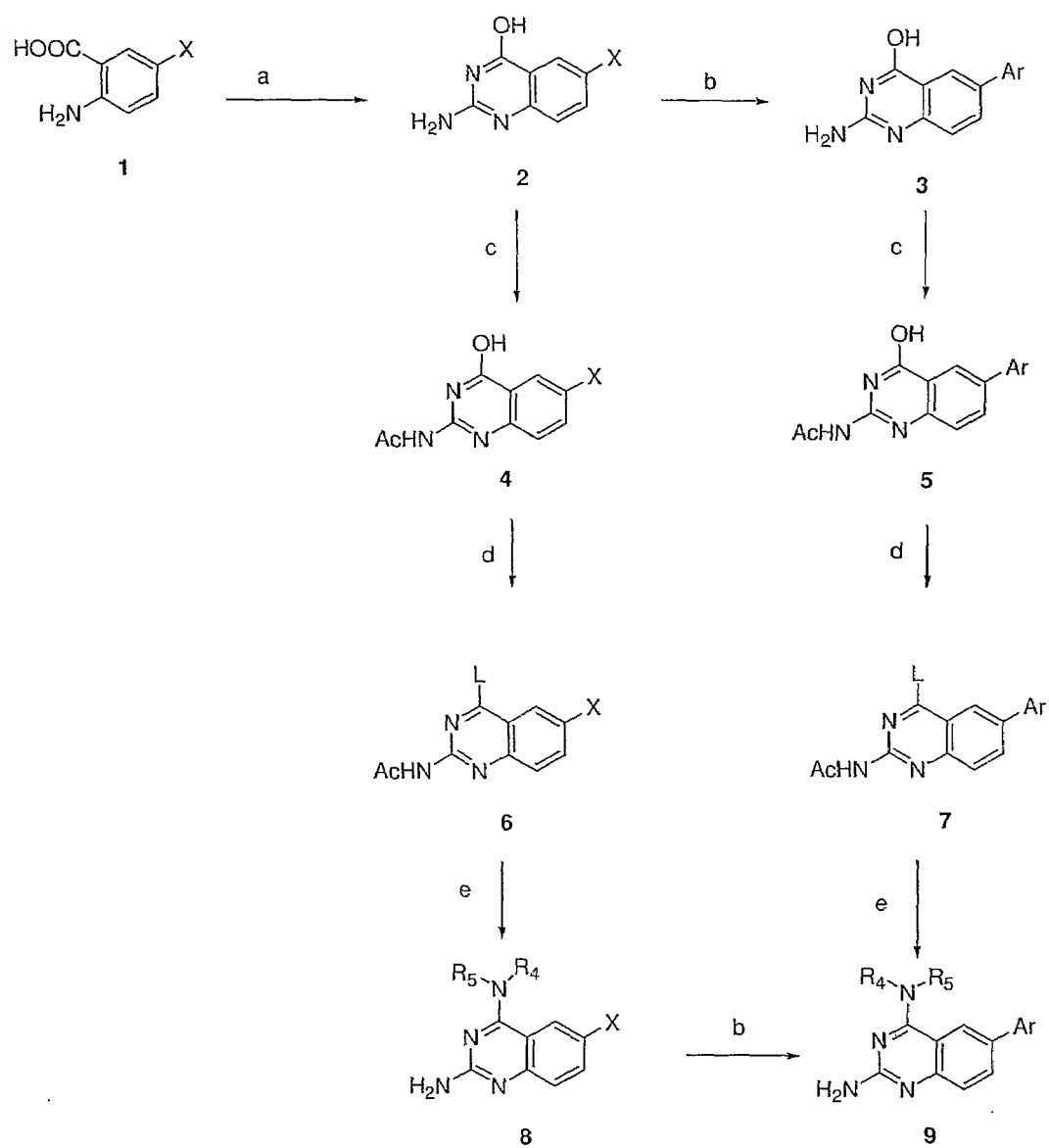
FIG. 1 schematically shows a synthetic pathway for the synthesis of 2-amino-4,6-disubstituted quinazoline derivatives according to one embodiment of the present invention.

In one aspect, the present invention relates to the antiviral activity of a class of 2,4,6-trisubstituted and 4,6-disubstituted quinazoline derivatives having the structural formula (I),

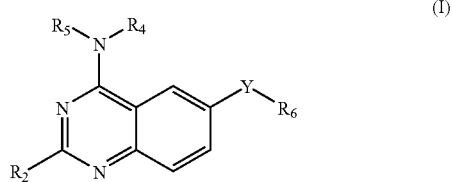

wherein:
$R_2$ is selected from the group consisting of hydrogen; NR'R"; $C_{1-7}$ alkyl optionally substituted with one or more groups selected from the group consisting of hydroxy, halogen, $C_{1-7}$ alkoxy, $C_{3-10}$ cycloalkyl and heterocyclyl; aryl$C_{1-7}$ alkyl; heterocyclyl; and $C_{3-10}$ cycloalkyl;
$R_4$ is selected from the group consisting of $C_{1-7}$ alkyl; $C_{2-7}$ alkenyl; $C_{3-10}$ cycloalkyl; $C_{3-10}$ cycloalkenyl; aryl; heterocyclic; arylalkyl; heterocyclic-substituted $C_{1-7}$ alkyl and $C_{3-10}$ cycloalkyl-$C_{1-7}$ alkyl; and wherein said $R_4$ is optionally substituted with one or more $R_7$;
$R_5$ is hydrogen or $C_{1-7}$ alkyl; or $R_5$ and $R_4$, together with the nitrogen atom to which they are attached, form a 5 to 7-membered heterocyclic ring comprising a nitrogen atom and further optionally comprising at least one heteroatom selected from N, O and S, said ring being optionally substituted with one or more $R_7$;
Y is selected from the group consisting of a single bond, $C_{1-7}$ alkylene, $C_{2-7}$ alkenylene (in particular —C=C—) and $C_{2-7}$ alkynylene (in particular —C≡C—);
$R_6$ is selected from the group consisting of halogen; fused benzo-$C_{5-8}$ cycloalkyl optionally substituted with oxo; heteroaryl and aryl, wherein said heteroaryl or aryl is optionally substituted with one or more $R_8$;
each $R_7$ and each $R_8$ is independently selected from the group consisting of halogen; nitro; hydroxyl; sulfhydryl; hydroxylamino; cyano; amino; $C_{1-7}$ alkyl; halo $C_{1-7}$ alkyl; $C_{2-7}$ alkenyl; $C_{2-7}$ alkynyl; $C_{1-7}$ alkoxy; halo $C_{1-7}$ alkoxy; $C_{1-7}$ alkylthio; formyl; —CO—NHR$_9$; —CO—NR$_9$R$_9$'; —CS—NHR$_9$; —NR$_{12}$—CO—NHR$_{12}$; —NR$_{12}$—CS—NHR$_{12}$; —SO$_2$NH$_2$; —NR$_{12}$—SO$_2$R$_{11}$; —NR$_{12}$—COR$_{10}$; —NR$_{12}$—CSR$_{10}$; alkoxyamino; mercaptoamino; thioalkylamino; alkylamino; alkenylamino; alkynylamino; alkylsulfoxide; alkylsulfone; hydroxyalkylamino; mercaptoalkylamino; hydrazino; alkylhydrazino; $C_{3-10}$ cycloalkyl; aryl optionally substituted with arylcarbonyl, aryloxy, (O,O-dialkylphosphonyl)-alkyl, alkanoyl, halo-$C_{1-7}$ alkoxy, hydroxy-$C_{1-7}$ alkoxy, hydroxy-$C_{1-7}$ alkyl, di-($C_{1-7}$ alkyl)amino $C_{1-7}$ alkyl, ω-carboxy-alkanoylamino, mono-($C_{3-7}$ cycloalkyl)aminocarbonyl, di-($C_{3-7}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy$C_{1-7}$ alkyl)aminocarbonyl, formylamino, —SO$_2$NH$_2$, arylamino-$C_{1-7}$ alkyl, $C_{1-7}$ alkylsulfonyl, heterocyclyl-carbonyl, heterocyclyl-$C_{1-7}$ alkyl or heterocyclyl, wherein said heterocyclyl is optionally substituted with $C_{3-7}$ alkenyloxycarbonyl, $C_{1-7}$ alkyl or $C_{1-7}$ alkyloxycarbonyl; carboxylic acid or esters or thioesters or halides or anhydrides or amides thereof; thiocarboxylic acid or esters or thioesters or halides or anhydrides or amides thereof; heterocyclyl (particularly heteroaryl) optionally substituted with one or more substituents independently selected from the group consisting of hydroxy, oxo, halogen, amino, $C_{1-7}$ alkyl, $C_{1-7}$ alkoxy, acylamino, $C_{1-7}$ alkylsulfonyl, arylsulfonyl, heterocyclyl-$C_{1-7}$ alkyl, heterocyclyl-$C_{1-7}$ alkylamino, aryl and heterocyclyl, wherein said heterocyclyl is optionally substituted with $C_{1-7}$ alkyl, arylsulfonyl or di-($C_{1-7}$ alkyl)amino-$C_{1-7}$ alkoxy; and non-aromatic heterocyclyl including a nitrogen atom substituted with heterocyclyl-$C_{1-7}$ alkyl or a carboxylic acid or a $C_{1-7}$ alkyl ester thereof;
$R_9$ and $R_9'$ are each independently selected from the group consisting of hydrogen, $C_{3-10}$ cycloalkyl optionally substituted with one more substituents independently selected from the group consisting of cyano, halogen, hydroxy, amino, $C_{1-7}$ alkyl and $C_{1-7}$ alkoxy; $C_{1-7}$ alkoxy; halo $C_{1-7}$ alkoxy; $C_{1-7}$ alkyl optionally substituted with one or more substituents independently selected from the group consisting of amino, alkylamino, cyano, dialkylamino, and heterocyclyl optionally substituted with $C_{1-7}$ alkyl; halo $C_{1-7}$ alkyl; heterocyclyl optionally substituted with $C_{1-7}$ alkyl; aryl and aryl$C_{1-7}$ alkyl wherein the aryl moiety is optionally substituted with one or more halogen; or $R_9$ and $R_9'$ together with the nitrogen atom to which they are attached form a nitrogen-containing heterocyclyl group;

$R_{10}$ and $R_{11}$ are each independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, alkylamino, cyano, dialkylamino, halogen, and heterocyclyl; heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, $C_{1-7}$ alkylamino, cyano, dialkylamino, halogen and heterocyclyl;

$R_{12}$ is selected from the group consisting of hydrogen and $C_{1-7}$ alkyl optionally substituted with one or more substituents independently selected from the group consisting of cyano, halogen and hydroxy;

R' and R" are each independently selected from the group consisting of hydrogen, $C_{1-7}$ alkyl-carbonyl and $C_{1-7}$ alkyl, wherein said $C_{1-7}$ alkyl is optionally substituted with one or more substituents independently selected from the group consisting of hydroxy, halogen, $C_{1-7}$ alkoxy, heterocyclic, aryl$C_{1-7}$ alkyl and $C_{3-10}$ cycloalkyl; or one of R' and R" is hydrogen and the other one of R' and R" is selected from the group consisting of —CHR$_{13}$R$_{14}$ and R$_{15}$, wherein at least one of R$_{13}$ and R$_{14}$ is aryl optionally substituted with one or more R$_{16}$, and the other one of R$_{13}$ and R$_{14}$ is hydrogen or $C_{1-7}$ alkyl optionally substituted with one or more substituents independently selected from the group consisting of halogen and $C_{1-7}$ alkoxy, $C_{3-10}$ cycloalkyl, heterocyclyl and aryl optionally substituted with one or more R$_{16}$;

$R_{15}$ is selected from the group consisting of $C_{3-10}$ cycloalkyl, heteroaryl and aryl wherein said heteroaryl or aryl is optionally substituted with one or more substituents independently selected from the group consisting of halogen and $C_{1-7}$ alkyl and wherein said $C_{3-10}$ cycloalkyl is optionally substituted, at the carbon position adjacent to the nitrogen atom to which it is attached, with aryl or heteroaryl wherein said aryl is optionally substituted with halogen; and each $R_{16}$ is independently selected from the group consisting of halogen, hydroxy, amino, nitro, cyano, trifluoromethyl, trifluoromethoxy, $C_{1-7}$ alkyl, $C_{1-7}$ alkoxy, di-$C_{1-7}$ alkylamino, mono-$C_{1-7}$ alkylamino, carboxamido, —SO$_2$NH$_2$, carbamoyl, —NR$_{12}$—SO$_2$R$_{11}$ and phenoxy;

provided that when $R_2$ is H and $R_4$ is phenyl, $R_7$ is not morpholino, and provided that when NR$_4$R$_5$ is piperazinyl, said NR$_4$R$_5$ is either non-substituted or substituted with methyl or acetyl, and/or a pharmaceutically acceptable addition salt thereof and/or a stereo-isomer thereof and/or a mono- or a di-N-oxide thereof and/or a solvate thereof and/or a pro-drug form thereof.

In another aspect, the present invention relates to a subclass of novel quinazoline derivatives represented by the structural formula (I)

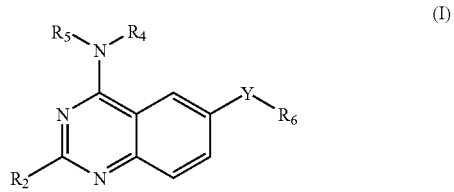

wherein:

$R_2$ is selected from the group consisting of hydrogen; NR'R"; $C_{1-7}$ alkyl optionally substituted with one or more groups selected from the group consisting of hydroxy, halogen, $C_{1-7}$ alkoxy, $C_{3-10}$ cycloalkyl and heterocyclyl; aryl$C_{1-7}$ alkyl; heterocyclyl; and $C_{3-10}$ cycloalkyl;

$R_4$ is selected from the group consisting of $C_{1-7}$ alkyl; $C_{2-7}$ alkenyl; $C_{3-10}$ cycloalkyl; $C_{3-10}$ cycloalkenyl; aryl; heterocyclic; arylalkyl; heterocyclic-substituted $C_{1-7}$ alkyl and $C_{3-10}$ cycloalkyl-$C_{1-7}$ alkyl; and wherein said $R_4$ is optionally substituted with one or more $R_7$;

$R_5$ is hydrogen or $C_{1-7}$ alkyl, or $R_5$ and $R_4$, together with the nitrogen atom to which they are attached, form a 5 to 7-membered heterocyclic ring comprising a nitrogen atom and further optionally comprising at least one heteroatom selected from N, O and S, said ring being optionally substituted with one or more $R_7$;

Y is a single bond;

$R_6$ is a fused benzo-$C_{5-8}$ cycloalkyl optionally substituted with oxo; or $R_6$ is aryl substituted with one or more substituents independently selected from the group consisting of aryl wherein said aryl is optionally substituted with arylcarbonyl, (O,O-dialkylphosphonyl)-alkyl, alkanoyl, halo-$C_{1-7}$ alkoxy, hydroxy-$C_{1-7}$ alkoxy, hydroxy-$C_{1-7}$ alkyl, di-$C_{1-7}$ alkyl-amino $C_{1-7}$ alkyl, ω-carboxy-alkanoylamino, mono-($C_{3-7}$ cycloalkyl)aminocarbonyl, di-($C_{3-7}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy$C_{1-7}$ alkyl)aminocarbonyl, formylamino, —SO$_2$NH$_2$, arylamino-$C_{1-7}$ alkyl, $C_{1-7}$ alkylsulfonyl, heterocyclyl-carbonyl, heterocyclyl-$C_{1-7}$ alkyl or heterocyclyl, wherein said heterocyclyl is optionally substituted with $C_{3-7}$ alkenyloxycarbonyl, $C_{1-7}$ alkyl or $C_{1-7}$ alkyloxycarbonyl; or $R_6$ is heterocyclyl substituted with one or more substituents independently selected from the group consisting of acylamino, $C_{1-7}$ alkylsulfonyl, arylsulfonyl, heterocyclyl-$C_{1-7}$ alkyl, heterocyclyl-$C_{1-7}$ alkylamino, aryl and heterocyclyl, wherein said heterocyclyl is optionally substituted with $C_{1-7}$ alkyl, arylsulfonyl or (di-$C_{1-7}$ alkylamino)-$C_{1-7}$ alkoxy, or said heterocyclyl is non-aromatic and includes a nitrogen atom substituted with heterocyclyl-$C_{1-7}$ alkyl or a carboxylic acid or a $C_{1-7}$ alkyl ester thereof;

each $R_7$ is independently selected from the group consisting of halogen; nitro; hydroxyl; sulfhydryl; hydroxylamino; cyano; amino; $C_{1-7}$ alkyl; halo $C_{1-7}$ alkyl; $C_{2-7}$ alkenyl; $C_{2-7}$ alkynyl; $C_{1-7}$ alkoxy; halo $C_{1-7}$ alkoxy; $C_{1-7}$ alkylthio; formyl; —CO—NHR$_9$; —CO—NR$_9$R$_9$'; —CS—NHR$_9$; —NR$_{12}$—CO—NHR$_{12}$; —NR$_{12}$—CS—NHR$_{12}$; —SO$_2$NH$_2$; —NR$_{12}$—SO$_2$R$_{11}$; —NR$_{12}$—COR$_{10}$; —NR$_{12}$—CSR$_{10}$; alkoxyamino; mercaptoamino; thioalkylamino; alkylamino; alkenylamino; alkynylamino; alkylsulfoxide; alkylsulfone; hydroxyalkylamino; mercaptoalkylamino; hydrazino;

alkylhydrazino; $C_{3-10}$ cycloalkyl; aryl optionally substituted with arylcarbonyl, aryloxy, (O,O-dialkylphosphonyl)-alkyl, alkanoyl, halo-$C_{1-7}$ alkoxy, hydroxy-$C_{1-7}$ alkoxy, hydroxy-$C_{1-7}$ alkyl, di-$C_{1-7}$ alkylamino $C_{1-7}$ alkyl, ω-carboxy-alkanoylamino, mono-($C_{3-10}$ cycloalkyl)aminocarbonyl, di-($C_{3-10}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy$C_{1-7}$ alkyl)aminocarbonyl, formylamino, —$SO_2NH_2$, arylamino-$C_{1-7}$ alkyl, $C_{1-7}$ alkylsulfonyl, heterocyclyl-carbonyl, heterocyclyl-$C_{1-7}$ alkyl and heterocyclyl, wherein said heterocyclyl is optionally substituted with $C_{3-7}$ alkenyloxycarbonyl, $C_{1-7}$ alkyl or $C_{1-7}$ alkyloxycarbonyl; carboxylic acid or esters or thioesters or halides or anhydrides or amides thereof; thiocarboxylic acid or esters or thioesters or halides or anhydrides or amides thereof; heterocyclyl (particularly heteroaryl) optionally substituted with one or more substituents selected from the group consisting of hydroxy, oxo, halogen, amino, $C_{1-7}$ alkyl, $C_{1-7}$ alkoxy, acylamino, $C_{1-7}$ alkylsulfonyl, arylsulfonyl, heterocyclyl-$C_{1-7}$ alkyl, heterocyclyl-$C_{1-7}$ alkylamino, aryl and heterocyclyl, wherein said heterocyclyl is optionally substituted with $C_{1-7}$ alkyl, arylsulfonyl or (di-$C_{1-7}$ alkylamino)-$C_{1-7}$ alkoxy; and non-aromatic heterocyclyl including a nitrogen atom substituted with heterocyclyl-$C_{1-7}$ alkyl or a carboxylic acid or a $C_{1-7}$ alkyl ester thereof;

$R_9$ and $R_9'$ are each independently selected from the group consisting of hydrogen, $C_{3-10}$ cycloalkyl optionally substituted with one more substituents independently selected from the group consisting of cyano, halogen, hydroxy, amino, $C_{1-7}$ alkyl and $C_{1-7}$ alkoxy; $C_{1-7}$ alkoxy; halo $C_{1-7}$ alkoxy; $C_{1-7}$ alkyl optionally substituted with one or more substituents independently selected from the group consisting of amino, alkylamino, cyano, dialkylamino, and heterocyclyl optionally substituted with $C_{1-7}$ alkyl; halo $C_{1-7}$ alkyl; heterocyclyl optionally substituted with $C_{1-7}$ alkyl; aryl and aryl$C_{1-7}$ alkyl wherein the aryl moiety is optionally substituted with one or more halogen; or $R_9$ and $R_9'$ together with the nitrogen atom to which they are attached form a nitrogen-containing heterocyclyl group;

$R_{10}$ and $R_{11}$ are each independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, alkylamino, cyano, dialkylamino, halogen, and heterocyclyl; heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, $C_{1-7}$ alkylamino, cyano, dialkylamino, halogen and heterocyclyl;

$R_{12}$ is selected from the group consisting of hydrogen and $C_{1-7}$ alkyl, wherein said $C_{1-7}$ alkyl is optionally substituted with one or more substituents independently selected from the group consisting of cyano, halogen and hydroxy;

R' and R" are each independently selected from the group consisting of hydrogen, $C_{1-7}$ alkyl-carbonyl and —$C_{1-7}$ alkyl, wherein said $C_{1-7}$ alkyl is optionally substituted with one or more substituents independently selected from the group consisting of hydroxy, halogen, $C_{1-7}$ alkoxy, heterocyclyl, aryl$C_{1-7}$ alkyl and $C_{3-10}$ cycloalkyl; or one of R' and R" is hydrogen and the other one of R' and R" is selected from the group consisting of —$CHR_{13}R_{14}$ and $R_{15}$, wherein at least one of $R_{13}$ and $R_{14}$ is aryl optionally substituted with one or more $R_{16}$, and the other one of $R_{13}$ and $R_{14}$ is hydrogen, $C_{1-7}$ alkyl optionally substituted with one or more substituents independently selected from the group consisting of halogen and $C_{1-7}$ alkoxy, $C_{3-10}$ cycloalkyl, heterocyclyl, and aryl optionally substituted with one or more $R_{16}$;

$R_{15}$ is selected from the group consisting of $C_{3-10}$ cycloalkyl, heteroaryl and aryl wherein said heteroaryl or aryl is optionally substituted with one or more substituents independently selected from the group consisting of halogen and $C_{1-7}$ alkyl and wherein said $C_{3-10}$ cycloalkyl is optionally substituted at the carbon position adjacent to the nitrogen atom to which it is attached with aryl or heteroaryl wherein said aryl is optionally substituted with halogen; and each $R_{16}$ is independently selected from the group consisting of halogen, hydroxy, amino, nitro, cyano, trifluoromethyl, trifluoromethoxy, $C_{1-7}$ alkyl, $C_{1-7}$ alkoxy, di-$C_{1-7}$ alkylamino, mono-$C_{1-7}$ alkylamino, carboxamido, —$SO_2NH_2$, carbamoyl, —$NR_{12}$—$SO_2R_{11}$ and phenoxy;

and/or a pharmaceutically acceptable addition salt thereof and/or a stereo-isomer thereof and/or a mono- or a di-N-oxide thereof and/or a solvate thereof and/or a pro-drug form thereof.

These compounds are useful as biologically active ingredients for manufacturing medicaments or pharmaceutical compositions for the prevention or treatment of viral infections, in particular infections by Flaviridae, and pathologic conditions associated therewith such as, but not limited to, hepatitis C.

In both said aspects of the present invention, the quinazoline derivatives are as defined in the structural formula (I), wherein each of the substituents Y, R', R", $R_2$, $R_4$, $R_5$, $R_6$, $R_7$, $R_8$, $R_9$, $R_9'$, $R_{10}$, $R_{11}$, $R_{12}$, $R_{13}$, $R_{14}$, $R_{15}$ and $R_{16}$ may independently correspond to any part of the definitions given herein-above, in particular with any of the individual meanings (such as illustrated above) of generic terms used for substituting groups such as, but not limited to, "$C_{1-7}$ alkyl", "halo $C_{1-7}$ alkyl", "$C_{3-10}$ cycloalkyl", "$C_{2-7}$ alkenyl", "$C_{3-10}$ cycloalkenyl", "$C_{2-7}$ alkynyl", "aryl", "heterocyclic", "halogen", "$C_{3-10}$ cycloalkenyl", "alkylaryl", "arylalkyl", "alkylamino", "alkenylamino", "alkynylamino", "heterocyclic-substituted $C_{1-7}$ alkyl", "hydroxyalkylamino", "mercaptoalkylamino", "$C_{1-7}$ alkoxy", "halo $C_{1-7}$ alkoxy", "$C_{1-7}$ alkylthio", and the like.

Stereoisomers of the disubstituted and trisubstituted quinazoline derivatives of this invention may be formed by using reactants in their single enantiomeric form wherever possible in the manufacturing process, or by resolving a mixture of stereoisomers by conventional methods. One such method is liquid chromatography using one or more suitable chiral stationary phases including, for example, polysaccharides, in particular cellulose or amylose derivatives. Commercially available, but non limiting, suitable polysaccharide-based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide-based chiral stationary phases are hydrocarbons such as hexane and the like, optionally admixed with an alcohol such as ethanol, isopropanol and the like. The above mixture of enantiomers may alternatively be separated by making use of microbial resolution or by resolving the diastereoisomeric salts formed with chiral acids such as mandelic acid, camphorsulfonic acid, tartaric acid, lactic acid and the like or with chiral bases such as brucine and the like. The resolving agent may be cleaved from the separated diastereoisomers, e.g. by treatment with acids or bases, in order to generate the pure enantiomers of the compounds of the invention. Conventional resolution methods were compiled e.g. by Jaques et al. in "Enantiomers, Racemates and Resolution" (Wiley Interscience, 1981).

Both aspects of the present invention include the medicinal use, in particular the anti-viral use, of any therapeutically active non-toxic addition salt which the quinazoline derivatives represented by the structural formula (I) are able to form with a salt-forming agent. Such addition salts may conveniently be obtained by treating a quinazoline derivative of this invention with an appropriate salt-forming acid or base. For instance, 4,6-di- and 2,4,6-trisubstituted quinazoline derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butenedioic, (E)-2-butenedioic, 2-hydroxybutanedioic, 2,3-dihydroxybutane-dioic, 2-hydroxy-1,2,3-propanetricarboxylic and cyclohexane-sulfamic acids and the like.

4,6-di- and 2,4,6-trisubstituted quinazoline derivatives having the structural formula (I) and having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylenediamine, N-methylglucamine, procaine and the like.

Reaction conditions for treating the 4,6-di- and 2,4,6-trisubstituted quinazoline derivatives represented by the structural formula (I) of this invention with an appropriate salt-forming acid or base are similar to standard conditions involving the same acid or base but different organic compounds with basic or acidic properties, respectively. In particular, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the quinazoline derivative of this invention.

As noted above, one particular embodiment of this invention includes the various precursors or "pro-drug" forms of the disubstituted and trisubstituted quinazoline derivatives of the present invention. It may be desirable to formulate the compounds of the present invention in the form of a chemical species which itself is not significantly biologically-active but which, when delivered to the body of a human being or higher mammal, will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

In particular, in said aspect the invention provides the use of a disubstituted or trisubstituted quinazoline derivative having the structural formula (I) as defined herein-above for the manufacture of a medicament for treating or preventing a viral infection, and the corresponding method of treatment of a viral infection and pathologic conditions associated therewith, by administering an effective amount of such a quinazoline derivative to a patient in need thereof. In one embodiment, said viral infection may be an infection caused by a virus being a member of the Flaviviridae family. The Flaviviridae family is a family of positive-strand RNA viruses which includes the following genera:

Genus *Flavivirus* (type species include Yellow fever virus, West Nile virus and Dengue Fever), Genus *Hepacivirus* (type species includes Hepatitis C virus), and Genus *Pestivirus* (type species include Bovine viral diarrhea virus, classical swine fever and hog cholera).

In a particular embodiment of this aspect of the invention, said *Flavivirus* is the Hepatitis C virus (hereinafter referred as HCV).

The invention further relates to a method of treament or prevention of viral infections by administering a patient in need thereof a pharmaceutical composition comprising:

(a) one or more 4,6-di- and 2,4,6-trisubstituted quinazoline derivatives represented by the structural formula (I), and (b) one or more pharmaceutically acceptable carriers.

In another embodiment, this invention provides a method of treatment or prevention of viral infections by administering a patient in need thereof combinations, preferably synergistic combinations, of one or more 4,6-di- and 2,4,6-trisubstituted quinazoline derivatives represented by the structural formula (I) with one or more other antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, anti-viral activity against HCV.

The present invention further relates to a pharmaceutical composition or combined preparation having synergistic effects against a viral infection, especially a hepatitis C virus infection, and containing:

(a) one or more anti-viral agents, and (b) at least one 4,6-di- and 2,4,6-trisubstituted quinazoline derivative represented by the structural formula (I), and (c) optionally one or more pharmaceutical excipients or pharmaceutically acceptable carriers, for simultaneous, separate or sequential use in the treatment of HCV infection.

Suitable anti-viral agents for inclusion into the synergistic antiviral compositions or combined preparations of this invention include, for instance, retroviral enzyme inhibitors belonging to categories well known in the art, such as HIV-1 1N inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of hepatitis C virus, in particular in human beings. Therefore, of particular relevance in the context of HCV prevention or treatment is co-administration with one or more other agents aiming at HCV inhibition well known in the art, such as but not limited to, (pegylated) interferon alpha, ribavirin, an NS3 protease inhibitor (such as telaprivir), or nucleoside- or non-nucleoside-based inhibitors of NS5B polymerase. Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the 4,6-di- and 2,4,6-trisubstituted quinazoline derivative represented by the structural formula (I) over a broad content range depending on the contemplated use and the expected effect of the preparation. Generally, the 4,6-di- and 2,4,6-trisubstituted quinazoline derivative content of the combined preparation is within the range of from 0.1 to 99.9% by weight, preferably from 1 to 99% by weight, more preferably from about 5 to 95% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed herein below and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperitoneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the 4,6-di- and 2,4,6-trisubstituted quinazoline derivative represented by the general formula (I), and optionally the one or more other antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the quinazoline derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alkanolamine salts of dodecylbenzene sulphonic acid or dibutyl-naphthalenesulphonic acid or a naphthalenesulphonic acid/formaldehyde condensation product. Also suitable are the corresponding phosphates, e.g. salts of phosphoric acid ester and an adduct of pnonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof.

Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyaminoacids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including the 4,6-di- and 2,4,6-trisubstituted quinazoline derivative of this invention and one or more other antiviral agents, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating hepatitis C in a patient, in particular a mammal, more particularly a human being in need thereof. The method of this invention consists of administering to the patient in need thereof an effective amount of a 4,6-di- and 2,4,6-trisubstituted quinazoline derivative having the general formula (I), optionally together with an effective amount of one or more other antiviral agents, or a pharmaceutical composition comprising the same, such as disclosed above in extensive details.

The therapeutically effective amount of a 4,6-di- or 2,4,6-trisubstituted quinazoline derivative having the structural formula (I) is, for the purpose of the method of treatment of this invention, usually in the range of about 0.01 mg to 20 mg, preferably about 0.1 mg to 5 mg, per day per kg bodyweight for human beings. Depending upon the severity of the pathologic condition to be treated and upon the patient's condition, the said effective amount may be divided into several sub-units per day or may be administered at more than one day intervals. The patient to be treated may be any warm-blooded animal, preferably a mammal, more preferably a human being, suffering from said pathologic condition.

It is another aspect of the present invention to provide a series of individual 4,6-di- and 2,4,6-trisubstituted quinazoline derivatives represented by the structural formula (I) which are not yet known in the art. Without limitation, this series includes quinazoline derivatives selected from the group consisting of:

2-amino-6-(3,4-dimethoxyphenyl)-4-(N-morpholino)-quinazoline,
2-amino-6-(3,4-dimethoxyphenyl)-4-[N-(3-bromo)-anilino)]-quinazoline, 2-amino-6-(3,4-dimethoxyphenyl)-4-[N-(3-methylphenylarbamoyl)-piperazin-1-yl]-quinazoline,
2-amino-6-(3,4-dimethoxyphenyl)-4-[N-(4-methylphenyl)piperazin-1-yl]-quinazoline,
2-amino-6-(3,4-dimethoxyphenyl)-4-(N-acetylpiperazino)-quinazoline,
2-amino-6-(3,4-dimethoxyphenyl)-4-(N-cyclohexylamino)-quinazoline,
2-amino-6-(3,4-dimethoxyphenyl)-4-(N-methylpiperazino)-quinazoline
2-amino-6-(3,4-dimethoxyphenyl)-4-(N-piperidino)-quinazoline
2-amino-6-(3,4-dimethoxyphenyl)-4-[N-(3-methyl)-anilino]-quinazoline
2-amino-6-(3,4-dimethoxyphenyl)-4-hydrazino-quinazoline
2-amino-6-(3,4-dimethoxyphenyl)-4-(N,N-dimethylamino)-quinazoline
2-amino-6-(3,4-dimethoxyphenyl)-4-(N-butylamino)-quinazoline
2-amino-6-(3,4-dimethoxyphenyl)-4-(N-cyclopentylamino)-quinazoline
2-amino-6-(3,4-dimethoxyphenyl)-4-(N-cyclopropylamino)-quinazoline
2-amino-6-(3,4-dimethoxyphenyl)-4-(N-isopentylamino)-quinazoline
2-amino-6-(3,4-dimethoxyphenyl)-4-(N-propylamino)-quinazoline
2-amino-6-(3,4-dimethoxyphenyl)-4-amino-quinazoline
2-amino-6-(4-acetamidophenyl)-4-(N-morpholino)-quinazoline
2-amino-6-(4-acetamidophenyl)-4-[N-(3-bromo)-anilino)]-quinazoline
2-amino-6-(4-acetamidophenyl)-4-[N-(3-methylphenylcarbamoyl)-piperazin-1-yl]-quinazoline
2-amino-6-(4-acetamidophenyl)-4-[N-(4-methylphenyl)piperazin-1-yl]-quinazoline
2-amino-6-(4-acetamidophenyl)-4-(N-acetylpiperazino)-quinazoline
2-amino-6-(4-acetamidophenyl)-4-(N-cyclohexylamino)-quinazoline 2-amino-6-(4-acetamidophenyl)-4-(N-methylpiperazino)-quinazoline
2-amino-6-(4-acetamidophenyl)-4-(N-piperidino)-quinazoline
2-amino-6-(4-acetamidophenyl)-4-[N-(3-methyl)-anilino]-quinazoline
2-amino-6-(4-acetamidophenyl)-4-hydrazino-quinazoline
2-amino-6-(4-acetamidophenyl)-4-(N,N-dimethylamino)-quinazoline
2-amino-6-(4-acetamidophenyl)-4-(N,N-dimethylamino)-quinazoline
2-amino-6-(4-acetamidophenyl)-4-(N-butylamino)-quinazoline
2-amino-6-(4-acetamidophenyl)-4-(N-cyclopentylamino)-quinazoline
2-amino-6-(4-acetamidophenyl)-4-(N-cyclopropylamino)-quinazoline
2-amino-6-(4-acetamidophenyl)-4-(N-isopentylamino)-quinazoline
2-amino-6-(4-acetamidophenyl)-4-(N-propylamino)-quinazoline
2-amino-6-(4-acetamidophenyl)-4-amino-quinazoline
2-amino-6-(4-chlorophenyl)-4-(N-morpholino)-quinazoline
2-amino-6-(4-chlorophenyl)-4-[N-(3-bromo)-anilino)]-quinazoline
2-amino-6-(4-chlorophenyl)-4-[N-(3-methylphenylcarbamoyl)-piperazin-1-yl]-quinazoline,
2-amino-6-(4-chlorophenyl)-4-[N-(4-methylphenyl)piperazin-1-yl]-quinazoline
2-amino-6-(4-chlorophenyl)-4-(N-acetylpiperazino)-quinazoline
2-amino-6-(4-chlorophenyl)-4-(N-cyclohexylamino)-quinazoline
2-amino-6-(4-chlorophenyl)-4-(N-methylpiperazino)-quinazoline
2-amino-6-(4-chlorophenyl)-4-(N-piperidino)-quinazoline
2-amino-6-(4-chlorophenyl)-4-[N-(3-methyl)-anilino]-quinazoline
2-amino-6-(4-chlorophenyl)-4-hydrazino-quinazoline
2-amino-6-(4-chlorophenyl)-4-(N,N-dimethylamino)-quinazoline
2-amino-6-(4-chlorophenyl)-4-(N-butylamino)-quinazoline
2-amino-6-(4-chlorophenyl)-4-(N-cyclopentylamino)-quinazoline
2-amino-6-(4-chlorophenyl)-4-(N-cyclopropylamino)-quinazoline
2-amino-6-(4-chlorophenyl)-4-(N-isopentylamino)-quinazoline
2-amino-6-(4-chlorophenyl)-4-(N-propylamino)-quinazoline
2-amino-6-(4-chlorophenyl)-4-amino-quinazoline
2-amino-6-(4-fluorophenyl)-4-(N-morpholino)-quinazoline
2-amino-6-(4-fluorophenyl)-4-[N-(3-bromo)-anilino)]-quinazoline
2-amino-6-(4-fluorophenyl)-4-[N-(3-methylphenylcarbamoyl)-piperazin-1-yl]-quinazoline
2-amino-6-(4-fluorophenyl)-4-[N-(4-methylphenyl)piperazin-1-yl]-quinazoline
2-amino-6-(4-fluorophenyl)-4-(N-acetylpiperazino)-quinazoline
2-amino-6-(4-fluorophenyl)-4-(N-cyclohexylamino)-quinazoline
2-amino-6-(4-fluorophenyl)-4-(N-methylpiperazino)-quinazoline
2-amino-6-(4-fluorophenyl)-4-(N-piperidino)-quinazoline
2-amino-6-(4-fluorophenyl)-4-[N-(3-methyl)-anilino]-quinazoline
2-amino-6-(4-fluorophenyl)-4-hydrazino-quinazoline
2-amino-6-(4-fluorophenyl)-4-(N,N-dimethylamino)-quinazoline
2-amino-6-(4-fluorophenyl)-4-(N,N-dimethylamino)-quinazoline
2-amino-6-(4-fluorophenyl)-4-(N-butylamino)-quinazoline
2-amino-6-(4-fluorophenyl)-4-(N-cyclopentylamino)-quinazoline
2-amino-6-(4-fluorophenyl)-4-(N-cyclopropylamino)-quinazoline
2-amino-6-(4-fluorophenyl)-4-(N-isopentylamino)-quinazoline
2-amino-6-(4-fluorophenyl)-4-(N-propylamino)-quinazoline
2-amino-6-(4-fluorophenyl)-4-amino-quinazoline
2-amino-6-bromo-4-(N-morpholino)-quinazoline
2-amino-6-bromo-4-[N-(3-bromo)-anilino)]-quinazoline
2-amino-6-bromo-4-[N-(3-methylphenylcarbamoyl)-piperazin-1-yl]-quinazoline
2-amino-6-bromo-4-[N-(4-methylphenyl)piperazin-1-yl]-quinazoline
2-amino-6-bromo-4-(N-acetylpiperazino)-quinazoline
2-amino-6-bromo-4-(N-cyclohexylamino)-quinazoline
2-amino-6-bromo-4-(N-methylpiperazino)-quinazoline
2-amino-6-bromo-4-(N-piperidino)-quinazoline
2-amino-6-bromo-4-[N-(3-methyl)-anilino]-quinazoline
2-amino-6-bromo-4-hydrazino-quinazoline
2-amino-6-bromo-4-(N,N-dimethylamino)-quinazoline
2-amino-6-bromo-4-(N,N-dimethylamino)-quinazoline
2-amino-6-bromo-4-(N-butylamino)-quinazoline
2-amino-6-bromo-4-(N-cyclopentylamino)-quinazoline
2-amino-6-bromo-4-(N-cyclopropylamino)-quinazoline
2-amino-6-bromo-4-(N-isopentylamino)-quinazoline
2-amino-6-bromo-4-(N-propylamino)-quinazoline
2-amino-6-bromo-4-amino-quinazoline
2-acetamino-6-(3,4-dimethoxyphenyl)-4-(N-morpholino)-quinazoline
2-acetamino-6-(3,4-dimethoxyphenyl)-4-[N-(3-bromo)-anilino)]-quinazoline
2-acetamino-6-(3,4-dimethoxyphenyl)-4-[N-(3-methylphenylcarbamoyl)-piperazin-1-yl]-quinazoline
2-acetamino-6-(3,4-dimethoxyphenyl)-4-[N-(4-methylphenyl)piperazin-1-yl]-quinazoline
2-acetamino-6-(3,4-dimethoxyphenyl)-4-(N-acetylpiperazino)-quinazoline
2-acetamino-6-(3,4-dimethoxyphenyl)-4-(N-cyclohexylamino)-quinazoline
2-acetamino-6-(3,4-dimethoxyphenyl)-4-(N-methylpiperazino)-quinazoline
2-acetamino-6-(3,4-dimethoxyphenyl)-4-(N-piperidino)-quinazoline
2-acetamino-6-(3,4-dimethoxyphenyl)-4-[N-(3-methyl)-anilino]-quinazoline
2-acetamino-6-(3,4-dimethoxyphenyl)-4-hydrazino-quinazoline
2-acetamino-6-(3,4-dimethoxyphenyl)-4-(N,N-dimethylamino)-quinazoline
2-acetamino-6-(3,4-dimethoxyphenyl)-4-(N,N-dimethylamino)-quinazoline
2-acetamino-6-(3,4-dimethoxyphenyl)-4-(N-butylamino)-quinazoline
2-acetamino-6-(3,4-dimethoxyphenyl)-4-(N-cyclopentylamino)-quinazoline
2-acetamino-6-(3,4-dimethoxyphenyl)-4-(N-cyclopropylamino)-quinazoline
2-acetamino-6-(3,4-dimethoxyphenyl)-4-(N-isopentylamino)-quinazoline 2-acetamino-6-(3,4-dimethoxyphenyl)-4-(N-propylamino)-quinazoline
2-acetamino-6-(3,4-dimethoxyphenyl)-4-amino-quinazoline
2-acetamino-6-(4-acetamidophenyl)-4-(N-morpholino)-quinazoline
2-acetamino-6-(4-acetamidophenyl)-4-[N-(3-bromo)-anilino)]-quinazoline
2-acetamino-6-(4-acetamidophenyl)-4-[N-(3-methylphenyl-carbamoy)-piperazin-1-yl]-quinazoline
2-acetamino-6-(4-acetamidophenyl)-4-[N-(4-methylphenyl)piperazin-1-yl]-quinazoline
2-acetamino-6-(4-acetamidophenyl)-4-(N-acetylpiperazino)-quinazoline
2-acetamino-6-(4-acetamidophenyl)-4-(N-cyclohexylamino)-quinazoline
2-acetamino-6-(4-acetamidophenyl)-4-(N-methylpiperazino)-quinazoline
2-acetamino-6-(4-acetamidophenyl)-4-(N-piperidino)-quinazoline
2-acetamino-6-(4-acetamidophenyl)-4-[N-(3-methyl)-anilino]-quinazoline
2-acetamino-6-(4-acetamidophenyl)-4-hydrazino-quinazoline
2-acetamino-6-(4-acetamidophenyl)-4-(N,N-dimethylamino)-quinazoline
2-acetamino-6-(4-acetamidophenyl)-4-(N,N-dimethylamino)-quinazoline
2-acetamino-6-(4-acetamidophenyl)-4-(N-butylamino)-quinazoline
2-acetamino-6-(4-acetamidophenyl)-4-(N-cyclopentylamino)-quinazoline
2-acetamino-6-(4-acetamidophenyl)-4-(N-cyclopropylamino)-quinazoline
2-acetamino-6-(4-acetamidophenyl)-4-(N-isopentylamino)-quinazoline
2-acetamino-6-(4-acetamidophenyl)-4-(N-propylamino)-quinazoline
2-acetamino-6-(4-acetamidophenyl)-4-amino-quinazoline
2-acetamino-6-(4-chlorophenyl)-4-(N-morpholino)-quinazoline
2-acetamino-6-(4-chlorophenyl)-4-[N-(3-bromo)-anilino)]-quinazoline
2-acetamino-6-(4-chlorophenyl)-4-[N-(3-methylphenylcarbamoyl)-piperazin-1-yl]-quinazoline
2-acetamino-6-(4-chlorophenyl)-4-[N-(4-methylphenyl)piperazin-1-yl]-quinazoline
2-acetamino-6-(4-chlorophenyl)-4-(N-acetylpiperazino)-quinazoline
2-acetamino-6-(4-chlorophenyl)-4-(N-cyclohexylamino)-quinazoline
2-acetamino-6-(4-chlorophenyl)-4-(N-methylpiperazino)-quinazoline
2-acetamino-6-(4-chlorophenyl)-4-(N-piperidino)-quinazoline
2-acetamino-6-(4-chlorophenyl)-4-[N-(3-methyl)-anilino]-quinazoline
2-acetamino-6-(4-chlorophenyl)-4-hydrazino-quinazoline
2-acetamino-6-(4-chlorophenyl)-4-(N,N-dimethylamino)-quinazoline
2-acetamino-6-(4-chlorophenyl)-4-(N,N-dimethylamino)-quinazoline
2-acetamino-6-(4-chlorophenyl)-4-(N-butylamino)-quinazoline
2-acetamino-6-(4-chlorophenyl)-4-(N-cyclopentylamino)-quinazoline
2-acetamino-6-(4-chlorophenyl)-4-(N-cyclopropylamino)-quinazoline
2-acetamino-6-(4-chlorophenyl)-4-(N-isopentylamino)-quinazoline
2-acetamino-6-(4-chlorophenyl)-4-(N-propylamino)-quinazoline
2-acetamino-6-(4-chlorophenyl)-4-amino-quinazoline
2-acetamino-6-(4-fluorophenyl)-4-(N-morpholino)-quinazoline
2-acetamino-6-(4-fluorophenyl)-4-[N-(3-bromo)-anilino)]-quinazoline
2-acetamino-6-(4-fluorophenyl)-4-[N-(3-methylphenylcarbamoyl)-piperazin-1-yl]-quinazoline
2-acetamino-6-(4-fluorophenyl)-4-[N-(4-methylphenyl)piperazin-1-yl]-quinazoline
2-acetamino-6-(4-fluorophenyl)-4-(N-acetylpiperazino)-quinazoline
2-acetamino-6-(4-fluorophenyl)-4-(N-cyclohexylamino)-quinazoline
2-acetamino-6-(4-fluorophenyl)-4-(N-methylpiperazino)-quinazoline
2-acetamino-6-(4-fluorophenyl)-4-(N-piperidino)-quinazoline
2-acetamino-6-(4-fluorophenyl)-4-[N-(3-methyl)-amino]-quinazoline
2-acetamino-6-(4-fluorophenyl)-4-hydrazino-quinazoline
2-acetamino-6-(4-fluorophenyl)-4-(N,N-dimethylamino)-quinazoline
2-acetamino-6-(4-fluorophenyl)-4-(N-butylamino)-quinazoline
2-acetamino-6-(4-fluorophenyl)-4-(N-cyclopentylamino)-quinazoline
2-acetamino-6-(4-fluorophenyl)-4-(N-cyclopropylamino)-quinazoline
2-acetamino-6-(4-fluorophenyl)-4-(N-isopentylamino)-quinazoline
2-acetamino-6-(4-fluorophenyl)-4-(N-propylamino)-quinazoline
2-acetamino-6-(4-fluorophenyl)-4-amino-quinazoline
2-acetamino-6-bromo-4-(N-morpholino)-quinazoline
2-acetamino-6-bromo-4-[N-(3-bromo)-anilino)]-quinazoline
2-acetamino-6-bromo-4-[N-(3-methylphenylcarbamoyl)-piperazin-1-yl]-quinazoline 2-acetamino-6-bromo-4-[N-(4-methylphenyl)piperazin-1-yl]-quinazoline
2-acetamino-6-bromo-4-(N-acetylpiperazino)-quinazoline
2-acetamino-6-bromo-4-(N-cyclohexylamino)-quinazoline
2-acetamino-6-bromo-4-(N-methylpiperazino)-quinazoline
2-acetamino-6-bromo-4-(N-piperidino)-quinazoline
2-acetamino-6-bromo-4-[N-(3-methyl)-anilino]-quinazoline
2-acetamino-6-bromo-4-hydrazino-quinazoline
2-acetamino-6-bromo-4-(N,N-dimethylamino)-quinazoline
2-acetamino-6-bromo-4-(N,N-dimethylamino)-quinazoline
2-acetamino-6-bromo-4-(N-butylamino)-quinazoline
2-acetamino-6-bromo-4-(N-cyclopentylamino)-quinazoline
2-acetamino-6-bromo-4-(N-cyclopropylamino)-quinazoline
2-acetamino-6-bromo-4-(N-isopentylamino)-quinazoline
2-acetamino-6-bromo-4-(N-propylamino)-quinazoline
2-acetamino-6-bromo-4-amino-quinazoline
6-(3,4-dimethoxyphenyl)-4-(N-morpholino)-quinazoline
6-(3,4-dimethoxyphenyl)-4-[N-(3-bromo)-anilino)]-quinazoline
6-(3,4-dimethoxyphenyl)-4-[N-(3-methylphenylcarbamoyl)-piperazin-1-yl]-quinazoline
6-(3,4-dimethoxyphenyl)-4-[N-(4-methylphenyl)piperazin-1-yl]-quinazoline 6-(3,4-dimethoxyphenyl)-4-(N-acetylpiperazino)-quinazoline
6-(3,4-dimethoxyphenyl)-4-(N-cyclohexylamino)-quinazoline
6-(3,4-dimethoxyphenyl)-4-(N-methylpiperazino)-quinazoline
6-(3,4-dimethoxyphenyl)-4-(N-piperidino)-quinazoline
6-(3,4-dimethoxyphenyl)-4-[N-(3-methyl)-anilino]-quinazoline
6-(3,4-dimethoxyphenyl)-4-hydrazino-quinazoline
4-(N,N-dimethylamino)-6-(3,4-dimethoxyphenyl)-quinazoline
4-(N,N-dimethylamino)-6-(3,4-dimethoxyphenyl)-quinazoline
4-(N-butylamino)-6-(3,4-dimethoxyphenyl)-quinazoline
4-(N-cyclopentylamino)-6-(3,4-dimethoxyphenyl)-quinazoline
4-(N-cyclopropylamino)-6-(3,4-dimethoxyphenyl)-quinazoline
4-(N-isopentylamino)-6-(3,4-dimethoxyphenyl)-quinazoline
4-(N-propylamino)-6-(3,4-dimethoxyphenyl)-quinazoline
4-amino-6-(3,4-dimethoxyphenyl)-quinazoline
6-(4-acetamidophenyl)-4-(N-morpholino)-quinazoline
6-(4-acetamidophenyl)-4-[N-(3-bromo)-anilino)]-quinazoline
6-(4-acetamidophenyl)-4-[N-(3-methylphenylcarbamoyl)-piperazin-1-yl]-quinazoline
6-(4-acetamidophenyl)-4-[N-(4-methylphenyl)piperazin-1-yl]-quinazoline
6-(4-acetamidophenyl)-4-(N-acetylpiperazino)-quinazoline
6-(4-acetamidophenyl)-4-(N-cyclohexylamino)-quinazoline
6-(4-acetamidophenyl)-4-(N-methylpiperazino)-quinazoline
6-(4-acetamidophenyl)-4-(N-piperidino)-quinazoline
6-(4-acetamidophenyl)-4-[N-(3-methyl)-anilino]-quinazoline
6-(4-acetamidophenyl)-4-hydrazino-quinazoline
4-(N,N-dimethylamino)-6-(4-acetamidophenyl)-quinazoline
4-(N,N-dimethylamino)-6-(4-acetamidophenyl)-quinazoline
4-(N-butylamino)-6-(4-acetamidophenyl)-quinazoline
4-(N-cyclopentylamino)-6-(4-acetamidophenyl)-quinazoline
4-(N-cyclopropylamino)-6-(4-acetamidophenyl)-quinazoline
4-(N-isopentylamino)-6-(4-acetamidophenyl)-quinazoline
4-(N-propylamino)-6-(4-acetamidophenyl)-quinazoline
4-amino-6-(4-acetamidophenyl)-quinazoline
6-(4-chlorophenyl)-4-(N-morpholino)-quinazoline
6-(4-chlorophenyl)-4-[N-(3-bromo)-anilino)]-quinazoline
6-(4-chlorophenyl)-4-[N-(3-methylphenylcarbamoyl)-piperazin-1-yl]-quinazoline
6-(4-chlorophenyl)-4-[N-(4-methylphenyl)piperazin-1-yl]-quinazoline
6-(4-chlorophenyl)-4-(N-acetylpiperazino)-quinazoline
6-(4-chlorophenyl)-4-(N-cyclohexylamino)-quinazoline
6-(4-chlorophenyl)-4-(N-methylpiperazino)-quinazoline
6-(4-chlorophenyl)-4-(N-piperidino)-quinazoline
6-(4-chlorophenyl)-4-[N-(3-methyl)-anilino]-quinazoline
6-(4-chlorophenyl)-4-hydrazino-quinazoline
4-(N,N-dimethylamino)-6-(4-chlorophenyl)-quinazoline
4-(N,N-dimethylamino)-6-(4-chlorophenyl)-quinazoline
4-(N-butylamino)-6-(4-chlorophenyl)-quinazoline
4-(N-cyclopentylamino)-6-(4-chlorophenyl)-quinazoline
4-(N-cyclopropylamino)-6-(4-chlorophenyl)-quinazoline
4-(N-isopentylamino)-6-(4-chlorophenyl)-quinazoline
4-(N-propylamino)-6-(4-chlorophenyl)-quinazoline
4-amino-6-(4-chlorophenyl)-quinazoline
6-(4-fluorophenyl)-4-(N-morpholino)-quinazoline
6-(4-fluorophenyl)-4-[N-(3-bromo)-anilino)]-quinazoline
6-(4-fluorophenyl)-4-[N-(3-methylphenylcarbamoyl)-piperazin-1-yl]-quinazoline
6-(4-fluorophenyl)-4-[N-(4-methylphenyl)piperazin-1-yl]-quinazoline
6-(4-fluorophenyl)-4-(N-acetylpiperazino)-quinazoline
6-(4-fluorophenyl)-4-(N-cyclohexylamino)-quinazoline
6-(4-fluorophenyl)-4-(N-methylpiperazino)-quinazoline
6-(4-fluorophenyl)-4-(N-piperidino)-quinazoline
6-(4-fluorophenyl)-4-[N-(3-methyl)-anilino]-quinazoline
6-(4-fluorophenyl)-4-hydrazino-quinazoline
4-(N,N-dimethylamino)-6-(4-fluorophenyl)-quinazoline
4-(N-butylamino)-6-(4-fluorophenyl)-quinazoline
4-(N-cyclopentylamino)-6-(4-fluorophenyl)-quinazoline
4-(N-cyclopropylamino)-6-(4-fluorophenyl)-quinazoline
4-(N-isopentylamino)-6-(4-fluorophenyl)-quinazoline
4-(N-propylamino)-6-(4-fluorophenyl)-quinazoline
4-amino-6-(4-fluorophenyl)-quinazoline
6-bromo-4-(N-morpholino)-quinazoline
6-bromo-4-[N-(3-bromo)-anilino)]-quinazoline
6-bromo-4-[N-(3-methylphenylcarbamoyl)-piperazin-1-yl]-quinazoline
6-bromo-4-[N-(4-methylphenyl)piperazin-1-yl]-quinazoline
6-bromo-4-(N-acetylpiperazino)-quinazoline
6-bromo-4-(N-cyclohexylamino)-quinazoline
6-bromo-4-(N-methylpiperazino)-quinazoline
6-bromo-4-(N-piperidino)-quinazoline
6-bromo-4-[N-(3-methyl)-anilino]-quinazoline
6-bromo-4-hydrazino-quinazoline
4-(N,N-dimethylamino)-6-bromo-quinazoline
4-(N,N-dimethylamino)-6-bromo-quinazoline
4-(N-butylamino)-6-bromo-quinazoline
4-(N-cyclopentylamino)-6-bromo-quinazoline
4-(N-cyclopropylamino)-6-bromo-quinazoline
4-(N-isopentylamino)-6-bromo-quinazoline
4-(N-propylamino)-6-bromo-quinazoline
4-amino-6-bromo-quinazoline,
(N2-(4-fluoro-benzyl)-6-(4-fluoro-phenyl)-N4-(2,2,2-trifluoro-ethyl)-quinazoline-2,4-diamine,
N-cyclopropyl-4-[2-(4-fluoro-benzylamino)-4-(2,2,2-trifluoro-ethylamino)quinazolin-6-yl]-benzamide,
N-cyclopropyl-4-[2-(4-sulfamoyl-benzylamino)-4-(2,2,2-trifluoro-ethylamino)quinazolin-6-yl]-benzamide,
4-{[6-(4-fluoro-phenyl)-4-(2,2,2-trifluoro-ethylamino)-quinazolin-2-ylamino]-methyl}-benzenesulfonamide,
cyclopropyl-[6-(4-fluoro-phenyl)-2-(2H-pyrazol-3-yl)-quinazolin-4-yl]-amine
N4-cyclopropyl-6-(4-fluoro-phenyl)-N2-(1-methyl-1H-pyrazol-3-yl)-quinazoline-2,4-diamine,
N4,N2-bis-n-butyl-6-(4-fluoro-phenyl)-quinazoline-2,4-diamine, and
4-[2-amino-4-(2-methoxy-ethylamino)-quinazolin-6-yl]-N-cyclopropyl-benzamide,
6-bromo-N2-(4-fluoro-benzyl)-N4-(2,2,2-trifluoro-ethyl)-quinazoline-2,4-diamine,
4-{[6-bromo-4-(2,2,2-trifluoro-ethylamino)-quinazolin-2-ylamino]-methyl}-benzenesulfonamide, and
6-bromo-N4-(2-methoxy-ethyl)-quinazoline-2,4-diamine,
and/or a pharmaceutically acceptable addition salt thereof and/or a stereo-isomer thereof and/or a mono- or a di-N-oxide thereof and/or a solvate thereof and/or a pro-drug form thereof.

The present invention provides different methods for making disubstituted and trisubstituted quinazoline derivatives having the structural formula (I) as defined above with respect to the first aspect of the invention. Methods of manufacture have been developed by the present inventors which may be used alternatively to, or may be combined with, the methods of synthesis already known in the art of quinazoline derivatives (depending upon the targeted final compound). For instance, synthesis of mono- and di-N-oxides of the quinazoline derivatives of this invention can easily be achieved by treating the said derivatives with an oxidizing agent such as, but not limited to, hydrogen peroxide (e.g. in the presence of acetic acid) or a peracid such as, but not limited to, chloroperbenzoic acid. The methods for making the quinazoline derivatives of the present invention will now be explained in more details by reference to the appended FIGS. 1 to 8 wherein the notation "Ar" stands for aryl, "Ac" stands for acetyl, "L" indicated a good leaving group for nucleophilic displacement reactions, and wherein $R_2$, $R_4$ and $R_5$ are as defined in the above structural formula (I) and more specifically may correspond to any of the individual meanings disclosed above.

In the following description of certain reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

The disubstituted and trisubstituted quinazoline derivatives having the structural formula (I) can be synthesized, without limitation, according to one or more of the following procedures.

FIG. 1 schematically shows a method for making 2-amino-4,6-disubstituted quinazoline analogues. In step (a), a 5-haloanthranilic acid (X is preferably chlorine, bromine or iodine), is condensed with chloroformamidine in order to construct a 2-amino-4-hydroxy-6-haloquinazoline scaffold. Although FIG. 1 shows only an aryl substituent on position 6 of the quinazoline scaffold, the present method is not limited thereto and is also applicable to quinazoline derivatives wherein the 6-substituent is other than aryl, e.g. a heteroaryl, or a C-linked unsaturated substituent such as alkenyl or alkynyl. The halogen at position 6 (X is preferably chlorine, bromine or iodine) of this quinazoline scaffold can be used in step (b) for a wide variety of palladium-catalyzed cross-coupling reactions, such as, but not limited to, a Suzuki reaction (i.e. a reaction with an arylboronic acid, a heteroarylboronic acid or a pinacol ester thereof, leading to the formation of 2-amino-4-hydroxy-6-(hetero)arylquinazolines as shown in FIG. 1), a Heck reaction (i.e. a reaction with a terminal alkene affording the corresponding 2-amino-4-hydroxy-6-alkenylquinazoline derivatives, not shown in FIG. 1), or a Sonogashira reaction (i.e. a reaction with a terminal alkyne affording the corresponding 2-amino-4-hydroxy-6-alkynylquinazoline derivatives, not shown in FIG. 1).

As shown in step (c), the amino group at position 2 of the quinazoline scaffold is then protected from further reactions with for example (but not limited to) an acetyl group (as shown in the figure, e.g. by reaction with acetic anhydride in pyridine) or a pivaloyl group (e.g. by reaction with pivaloyl anhydride in pyridine, not shown in the figure). Activation of the tautomeric hydroxyl group at position 4 of the quinazoline scaffold occurs in step (d) by introducing a good leaving group at position 4 of the quinazoline scaffold (indicated by the letter L in FIG. 1). Good leaving groups are for example but not limited to chlorine or 1,2,4-triazolyl. The 4-(1,2,4-triazolyl) derivative can be obtained by treating the 4-hydroxy-quinazoline derivative with $POCl_3$ or 4-chloro-phenyl phosphorodichloridate and 1,2,4-triazole in an appropriate solvent such as, for example, but not limited to, pyridine, acetonitrile or dichloromethane. The 4-chloro derivative can be obtained by treating the 4-hydroxyquinazoline derivative with thionylchloride or $POCl_3$.

Nucleophilic displacement of L, for example the triazolyl group or the chlorine, occurs in step (e) by reaction with an appropriate amine, bearing the general formula $NHR_4R_5$, such as for example but not limited to alkylamine, alkenylamino, cycloalkylamine, cycloalkenylamine, arylamine, arylalkylamine, cycloalkyl alkamine, heterocyclic amine or heterocyclic-substituted alkyl amine, in an aprotic solvent such as for example dioxane or tetrahydrofuran. Introduction of an amino-substituent in step (e) may concomitantly lead to deprotection of the protecting group of the amino group at position 2. If no deprotection is observed during the introduction of the nucleophile, then in the final step, the protecting group has to be cleaved off using standard deprotection sequences, such as but not limited to acidic or basic hydrolysis.

Figure 2:
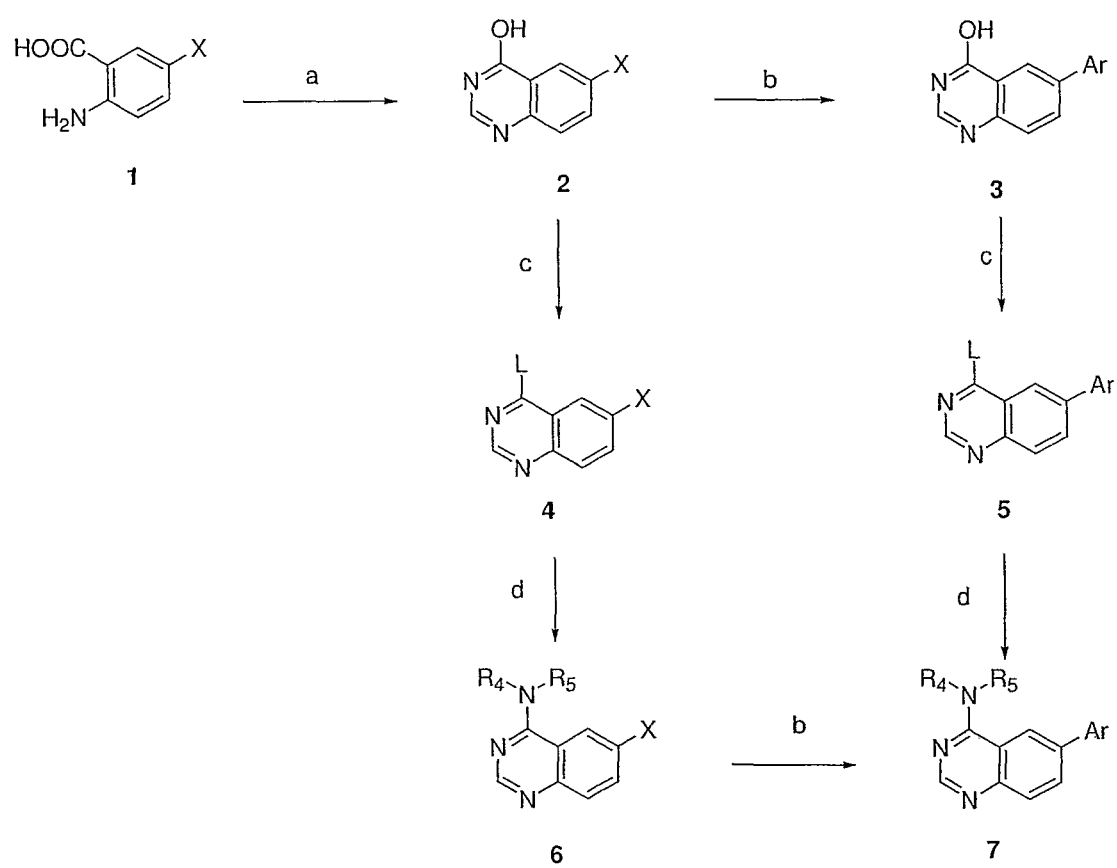
FIG. 2 schematically shows a synthetic pathway for the synthesis of 4,6-disubstituted quinazoline derivatives according to one embodiment of the present invention.

FIG. 2 schematically shows a method for making 4,6-disubstituted quinazoline derivatives according to the present invention. Although FIG. 2 shows only an aryl substituent on position 6 of the quinazoline scaffold, the present method is not limited thereto and is also applicable to quinazoline derivatives wherein the 6-substituent is other than aryl, e.g. a heteroaryl, or a C-linked unsaturated substituent such as alkenyl or alkynyl. In step (a) 5-halo-anthranilic acid represented by the formula I (wherein X is preferably chlorine, bromine or iodine) is condensed with formamide in order to construct the 4-hydroxy-6-haloquinazoline scaffold. In step (b) the halogen atom at position 6 of this scaffold can be used for a wide variety of palladium-catalyzed cross-coupling reactions, such as for example, but not limited to, Suzuki reactions (reactions with an arylboronic acid, a heteroarylboronic acid or a pinacol ester thereof, leading to the formation of 4-hydroxy-6-arylquinazolines (as shown in FIG. 2) or 4-hydroxy-6-heteroarylquinazolines, Heck reactions (reaction with terminal alkenes affording 4-hydroxy-6-alkenylquinazolines, not shown in FIG. 2), Sonogashira reaction (reaction with terminal alkynes giving rise to 4-hydroxy-6-alkynyl quinazoline derivatives, not shown in FIG. 2). Activation of the tautomeric hydroxyl group at position 4 of the quinazoline scaffold occurs in step (c) by introducing a readily leaving group (indicated by the letter L in FIG. 2) at position 4 of the quinazoline scaffold, in a manner similar as described with respect to FIG. 1. Nucleophilic displacement of the leaving group L (e.g. triazolyl or chloro) occurs in step (d) by reaction with an appropriate nucleophilic reagent $NHR_4R_5$, as previously described with respect to FIG. 1.

Figure 3:
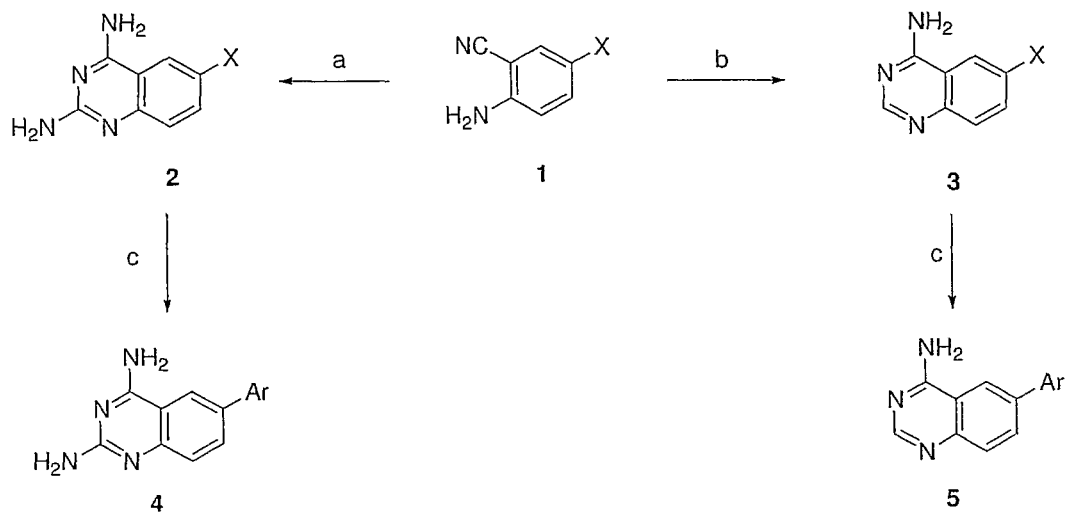
FIG. 3 schematically shows a synthetic pathway for the synthesis of 4-amino-2,6-disubstituted and 4-amino-6-substituted quinazolines according to one embodiment of the present invention.

FIG. 3 schematically shows a method for making 2,4-diamino-6-substituted-quinazoline analogues and 4-amino-6-substituted-quinazoline analogues. Although FIG. 3 shows only an aryl substituent on position 6 of the quinazoline scaffold, the present method is not limited thereto and is also applicable to quinazoline derivatives wherein the 6-substituent is other than aryl, e.g. a heteroaryl, or a C-linked unsaturated substituent such as alkenyl or alkynyl. In step (a), 2-amino-5-chloro-benzonitrile is condensed with chloroformamidine in order to construct the 2,4-diamino-quinazoline scaffold. Alternatively, a similar ring closure reaction with formamide (step (b)) gives rise to the 4-amino-quinazoline scaffold. The halogen at position 6 of the quinazoline scaffold can be used for a wide variety of palladium-catalyzed cross-coupling reactions, in a manner similar as described with respect to step (b) in FIG. 1.

Figure 4:
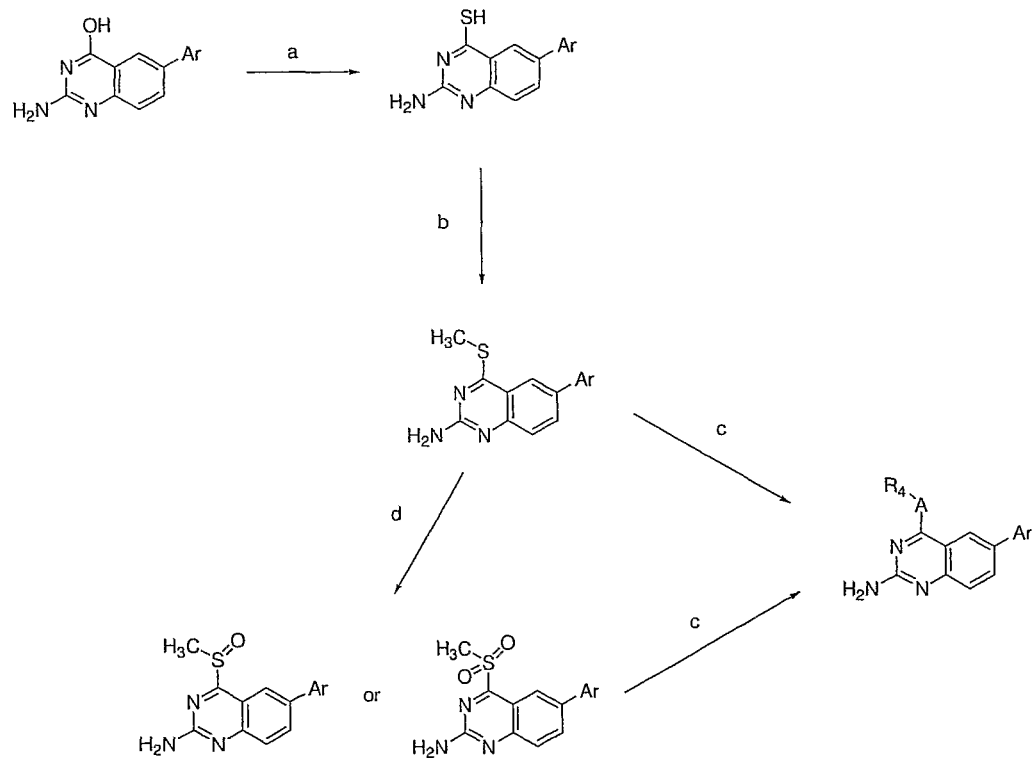
FIG. 4 schematically shows an alternative synthetic pathway for the synthesis of 2-amino-4,6-disubstituted quinazolines according to one embodiment of the present invention.

FIG. 4 schematically shows an alternative method for making 2-amino-4,6-disubstituted quinazoline analogues. Although FIG. 4 shows only an aryl substituent on position 6 of the quinazoline scaffold, the present method is not limited thereto and is also applicable to quinazoline derivatives wherein the 6-substituent is other than aryl, e.g. a heteroaryl, or a C-linked unsaturated substituent such as alkenyl or alkynyl. FIG. 4 also shows the substituent -A-$R_4$ on position 4 of the quinazoline scaffold wherein "A" stands for "$NR_5$" In step (a), the oxo group is converted to the sulfhydryl group by treatment with phosphorus pentasulfide or Lawesson's reagent. The thio analogue can be alkylated in step (b) using an appropriate halogenated reagent under alkaline conditions (e.g. an aqueous sodium hydroxide solution). In the specific case where a thiomethyl analogue has been synthesized in step (b), by treatment with iodomethane, the thiomethyl group acts as a good leaving group and might be replaced by suitable nucleophiles, such as various primary or secondary amines such as but not limited to alkylamine, alkenylamino, cycloalkylamine, cycloalkenylamine, arylamine, arylalkylamine, cycloalkyl alklamine, heterocyclic amine or heterocyclic-substituted alkyl amine. In some cases (for example when less reactive nucleophiles are used, such as for example aniline analogues), it might be necessary to oxidize the sulfur to its corresponding sulfoxide or sulfone in step (d). This might be achieved by using oxidizing agents, such as for example, but not limited to hydrogen peroxide, sodium periodate or m-chloro-perbenzoic acid. The sulfone or sulfoxide is then easily displaced by a wide range of amines such as the ones referred to earlier in this paragraph.

Figure 5:
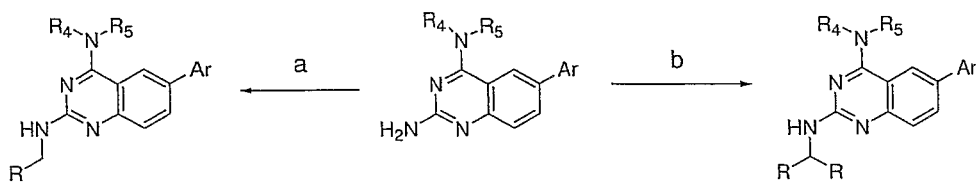
FIG. 5 schematically shows a synthetic pathway for the synthesis of 2-(substituted-amino)-4,6-disubstituted quinazolines according to one embodiment of the present invention.

FIG. 5 schematically shows a method for making 2-alkylamino-4,6-substituted quinazoline compounds according to one embodiment of the present invention. Although FIG. 5 shows only an aryl substituent on position 6 of the quinazoline scaffold, the present method is not limited thereto and is also applicable to quinazoline derivatives wherein the 6-substituent is, other than aryl, a heteroaryl or a C-linked unsaturated substituent, such as alkenyl or alkynyl, the construction of which has been previously described with respect to FIG. 1 (Heck reaction and Sonogashira reaction). In step (a), the 2-amino-4,6-disubstituted quinazoline derivative is condensed with an aldehyde having the structural formula RC(O)H in an appropriate solvent and in the presence of a suitable reducing agent. Suitable (and preferably commercially available) aldehydes include, but are not limited to, acetaldehyde, benzaldehyde and derivatives thereof (such as listed below), propionaldehyde, naphthaldehyde, salicylaldehyde and the like. Suitable solvents are for example methanol and acetonitrile. Suitable reducing agents include, but are not limited to, sodium cyanoborohydride, sodium triacetoxyborohydride and sodium borohydride.

Alternatively this reductive amination reaction can also be carried out in step (b) by means of a ketone having the structural formula RC(O)R, wherein R and R may be the same or different and may be defined as with respect to formula (I). Suitable ketones include, but are not limited to, acetone, methylethylketone and acetophenone.

In particular, optionally mono-substituted or di-substituted benzaldehydes suitable as starting materials for the condensation reaction of step (a) of the method illustrated by FIG. 5 include, but are not limited to, benzaldehyde, salicylaldehyde, otolualdehyde, m-tolualdehyde, p-tolualdehyde, o-anisaldehyde, m-anisaldehyde, panisaldehyde, 2,5-dihydroxybenzaldehyde, 4-propoxy-benzaldehyde, 4-phenoxybenzaldehyde, 3-(3,4-dichlorophenoxy)benzaldehyde, 3-(3,5-dichlorophenoxy)benzaldehyde, 2-bromo-benzaldehyde, 3-bromobenzaldehyde, 4-bromo-benzaldehyde, 2-chlorobenzaldehyde, 3-chlorobenzaldehyde, 4-chlorobenzaldehyde, 2-fluorobenzaldehyde, 3-fluorobenzaldehyde, 4-fluorobenzaldehyde, 2,3-dichlorobenzaldehyde, 2,4-dichlorobenzaldehyde, 2,6-dichlorobenzaldehyde, 3,4-dichlorobenzaldehyde, 3,5-dichloro-benzaldehyde, 2,3-difluoro-benzaldehyde, 2,4-difluorobenzaldehyde, 2,5-difluoro-benzaldehyde, 2,6-difluorobenzaldehyde, 3,4-difluorobenzaldehyde, 3,5-difluoro-benzaldehyde, 2,3,4-trifluorobenzaldehyde, 2-(trifluoromethyl)benzaldehyde, 3-(trifluoromethyl)benzaldehyde, 4-(trifluoromethyl)benzaldehyde, 3-(trifluoro-methoxy)benzaldehyde, 5-(trifluoromethoxy)salicylaldehyde, 3,5-dichloro-salicyl-aldehyde, 2-nitrobenzaldehyde, 3-nitrobenzaldehyde, 4-nitrobenzaldehyde, 3-cyanobenzaldehyde, 4-cyano-benzaldehyde, 4-dimethylamino-1-naphthaldehyde, 4-(dimethylamino)benzaldehyde, 4-(diethylamino)benzaldehyde and 3,4,5-trimethoxybenzaldehyde.

Figure 6:
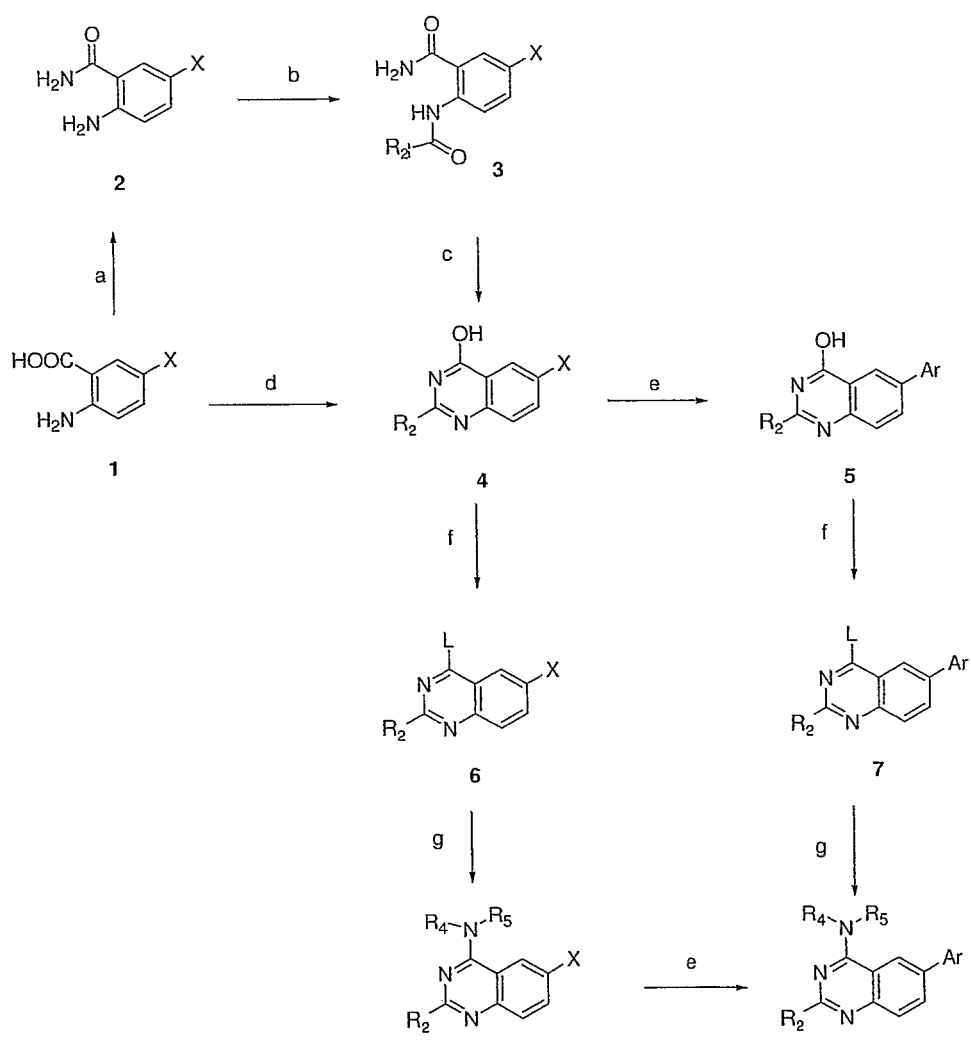
FIG. 6 schematically shows a method for making 2,4,6-trisubstituted quinazolines bearing C-linked substituents on position 2 according to one embodiment of the present invention.

FIG. 6 schematically shows a method for making 2,4,6-trisubstituted quinazoline derivatives according to one embodiment of this invention, said derivatives having a C-linked substituent on position 2 of the quinazoline scaffold such as, but not limited to, 2-alkyl-4,6-substituted quinazoline derivatives, 2-cycloalkyl-4,6-substituted quinazoline derivatives, 2-arylalkyl-4,6-substituted quinazoline derivatives, 2-aryl-4,6-substituted quinazoline derivatives, 2-alkenyl-4,6-substituted quinazoline derivatives, 2-cycloalkenyl-4,6-substituted quinazoline derivatives, 2-heterocyclic-4,6-substituted quinazoline derivatives, 2-[(heterocyclic-substituted) alkyl]-4,6-substituted quinazoline derivatives, or 2-[(cycloalkyl)alkyl]-4,6-substituted quinazoline derivatives, wherein each of said C-linked substituent on position 2 may optionally be further substituted. Although FIG. 6 shows only a halo substituent X or an aryl substituent on position 6 of the quinazoline scaffold, the present method is not limited thereto and is also applicable to quinazoline derivatives wherein the 6-substituent is a heteroaryl or a C-linked unsaturated substituent, such as, alkenyl or alkynyl, the construction of which has been previously described with respect to FIG. 1 (e.g. through a cross-coupling reaction such as, but not limited to, Heck reaction and Sonogashira reaction). In step (a), the carboxylic acid moiety of a 5-halo-anthranilic acid (wherein preferably X is iodine, bromine or chlorine) is converted to the corresponding amide e.g. by treatment with suitable amounts of thionylchloride (or N,N'-dicyclohexylcarbodiimide) and ammonia. In step (b), the amino group is condensed with a suitable aliphatic or cycloaliphatic monocarboxylic acid halide having the structural formula $R_2C(O)X$ wherein X is a halogen, preferably chlorine, and wherein $R_2$ may be alkyl, alkenyl, cycloalkyl, cycloalkenyl, aryl, heterocyclic, arylalkyl, heterocyclic-substituted alkyl or cycloalkyl-alkyl, to provide the corresponding amide derivative 3. Non-limiting examples of suitable aliphatic or cycloaliphatic monocarboxylic acid halides include acetyl chloride, benzoyl chloride, propionyl chloride, as well as other acyl halides mentioned with respect to the definition of "acyl", and the like. In step (c), ring closure is effected by heating compound 3 under alkaline conditions, thus affording a 2-R-4-hydroxy-6-haloquinazoline derivative. Alternatively in step (d), a 5-halo-anthranilic acid (wherein preferably X is iodine, bromine or chlorine) is condensed in the presence of ammonium acetate with an appropriate ortho-ester having the structural formula $RC(OEt)_3$ wherein "Et" is ethyl and wherein R may be alkyl, alkenyl, cycloalkyl, cycloalkenyl, aryl, heterocyclic, arylalkyl, heterocyclic-substituted alkyl or cycloalkyl-alkyl in order to directly afford a 2-R-4-hydroxy-6-haloquinazoline derivative. The halogen atom at position 6 (preferably chlorine, bromine or iodine) of the quinazoline scaffold can then be used in step (e) for a wide variety of palladium-catalyzed cross-coupling reactions, such as for example, but not limited to, Suzuki reactions (reactions with arylboronic acids, heteroarylboronic acids, or pinacol esters thereof), Heck reactions (reaction with terminal), and Sonogashira reactions (reaction with terminal alkynes) as previously described with respect to FIG. 1. Activation of the tautomeric hydroxyl group at position 4 of the quinazoline scaffold occurs in step (f) by introducing a readily leaving group (indicated by the letter L in FIG. 6) at position 4 of the quinazoline scaffold, as previously described with respect to FIG. 1. Nucleophilic displacement of the L group (e.g. triazolyl or chlorine) then occurs in step (g) by reaction, preferably in an aprotic solvent such as for example dioxane or tetrahydrofuran, with an appropriate nucleophile having the structural formula $R_4R_5NH$ as previously described with respect to FIG. 1.

Figure 7:
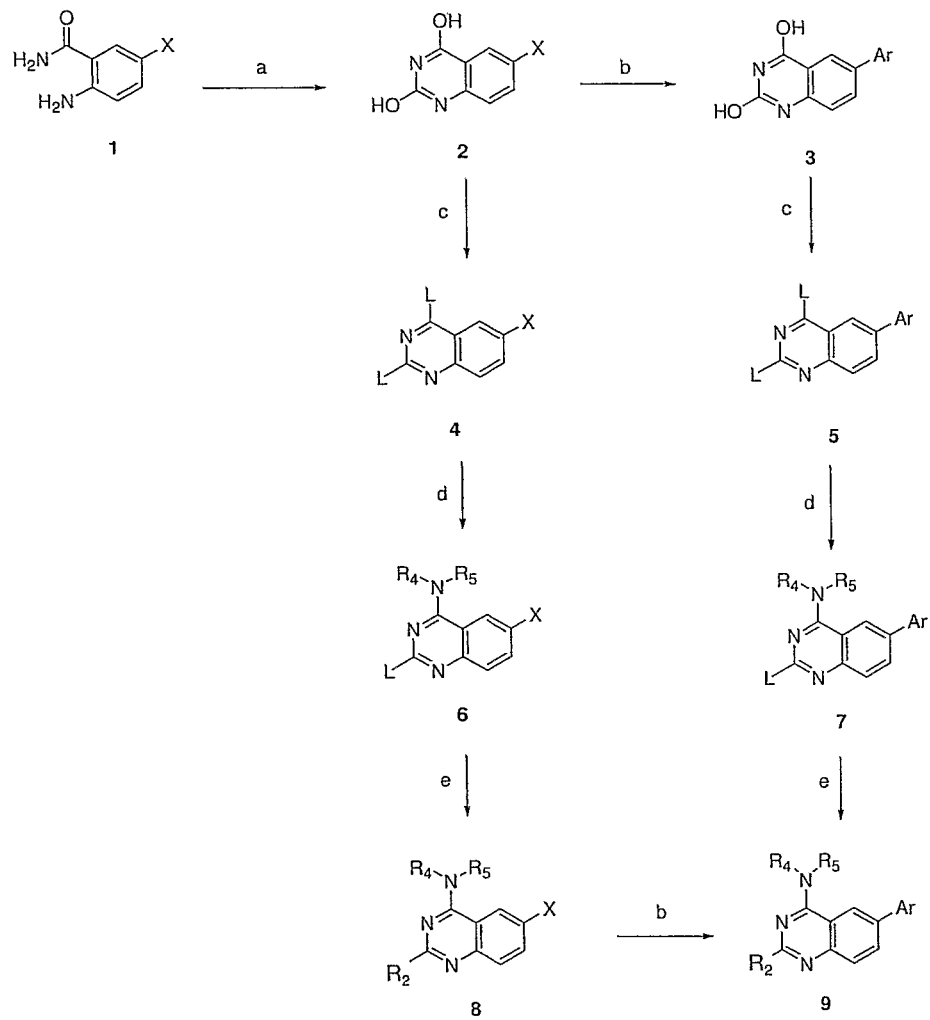
FIG. 7 schematically shows another method for making 2,4,6-trisubstituted quinazoline derivatives according to one embodiment of the present invention.

FIG. 7 schematically shows another method for making 2,4,6-trisubstituted quinazoline derivatives according to an embodiment of the present invention. In step (a), compound 1 is condensed with triphosgene in order to obtain a 2,4-dihydroxy-6-haloquinazoline (wherein preferably X is iodine, bromine or chlorine). The halogen atom at position 6 (preferably chlorine, bromine or iodine) of the quinazoline scaffold can then be used in step (b) for a wide variety of palladium-catalyzed cross-coupling reactions, such as for example, but not limited to, Suzuki reactions (reactions with aryl boronic acids, heteroaryl boronic acids, or esters thereof), Heck reactions (reaction with terminal alkene), and Sonogashira reactions (reaction with terminal alkynes) as previously described with respect to FIG. 1. Simultaneous activation of the tautomeric hydroxyl groups at positions 2 and 4 of the quinazoline scaffold occurs in step (c) by introducing readily leaving groups (indicated by the letter L in FIG. 7) at these positions in a manner similar as previously described with respect to FIG. 1. The leaving capacity of the L groups at positions 2 and 4 of the quinazoline scaffold is however usually different, which makes it possible to selectively displace the L group (e.g. chlorines or 1,2,4-triazolyl) at position 4, in step (d), by reaction with a first appropriate nucleophilic reagent having the structural formula $R_4R_5NH$ as previously described with respect to FIG. 1. In the next step (e), the L group at position 2 (e.g. chlorine or 1,2,4-triazolyl) is displaced by a second nucleophilic reagent, which can be the same as or can be different from the first nucleophilic reagent used in step (d). The nucleophilic reagent may have the structural formula NHR'R" wherein R' and R" are as defined herein above with respect to structural formula (I). Alternatively, in order to introduce a carbon substituent on position 2, a nucleophilic displacement reaction can be effected through reaction with an appropriate Grignard reagent in a dry, polar, aprotic solvent such as for example 1,4-dioxane, diethyl ether or tetrahydrofuran. A broad range of suitable Grignard reagents is commercially available such as, but not limited to, benzylmagnesium chloride, methylmagnesium bromide, methylmagnesium chloride, methylmagnesium iodide, ethylmagnesium bromide, ethylmagnesium chloride, propylmagnesium chloride, isopropylmagnesium bromide, isopropylmagnesium chloride, n-butylmagnesium chloride, sec-butylmagnesium chloride, tert-butylmagnesium chloride, pentylmagnesium bromide, 3-hexylmagnesium bromide, n-hexylmagnesium bromide, 3-heptylmagnesium bromide, n-heptylmagnesium bromide, n-octylmagnesium bromide, n-decylmagnesium bromide, allylmagnesium bromide, allylmagnesium chloride, ethynylmagnesium chloride, (trimethylsilyl)methylmagnesium chloride, phenylmagnesium bromide, 4-methoxyphenylmagnesium bromide, 4-chlorophenylmagnesium bromide, 4-fluorophenylmagnesium bromide, 1-naphthylmagnesium bromide, phenylmagnesium chloride, vinylmagnesium bromide, vinylmagnesium chloride, cyclohexylmagnesium chloride, cyclopentylmagnesium chloride, cyclopropylmagnesium chloride, 4-but-3-enylmagnesium bromide, benzylmagnesium bromide, benzylmagnesium chloride, otolylmagnesium bromide, m-tolylmagnesium bromide, p-tolylmagnesium bromide, otolylmagnesium chloride, m-tolylmagnesium chloride, 2-pyridylmagnesium bromide, 1,3-dioxan-2-ylmethylmagnesium bromide, 3,4-dichlorophenylmagnesium bromide, 3,5-dichlorophenylmagnesium bromide, 3,4-difluorophenylmagnesium bromide, 3,5-difluorophenylmagnesium bromide, 3-chloro-4-fluorophenylmagnesium bromide, 3-chloro-5-fluorophenylmagnesium bromide, 4-chloro-3-fluorophenylmagnesium bromide, 3,5-dimethylphenylmagnesium bromide, 3,4-dimethylphenylmagnesium bromide, 2,3-dimethylphenylmagnesium bromide, 2,4-dimethylphenylmagnesium bromide, 2,5-dimethylphenylmagnesium bromide, 2,6-dimethylphenylmagnesium bromide, 2,4-dimethoxyphenylmagnesium bromide, 2,5-dimethoxyphenylmagnesium bromide, 3,4-dimethoxyphenylmagnesium bromide, 3,5-dimethoxyphenylmagnesium bromide, 3,4,5-trimethoxyphenylmagnesium bromide, 2,4,5-trimethylphenylmagnesium bromide, 4-ethylphenylmagnesium bromide, 4-ethoxyphenylmagnesium bromide, 2,4,6-trimethylphenylmagnesium bromide, 4-methylbenzylmagnesium chloride, 3-methylbenzylmagnesium chloride, 2-methylbenzylmagnesium chloride, 4-methoxybenzylmagnesium chloride, 3-methoxybenzylmagnesium chloride, 2-methoxybenzylmagnesium chloride, 4-chlorobenzylmagnesium chloride, 3-chlorobenzylmagnesium chloride, 2-chlorobenzylmagnesium chloride, 4-fluorobenzylmagnesium chloride, 3-fluorobenzylmagnesium chloride, 2-fluorobenzylmagnesium chloride, 4-bromobenzylmagnesium bromide, 3-bromobenzylmagnesium bromide, 2-bromobenzylmagnesium bromide, 2-biphenylmagnesium bromide, 4-biphenylmagnesium bromide, 3-fluoro-4-biphenylmagnesium bromide, 2-naphthylmagnesium bromide, 3-thienylmagnesium iodide and the like. Alternatively, the above-listed Grignard reagents as well as those which are not commercially available are obtainable using methods well known to the skilled person, or can be made in situ if desired. Alternatively, 2-chloro-4,6-disubstituted quinazoline derivatives can also serve as excellent starting materials for a wide variety of organometallic cross-coupling reactions, which are well known in the art (see e.g. F. Diederich et al., *Metal-Catalyzed Cross-Coupling reactions*, Wiley-VCH, New York, 1998). Examples of cross-coupling reactions include, but are not limited to, a Negishi reaction (i.e. a nickel or palladium catalyzed coupling of organozinc compounds with an aryl- or heteroarylhalide), Stille coupling (i.e. a palladium catalysed coupling reaction between an aryl- or heteroaryl halide and a stannane), Suzuki coupling (i.e. a palladium catalysed cross coupling reaction between an organoboronic acid and an aryl- or heteroarylhalide), Kumada coupling (which is a palladium or nickel catalyzed coupling of a Grignard reagent with an aryl- or heteroarylhalide), Heck reaction (which is the palladium-catalyzed C—C coupling between an aryl- or heteroaryl halide and an activated alkene in the presence of a base), Sonogashira reaction (i.e. the coupling of a terminal alkyne with an aryl- or heteroarylhalide with a palladium catalyst, a copper (I) co-catalyst, and an amine base). In each of the above types of reaction, the 2-chloroquinazoline moiety will serve as the heteroaryl halide.

Figure 8:
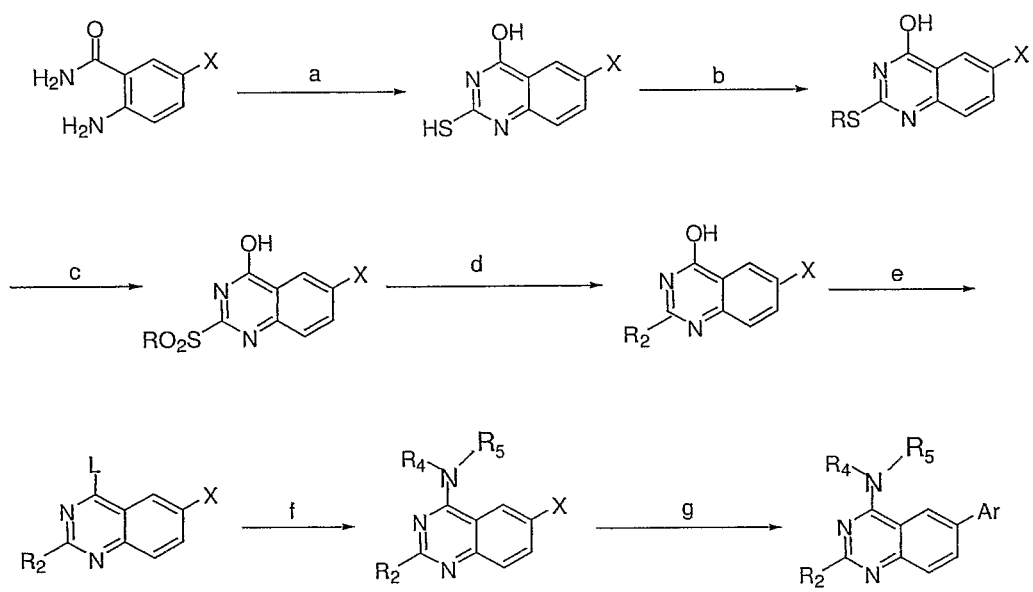
FIG. 8 schematically shows another method for making 2,4,6-trisubstituted quinazoline derivatives according to one embodiment of the present invention, particularly those bearing a substituted amino substituent at the 2-position.

FIG. 8 schematically shows an alternative method for making 2,4,6-trisubstituted quinazolines. In step (a), treatment of a 3-amino-6-halo-pyridine-2-carboxylic acid amide (X is preferably chlorine, bromine or iodine) with thiophosgene in an aprotic solvent gives the 2-thio-4-oxo-quinazoline scaffold. In step (b), the sulfhydryl group at position 2 is alkylated with an alkylating reagent such as methyl iodide in the presence of a base, such as a metal alkoxide, in an aprotic solvent. In step (c), the resulting 2-alkylthio-4-oxoquinazoline is oxidized to the sulfoxide or sulfone with an oxidant such as m-chloroperbenzoic acid, facilitating nucleophilic displacement at the 2-position with nucleophiles having the general formula $R_2H$ wherein $R_2$ is as defined here above, in particular wherein $R_2$ is NR'R", such as alkyl, benzyl- or arylamines, as depicted in step (d). Activation of the tautomeric hydroxyl group at position 4 of the quinazoline scaffold for the subsequent nucleophilic displacement reaction occurs in step (e) by preparing the corresponding 4-(1,2,4-triazolyl)-quinazoline or 4-chloro-quinazoline derivatives. The 4-triazolyl derivative can be obtained by treating the 4-oxo-quinazoline derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-quinazoline derivative with thionyl chloride or $POCl_3$. The chlorine atom or triazolyl group is designated as L in FIG. 7. Nucleophilic displacement of the triazolyl group or chlorine atom occurs in step (f) by reaction with an appropriate nucleophile having the general formula $NHR_4R_5$ in a polar aprotic solvent. Suitable examples of nucleophilic reagents include primary or secondary amines according to the general formula $NHR_4R_5$ wherein $R_4$ and $R_5$ are as defined herein above. Palladium-mediated aryl-aryl cross coupling (Suzuki type) occurs in step (g) by treating the 6-haloquinazoline with an arylboronic acid, a heteroarylboronic acid, or a pinacol ester thereof, in the presence of aqueous base and a palladium(0) catalyst such as $Pd(PPh_3)_4$ to give the desired 6-arylquinazolines.

Suitable commercially available reagents for use in step (d) of FIG. 8 include, but are not limited to, 2-chlorobenzylamine, 4-chlorobenzylamine, 2,4-dichlorobenzylamine, 3,4-dichlorobenzylamine, 4-methoxybenzylamine, 4-methylbenzylamine, piperonylamine, 3,4-dimethoxybenzylamine, 3-methyl-benzylamine, 3-fluorobenzylamine, 2-methylbenzylamine, 2-methoxybenzylamine, 3-methoxybenzylamine, 2-fluorobenzylamine, 4-fluorobenzylamine, 3,4-dihydroxy-benzylamine, 3-chlorobenzylamine, 4-(trifluoromethoxy)benzylamine, 2,6-difluorobenzylamine, 3,5-bis(trifluoromethyl)benzylamine, 2,4-difluorobenzylamine, 2,5-difluorobenzylamine, 3,4-difluorobenzylamine, 2-(trifluoromethyl)benzylamine, 3-(trifluoromethyl)benzylamine, 2-bromobenzylamine, 4-bromobenzylamine, 2-chloro-6-fluorobenzylamine, 2,5-dimethylbenzylamine, 3,4,5-trimethoxybenzylamine, 2,4,6-trimethylbenzylamine, 2,4-dimethylbenzylamine, 2,3-dichlorobenzylamine, 1-naphthalenemethylamine, 3-Iodobenzylamine, 2-hydroxybenzylamine, 3-bromo-benzylamine, 2,6-dichlorobenzylamine, 3,4-dihydro-2H-1,5-benzodioxepin-6-ylmethylamine, 2,3-dihydro-1,4-benzodioxin-6-ylmethylamine, 2,3-dihydro-1,4-benzodioxin-5-ylmethylamine, 1-benzofuran-5-ylmethylamine, 4-(2-thienyl)benzyl-amine, 3,4-dihydro-2H-1,5-benzodioxepin-7-ylmethylamine, 4-morpholinobenzyl-amine, 4-(1H-pyrazol-1-yl)benzylamine, 4-(4-methylpiperazino) benzylamine, 2-Piperidinobenzylamine, 3-(1H-Pyrrol-1-yl) benzylamine, 2-morpholinobenzylamine, 4-(1H-pyrrol-1-yl) benzylamine, 2-chloro-6-phenoxy benzylamine, 2-(methylthio)-benzylamine, 2-(trifluoromethoxy)benzylamine, 2,3-dimethylbenzylamine, 4-(trifluoromethyl)benzylamine, 3,5-dichlorobenzylamine, 2-(Aminomethyl)-3-fluoroaniline, 3-chloro-4-fluorobenzylamine, 2,5-dimethoxybenzylamine, 2,5-dichlorobenzylamine, 2,6-dimethoxybenzylamine, 2,4-dichloro-6-methylbenzylamine, 3-chloro-4-methylbenzylamine, 4-fluoro-3-(trifluoromethyl)benzylamine, 4-fluoro-2-(trifluoromethyl)benzylamine, 3-piperidin-1-ylmethyl benzylamine, 1-benzothiophen-5-ylmethylamine, 4-(Morpholinomethyl) benzylamine, (3-((4-methylpiperidino)methyl)phenyl) methanamine, (4-Piperidinophenyl)methylamine, (3-piperidinophenyl)methylamine, 1-[2-(4-methylpiperazin-1-yl)phenyl]methanamine, (1,4-dimethyl-1,2,3,4-tetrahydroquinoxalin-6-yl)methylamine, 3-(trifluoromethoxy)benzylamine, 4-bromo-2-fluorobenzylamine, 2-(1 h-pyrazol-1-yl)benzylamine, tert-butyl 4-(2-(aminomethyl)phenyl) piperazine-1-carboxylate, (3-morpholinophenyl) methylamine, tert-butyl-N-[4-(aminomethyl)phenyl] carbamate, [2-(1H-pyrrol-1-yl)phenyl]methylamine, 1-[3-(4-methylpiperazin-1-yl)phenyl]methanamine, [4-(1-pyrrolidinyl)phenyl]methylamine, (3-pyrrolidin-1-ylphenyl)methylamine, [4-(2-morpholinoethoxy)-phenyl] methylamine, [2-(2-Morpholinoethoxy)phenyl] methylamine, [3-(2-morpholinoethoxy)phenyl] methylamine, [3-(morpholinomethyl)phenyl]-methylamine, [4-(piperidinomethyl)phenyl]methylamine, {[(4-methylpiperazin-1-yl)methyl]-phenyl}methylamine, [4-(2-furyl)phenyl]methylamine, tert-Butyl 4-[4-(aminomethyl)phenyl]tetrahydro-1(2H)-pyrazinecarboxylate, (2,2-dimethyl-2,3-dihydro-1-benzo-furan-7-yl)methylamine, [3-(1H-1,2,4-triazol-1-yl)phenyl]methylamine, (4-thien-3-ylphenyl) methylamine, 1-[2-(morpholin-4-ylmethyl)phenyl] methanamine, {2-[(4-methylpiperazin-1-yl)methyl] phenyl}methylamine, [3-(2-furyl)phenyl]methylamine, (3-thien-2-ylphenyl)methylamine, [2-(2-furyl)phenyl]methylamine, 4-(pyrrolidin-1-ylmethyl)benzylamine, 4-[(4-methylperhydro-1,4-diazepin-1-yl)methyl]benzylamine, 4-[2-(dimethylamino)ethoxy]benzylamine, (2-Pyrrolidin-1-ylphenyl)methylamine, [3-(1-Pyrrolidinylmethyl)phenyl] methanamine, (3-thien-3-ylphenyl)methylamine, 2-[2-(dimethylamino)ethoxy]benzylamine, 2-(phenoxymethyl) benzylamine, (1-methyl-1h-indol-4-yl)methylamine, 4-(4-methylperhydro-1,4-diazepin-1-yl)benzylamine, (1-methyl-1H-indol-6-yl)methylamine, [3-(1,3-thiazol-2-yl)phenyl]-methylamine, 3-(1H-pyrazol-1-ylmethyl)benzylamine, (1-methyl-1H-indol-5-yl)methylamine, 3-(phenoxy-methyl) benzylamine, 2-morpholino-5-(trifluoromethyl)benzylamine, [4-(1,3-thiazol-2-yl)phenyl]methylamine, 3-(1-methyl-1H-pyrazol-3-yl)benzylamine, 2-(4-methyl-perhydro-1,4-diazepin-1-yl)benzylamine, 4-[3-(dimethylamino)propoxy]benzylamine, 3-(2-Methyl-1H-imidazol-1-yl)benzylamine, 4-(2-methyl-1H-imidazol-1-yl)benzyl-amine, 2-(2-methyl-1H-imidazol-1-yl)benzylamine, [4-(tetrahydropyran-4-yloxy)-phenyl]methylamine, 3-[3-(dimethylamino)propoxy]benzylamine, 2-[3-(dimethylamino) propoxy]benzylamine, 3-pyrimidin-2-ylbenzylamine, 4-(1-methyl-1H-pyrazol-3-yl)benzylamine, 3-(1-methyl-1h-pyrazol-5-yl)benzylamine and 1-(1-benzothien-7-yl)methanamine.

Most of these methods make use of a boronic acid, or a pinacol ester thereof, for introducing a substituent at position 6 of the pteridine core structure. For this purpose, suitable aryl-boronic acids include, but are not limited to, the following commercially available materials wherein the aryl group is 3-acetamidophenyl, 4-acetamidophenyl, 4-acetylphenyl, 3-acetylphenyl, 2-acetylphenyl, 5-acetyl-2-chlorophenyl, 4-acetyl-3-fluorophenyl, 5-acetyl-2-fluorophenyl, 4-(4'-allyloxycarbonylpiperazino)phenyl, 3-aminocarbonyl-phenyl, 4-aminocarbonylphenyl, 2-amino-5-chlorophenyl, 4-amino-3-methoxyphenyl, 3-aminophenyl, 2-amino-4-methylphenyl, 2-amino-5-methylphenyl, 4-amino-2-methylphenyl, 5-amino-2-methylphenyl, 4-amino-3-nitrophenyl, 3-aminophenyl, 2-aminophenyl, 4-aminophenyl, 4-benzyloxyphenyl, 3-benzyloxyphenyl, 2-benzyloxyphenyl, 4-benzyloxy-2-fluorophenyl, 4-benzyloxy-3-fluorophenyl, 3-benzyloxy-4-methoxyphenyl, 4-biphenyl, 3,5-bis(trifluoromethyl)benzene, 4-bromophenyl, 3-bromophenyl, 4-bromo-2,5-dimethylphenyl, 2-bromo-5-fluorophenyl, 2-bromo-6-fluorophenyl, 4-n-butylphenyl, 4-isobutylphenyl, 4-carboxyphenyl, 3-carboxyphenyl, 2-carboxyphenyl, 2-carboxy-5-fluorophenyl, 4-carboxy-3-fluorophenyl, 4-carboxy-2-chlorophenyl, 5-carboxy-2-chlorophenyl, 4-carboxy-3-chlorophenyl, 3-carboxyphenyl, 3-(3-carboxypropionylamino)phenyl, 4-(3-carboxypropionylamino)phenyl, 2-chloro-5-formylphenyl, 3-chloro-4-fluorophenyl, 2-chloro-4-fluorophenyl, 4-chloro-2-fluorophenyl, 3-chloro-4-hydroxy-5-methoxyphenyl, 2-chloro-5-hydroxymethylphenyl, 3-chloro-5-methoxyphenyl, 2-chloro-4-methylphenyl, 2-chloro-5-methylphenyl, 2-chloro-5-trifluoromethoxyphenyl, 3-chloro-5-trifluoromethylphenyl, 4-chloro-2-trifluoromethylphenyl, 4-chlorophenyl, 3-chlorophenyl, 2-chlorophenyl, 4-cyanomethoxyphenyl, 3-cyanomethoxyphenyl, 2-cyanomethoxyphenyl, 4-cyanomethoxyphenyl, 3-cyanomethoxyphenyl, 2-cyanomethoxyphenyl, 4-cyanophenyl, 3-cyanophenyl, 2-cyanophenyl, 3,5-dibromophenyl, 3-(N-cyclopropylaminocarbonyl)phenyl, 2,6-dichlorophenyl, 3,4-dichlorophenyl, 2,4-dichlorophenyl, 2,3-dichlorophenyl, 3,5-dichlorophenyl, 3-(N,N-diethylaminocarbonyl)phenyl, 3,5-difluorophenyl, 3,5-difluoro-2-methoxyphenyl, 3,4-difluorophenyl, 2,6-difluorophenyl, 2,5-difluorophenyl, 2,4-difluorophenyl, 2,3-difluorophenyl, 4-(N,N-dimethylamino)phenyl, 3-(N,N-dimethylamino)phenyl, 2-(N,N-dimethylamino)phenyl, 3-(N,N-dimethylaminocarbonyl)phenyl, 3-[(N',N'-dimethylamino)ethylaminocarbonyl]phenyl, 4-[(N',N'-dimethylamino)ethylaminocarbonyl]phenyl, 3,5-dimethylphenyl, 3,4-dimethylphenyl, 2,6-dimethylphenyl, 2,6-dimethoxyphenyl, 2,5-dimethoxyphenyl, 2,4-dimethoxyphenyl, 3-[1,3]dioxolan-2-ylmethoxyphenyl, 4-ethoxyphenyl, 2-ethoxyphenyl, 3-(ethoxycarbonyl)methoxyphenyl, 4-(ethoxycarbonyl)methoxyphenyl, 4-ethoxycarbonylphenyl, 3-ethoxycarbonylphenyl, 2-ethoxycarbonylphenyl, 4-(3-ethoxycarbonylpiperidino)carboxamidophenyl, 4-ethylphenyl, 4-fluorophenyl, 3-fluorophenyl, 2-fluorophenyl, 3-fluoro-4-formylphenyl, 4-fluoro-3-formylphenyl, 4-fluoro-2-methylphenyl, 2-fluoro-5-methylphenyl, 2-fluoro-5-methoxyphenyl, 3-fluoro-4-methoxyphenyl, 5-fluoro-2-methoxycarbonylphenyl, 2-fluoro-4-trifluoromethylphenyl, 2-formylaminophenyl, 3-formylaminophenyl, 4-formylaminophenyl, 2-formyl-5-methoxyphenyl, 3-formyl-4-methoxyphenyl, 5-formyl-2-methoxyphenyl, 2-formyl-5-methylphenyl, 4-formylphenyl, 3-formylphenyl, 2-formylphenyl, 4-hydroxy-3,5-dimethylphenyl, 3-(2-hydroxyethyl)aminocarbonylphenyl, 4-(2-hydroxyethyl)aminocarbonyl-phenyl, 3-hydroxy-4-methoxycarbonylphenyl, 4-hydroxy-3-methoxyphenyl, 4-(hydroxymethyl)phenyl, 3-(hydroxymethyl)phenyl, 4-hydroxy-3-nitrophenyl, 4-hydroxyphenyl, 3-hydroxyphenyl, 2-hydroxyphenyl, 4-isopropoxyphenyl, 4-(4-isopropylpiperazinyl)phenyl, 4-isopropylphenyl, 4-methanesulfonamido-phenyl, 3-methanesulfonamidophenyl, 2-methanesulfonamidophenyl, 4-methanesulfonylphenyl, 2-methoxy-5-formylphenyl, 5-methoxy-2-formylphenyl, 4-methoxy-2-formylphenyl, 4-methoxycarbonylphenyl, 3-methoxycarbonylphenyl, 2-methoxycarbonylphenyl, 3-methoxy-4-methoxycarbonylphenyl, 4-methoxy-3-nitrophenyl, 4-methoxyphenyl, 3-methoxyphenyl, 2-methoxyphenyl, 2-methoxy-5-methylphenyl, 4-N-methylcarboxamidophenyl, 4-methylphenyl, 3-methylphenyl, 2-methylphenyl, 4-(N-methylamino)phenyl, 3-(4-methylpiperazine-1-carbonyl)phenyl, 4-(4-methylpiperazine-1-carbonyl)phenyl, 4-(methylthio)phenyl, 3-(methylthio)phenyl, 2-(methylthio)phenyl, 4-morpholinophenyl, 4-(morpholinocarbonyl)phenyl, 2-morpholinomethyl)phenyl, 4-nitrophenyl, 3-nitrophenyl, 2-nitrophenyl, 4-phenoxyphenyl, 4-(N-phenylaminomethyl)phenyl, 4-(phenylcarbonyl)phenyl, 4-(piperazine-1-carbonyl)phenyl, 4-piperazinylphenyl, 3-succinamidophenyl, 4-succinamidophenyl, sulfamoylphenyl, 2-(toluene-4-sulfonamido)phenyl, 3-(toluene-4-sulfonamido)phenyl, 4-(toluene-4-sulfonamido)phenyl, 4-(tert-butoxycarbonylamino)-3-methoxyphenyl, 2-(tert-butoxycarbonyl)phenyl, 3-(tert-butoxycarbonyl)phenyl, 4-(tert-butoxycarbonyl)phenyl, 4-tert-butylphenyl, 4-(tetrahydro-2H-pyran-2-yloxy)phenyl, 4-(2-thienyl)phenyl, 4-trifluoromethoxyphenyl, 4-(trimethylammonium)methylphenyl, 2,4,6-trimethylphenyl, 3,4,5-trifluorophenyl, 2,3,4-trifluorophenyl, 3-trifluoromethylphenyl, 4-trifluoromethoxyphenyl, 3-trifluoromethoxyphenyl, 2-trifluoromethylphenyl, 3-trifluoromethylphenyl, 4-trifluoromethylphenyl, 3,4,5-trimethoxyphenyl, 4-vinylphenyl, 6-benzyloxy-2-naphthyl, 1-naphthalyl, 2-naphthalyl, (O,O-dimethylphosphonyl)methyl-phenyl or 1-biphenylyl.

For the purpose of making the compounds of the present invention, suitable heterocyclic-boronic acids or pinacol esters thereof include, but are not limited to, the following commercially available materials wherein the heterocyclic group is 3,4-methylenedioxyphenyl (benzodioxolyl), 2-acetamidopyridin-5-yl, 2-aminopyridin-5-yl, 2-aminopyrimidin-5-yl, 1,4-benzodioxan-6-yl, 2-benzothienyl, 1-benzothiophen-3-yl, 1-benzothiophen-2-yl, 2-benzyloxypyridin-5-yl, 1-benzyl-1H-pyrazol-4-yl, 2-bromo-3-chloropyridin-4-yl, 5-bromo-2,3-dihydrobenzo[b]furan-7-yl, 2-bromo-3-methylpyridin-5-yl, 3-bromopyridin-5-yl, 2-bromopyridin-5-yl, 5-bromothien-2-yl, 2-chloro-6-isopropylpyridin-3-yl, 2-chloro-3-methylpyridin-5-yl, 2-[4-(4-chlorophenylsulfonyl)piperazin-1-yl]pyridin-5-yl, 2-chloropyrid-4-yl, 2-chloropyrid-5-yl, 5-chlorothien-2-yl, dibenzo[b,d]furan-4-yl, 2-chloro-3-fluoropyridin-4-yl, dibenzo[b,d]thien-4-yl, 3,4-dihydro-2H-1,5-benzodioxepin-7-yl, 3,6-dihydro-2H-pyridine-1-tert-butoxycarbonyl, 2,5-dibromo-3-pyridinyl, 2,6-dichloro-pyridin-3-yl, 2,3-dihydro-1-benzofuran-5-yl, 2,6-dimethoxypyridin-5-yl, 2,6-dimethoxypyridin-3-yl, 2,4-dimethoxypyrimidin-5-yl, 3,5-dimethylisoxazol-4-yl, 2-(3-N,N-dimethylaminopropoxy)

pyridin-5-yl, 3,5-dimethylpyrazol-4-yl, 1-[1,3]dioxolan-2-ylmethyl-1H-pyrazol-4-yl, 2,4-dioxo-1,2,3,4-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthien-2-yl, furan-3-yl, furan-2-yl, 2-hydroxypyridin-5-yl, 5-indolyl, 1-isobutyl-1H-pyrazol-4-yl, isoquinolin-4-yl, 2-methoxypyridin-3-yl, 2-methoxypyrimidin-5-yl, 5-methyl-1-benzothiophen-2-yl, 1-(3-methylbutyl)-1H-pyrazol-4-yl, 5-methylfuran-2-yl, 1-methylindol-5-yl, 5-methyl-3-phenyl-4-isoxazolyl, 5-(methylthio)thien-2-yl, 2-(4-methylpiperazinyl)pyridin-4-yl, 2-(4-methylpiperazinyl)pyridin-5-yl, 1-methyl-1H-pyrazol-4-yl, 3-methylpyridin-2-yl, 5-methylpyridin-2-yl, 5-methylpyridin-3-yl, 4-methylthien-2-yl, 5-methylthien-2-yl, 2-methoxypyridin-5-yl, 2-(2-morpholinoethylamino)-pyridin-5-yl, 2-(2-morpholinoethyl)-1H-pyrazol-4-yl, 2-(morpholin-1-yl)-pyridin-5-yl, 1-(phenylsulfonyl)-1H-indol-3-yl, 5-phenyl-2-thienyl, 2-(piperazin-1-yl)-pyridin-5-yl, 2-(piperazin-1-yl)-pyridin-4-yl, 1-propyl-1H-pyrazol-4-yl, pyrazol-4-yl, pyridin-4-yl, pyridin-3-yl, pyrimidin-5-yl, 4-phenoxathiinyl, quinolin-8-yl, quinolin-3-yl, 2-(4-tertbutoxycarbonylpiperazinyl)-pyrid-4-yl, 1-tert-butoxycarbonyl-1H-pyrazol-4-yl, 1-tertbutoxycarbonyl-2-pyrrolyl, 1-(tert-butoxycarbonyl)-5-bromo-1H-indol-2-yl, 1-(tert-butoxycarbonyl)-1H-indol-5-yl, 1-(tert-butoxycarbonyl)-5-methoxy-1H-indol-2-yl, 1-thianthrenylthien-3-yl, thien-3-yl, thien-2-yl or 1,3,5-trimethyl-1H-pyrazol-4-yl.

The present invention will be further described with reference to certain more specific embodiments and examples, but the present invention is not limited thereto but only by the attached claims. The following examples are given by way of illustration only. In each formula, "Me" stands for methyl, and "Ac" stands for acetyl.

Example 1

Synthesis of 2-amino-4-hydroxy-6-bromo-quinazoline

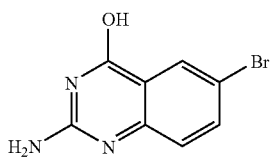 [SMILES: Nc1nc(O)c2cc(Br)ccc2n1]

This compound may be made by any of the two following methods:

Method A

This method has been described by O'Hara et al. in *J. Org. Chem.* (1991) 56, 776-785. A solution consisting of 2-amino-5-bromobenzoic acid (8.64 g, 40 mmol), cyanamide (2.52 g, 60 mmol) and concentrated hydrochloric acid (3 ml) in absolute ethanol (100 ml) was refluxed for 6 hours. At 1 hour intervals, 0.5 ml concentrated hydrochloric acid was added to the reaction mixture. After cooling to room temperature, the precipitate was collected by filtration, washed with ethanol yielding the title compound as a white solid (3.5 g, yield: 36%).

Method B

A mixture of 2-amino-5-bromobenzoic acid (5.4 g, 25 mmol), chloroformamidine hydrochloride (5.75 g, 50 mmol), sulfolane (1 ml) and dimethylsulfone (12 g) was heated at 165° C. for 30 minutes. Then, water (100 ml) was added to the reaction mixture and the pH was adjusted to 7-8 by the addition of a 33% aqueous ammonia solution in water. The precipitate was collected by filtration, washed with water and dried over $P_2O_5$, yielding the title compound as a yellowish solid (5.7 g, yield: 95%) which was characterized by its mass spectrum as follows: MS (m/z): 240 ([M+H]$^+$, 100).

Example 2

Synthesis of 6-bromo-4-hydroxy-quinazoline

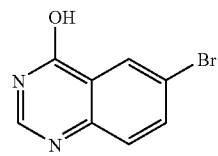 [SMILES: Oc1ncnc2ccc(Br)cc12]

A suspension of 2-amino-5-bromobenzoic acid (5.4 g, 25 mmol) in formamide (40 ml) was heated at 165° C. for 6 hours. After cooling to room temperature, water (100 ml) was added to the reaction mixture. The precipitate was collected by filtration, washed with water and dried over $P_2O_5$, yielding the title compound as a white solid (5.3 g, yield: 95%) which was characterized by its mass spectrum as follows: MS (m/z): 225 ([M+H]$^+$, 100).

Example 3

Synthesis of 6-chloro-2,4-diamino-quinazoline

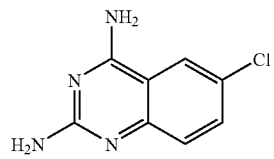

A mixture of 2-amino-5-chlorobenzonitrile (1.07 g, 7.0 mmol), chloroformamidine hydrochloride (1.6 g, 14 mmol), sulfolane (0.5 ml) and dimethylsulfone (3 g) was heated at 165° C. for 30 minutes. Then, water (30 ml) was added to the reaction mixture. The pH was adjusted to 7-8 by the addition of a 33% aqueous ammonia solution in water. The precipitate was collected by filtration and dried over $P_2O_5$, yielding the title compound as a yellowish solid (1.35 g, yield: 99%) which was characterized by its mass spectrum as follows: MS (m/z): 195 ([M+H]$^+$, 100).

Example 4

Synthesis of 4-amino-6-chloro-quinazoline

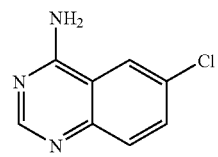 [SMILES: Nc1ncnc2ccc(Cl)cc12]

A solution of 2-amino-5-chlorobenzonitrile (1.07 g, 7.0 mmol) in formamide (20 ml) was heated at 180° C. for 6 hours. After cooling to room temperature, water (30 ml) was added to the reaction mixture. The precipitate was collected by filtration, washed with water and dried over P$_2$O$_5$, yielding the title compound as a grey solid (1.2 g, yield: 95%) which was characterized by its mass spectrum as follows: MS (m/z): 180 ([M+H]$^+$, 100).

Example 5

Synthesis of 2-amino-6-(3,4-dimethoxyphenyl)-4-hydroxy-quinazoline

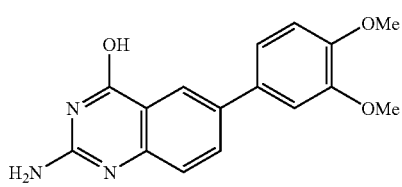 [SMILES: COc1ccc(-c2ccc3nc(N)nc(O)c3c2)cc1OC]

A mixture of the compound of example 1 (2.4 g, 10 mmol), 3,4-dimethoxyphenylboronic acid (1.82 g, 10 mmol), K$_2$CO$_3$ (4.15 g, 30 mmol) and tetrakis(triphenylphosphine)palladium(0) (0.5 g, 0.43 mmol) in dioxane (150 ml) and water (50 ml) was heated under reflux till the starting materials disappeared on TLC. After cooling to room temperature, the reaction mixture was neutralized with acetic acid till pH 6-7. The precipitate was collected by filtration, washed with water and diethyl ether to yield the title compound as a grey solid (3.0 g, yield: 90%). The crude product was used in the following step without further purification and was characterized by its mass spectrum as follows: MS (m/z): 298 ([M+H]$^+$, 100).

Example 6

Synthesis of 2-amino-6-(4-fluorophenyl)-4-hydroxy-quinazoline

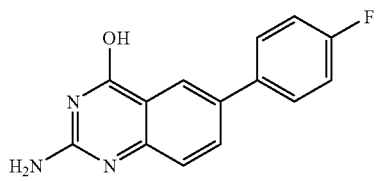

This compound, obtained from 4-fluorophenylboronic acid in 90% yield using the same procedure as in example 5, was characterized by its mass spectrum as follows: MS (m/z): 256 ([M+H]$^+$, 100).

Example 7

Synthesis of 6-(4-fluorophenyl)-4-hydroxy-quinazoline

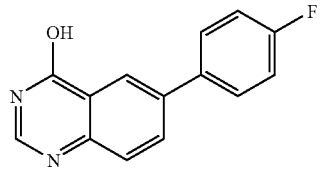

A mixture of 6-bromo-4-hydroxy-quinazoline (2.4 g, 10 mmol), 4-fluorophenylboronic acid (1.54 g, 11 mmol), K$_2$CO$_3$ (4.15 g, 30 mmol) and tetrakis(triphenylphosphine) palladium(0) (0.5 g, 0.43 mmol) in dioxane (150 ml) and water (50 ml) was heated under reflux for 12 hours. After cooling to room temperature, the reaction mixture was neutralized with acetic acid to pH 6-7. The precipitate was collected by filtration, washed with water and diethyl ether to yield the crude product. The crude residue was purified by silica gel flash chromatography, the mobile phase being a mixture of methanol and dichloromethane (in a ratio of 1:40), yielding the pure title compound as a white solid (2.15 g, yield: 95%) which was characterized by its mass spectrum as follows: MS (m/z): 241 ([M+H]$^+$, 100).

Example 8

Synthesis of 2-acetamido-6-(3,4-dimethoxyphenyl)-4-hydroxyquinazoline

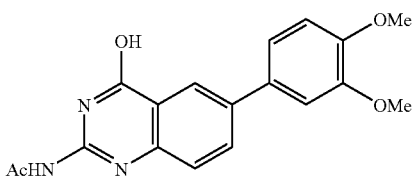 [SMILES: COc1ccc(-c2ccc3nc(NC(C)=O)nc(O)c3c2)cc1OC]

A suspension of the crude 2-amino-6-(3,4-dimethoxyphenyl)-4-hydroxyquinazoline from example 5 (3.0 g, 10 mmol) in acetic anhydride (20 ml) was refluxed for 40 minutes. After concentration under reduced pressure, the residue was purified by silica gel flash chromatography, the mobile phase being a mixture of methanol and dichloromethane (in a ratio of 1:40), yielding the title compound as a white solid (3.05 g, yield: 90%) which was characterized by its mass spectrum as follows: MS (m/z): 340 ([M+H]$^+$, 100).

Example 9

Synthesis of 2-acetamido-6-bromo-4-hydroxy-quinazoline

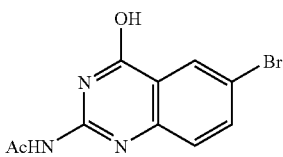 [SMILES: CC(=O)Nc1nc(O)c2cc(Br)ccc2n1]

This compound, synthesized from 2-amino-6-bromo-4-hydroxy-quinazoline in 85% yield using the procedure as in example 8, was characterized by its mass spectrum as follows: MS (m/z): 282 ([M+H]$^+$, 100).

Example 10

Synthesis of 2-acetamido-6-(4-fluorophenyl)-4-hydroxy-quinazoline

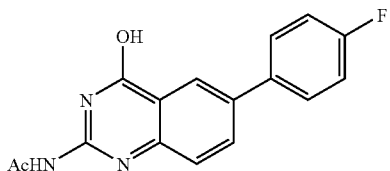 [SMILES: CC(=O)Nc1nc(O)c2cc(-c3ccc(F)cc3)ccc2n1]

This compound, prepared from 2-amino-6-(4-fluorophenyl)-4-hydroxyquinazoline in 95% yield using the same procedure as in example 8, was characterized by its mass spectrum as follows: MS (m/z): 298 ([M+H]$^+$, 100).

Example 11

Synthesis of 2-acetamido-6-bromo-4-(1,2,4-triazolyl)-quinazoline

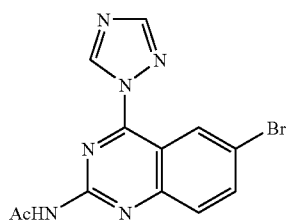 [SMILES: CC(=O)Nc1nc(-n2cncn2)c2cc(Br)ccc2n1]

To a mixture of 2-acetamido-6-bromo-4-hydroxy-quinazoline (2.82 g, 10 mmol) and 1,2,4-triazole (6.9 g, 100 mmol) in acetonitrile (100 ml) was added diisopropylethylamine (3.5 ml, 30 mmol) and POCl$_3$ (2.8 ml, 30 mmol). The mixture was stirred at room temperature for 12 hours. The precipitate was collected, washed with ethanol, diethylether, and dried over P$_2$O$_5$ in a vacuum dessicator to yield the title compound as yellow solid (3.3 g). The crude product was used in the following reaction without further purification and was characterized by its mass spectrum as follows: MS (m/z): 333 ([M+H]$^+$, 100).

Example 12

Synthesis of 2-acetamido-6-(3,4-dimethoxyphenyl)-4-(1,2,4-triazolyl)quinazoline

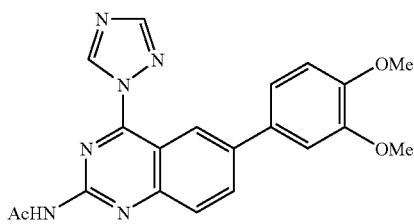 [SMILES: COc1ccc(-c2ccc3nc(NC(C)=O)nc(-n4cncn4)c3c2)cc1OC]

This compound, synthesized from the 2-acetamido-6-(3,4-dimethoxyphenyl)-4-hydroxy-quinazoline of example 8, using the same procedure as in example 11, was characterized by its mass spectrum as follows: MS (m/z): 391 ([M+H]$^+$, 100).

Example 13

Synthesis of 2-acetamido-6-(4-fluorophenyl)-4-(1,2,4-triazolyl)-quinazoline

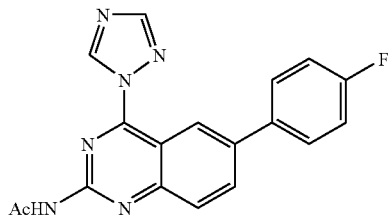 [SMILES: CC(=O)Nc1nc(-n2cncn2)c2cc(-c3ccc(F)cc3)ccc2n1]

This compound, synthesized from the 2-acetamido-6-(4-fluorophenyl)-4-hydroxy-quinazoline of example 10, and using the same procedure as in example 11, was characterized by its mass spectrum as follows: MS (m/z): 349 ([M+H]$^+$, 100).

Example 14

Synthesis of 2-amino-6-(3,4-dimethoxyphenyl)-4-(N-morpholino)quinazoline

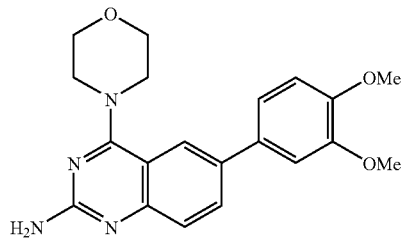 [SMILES: COc1ccc(-c2ccc3nc(N)nc(N4CCOCC4)c3c2)cc1OC]

A mixture of the compound of example 12 (195 mg, 0.5 mmol) and morpholine (0.5 ml) in dioxane (10 ml) was refluxed for 1 hour. The solvents were concentrated under reduced pressure to yield a residue, which was redissolved in methanol (10 ml). Then, water (5 ml) and K$_2$CO$_3$ (0.5 g) were added. The resulting mixture was refluxed for 2 hour. After cooling to room temperature, the reaction mixture was extracted with dichloromethane and washed with water. The combined organic layers were concentrated under reduced pressure to yield a crude product. The crude residue was purified by silica gel flash chromatography, the mobile phase being a mixture of methanol and dichloromethane (in a volume ratio of 1:40), yielding the title compound as a white solid in 74% yield (136 mg). The product was further characterized by its mass spectrum as follows:

MS (m/z): 367 ([M+H]$^+$, 100)

Examples 15 and 16

Synthesis of 2-amino-6-(3,4-dimethoxyphenyl)-4-hydrazinoquinazoline and 2-amino-6-(3,4-dimethoxyphenyl)-4-[N-(3-bromo)-anilino)]-quinazoline

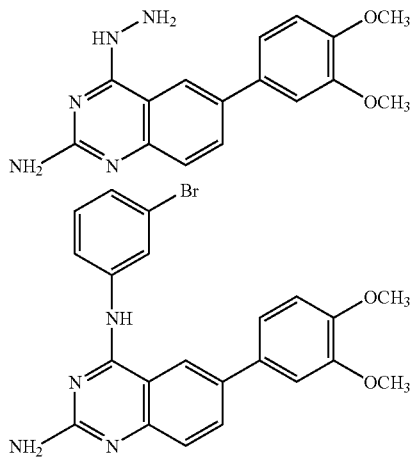

Both compounds were obtained from the product of example 12 and 3-bromoaniline, using the procedure described for the synthesis of example 14 resulting in:

2-amino-6-(3,4-dimethoxyphenyl)-4-hydrazino-quinazoline (example 15) in 35% yield as a yellowish solid which was characterized by its mass spectrum as follows: MS (m/z): 312 ([M+H]$^+$, 100); and 2-amino-6-(3,4-dimethoxyphenyl)-4-[N-(3-bromo)-anilino]-quinazoline (example 16) in 38% yield as a white solid which was characterized by its mass spectrum as follows: MS (m/z): 452 ([M+H]$^+$, 100).

Example 17

Synthesis of 2-amino-6-bromo-4-(N-morpholino)-quinazoline

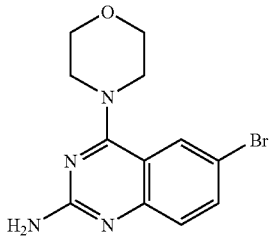 [SMILES: Nc1nc(N2CCOCC2)c2cc(Br)ccc2n1]

A mixture of the product of example 11, i.e. 2-acetamido-6-bromo-4-(1,2,4-triazolyl)-quinazoline (1.33 g, 4.0 mmol) and morpholine (5 ml) in dioxane (20 ml) was refluxed for 3 hours. The solvents were evaporated in vacuo. The crude residue was purified by silica gel flash chromatography, the mobile phase being a mixture of methanol and dichloromethane (in a ratio of 1:30), yielding the title compound as a white solid (1.2 g, yield: 97%), and characterized by its mass spectrum: MS (m/z): 309 ([M+H]$^+$, 100).

Example 18

Synthesis of 2-amino-6-bromo-4-(N-acetyl-piperazino)-quinazoline

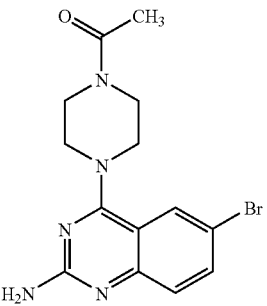 [SMILES: CC(=O)N1CCN(c2nc(N)nc3ccc(Br)cc23)CC1]

This compound was synthesized from the product of example 11 and 4-acetylpiperazine in 91% yield, using the procedure described for example 17, and was characterized by its mass spectrum as follows: MS (m/z): 350 ([M+H]$^+$, 100).

Example 19

Synthesis of 2-amino-6-bromo-4-(N-piperidino)-quinazoline

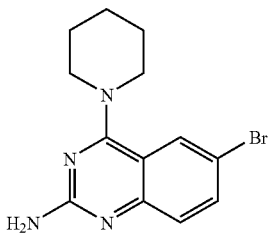 [SMILES: Nc1nc(N2CCCCC2)c2cc(Br)ccc2n1]

This compound was prepared from the product of example 11, i.e. 2-acetamido-6-bromo-4-(1,2,4-triazolyl)-quinazoline and piperidine in 85% yield using the procedure described for example 17. The product was characterized by its mass spectrum as follows: MS (m/z): 307 ([M+H]$^+$, 100).

Example 20

Synthesis of 2-amino-6-bromo-4-(N-cyclohexylamino)-quinazoline

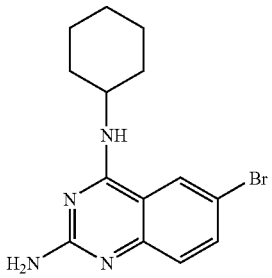 [SMILES: Nc1nc(NC2CCCCC2)c2cc(Br)ccc2n1]

This compound was synthesized from the product of example 11, i.e. 2-acetamido-6-bromo-4-(1,2,4-triazolyl)-quinazoline and cyclohexylamine in 93% yield, using the procedure described for example 17. The product was characterized by its mass spectrum as follows: MS (m/z): 321 ([M+H]+, 100).

Example 21

Synthesis of 2-amino-6-bromo-4-[N-(4-methyl)-piperazin-1-yl)quinazoline

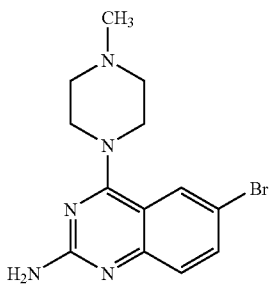 [SMILES: CN1CCN(c2nc(N)nc3ccc(Br)cc23)CC1]

This compound was synthesized from the product of example 11, i.e. 2-acetamido-6-bromo-4-(1,2,4-triazolyl)-quinazoline and 4-methylpiperazine in 93% yield, using the procedure described for example 17. The product was characterized by its mass spectrum as follows: MS (m/z): 322 ([M+H]+, 100).

Example 22

Synthesis of 2-amino-6-bromo-4-[N-(3-methyl)aniline]-quinazoline

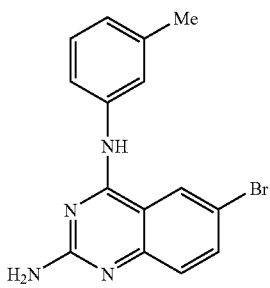 [SMILES: Cc1cccc(Nc2nc(N)nc3ccc(Br)cc23)c1]

This compound was synthesized from the product of example 11, i.e. 2-acetamido-6-bromo-4-(1,2,4-triazolyl)-quinazoline and 3-methylaniline in 88% yield, using the procedure described for example 17. The product was characterized by its mass spectrum as follows: MS (m/z): 328 ([M+H]+, 100).

Example 23

Synthesis of 2-amino-6-(4-fluorophenyl)-4-(N-piperidino)-quinazoline

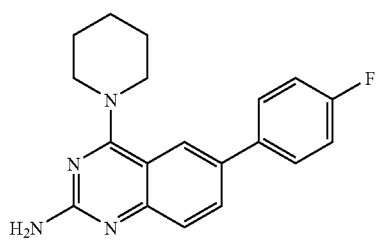 [SMILES: Nc1nc(N2CCCCC2)c2cc(-c3ccc(F)cc3)ccc2n1]

A mixture of the product of example 13, i.e. 2-acetamido-6-(4-fluorophenyl)-4-(1,2,4-triazolyl)-quinazoline (174 mg, 0.5 mmol) and piperidine (1 ml) in dioxane (20 ml) was refluxed for 3 hours. The solvents were concentrated in vacuo. The crude residue was purified by silica gel flash chromatography, the mobile phase being a mixture of methanol and dichloromethane (in a ratio of 1:35), yielding the title compound as a white solid (150 mg, yield: 93%). The product was characterized by its mass spectrum as follows: MS (m/z): 323 ([M+H]+, 100).

Example 24

Synthesis of 2-amino-6-(4-fluorophenyl)-4-(N-cyclohexylamino)quinazoline

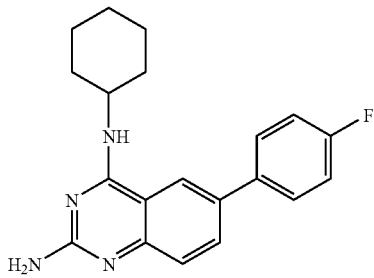 [SMILES: Nc1nc(NC2CCCCC2)c2cc(-c3ccc(F)cc3)ccc2n1]

This compound was synthesized from the product of example 13 and cyclohexylamine, in 85% yield, using the procedure described for example 23 and was characterized by its mass spectrum as follows: MS (m/z): 336 ([M+H]+, 100).

Example 25

Synthesis of 2-amino-6-(4-fluorophenyl)-4-[N-(4-methyl)-piperazin-1-yl]-quinazoline

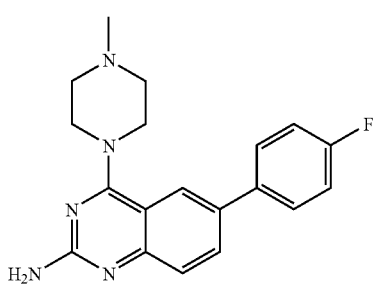 [SMILES: CN1CCN(c2nc(N)nc3ccc(-c4ccc(F)cc4)cc23)CC1]

This compound was synthesized from the product of example 13, i.e. 2-acetamido-6-(4-fluorophenyl)-4-(1,2,4-triazolyl)-quinazoline and 4-methyl-piperazine in 86% yield, using the procedure described for example 23. The product was characterized by its mass spectrum as follows: MS (m/z): 337 ([M+H]+, 100).

Example 26

Synthesis of 2-amino-6-(4-fluorophenyl)-4-[N-(3-methyl)-anilino]-quinazoline

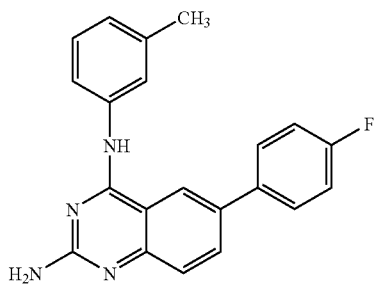 [SMILES: Cc1cccc(Nc2nc(N)nc3ccc(-c4ccc(F)cc4)cc23)c1]

This compound was obtained from the product of example 13, i.e. 2-acetamido-6-(4-fluorophenyl)-4-(1,2,4-triazolyl)-quinazoline and 3-methylaniline in 88% yield, using the procedure described for example 23. The product was characterized by its mass spectrum as follows: MS (m/z): 337 ([M+H]$^+$, 100).

Example 27

Synthesis of 2-amino-6-(4-chlorophenyl)-4-(N-morpholino)-quinazoline

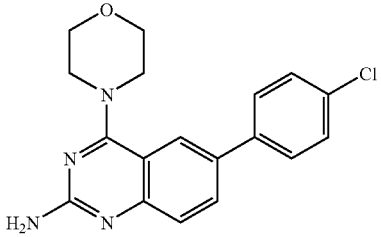 [SMILES: Nc1nc(N2CCOCC2)c2cc(-c3ccc(Cl)cc3)ccc2n1]

A mixture of the product of example 17, i.e. 2-amino-6-bromo-4-(N-morpholino)-quinazoline (351 mg, 1.14 mmol), 4-chlorophenylboronic acid (160 mg, 1.14 mmol), K$_2$CO$_3$ (480 mg, 3.5 mmol), and tetrakis(triphenylphosphine)palladium(0) (60 mg, 0.05 mmol) in dioxane (30 ml) and water (10 ml) was refluxed for 1 hour. After cooling to room temperature, the reaction mixture was extracted with dichloromethane. The combined organic layers were evaporated in vacuo and the crude residue was purified by silica gel flash chromatography, the mobile phase being a mixture of methanol/dichloromethane (in a volume ratio of 1:30), yielding the title compound in 82% as a white solid (320 mg). The product was characterized by its mass spectrum as follows: MS (m/z): 340 ([M+H]$^+$, 100).

Example 28

Synthesis of 2-amino-6-(4-fluorophenyl)-4-(N-morpholino)-quinazoline

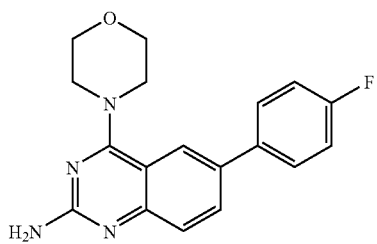 [SMILES: Nc1nc(N2CCOCC2)c2cc(-c3ccc(F)cc3)ccc2n1]

This compound was synthesized from the product of example 17 and 4-fluorophenylboronic acid in 91% yield, using the procedure described for example 7, and was characterized by its mass spectrum as follows: MS (m/z): 325 ([M+H]$^+$, 100).

Example 29

Synthesis of 2-amino-6-(4-fluorophenyl)-4-(N-acetylpiperazino)quinazoline

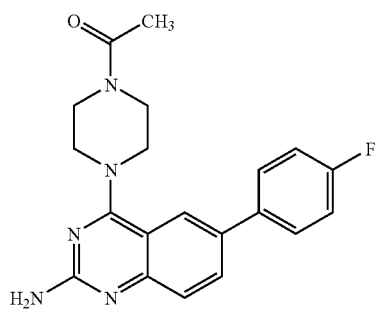 [SMILES: CC(=O)N1CCN(c2nc(N)nc3ccc(-c4ccc(F)cc4)cc23)CC1]

This compound was obtained from the product of example 18 and 4-fluorophenylboronic acid in 82% yield, using the procedure described for example 7, and was characterized by its mass spectrum as follows: MS (m/z): 366 ([M+H]$^+$, 100).

Example 30

Synthesis of 2-amino-6-(4-acetamidophenyl)-4-(N-morpholino)quinazoline

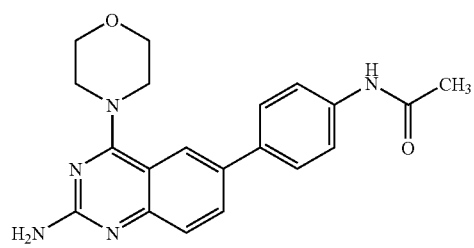 [SMILES: CC(=O)Nc1ccc(-c2ccc3nc(N)nc(N4CCOCC4)c3c2)cc1]

This compound was obtained from the product of example 17 and 4-acetamido-phenylboronic acid in 82% yield, using the procedure described for example 7, and was characterized by its mass spectrum as follows: MS (m/z): 364 ([M+H]$^+$, 100).

Example 31

Synthesis of 2-amino-6-(4-acetamidophenyl)-4-(N-piperidino)quinazoline

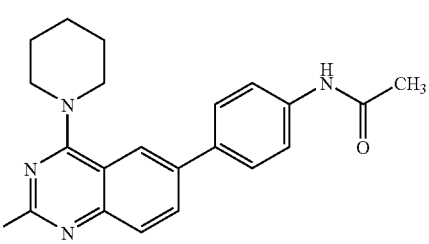

This compound was synthesized from the product of example 19 and 4-acetamido-phenylboronic acid in 91% yield, using the procedure described for example 7, and was characterized by its mass spectrum as follows: MS (m/z): 362 ([M+H]$^+$, 100).

Example 32

Synthesis of 2-amino-6-(4-acetamidophenyl)-4-(N-acetylpiperazino)quinazoline

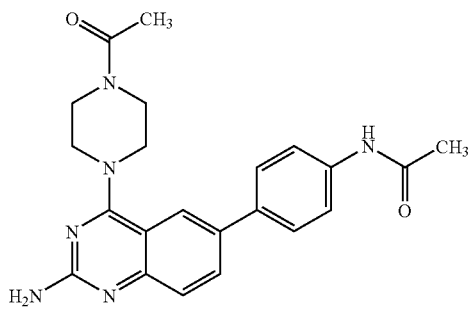 [SMILES: CC(=O)Nc1ccc(-c2ccc3nc(N)nc(N4CCN(C(C)=O)CC4)c3c2)cc1]

This compound was synthesized from the product of example 18 and 4-acetamidophenyl-boronic acid in 91% yield, using the procedure described for example 7, and was characterized by its mass spectrum as follows: MS (m/z): 405 ([M+H]$^+$, 100).

Example 33

Synthesis of 2-amino-6-(4-acetamidophenyl)-4-(N-cyclohexylamino)quinazoline

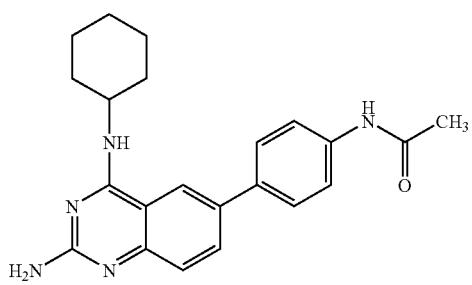 [SMILES: CC(=O)Nc1ccc(-c2ccc3nc(N)nc(NC4CCCCC4)c3c2)cc1]

This compound was synthesized from the product of example 20 and 4-acetamidophenyl-boronic acid, in 95% yield, using the procedure described for example 7, and was characterized by its mass spectrum as follows: MS (m/z): 376 ([M+H]$^+$, 100).

Example 34

Synthesis of 2-amino-6-(4-acetamidophenyl)-4-(N-methylpiperazino)quinazoline

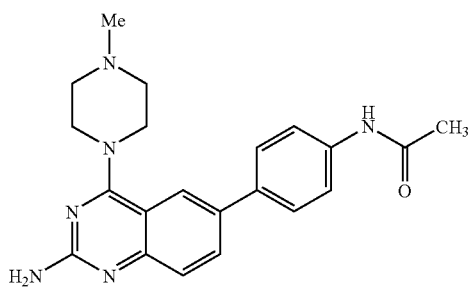 [SMILES: CC(=O)Nc1ccc(-c2ccc3nc(N)nc(N4CCN(C)CC4)c3c2)cc1]

This compound was obtained from the product of example 21 and 4-acetamidophenyl-boronic acid in 78% yield, using the procedure described for example 7, and was characterized by its mass spectrum as follows: MS (m/z): 377 ([M+H]$^+$, 100).

Example 35

Synthesis of 2-amino-6-(4-acetamidophenyl)-4-[N-(3-methyl)-anilino]-quinazoline

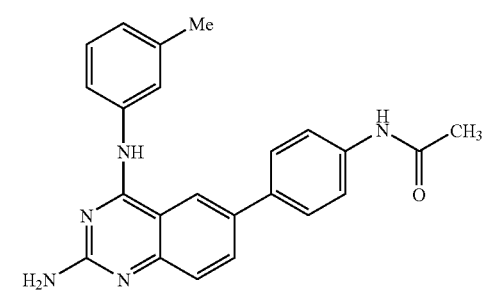 [SMILES: CC(=O)Nc1ccc(-c2ccc3nc(N)nc(Nc4cccc(C)c4)c3c2)cc1]

This compound was synthesized from 2-amino-6-bromo-4-[N-(3-methyl)anilino)-quinazoline and 4-acetamidophenylboronic acid in 94% yield, using the procedure described for the synthesis of 6-(4-fluorophenyl)-4-hydroxy-quinazoline. The product was characterized by its mass spectrum as follows: MS (m/z): 384 ([M+H]$^+$, 100).

Example 36

Synthesis of 4-chloro-6-(4-fluorophenyl)-quinazoline

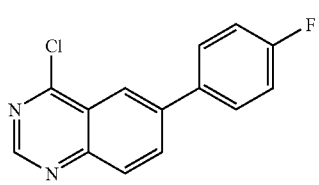 [SMILES: Fc1ccc(-c2ccc3ncnc(Cl)c3c2)cc1]

To a suspension of the product of example 7 (720 mg, 3 mmol) in toluene (20 ml) was added diisopropylethylamine (1.5 ml, 9 mmol) and POCl$_3$ (0.84 ml, 9 mmol). The mixture was refluxed for 1 hour. The solvents were evaporated in vacuo. The residue was redissolved in dichloromethane and the organic layer was washed with ice water till pH 6-7. The combined organic layers were dried over MgSO$_4$ and concentrated to yield the title compound as a yellow solid (700 mg, yield: 90%) which was characterized by its mass spectrum as follows: MS (m/z): 259 ([M+H]$^+$, 100).

Example 37

Synthesis of 6-(4-fluorophenyl)-4-(N-morpholino)-quinazoline

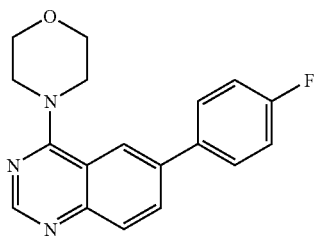 [SMILES: Fc1ccc(-c2ccc3ncnc(N4CCOCC4)c3c2)cc1]

To a solution of morpholine (0.5 ml) in dioxane (10 ml) was added 4-chloro-6-(4-fluorophenyl)-quinazoline (52 mg, 0.2 mmol). The resulting mixture was refluxed for 1 hour. The solvents were evaporated under reduced pressure and the residue was purified by silica gel flash chromatography, the mobile phase being a mixture of methanol and dichloromethane (in a ratio of 1:80), yielding the pure title compound as a white solid (52 mg, yield: 84%). The product was characterized by its mass spectrum as follows: MS (m/z): 310 ([M+H]$^+$, 100).

Example 38

Synthesis of 6-(4-fluorophenyl)-4-[N-(3-methyl)anilino)-quinazoline

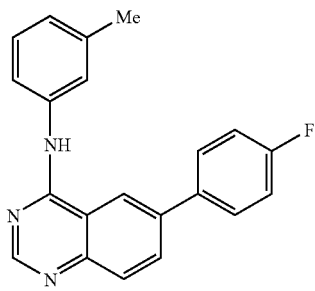 [SMILES: Cc1cccc(Nc2ncnc3ccc(-c4ccc(F)cc4)cc23)c1]

This compound was synthesized from 4-chloro-6-(4-fluorophenyl)-quinazoline and 3-methylaniline in 80% yield, using the procedure described for example 37, and was characterized by its mass spectrum as follows: MS (m/z): 330 ([M+H]$^+$, 100).

Example 39

Synthesis of 4-amino-6-(4-fluorophenyl)-quinazoline

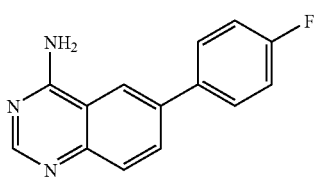 [SMILES: Nc1ncnc2ccc(-c3ccc(F)cc3)cc12]

This compound was synthesized from 4-chloro-6-(4-fluorophenyl)-quinazoline and a 7 N ammonia solution in methanol in 84%, using the procedure described for example 37. The product was characterized by its mass spectrum as follows: MS (m/z): 240 ([M+H]$^+$, 100).

Example 40

Synthesis of 4-(N-cyclohexylamino)-6-(4-fluorophenyl)-quinazoline

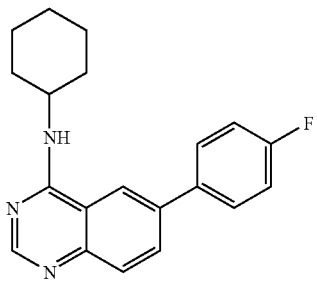 [SMILES: Fc1ccc(-c2ccc3ncnc(NC4CCCCC4)c3c2)cc1]

This compound was synthesized from 4-chloro-6-(4-fluorophenyl)-quinazoline and cyclohexylamine in 78% yield, using the procedure described for example 37. The product was characterized by its mass spectrum as follows: MS (m/z): 322 ([M+H]$^+$, 100).

Example 41

Synthesis of 4-(N-butylamino)-6-(4-fluorophenyl)-quinazoline

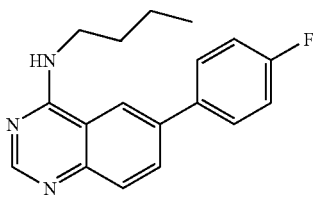 [SMILES: CCCCNc1ncnc2ccc(-c3ccc(F)cc3)cc12]

This compound was synthesized from 4-chloro-6-(4-fluorophenyl)-quinazoline and n-butylamine in 68% yield, using the procedure described for example 37. The product was characterized by its mass spectrum as follows: MS (m/z): 296 ([M+H]$^+$, 100).

Example 42

Synthesis of 4-(N-isopentylamino)-6-(4-fluorophenyl)-quinazoline

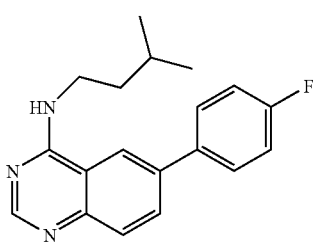 [SMILES: CC(C)CCNc1ncnc2ccc(-c3ccc(F)cc3)cc12]

This compound was synthesized from 4-chloro-6-(4-fluorophenyl)-quinazoline and isopentylamine in 75% yield using the procedure described for example 37, and was characterized by its mass spectrum as follows: MS (m/z): 310 ([M+H]$^+$, 100).

Example 43

Synthesis of 4-(N-propylamino)-6-(4-fluorophenyl)-quinazoline

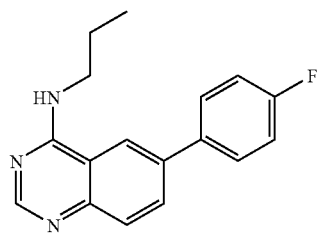 [SMILES: CCCNc1ncnc2ccc(-c3ccc(F)cc3)cc12]

This compound was synthesized from 4-chloro-6-(4-fluorophenyl)-quinazoline and n-propylamine in 83% yield, using the procedure described for example 37, and was characterized by its mass spectrum as follows: MS (m/z): 282 ([M+H]$^+$, 100).

Example 44

Synthesis of 4-(N-propylamino)-6-(4-fluorophenyl)-quinazoline

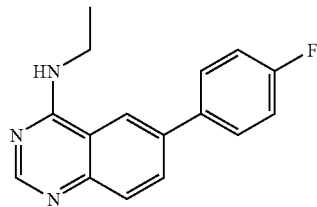 [SMILES: CCNc1ncnc2ccc(-c3ccc(F)cc3)cc12]

This compound was synthesized from 4-chloro-6-(4-fluorophenyl)-quinazoline and ethylamine, in 75% yield, using the procedure described for example 37 and was characterized by its mass spectrum as follows: MS (m/z): 268 ([M+H]$^+$, 100).

Example 45

Synthesis of 4-(N,N-dimethylamino)-6-(4-fluorophenyl)-quinazoline

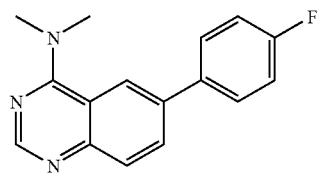 [SMILES: CN(C)c1ncnc2ccc(-c3ccc(F)cc3)cc12]

This compound was synthesized from 4-chloro-6-(4-fluorophenyl)-quinazoline and dimethylamine in 76% yield, using the procedure described for example 37 and was characterized by its mass spectrum as follows: MS (m/z): 268 ([M+H]$^+$, 100).

Example 46

Synthesis of 4-(N-cyclopentylamino)-6-(4-fluorophenyl)-quinazoline

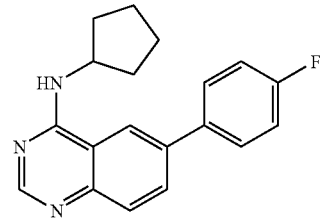 [SMILES: Fc1ccc(-c2ccc3ncnc(NC4CCCC4)c3c2)cc1]

This compound was synthesized from 4-chloro-6-(4-fluorophenyl)-quinazoline and cyclopentylamine in 78%, using the procedure described example 37 and was characterized by its mass spectrum as follows: MS (m/z): 308 ([M+H]$^+$, 100).

Example 47

Synthesis of 4-(N-cyclopropylamino)-6-(4-fluorophenyl)-quinazoline

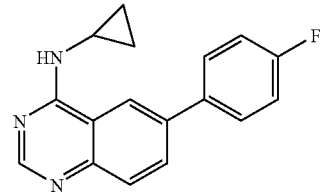 [SMILES: Fc1ccc(-c2ccc3ncnc(NC4CC4)c3c2)cc1]

This compound was synthesized from 4-chloro-6-(4-fluorophenyl)-quinazoline and cyclopropylamine in 80% yield, using the procedure described example 37 and was characterized by its mass spectrum as follows: MS (m/z): 298 ([M+H]$^+$, 100).

Example 48

Synthesis of 2-amino-6-(4-fluorophenyl)-4-(N-anilino)-quinazoline

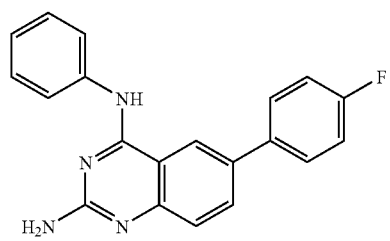 [SMILES: Nc1nc(Nc2ccccc2)c2cc(-c3ccc(F)cc3)ccc2n1]

This compound was obtained from the product of example 13 and aniline in 74% yield, using the procedure described for example 23, and was characterized by its mass spectrum as follows: MS (m/z): 331 ([M+H]+, 100).

In the description of the examples that follow, HPLC retention times are reported using the following chromatographic conditions:

Method A
Column: 50×4.6 mm
Packing: Synergi 4μ Polar RP 80 Å
Detection: UV 254 and 270 nm
Temperature: ambient
Eluents:

| start time (minutes) | duration (minutes) | Flow μl/minute | Water + 0.1% TFA | ACN + 0.1% TFA |
|---|---|---|---|---|
| 0 | 3 | 3000 | 98 | 2 |
| 3.0 | 1.5 | 3000 | 2 | 98 |
| 4.5 | 0.1 | 3000 | 98 | 2 |
| 4.51 | 0.89 | 3000 | 98 | 2 |

Method B
Column: 3×2 mm
Packing: Synergi 4μ Polar RP 80 Å
Detection: UV 254 and 280 nm
Temperature: ambient
Eluents:

| start time (minutes) | duration (minutes) | Flow μl/minute | Water + 1% Acetic acid | MeOH + 1% Acetic acid |
|---|---|---|---|---|
| 0 | 0.1 | 2000 | 100 | 0 |
| 0.1 | 2.5 | 2000 | 0 | 100 |
| 2.6 | 0.5 | 2000 | 0 | 100 |
| 3.1 | 0.1 | 2000 | 100 | 0 |
| 3.2 | 0.4 | 2000 | 100 | 0 |

Example 49

Synthesis of (N2-(4-fluorobenzyl)-6-(4-fluorophenyl)-N4-(2,2,2-trifluoroethyl)-quinazoline-2,4-diamine

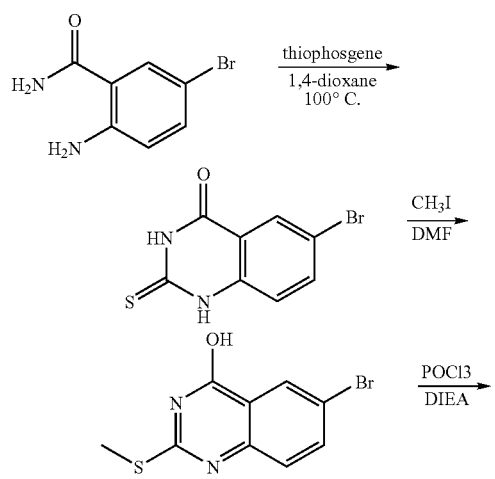

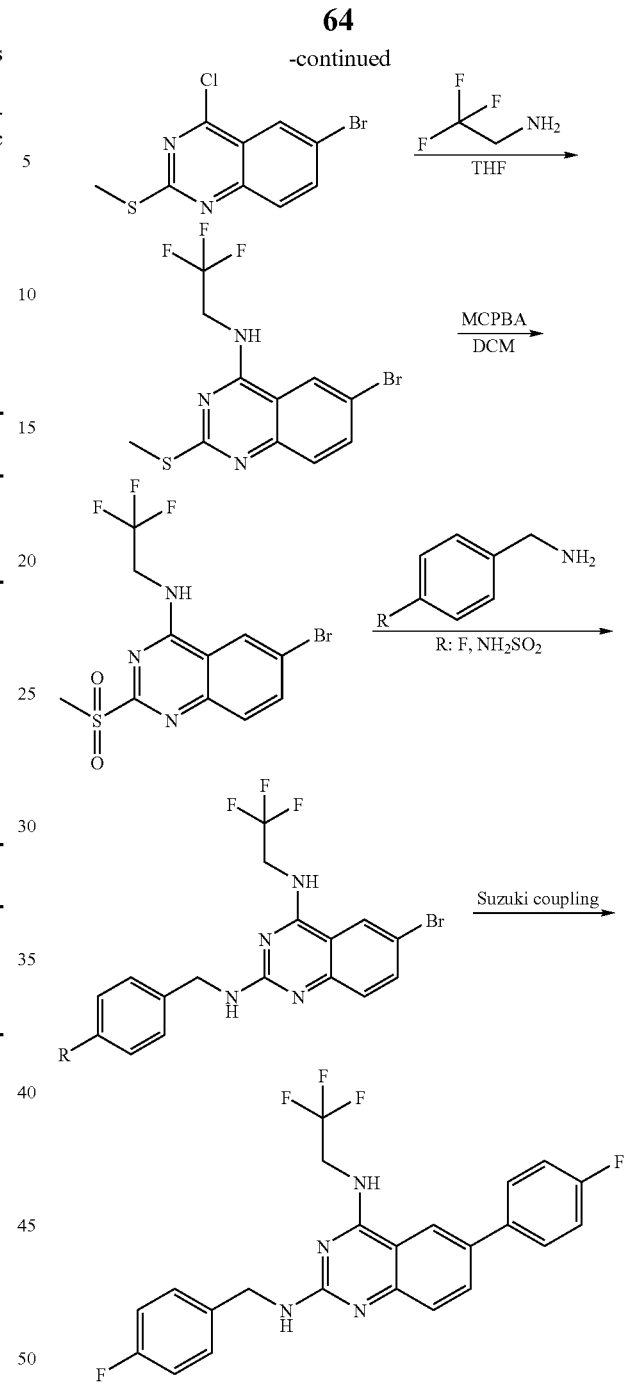

A suspension of 2-amino-5-bromobenzamide (250 mg, 1.16 mmol) and thiophosgene (200 mg, 1.74 mmol) in 1,4-dioxane (10 mL) was heated at 100° C. for 1 hour. Solvent was removed to provide 0.32 g of crude product-6-bromo-2-mercaptoquinazolin-4-ol-which was used without further purification.

6-bromo-2-(methylthio)-quinazolin-4-ol

A solution of 6-bromo-2-mercapto-quinazolin-4-ol (0.32 g, 1.26 mmol), methyl iodide and sodium ethoxide in DMF (5 mL) was stirred at room temperature for 3 hours. HCl (1N, 3 ml) was added and the mixture was extracted with ethyl acetate. The organic layer was dried and concentrated to provide 0.31 g of crude product which was used without further purification. The product was characterized as follows: MS (m/z) 271 [M+H]⁺; HPLC retention time (R$_t$)=1.87 minutes (Method B).

6-bromo-4-chloro-2-(methylthio)quinazoline

Diisopropylethylamine (0.65 ml, 3.69 mmol) was added to a suspension of 6-bromo-2-(methylthio)-quinazolin-4-ol (500 mg, 1.85 mmol) in POCl₃ (6.5 ml). The reaction was heated at reflux for 6 hours and then cooled to room temperature. The POCl₃ was removed under reduced pressure. The residue was diluted with EtOAc (30 ml) and poured onto ice. The organic layer was washed twice with brine (2×30 ml), then dried over sodium sulfate and concentrated. The product thus obtained was used without further purification.

(6-bromo-2-methylthio)-quinazolin-4-yl)-(2,2,2-trifluoro-ethyl)-amine

Diisopropylethylamine (1.6 ml, 9.25 mmol) was added to a solution of 6-bromo-4-chloro-2-(methylthio)-quinazoline and 2,2,2-trifluoroethylamine hydrochloride (752 mg, 5.55 mmol) in THF. The reaction was heated at 50° C. for 16 hours. After cooling to room temperature, the reaction was diluted with EtOAc and washed with brine twice. The organic layer was dried with sodium sulfate and concentrated under reduced pressure. The crude product was purified by flash column on silica gel (Rf: 0.3, 5% of EtOAc/Hexane). The yield was 62.5% for the two steps. The product was characterized as follows: MS (m/z) 352 [M+H]⁺; HPLC R$_t$=2.97 minutes (Method B).

(6-Bromo-2-methanesulfonyl-quinazolin-4-yl)-(2,2,2-trifluoroethyl)-amine m-chloroperbenzoic acid (MCPBA) (250 mg, 77% pure, 1.1 mmol) was added to a solution of (6-Bromo-2-(methylthio)-quinazolin-4-yl)-(2,2,2-trifluoroethyl)-amine (195 mg, 0.554 mmol) in DCM (5 ml). The white cloudy mixture was stirred for 1 hour, and the solvent was removed. The crude product was used without further purification.

6-Bromo-N2-(4-fluorobenzyl)-N4-(2,2,2-trifluoro-ethyl)-quinazoline-2,4-diamine Diisopropylethylamine (1 ml) was added to a solution of 6-Bromo-2-methanesulfonylquinazolin-4-yl)-(2,2,2-trifluoroethyl)-amine and 4-fluorobenzyl-amine (0.2 ml, 1.66 mmol) in 1,4-dioxane. The reaction was heated to 100° C. for 16 hours. The reaction was then cooled to room temperature and poured into to HCl (1N, 30 ml). The resulting suspension was filtered and the solid collected was dried under vacuum for 6 hours. The crude product (190 mg, 0.44 mmol, 80% yield) was used without further purification.

N2-(4-Fluoro-benzyl)-6-(4-fluoro-phenyl)-N4-(2,2,2-trifluoro-ethyl)-quinazoline-2,4-diamine A mixture of 6-Bromo-N2-(4-fluoro-benzyl)-N4-(2,2,2-trifluoro-ethyl)-quinazoline-2,4-diamine (34 mg, 0.08 mmol), potassium carbonate (0.4M. 0.4 ml)), tetrakis(triphenylphosphine) palladium (10 mg) and 4-fluorophenyl boronic acid in DMF (1 ml) was heated to 170° C. for 5 minutes by microwave. The residue was purified by RP HPLC, eluting with 0.1% TFA-acetonitrile, to provide the desired product (20 mg). The product was characterized as follows: MS (m/z): 445 ([M+H]⁺, 100); HPLC R$_t$=3.10 minutes (Method A).

Example 50

Synthesis of N-Cyclopropyl-4-[2-(4-fluoro-benzylamino)-4-(2,2,2-trifluoroethylamino)-quinazolin-6-yl]-benzamide N-Cyclopropyl-4-[2-(4-fluoro-benzylamino)-4-(2,2,2-trifluoro-ethylamino)quinazolin-6-yl]-benzamide was prepared by analogy to the procedure of example 59, using 4-(cyclopropylamido)benzene boronic acid. The resulting product was characterized as follows: MS (m/z): 570 ([M+H]⁺, 100); HPLC R$_t$=2.93 minutes (Method A).

Example 51

Synthesis of N-Cyclopropyl-4-[2-(4-sulfamoyl-benzylamino)-4-(2,2,2-trifluoroethylamino)-quinazolin-6-yl]-benzamide

4-{[6-bromo-4-(2,2,2-trifluoro-ethylamino)-quinazolin-2-ylamino]-methyl}-benzenesulfonamide 6-Bromo-2-methanesulfonyl-quinazolin-4-yl)-(2,2,2-trifluoro-ethyl)-amine was reacted with 4-Aminomethyl-benzenesulfonamide in a manner analogous to 6-Bromo-N2-(4-fluoro-benzyl)-N4-(2,2,2-trifluoro-ethyl)-quinazoline-2,4-diamine as described in Example 49. The product was characterized as follows: MS (m/z) 490 [M+H]⁺; HPLC R$_t$=1.90 minutes (Method B).

N-Cyclopropyl-4-[2-(4-sulfamoyl-benzylamino)-4-(2,2,2-trifluoro-ethylamino)-quinazolin-6-yl]-benzamide The title compound was synthesized in an analogous manner to Example 51, using 4-{[6-Bromo-4-(2,2,2-trifluoroethylamino)-quinazolin-2-ylamino]-methyl}-benzenesulfonamide and 4-(cyclopropylamido)benzene boronic acid. The product was characterized as follows: MS (m/z): 571 ([M+H]⁺, 100); HPLC R$_t$=2.65 minutes (Method A).

Example 52

Synthesis of 4-{[6-(4-Fluoro-phenyl)-4-(2,2,2-trifluoro-ethylamino)quinazolin-2-ylamino]-methyl}-benzenesulfonamide The title compound was synthesized by analogy to Example 51 using 4-{[6-bromo-4-(2,2,2-trifluoro-ethylamino)-quinazolin-2-ylamino]-methyl}-benzenesulfonamide and 4-fluorobenzene boronic acid. The resulting product was characterized as follows: MS (m/z): 506 ([M+H]⁺, 100); HPLC R$_t$=2.85 minutes (Method A).

Example 53

Synthesis of Cyclopropyl-[6-(4-fluoro-phenyl)-2-(2H-pyrazol-3-yl)quinazolin-4-yl]-amine

6-bromo-quinazoline-2,4-diol

Triphosgene (173 g, 0.58 mmol) was added to a solution of 2-Amino-5-bromobenzamide (250 mg, 1.162 mmol) in 1,4- dioxane (12 mL). The reaction was heated at 100° C. for 1.5 hours, cooled to room temperature and quenched with water (1 ml). The solid was filtered and washed with EtOAc twice to provide crude product (230 mg), which was used without further purification.

6-(4-fluorophenyl)-quinazoline-2,4-diol

A mixture of 6-Bromo-quinazoline-2,4-diol (1 g, 4.15 mmol), potassium carbonate (11.6 ml, 0.4 M), tetrakis(triphenylphosphine) palladium (550 mg) and 4-fluorophenyl boronic acid (0.716 g, 5.1 mmol) in DME (40 ml) was heated at 170° C. for 10 minutes by microwave. Solvents were concentrated in vacuo and the residue was purified by RP HPLC with a gradient of $H_2O$, 0.1% TFA-acetonitrile, to provide the desired product in 66% yield (760 mg).

2,4-Dichloro-6-(4-fluorophenyl)-quinazoline

A mixture of 6-(4-Fluoro-phenyl)-quinazoline-2,4-diol (760 mg, 2.95 mmol), $POCl_3$ (20 ml) and N,N-di-isopropyl ethyl amine (DIEA, 2 ml) was heated to reflux for 16 hours. The $POCl_3$ was removed by concentration under reduced pressure and the residue was dissolved in EtOAc. The organic solution was extracted with brine three times, then dried over sodium sulfate and concentrated to provide crude product (700 mg), which used without further purification.

[2-Chloro-6-(4-fluoro-phenyl)-quinazolin-4-yl]-cyclopropyl-amine

Cyclopropylamine (408 mg, 7.17 mmol) was added to a solution of 2,4-dichloro-6-(4-fluoro-phenyl)-quinazoline (700 mg, 2.39 mmol) in 1,4-dioxane. The reaction mixture was stirred for 30 min. at room temperature then diluted with EtOAc and washed with brine. The organic layer was dried and concentrated. The crude product (680 mg, 90.7% yield) was used without further purification. cyclopropyl-[6-(4-fluoro-phenyl)-2-(1H-pyrazol-3-yl)-quinazolin-4-yl]-amine:

A mixture of [2-Chloro-6-(4-fluoro-phenyl)-quinazolin-4-yl]-cyclopropyl-amine (50 mg, 0.16 mmol), potassium carbonate (44 ml, 0.32 mmol), tetrakis(triphenylphosphine) palladium (20 mg) and 1H-pyrazol-3-yl boronic acid (27 mg, 0.24 mmol) in DMF (1 mL) and water (0.3 ml) was heated to 150° C. for 5 minutes by microwave. The residue was purified by RP HPLC with a gradient of $H_2O$, 0.1% TFA-acetonitrile, to provide the desired product (15 mg) which was characterized as follows: MS (m/z): 346 ([M+H]$^+$, 100). HPLC $R_t$=1.50 minutes (Method B).

Example 54

Synthesis of N4-cyclopropyl-6-(4-fluoro-phenyl)-N2-(1-methyl-1H-pyrazol-3-yl)-quinazoline-2,4-diamine To a solution of [2-Chloro-6-(4-fluoro-phenyl)-quinazolin-4-yl]-cyclopropylamine (150 mg, 0.48 mmol) and 1-Methyl-1H-pyrazol-3-ylamine (70 mg, 0.72 mmol) in 1,4-dioxane (5 ml) was added 2,6-lutidine (2 equiv.; 102 mg, 0.96 mmol). The solution was heated to 100° C. for 3 hours, then cooled and purified by RP HPLC with a gradient of $H_2O$, 0.1% TFA-acetonitrile, to provide the desired product (140 mg, 0.287 mmol, 60% yield). The product was characterized as follows: MS (m/z): 375 ([M+H]$^+$, 100); HPLC $R_t$=1.60 minutes (Method B).

Example 55

Synthesis of N4,N2-bis-n-butyl-6-(4-fluoro-phenyl)-quinazoline-2,4-diamine

To a solution of 2,4-Dichloro-6-(4-fluoro-phenyl)-quinazoline (20 mg, 0.068 mmol) in 1,4-dioxane was added n-butylamine (20 mg). The solution was heated to 60° C. for 2 hours, and subsequently cooled, diluted with EtOAc and washed with brine. The organic layer was dried and purified by RP HPLC with a gradient of $H_2O$, 0.1% TFA-acetonitrile, to provide the desired product (8 mg). The product was characterized as follows: MS (m/z): 367 ([M+H]$^+$, 100); HPLC $R_t$=1.69 minutes (Method A).

Example 56

Synthesis of 4-[2-Amino-4-(2-methoxy-ethylamino)-quinazolin-6-yl]-N cyclopropyl-benzamide

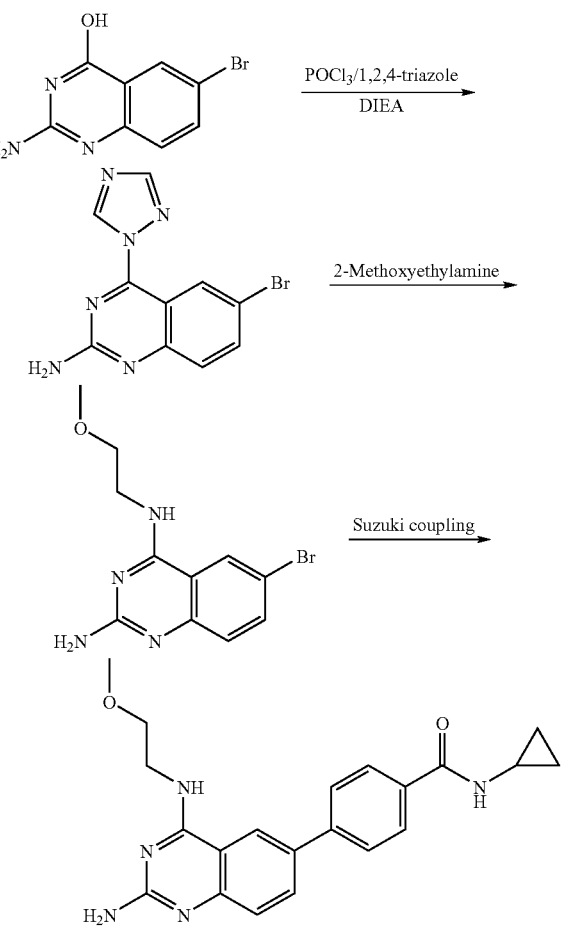

6-Bromo-4-[1,2,4]triazol-1-yl-quinazolin-2-ylamine

The title compound was synthesized from 2-amino-4-hydroxy-6-bromoquinazoline (see Example 1) by a procedure analogous to example 11 and was characterized as follows: MS (m/z): 291 ([M+H]$^+$, 100); HPLC $R_t$=1.47 minutes (Method B).

6-Bromo-N4-(2-methoxy-ethyl)-quinazoline-2,4-diamine

The title compound was synthesized by a method analogous to example 23 using 6-Bromo-4-[1,2,4]triazol-1-yl-quinazolin-2-ylamine and 2-methoxyethylamine. The product was characterized as follows: MS (m/z) 297[M+H]$^+$; HPLC $R_t$=1.05 minutes (Method B).

4-[2-Amino-4-(2-methoxy-ethylamino)-quinazolin-6-yl]-N-cyclopropyl-benzamide The title compound was synthesized in analogy to example 7, using 6-BromoN$^4$-(2-methoxy-ethyl)-quinazoline-2,4-diamine and 4-(cyclopropyl)-benzene boronic acid, and was characterized as follows: MS (m/z): 378 ([M+H]$^+$, 100); HPLC $R_t$=2.36 minutes (Method B).

Example 57

Anti-HCV Assay/Replicon Assay

The anti HCV activity of the quinazoline derivatives of this invention was tested in a human hepatoma Huh-7 cell line harbouring a HCV replicon. The assay comprised the following steps:

Step 1: compound preparation and serial dilution
1. for water soluble quinazoline derivatives, a volume of 500 µL of solution in cell media (DMEM, 10% FBS, P/S, L-Glutamine) was prepared with a concentration being twice the concentration of the starting final serial dilution concentration. A volume of 150 µL of the solution was added to the pre-specified wells in column 1 of a 96-well cell culture plate (PerkinElmer, white plate, cat. #6005181, for EC$_{50}$ assay; black plate, cat. #6005182 for CC$_{50}$ assay). The rest of the plate, columns 2-12, was filled with 100 µL of cell media. The plate was then placed on a Precision 2000 Workstation to start the serial dilution. Compounds were diluted three times each step from column 1 to column 10. Column 11 was used as a blank control (no compound added).
2. for quinazoline derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 µL of the solution was transferred from the 384-well plate to a 96-well cell culture plate containing 100 µL of cell media on a Biomek FX Workstation. The DMSO concentration in the final assay condition was 0.5% after cells are added to the plate and the total volume in each well is brought to 200 µL.

Step 2: to each well of the serial dilution plate prepared above, 100 µL of cell media containing 6000 suspended Huh-7 HCV replicon cells was added with a Multidrop workstation. The plates were incubated for 3 days at 37° C. with 5% CO$_2$.

Step 3: Detection:
a) for the EC$_{50}$ assay, the media in a 96-well cell culture plate was aspirated with a Biotek EL405 plate-washer. A volume of 200 µL of a solution containing a 1:1 mixture of cell-lysis buffer (Promega, Luciferase Cell Culture Lysis 5× Reagent, cat. #E1531) and luciferase substrate solution (Promega, Luciferase Assay, cat.# E4550) was added to each well of the plate with Multidrop. The plate was incubated for 30 minutes at room temperature before the luminescence signal was measured with a TopCount plate-reader.

b) for the CC$_{50}$ assay, a volume of 100 µL of pre-mixed CeliTiter-Glo (Promega, cat.# G7572) solution is added directly to the cell culture in each well of the plate and the luminescence signal is measured with a TopCount plate-reader after 10 minutes of incubation at room temperature.

The table below shows EC$_{50}$ and CC$_{50}$ values (expressed in nM and µM respectively, i.e. nmol/l and µmol/l) of a few quinazoline derivatives tested in this assay. Results in the table below are expressed by the following data:

the 50% cytostatic concentration (CC$_{50}$), i.e. the concentration that results in 50% inhibition of cell growth, and the 50% effective concentration (EC$_{50}$), i.e. the concentration that protects 50% of the cell monolayer from virus-induced cytopathic effect.

TABLE 1

| Example | EC$_{50}$ (A < 0.3 µM; 0.3 µM < B < 1 µM; 1 µM < C < 10 µM) | CC$_{50}$ (A < 10 µM; B 10-20 µM; C > 20 µM) |
|---------|---|---|
| 14 | A | A |
| 16 | A | C |
| 27 | B | B |
| 28 | B | A |
| 30 | C | B |
| 31 | C | B |
| 32 | C | C |
| 34 | C | B |
| 37 | C | C |
| 39 | C | C |
| 43 | C | C |
| 44 | B | C |
| 45 | C | C |
| 47 | C | C |
| 48 | B | A |
| 51 | A | C |
| 52 | A | A |
| 54 | A | A |
| 56 | C | C |

Examples 100 to 295

Synthesis of 2-amino-6-(3,4-dimethoxyphenyl)-4-hydrazinoquinazoline analogues The sequential experimental procedure of examples 5, 8, 12, 15 is repeated, except that in the initial step, 3,4-dimethoxyphenylboronic acid is replaced with another aryl or heteroaryl boronic acid. In this way, the following quinazoline derivatives are obtained in similar yields:

4-hydrazino-6-(4-(4'-allyloxycarbonylpiperazino)phenyl)quinazolin-2-ylamine, 4-hydrazino-6-(3-aminocarbonylphenyl)quinazolin-2-ylamine, 4-hydrazino-6-(4-aminocarbonylphenyl)quinazolin-2-ylamine, 4-hydrazino-6-(2-amino-5-chlorophenyl)quinazolin-2-ylamine, 4-hydrazino-6-(4-amino-3-ethoxyphenyl)quinazolin-2-ylamine, 4-hydrazino-6-(2-amino-4-methylphenyl)quinazolin-2-ylamine, 4-hydrazino-6-(2-amino-5-methylphenyl)quinazolin-2-ylamine, 4-hydrazino-6-(4-amino-2-methyl phenyl)quinazolin-2-ylamine, 4-hydrazino-6-(5-amino-2-methyl phenyl)quinazolin-2-ylamine,
4-hydrazino-6-(4-amino-3-nitrophenyl)quinazolin-2-ylamine,
4-hydrazino-6-(2-benzyloxyphenyl)quinazolin-2-ylamine,
4-hydrazino-6-(3-benzyloxy-4-ethoxyphenyl)quinazolin-2-ylamine,
4-hydrazino-6-(4-biphenyl)quinazolin-2-ylamine,
4-hydrazino-6-(4-n-butyl phenyl)quinazolin-2-ylamine,
4-hydrazino-6-(4-isobutylphenyl)quinazolin-2-ylamine,
4-hydrazino-6-(4-carboxy-3-fluorophenyl)quinazolin-2-ylamine,
4-hydrazino-6-(3-(3-carboxypropionylamino)phenyl) quinazolin-2-ylamine,
4-hydrazino-6-(4-(3-carboxypropionylamino)phenyl) quinazolin-2-ylamine,
4-hydrazino-6-(3-chloro-4-hydroxy-5-ethoxyphenyl) quinazolin-2-ylamine,
4-hydrazino-6-(2-chloro-5-hydroxymethylphenyl)quinazolin-2-ylamine,
4-hydrazino-6-(4-cyanoethoxyphenyl)quinazolin-2-ylamine,
4-hydrazino-6-(3-cyanoethoxyphenyl)quinazolin-2-ylamine,
4-hydrazino-6-(2-cyanoethoxyphenyl)quinazolin-2-ylamine,
4-hydrazino-6-(4-cyanophenyl)quinazolin-2-ylamine,
4-hydrazino-6-(3-cyanophenyl)quinazolin-2-ylamine,
4-hydrazino-6-(2-cyanophenyl)quinazolin-2-ylamine,
4-hydrazino-6-(3-(N-cyclopropylaminocarbonyl)phenyl) quinazolin-2-ylamine,
4-hydrazino-6-(3-(N,N-diethylaminocarbonyl)phenyl) quinazolin-2-ylamine,
4-hydrazino-6-(3-(N,N-dimethylamino)phenyl)quinazolin-2-ylamine,
4-hydrazino-6-(2-(N,N-dimethylamino)phenyl)quinazolin-2-ylamine,
4-hydrazino-6-(3-(N,N-dimethylaminocarbonyl)phenyl) quinazolin-2-ylamine,
4-hydrazino-6-(3-[(N',N'-dimethylamino)ethylaminocarbonyl]phenyl)quinazolin-2-ylamine,
4-hydrazino-6-(4-[(N',N'-dimethylamino)ethylaminocarbonyl]phenyl)quinazolin-2-ylamine,
4-hydrazino-6-(3-[1,3]dioxolan-2-ylethoxyphenyl)quinazolin-2-ylamine,
4-hydrazino-6-(3-(ethoxycarbonyl)ethoxyphenyl)quinazolin-2-ylamine,
4-hydrazino-6-(4-(ethoxycarbonyl)ethoxyphenyl)quinazolin-2-ylamine,
4-hydrazino-6-(4-ethoxycarbonylphenyl)quinazolin-2-ylamine,
4-hydrazino-6-(3-ethoxycarbonylphenyl)quinazolin-2-ylamine,
4-hydrazino-6-(2-ethoxycarbonylphenyl)quinazolin-2-ylamine,
4-hydrazino-6-(4-(3-ethoxycarbonylpiperidino)carboxamidophenyl)-quinazolin-2-ylamine,
4-hydrazino-6-(4-formylaminophenyl)quinazolin-2-ylamine,
4-hydrazino-6-(3-formylaminophenyl)quinazolin-2-ylamine,
4-hydrazino-6-(2-formylaminophenyl)quinazolin-2-ylamine,
4-hydrazino-6-(2-formyl-5-ethoxyphenyl)quinazolin-2-ylamine,
4-hydrazino-6-(3-formyl-4-ethoxyphenyl)quinazolin-2-ylamine,
4-hydrazino-6-(5-formyl-2-ethoxyphenyl)quinazolin-2-ylamine,
4-hydrazino-6-(2-formyl-5-methylphenyl)quinazolin-2-ylamine,
4-hydrazino-6-(4-formylphenyl)quinazolin-2-ylamine,
4-hydrazino-6-(3-formylphenyl)quinazolin-2-ylamine,
4-hydrazino-6-(2-formylphenyl)quinazolin-2-ylamine,
4-hydrazino-6-(4-hydroxy-3,5-dimethylphenyl)quinazolin-2-ylamine,
4-hydrazino-6-(3-(2-hydroxyethyl)-aminocarbonylphenyl) quinazolin-2-ylamine,
4-hydrazino-6-(4-(2-hydroxyethyl)aminocarbonylphenyl) quinazolin-2-ylamine,
4-hydrazino-6-(3-hydroxy-4-ethoxycarbonylphenyl) quinazolin-2-ylamine,
4-hydrazino-6-(4-hydroxy-3-ethoxyphenyl)quinazolin-2-ylamine,
4-hydrazino-6-(4-(hydroxymethyl)phenyl)quinazolin-2-ylamine,
4-hydrazino-6-(3-(hydroxymethyl)phenyl)quinazolin-2-ylamine,
4-hydrazino-6-(4-hydroxy-3-nitrophenyl)quinazolin-2-ylamine,
4-hydrazino-6-(4-isopropoxyphenyl)quinazolin-2-ylamine,
4-hydrazino-6-(4-(4-isopropylpiperazinyl)phenyl)quinazolin-2-ylamine,
4-hydrazino-6-(4-isopropylphenyl)quinazolin-2-ylamine,
4-hydrazino-6-(4-methanesulfonamidophenyl)quinazolin-2-ylamine,
4-hydrazino-6-(3-methanesulfonamidophenyl)quinazolin-2-ylamine,
4-hydrazino-6-(2-methanesulfonamido phenyl)quinazolin-2-ylamine,
4-hydrazino-6-(4-ethoxycarbonylphenyl)quinazolin-2-ylamine,
4-hydrazino-6-(3-ethoxycarbonylphenyl)quinazolin-2-ylamine,
4-hydrazino-6-(2-ethoxycarbonylphenyl)quinazolin-2-ylamine,
4-hydrazino-6-(3-ethoxy-4-ethoxycarbonylphenyl)quinazolin-2-ylamine,
4-hydrazino-6-(2-ethoxy-5-methylphenyl)quinazolin-2-ylamine,
4-hydrazino-6-(4-ethoxy-3-nitrophenyl)quinazolin-2-ylamine,
4-hydrazino-6-(4-ethoxyphenyl)quinazolin-2-ylamine,
4-hydrazino-6-(3-ethoxyphenyl)quinazolin-2-ylamine,
4-hydrazino-6-(4-N-methylcarboxamidophenyl)quinazolin-2-ylamine,
4-hydrazino-6-(4-(N-methylamino)phenyl)quinazolin-2-ylamine,
4-hydrazino-6-(3-(4-methylpiperazine-1-carbonyl)phenyl) quinazolin-2-ylamine,
4-hydrazino-6-(4-(4-methylpiperazine-1-carbonyl)phenyl) quinazolin-2-ylamine,
4-hydrazino-6-(4-(methylthio)phenyl)quinazolin-2-ylamine,
4-hydrazino-6-(3-(methylthio)phenyl)quinazolin-2-ylamine,
4-hydrazino-6-(2-(methylthio)phenyl)quinazolin-2-ylamine,
4-hydrazino-6-(4-(morpholinocarbonyl)phenyl)quinazolin-2-ylamine,
4-hydrazino-6-(4-morpholinophenyl)quinazolin-2-ylamine,
4-hydrazino-6-(2-(morpholinomethyl)phenyl)quinazolin-2-ylamine,
4-hydrazino-6-(4-nitrophenyl)quinazolin-2-ylamine, 4-hydrazino-6-(3-nitrophenyl)quinazolin-2-ylamine,
4-hydrazino-6-(2-nitrophenyl)quinazolin-2-ylamine,
4-hydrazino-6-(4-phenoxyphenyl)quinazolin-2-ylamine,
4-hydrazino-6-(4-(N-phenylaminomethyl)phenyl)quinazolin-2-ylamine,
4-hydrazino-6-(4-(phenylcarbonyl)phenyl)quinazolin-2-ylamine,
4-hydrazino-6-(4-(piperazine-1-carbonyl)phenyl)quinazolin-2-ylamine,
4-hydrazino-6-(4-piperazinylphenyl)quinazolin-2-ylamine,
4-hydrazino-6-(4-succinamidophenyl)quinazolin-2-ylamine,
4-hydrazino-6-(3-succinamidophenyl)quinazolin-2-ylamine,
4-hydrazino-6-(sulfamoylphenyl)quinazolin-2-ylamine,
4-hydrazino-6-(2-(toluene-4-sulfonamido)phenyl)quinazolin-2-ylamine,
4-hydrazino-6-(4-(toluene-4-sulfonamido)phenyl)quinazolin-2-ylamine,
4-hydrazino-6-(4-(tert-butoxycarbonylamino)-3-ethoxyphenyl)quinazolin-2-ylamine,
4-hydrazino-6-(2-(tert-butoxycarbonyl)phenyl)quinazolin-2-ylamine,
4-hydrazino-6-(3-(tert-butoxycarbonyl)phenyl)quinazolin-2-ylamine,
4-hydrazino-6-(4-(tert-butoxycarbonyl)phenyl)quinazolin-2-ylamine,
4-hydrazino-6-(2,3,4-trifluorophenyl)quinazolin-2-ylamine,
4-hydrazino-6-(4-tert-butylphenyl)quinazolin-2-ylamine,
4-hydrazino-6-(4-(tetrahydro-2H-pyran-2-yloxy)phenyl)quinazolin-2-ylamine,
4-hydrazino-6-(4-(2-thienyl)phenyl)quinazolin-2-ylamine,
4-hydrazino-6-(2,4,6-trimethylphenyl)quinazolin-2-ylamine,
4-hydrazino-6-(3,4,5-trimethoxyphenyl)quinazolin-2-ylamine,
4-hydrazino-6-(4-vinylphenyl)quinazolin-2-ylamine,
4-hydrazino-6-(4-(2-hydroxyhydrazino)phenyl)quinazolin-2-ylamine,
4-hydrazino-6-(6-benzyloxynaphth-2-yl)quinazolin-2-ylamine,
4-hydrazino-6-(naphth-1-yl)quinazolin-2-ylamine,
4-hydrazino-6-(naphth-2-yl)quinazolin-2-ylamine,
4-hydrazino-6-(4'-benzoyl[1,1'-biphenyl]-4-yl)quinazolin-2-ylamine,
4-hydrazino-6-(1-biphenylyl)quinazolin-2-ylamine,
4-hydrazino-6-(oxoindan-5-yl)quinazolin-2-ylamine,
4-hydrazino-6-(benzodioxolyl)quinazolin-2-ylamine,
4-hydrazino-6-(2-acetamidopyridin-5-yl)quinazolin-2-ylamine,
4-hydrazino-6-(2-aminopyridin-5-yl)quinazolin-2-ylamine,
4-hydrazino-6-(2-aminopyrimidin-5-yl)quinazolin-2-ylamine,
4-hydrazino-6-(1,4-benzodioxan-6-yl)quinazolin-2-ylamine,
4-hydrazino-6-(1-benzothien-3-yl)quinazolin-2-ylamine,
4-hydrazino-6-(2-benzyloxypyridin-5-yl)quinazolin-2-ylamine,
4-hydrazino-6-(1-benzyl-1H-pyrazol-4-yl)quinazolin-2-ylamine,
4-hydrazino-6-(2-bromo-3-chloropyridin-4-yl)quinazolin-2-ylamine,
4-hydrazino-6-(5-bromo-2,3-dihydrobenzo[b]furan-7-yl)quinazolin-2-ylamine,
4-hydrazino-6-(2-bromo-3-methylpyridin-5-yl)quinazolin-2-ylamine,
4-hydrazino-6-(2-bromopyridin-5-yl)quinazolin-2-ylamine,
4-hydrazino-6-(3-bromopyridin-5-yl)quinazolin-2-ylamine,
4-hydrazino-6-(5-bromothien-2-yl)quinazolin-2-ylamine,
4-hydrazino-6-(2-chloro-6-isopropylpyridin-3-yl)quinazolin-2-ylamine,
4-hydrazino-6-(2-chloro-3-methylpyridin-5-yl)quinazolin-2-ylamine,
4-hydrazino-6-(2-[4-(4-chlorophenylsulfonyl)piperazin-1-yl]pyridin-5-yl)quinazolin-2-ylamine,
4-hydrazino-6-(2-chloropyrid-4-yl)quinazolin-2-ylamine,
4-hydrazino-6-(2-chloropyrid-5-yl)quinazolin-2-ylamine,
4-hydrazino-6-(dibenzo[b,d]furan-4-yl)quinazolin-2-ylamine,
4-hydrazino-6-(2-chloro-3-fluoropyridin-4-yl)quinazolin-2-ylamine,
4-hydrazino-6-(dibenzo[b,d]thien-4-yl)quinazolin-2-ylamine,
4-hydrazino-6-(3,4-dihydro-2H-1,5-benzodioxepin-7-yl)quinazolin-2-ylamine,
4-hydrazino-6-(3,6-dihydro-2H-pyridine-1-tert-butoxycarbonyl)quinazolin-2-ylamine,
4-hydrazino-6-(2,5-dibromopyridin-3-yl)quinazolin-2-ylamine,
4-hydrazino-6-(2,6-dichloropyridin-3-yl)quinazolin-2-ylamine,
4-hydrazino-6-(2,3-dihydro-1-benzofuran-5-yl)quinazolin-2-ylamine,
4-hydrazino-6-(2,6-diethoxypyridin-5-yl)quinazolin-2-ylamine,
4-hydrazino-6-(2,6-diethoxypyridin-3-yl)quinazolin-2-ylamine,
4-hydrazino-6-(2,4-diethoxypyrimidin-5-yl)quinazolin-2-ylamine,
4-hydrazino-6-(3,5-dimethylisoxazol-4-yl)quinazolin-2-ylamine,
4-hydrazino-6-(2-(3-N,N-dimethylaminopropoxy)pyridin-5-yl)quinazolin-2-ylamine,
4-hydrazino-6-(3,5-dimethylpyrazol-4-yl)quinazolin-2-ylamine,
4-hydrazino-6-(1-[1,3]dioxolan-2-ylmethyl-1H-pyrazol-4-yl)quinazolin-2-ylamine,
4-hydrazino-6-(2,4-dioxo-1,2,3,4-tetrahydro-5-pyrimidinyl)quinazolin-2-ylamine,
4-hydrazino-6-(2,4-di(tert-butoxy)pyrimidin-5-yl)quinazolin-2-ylamine,
4-hydrazino-6-(2-hydrazinopyridin-3-yl)quinazolin-2-ylamine,
4-hydrazino-6-(2-fluoro-3-methylpyridin-5-yl)quinazolin-2-ylamine,
4-hydrazino-6-(2-fluoropyridin-5-yl)quinazolin-2-ylamine,
4-hydrazino-6-(5-formyl-2-furyl)quinazolin-2-ylamine,
4-hydrazino-6-(5-formylthien-2-yl)quinazolin-2-ylamine,
4-hydrazino-6-(furan-2-yl)quinazolin-2-ylamine,
4-hydrazino-6-(2-hydroxypyridin-5-yl)quinazolin-2-ylamine,
4-hydrazino-6-(1-isobutyl-1H-pyrazol-4-yl)quinazolin-2-ylamine,
4-hydrazino-6-(isoquinolin-4-yl)quinazolin-2-ylamine,
4-hydrazino-6-(2-ethoxypyridin-3-yl)quinazolin-2-ylamine,
4-hydrazino-6-(2-ethoxypyrimidin-5-yl)quinazolin-2-ylamine,
4-hydrazino-6-(5-methyl-1-benzothien-2-yl)quinazolin-2-ylamine,
4-hydrazino-6-(1-(3-methylbutyl)-1H-pyrazol-4-yl)quinazolin-2-ylamine,
4-hydrazino-6-(5-methylfuran-2-yl)quinazolin-2-ylamine,
4-hydrazino-6-(1-methylindol-5-yl)quinazolin-2-ylamine, 4-hydrazino-6-(5-methyl-3-phenyl-4-isoxazolyl)quinazolin-2-ylamine,
4-hydrazino-6-(5-(methylthio)thien-2-yl)quinazolin-2-ylamine,
4-hydrazino-6-(2-(4-methylpiperazinyl)pyridin-4-yl)quinazolin-2-ylamine,
4-hydrazino-6-(2-(4-methylpiperazinyl)pyridin-5-yl)quinazolin-2-ylamine,
4-hydrazino-6-(1-methyl-1H-pyrazol-4-yl)quinazolin-2-ylamine,
4-hydrazino-6-(3-methylpyridin-2-yl)quinazolin-2-ylamine,
4-hydrazino-6-(5-methylpyridin-2-yl)quinazolin-2-ylamine,
4-hydrazino-6-(5-methylpyridin-3-yl)quinazolin-2-ylamine,
4-hydrazino-6-(2-ethoxypyridin-5-yl)quinazolin-2-ylamine,
4-hydrazino-6-(4-methylthien-2-yl)quinazolin-2-ylamine,
4-hydrazino-6-(5-methylthien-2-yl)quinazolin-2-ylamine,
4-hydrazino-6-(2-(2-morpholinoethylamino)-pyridin-5-yl)quinazolin-2-ylamine,
4-hydrazino-6-(2-(2-morpholinoethyl)-1H-pyrazol-4-yl)quinazolin-2-ylamine,
4-hydrazino-6-(2-(morpholin-1-yl)-pyridin-5-yl)quinazolin-2-ylamine,
4-hydrazino-6-(1-(phenylsulfonyl)-1H-indol-3-yl)quinazolin-2-ylamine,
4-hydrazino-6-(5-phenyl-2-thienyl)quinazolin-2-ylamine,
4-hydrazino-6-(2-(piperazin-1-yl)-pyridin-5-yl)quinazolin-2-ylamine,
4-hydrazino-6-(2-(piperazin-1-yl)-pyridin-4-yl)quinazolin-2-ylamine,
4-hydrazino-6-(1-propyl-1H-pyrazol-4-yl)quinazolin-2-ylamine,
4-hydrazino-6-(pyrazol-4-yl)quinazolin-2-ylamine,
4-hydrazino-6-(pyridin-4-yl)quinazolin-2-ylamine,
4-hydrazino-6-(4-phenoxathiinyl)quinazolin-2-ylamine,
4-hydrazino-6-(quinolin-8-yl)quinazolin-2-ylamine,
4-hydrazino-6-(quinolin-3-yl)quinazolin-2-ylamine,
4-hydrazino-6-(2-(4-tert-butoxycarbonylpiperazinyl)-pyrid-4-yl)quinazolin-2-ylamine,
4-hydrazino-6-(1-tert-butoxycarbonyl-1H-pyrazol-4-yl)quinazolin-2-ylamine,
4-hydrazino-6-(1-tert-butoxycarbonyl-2-pyrrolyl)quinazolin-2-ylamine,
4-hydrazino-6-(1-(tert-butoxycarbonyl)-5-bromo-1H-indol-2-yl)quinazolin-2-ylamine,
4-hydrazino-6-(1-(tert-butoxycarbonyl)-1H-indol-5-yl)quinazolin-2-ylamine,
4-hydrazino-6-(1-(tert-butoxycarbonyl)-5-methoxy-1H-indol-2-yl)quinazolin-2-ylamine,
4-hydrazino-6-(1-thianthrenylthien-3-yl)quinazolin-2-ylamine, and
4-hydrazino-6-(1,3,5-trimethyl-1H-pyrazol-4-yl)quinazolin-2-ylamine.

Examples 300 to 495

Synthesis of 2-amino-6-(3,4-dimethoxyphenyl)-4-[(3-bromo)anilino]-quinazoline analogues The sequential experimental procedure of examples 5, 8, 12 and 16 is repeated, except that in the initial step, 3,4-dimethoxyphenylboronic acid is replaced with another aryl or heteroaryl boronic acid. In this way, the following quinazoline derivatives are obtained in similar yields:
4-((3-bromo)-anilino)-6-(4-(4'-allyloxycarbonylpiperazino)phenyl)quinazolin-2-ylamine,
4-((3-bromo)-anilino)-6-(3-aminocarbonylphenyl)quinazolin-2-ylamine,
4-((3-bromo)-anilino)-6-(4-aminocarbonylphenyl)quinazolin-2-ylamine,
4-((3-bromo)-anilino)-6-(2-amino-5-chlorophenyl)quinazolin-2-ylamine,
4-((3-bromo)-anilino)-6-(4-amino-3-ethoxyphenyl)quinazolin-2-ylamine,
4-((3-bromo)-anilino)-6-(2-amino-4-methylphenyl)quinazolin-2-ylamine,
4-((3-bromo)-anilino)-6-(2-amino-5-methylphenyl)quinazolin-2-ylamine,
4-((3-bromo)-anilino)-6-(4-amino-2-methylphenyl)quinazolin-2-ylamine,
4-((3-bromo)-anilino)-6-(5-amino-2-methylphenyl)quinazolin-2-ylamine,
4-((3-bromo)-anilino)-6-(4-amino-3-nitrophenyl)quinazolin-2-ylamine,
4-((3-bromo)-anilino)-6-(2-benzyloxyphenyl)quinazolin-2-ylamine,
4-((3-bromo)-anilino)-6-(3-benzyloxy-4-ethoxyphenyl)quinazolin-2-ylamine,
4-((3-bromo)-anilino)-6-(4-biphenyl)quinazolin-2-ylamine,
4-((3-bromo)-anilino)-6-(4-n-butyl phenyl)quinazolin-2-ylamine,
4-((3-bromo)-anilino)-6-(4-isobutylphenyl)quinazolin-2-ylamine,
4-((3-bromo)-anilino)-6-(4-carboxy-3-fluorophenyl)quinazolin-2-ylamine,
4-((3-bromo)-anilino)-6-(3-(3-carboxypropionylamino)phenyl)quinazolin-2-ylamine,
4-((3-bromo)-anilino)-6-(4-(3-carboxypropionylamino)phenyl)quinazolin-2-ylamine,
4-((3-bromo)-anilino)-6-(3-chloro-4-hydroxy-5-ethoxyphenyl)quinazolin-2-ylamine,
4-((3-bromo)-anilino)-6-(2-chloro-5-hydroxymethylphenyl)quinazolin-2-ylamine,
4-((3-bromo)-anilino)-6-(4-cyanoethoxyphenyl)quinazolin-2-ylamine,
4-((3-bromo)-anilino)-6-(3-cyanoethoxyphenyl)quinazolin-2-ylamine,
4-((3-bromo)-anilino)-6-(2-cyanoethoxyphenyl)quinazolin-2-ylamine,
4-((3-bromo)-anilino)-6-(4-cyanophenyl)quinazolin-2-ylamine,
4-((3-bromo)-anilino)-6-(3-cyanophenyl)quinazolin-2-ylamine,
4-((3-bromo)-anilino)-6-(2-cyanophenyl)quinazolin-2-ylamine,
4-((3-bromo)-anilino)-6-(3-(N-cyclopropylaminocarbonyl)phenyl)quinazolin-2-ylamine,
4-((3-bromo)-anilino)-6-(3-(N,N-diethylaminocarbonyl)phenyl)quinazolin-2-ylamine,
4-((3-bromo)-anilino)-6-(3-(N,N-dimethylamino)phenyl)quinazolin-2-ylamine,
4-((3-bromo)-anilino)-6-(2-(N,N-dimethylamino)phenyl)quinazolin-2-ylamine,
4-((3-bromo)-anilino)-6-(3-(N,N-dimethylaminocarbonyl)phenyl)quinazolin-2-ylamine,
4-((3-bromo)-anilino)-6-(3-[(N',N'-dimethylamino)ethylaminocarbonyl]phenyl)quinazolin-2-ylamine,
4-((3-bromo)-anilino)-6-(4-[(N',N'-dimethylamino)ethylaminocarbonyl]phenyl)quinazolin-2-ylamine,
4-((3-bromo)-anilino)-6-(3-[1,3]dioxolan-2-ylethoxyphenyl)quinazolin-2-ylamine,
4-((3-bromo)-anilino)-6-(3-(ethoxycarbonyl)ethoxyphenyl)quinazolin-2-ylamine,
4-((3-bromo)-anilino)-6-(4-(ethoxycarbonyl)ethoxyphenyl)quinazolin-2-ylamine, 4-((3-bromo)-anilino)-6-(4-ethoxycarbonylphenyl)quinazolin-2-ylamine,
4-((3-bromo)-anilino)-6-(3-ethoxycarbonylphenyl)quinazolin-2-ylamine,
4-((3-bromo)-anilino)-6-(2-ethoxycarbonylphenyl)quinazolin-2-ylamine,
4-((3-bromo)-anilino)-6-(4-(3-ethoxycarbonylpiperidino)carboxamidophenyl)quinazolin-2-ylamine,
4-((3-bromo)-anilino)-6-(4-formylaminophenyl)quinazolin-2-ylamine,
4-((3-bromo)-anilino)-6-(3-formylaminophenyl)quinazolin-2-ylamine,
4-((3-bromo)-anilino)-6-(2-formylaminophenyl)quinazolin-2-ylamine,
4-((3-bromo)-anilino)-6-(2-formyl-5-ethoxyphenyl)quinazolin-2-ylamine,
4-((3-bromo)-anilino)-6-(3-formyl-4-ethoxyphenyl)quinazolin-2-ylamine,
4-((3-bromo)-anilino)-6-(5-formyl-2-ethoxyphenyl)quinazolin-2-ylamine,
4-((3-bromo)-anilino)-6-(2-formyl-5-methylphenyl)quinazolin-2-ylamine,
4-((3-bromo)-anilino)-6-(4-formylphenyl)quinazolin-2-ylamine,
4-((3-bromo)-anilino)-6-(3-formylphenyl)quinazolin-2-ylamine,
4-((3-bromo)-anilino)-6-(2-formylphenyl)quinazolin-2-ylamine,
4-((3-bromo)-anilino)-6-(4-hydroxy-3,5-dimethylphenyl)quinazolin-2-ylamine,
4-((3-bromo)-anilino)-6-(3-(2-hydroxyethyl)-aminocarbonylphenyl)quinazolin-2-ylamine,
4-((3-bromo)-anilino)-6-(4-(2-hydroxyethyl)aminocarbonyl)phenyl)quinazolin-2-ylamine,
4-((3-bromo)-anilino)-6-(3-hydroxy-4-ethoxycarbonylphenyl)quinazolin-2-ylamine,
4-((3-bromo)-anilino)-6-(4-hydroxy-3-ethoxyphenyl)quinazolin-2-ylamine,
4-((3-bromo)-anilino)-6-(4-(hydroxymethyl)phenyl)quinazolin-2-ylamine,
4-((3-bromo)-anilino)-6-(3-(hydroxymethyl)phenyl)quinazolin-2-ylamine,
4-((3-bromo)-anilino)-6-(4-hydroxy-3-nitrophenyl)quinazolin-2-ylamine,
4-((3-bromo)-anilino)-6-(4-isopropoxyphenyl)quinazolin-2-ylamine,
4-((3-bromo)-anilino)-6-(4-(4-isopropylpiperazinyl)phenyl)quinazolin-2-ylamine,
4-((3-bromo)-anilino)-6-(4-isopropylphenyl)quinazolin-2-ylamine,
4-((3-bromo)-anilino)-6-(4-methanesulfonamidophenyl)quinazolin-2-ylamine,
4-((3-bromo)-anilino)-6-(3-methanesulfonamidophenyl)quinazolin-2-ylamine,
4-((3-bromo)-anilino)-6-(2-methanesulfonamido phenyl)quinazolin-2-ylamine,
4-((3-bromo)-anilino)-6-(4-ethoxycarbonylphenyl)quinazolin-2-ylamine,
4-((3-bromo)-anilino)-6-(3-ethoxycarbonylphenyl)quinazolin-2-ylamine,
4-((3-bromo)-anilino)-6-(2-ethoxycarbonylphenyl)quinazolin-2-ylamine,
4-((3-bromo)-anilino)-6-(3-ethoxy-4-ethoxycarbonylphenyl)quinazolin-2-ylamine,
4-((3-bromo)-anilino)-6-(2-ethoxy-5-methylphenyl)quinazolin-2-ylamine,
4-((3-bromo)-anilino)-6-(4-ethoxy-3-nitrophenyl)quinazolin-2-ylamine,
4-((3-bromo)-anilino)-6-(4-ethoxyphenyl)quinazolin-2-ylamine,
4-((3-bromo)-anilino)-6-(3-ethoxyphenyl)quinazolin-2-ylamine,
4-((3-bromo)-anilino)-6-(4-N-methylcarboxamidophenyl)quinazolin-2-ylamine,
4-((3-bromo)-anilino)-6-(4-(N-methylamino)phenyl)quinazolin-2-ylamine,
4-((3-bromo)-anilino)-6-(3-(4-methylpiperazine-1-carbonyl)phenyl)quinazolin-2-ylamine,
4-((3-bromo)-anilino)-6-(4-(4-methylpiperazine-1-carbonyl)phenyl)quinazolin-2-ylamine,
4-((3-bromo)-anilino)-6-(4-(methylthio)phenyl)quinazolin-2-ylamine,
4-((3-bromo)-anilino)-6-(3-(methylthio)phenyl)quinazolin-2-ylamine,
4-((3-bromo)-anilino)-6-(2-(methylthio)phenyl)quinazolin-2-ylamine,
4-((3-bromo)-anilino)-6-(4-(morpholinocarbonyl)phenyl)quinazolin-2-ylamine,
4-((3-bromo)-anilino)-6-(4-morpholinophenyl)quinazolin-2-ylamine,
4-((3-bromo)-anilino)-6-(2-(morpholinomethyl)phenyl)quinazolin-2-ylamine,
4-((3-bromo)-anilino)-6-(4-nitrophenyl)quinazolin-2-ylamine,
4-((3-bromo)-anilino)-6-(3-nitrophenyl)quinazolin-2-ylamine,
4-((3-bromo)-anilino)-6-(2-nitrophenyl)quinazolin-2-ylamine,
4-((3-bromo)-anilino)-6-(4-phenoxyphenyl)quinazolin-2-ylamine,
4-((3-bromo)-anilino)-6-(4-(N-phenylaminomethy))phenyl)quinazolin-2-ylamine,
4-((3-bromo)-anilino)-6-(4-(phenylcarbonyl)phenyl)quinazolin-2-ylamine,
4-((3-bromo)-anilino)-6-(4-(piperazine-1-carbonyl)phenyl)quinazolin-2-ylamine,
4-((3-bromo)-anilino)-6-(4-piperazinylphenyl)quinazolin-2-ylamine,
4-((3-bromo)-anilino)-6-(4-succinamidophenyl)quinazolin-2-ylamine,
4-((3-bromo)-anilino)-6-(3-succinamidophenyl)quinazolin-2-ylamine,
4-((3-bromo)-anilino)-6-(sulfamoylphenyl)quinazolin-2-ylamine,
4-((3-bromo)-anilino)-6-(2-(toluene-4-sulfonamido)phenyl)quinazolin-2-ylamine,
4-((3-bromo)-anilino)-6-(4-(toluene-4-sulfonamido)phenyl)quinazolin-2-ylamine,
4-((3-bromo)-anilino)-6-(4-(tert-butoxycarbonylamino)-3-ethoxyphenyl)quinazolin-2-ylamine,
4-((3-bromo)-anilino)-6-(2-(tert-butoxycarbonyl)phenyl)quinazolin-2-ylamine,
4-((3-bromo)-anilino)-6-(3-(tert-butoxycarbonyl)phenyl)quinazolin-2-ylamine,
4-((3-bromo)-anilino)-6-(4-(tert-butoxycarbonyl)phenyl)quinazolin-2-ylamine,
4-((3-bromo)-anilino)-6-(2,3,4-trifluorophenyl)quinazolin-2-ylamine,
4-((3-bromo)-anilino)-6-(4-tert-butylphenyl)quinazolin-2-ylamine,
4-((3-bromo)-anilino)-6-(4-(tetrahydro-2H-pyran-2-yloxy)phenyl)quinazolin-2-ylamine, 4-((3-bromo)-anilino)-6-(4-(2-thienyl)phenyl)quinazolin-2-ylamine,
4-((3-bromo)-anilino)-6-(2,4,6-trimethylphenyl)quinazolin-2-ylamine,
4-((3-bromo)-anilino)-6-(3,4,5-trimethoxyphenyl)quinazolin-2-ylamine,
4-((3-bromo)-anilino)-6-(4-vinylphenyl)quinazolin-2-ylamine,
4-((3-bromo)-anilino)-6-(4-(2-hydroxyethoxyphenyl)quinazolin-2-ylamine,
4-((3-bromo)-anilino)-6-(6-benzyloxynaphth-2-yl)quinazolin-2-ylamine,
4-((3-bromo)-anilino)-6-(naphth-1-yl)quinazolin-2-ylamine,
4-((3-bromo)-anilino)-6-(naphth-2-yl)quinazolin-2-ylamine,
4-((3-bromo)-anilino)-6-(4'-benzoyl[1,1'-biphenyl]-4-yl)quinazolin-2-ylamine,
4-((3-bromo)-anilino)-6-(1-biphenylyl)quinazolin-2-ylamine,
4-((3-bromo)-anilino)-6-(oxoindan-5-yl)quinazolin-2-ylamine,
4-((3-bromo)-anilino)-6-(benzodioxolyl)quinazolin-2-ylamine,
4-((3-bromo)-anilino)-6-(2-acetamidopyridin-5-yl)quinazolin-2-ylamine,
4-((3-bromo)-anilino)-6-(2-aminopyridin-5-yl)quinazolin-2-ylamine,
4-((3-bromo)-anilino)-6-(2-aminopyrimidin-5-yl)quinazolin-2-ylamine,
4-((3-bromo)-anilino)-6-(1,4-benzodioxan-6-yl)quinazolin-2-ylamine,
4-((3-bromo)-anilino)-6-(1-benzothien-3-yl)quinazolin-2-ylamine,
4-((3-bromo)-anilino)-6-(2-benzyloxypyridin-5-yl)quinazolin-2-ylamine,
4-((3-bromo)-anilino)-6-(1-benzyl-1H-pyrazol-4-yl)quinazolin-2-ylamine,
4-((3-bromo)-anilino)-6-(2-bromo-3-chloropyridin-4-yl)quinazolin-2-ylamine,
4-((3-bromo)-anilino)-6-(5-bromo-2,3-dihydrobenzo[b]furan-7-yl)quinazolin-2-ylamine,
4-((3-bromo)-anilino)-6-(2-bromo-3-methylpyridin-5-yl)quinazolin-2-ylamine,
4-((3-bromo)-anilino)-6-(2-bromopyridin-5-yl)quinazolin-2-ylamine,
4-((3-bromo)-anilino)-6-(3-bromopyridin-5-yl)quinazolin-2-ylamine,
4-((3-bromo)-anilino)-6-(5-bromothien-2-yl)quinazolin-2-ylamine,
4-((3-bromo)-anilino)-6-(2-chloro-6-isopropylpyridin-3-yl)quinazolin-2-ylamine,
4-((3-bromo)-anilino)-6-(2-chloro-3-methylpyridin-5-yl)quinazolin-2-ylamine,
4-((3-bromo)-amino-6-(2-[4-(4-chlorophenylsulfonyl)piperazin-1-yl]pyridin-5-yl)quinazolin-2-ylamine,
4-((3-bromo)-anilino)-6-(2-chloropyrid-4-yl)quinazolin-2-ylamine,
4-((3-bromo)-anilino)-6-(2-chloropyrid-5-yl)quinazolin-2-ylamine,
4-((3-bromo)-anilino)-6-(dibenzo[b,d]furan-4-yl)quinazolin-2-ylamine,
4-((3-bromo)-anilino)-6-(2-chloro-3-fluoropyridin-4-yl)quinazolin-2-ylamine,
4-((3-bromo)-anilino)-6-(dibenzo[b,d]thien-4-yl)quinazolin-2-ylamine,
4-((3-bromo)-anilino)-6-(3,4-dihydro-2H-1,5-benzodioxepin-7-yl)quinazolin-2-ylamine,
4-((3-bromo)-anilino)-6-(3,6-dihydro-2H-pyridine-1-tertbutoxycarbonyl)quinazolin-2-ylamine,
4-((3-bromo)-anilino)-6-(2,5-dibromopyridin-3-yl)quinazolin-2-ylamine,
4-((3-bromo)-anilino)-6-(2,6-dichloropyridin-3-yl)quinazolin-2-ylamine,
4-((3-bromo)-anilino)-6-(2,3-dihydro-1-benzofuran-5-yl)quinazolin-2-ylamine,
4-((3-bromo)-anilino)-6-(2,6-diethoxypyridin-5-yl)quinazolin-2-ylamine,
4-((3-bromo)-anilino)-6-(2,6-diethoxypyridin-3-yl)quinazolin-2-ylamine,
4-((3-bromo)-anilino)-6-(2,4-diethoxypyrimidin-5-yl)quinazolin-2-ylamine,
4-((3-bromo)-anilino)-6-(3,5-dimethylisoxazol-4-yl)quinazolin-2-ylamine,
4-((3-bromo)-anilino)-6-(2-(3-N,N-dimethylaminopropoxy)pyridin-5-yl)quinazolin-2-ylamine,
4-((3-bromo)-anilino)-6-(3,5-dimethylpyrazol-4-yl)quinazolin-2-ylamine,
4-((3-bromo)-anilino)-6-(1-[1,3]dioxolan-2-ylmethyl-1H-pyrazol-4-yl)quinazolin-2-ylamine,
4-((3-bromo)-anilino)-6-(2,4-dioxo-1,2,3,4-tetrahydro-5-pyrimidinyl)quinazolin-2-ylamine,
4-((3-bromo)-anilino)-6-(2,4-di(tert-butoxy)pyrimidin-5-yl)quinazolin-2-ylamine,
4-((3-bromo)-anilino)-6-(2-ethoxypyridin-3-yl)quinazolin-2-ylamine,
4-((3-bromo)-anilino)-6-(2-fluoro-3-methylpyridin-5-yl)quinazolin-2-ylamine,
4-((3-bromo)-anilino)-6-(2-fluoropyridin-5-yl)quinazolin-2-ylamine,
4-((3-bromo)-anilino)-6-(5-formyl-2-furyl)quinazolin-2-ylamine,
4-((3-bromo)-anilino)-6-(5-formylthien-2-yl)quinazolin-2-ylamine,
4-((3-bromo)-anilino)-6-(furan-2-yl)quinazolin-2-ylamine,
4-((3-bromo)-anilino)-6-(2-hydroxypyridin-5-yl)quinazolin-2-ylamine,
4-((3-bromo)-anilino)-6-(1-isobutyl-1H-pyrazol-4-yl)quinazolin-2-ylamine,
4-((3-bromo)-anilino)-6-(isoquinolin-4-yl)quinazolin-2-ylamine,
4-((3-bromo)-anilino)-6-(2-ethoxypyridin-3-yl)quinazolin-2-ylamine,
4-((3-bromo)-anilino)-6-(2-ethoxypyrimidin-5-yl)quinazolin-2-ylamine,
4-((3-bromo)-anilino)-6-(5-methyl-1-benzothien-2-yl)quinazolin-2-ylamine,
4-((3-bromo)-anilino)-6-(1-(3-methylbutyl)-1H-pyrazol-4-yl)quinazolin-2-ylamine,
4-((3-bromo)-anilino)-6-(5-methylfuran-2-yl)quinazolin-2-ylamine,
4-((3-bromo)-anilino)-6-(1-methylindol-5-yl)quinazolin-2-ylamine,
4-((3-bromo)-anilino)-6-(5-methyl-3-phenyl-4-isoxazolyl)quinazolin-2-ylamine,
4-((3-bromo)-anilino)-6-(5-(methylthio)thien-2-yl)quinazolin-2-ylamine,
4-((3-bromo)-anilino)-6-(2-(4-methylpiperazinyl)pyridin-4-yl)quinazolin-2-ylamine,
4-((3-bromo)-anilino)-6-(2-(4-methylpiperazinyl)pyridin-5-yl)quinazolin-2-ylamine,
4-((3-bromo)-anilino)-6-(1-methyl-1H-pyrazol-4-yl)quinazolin-2-ylamine, 4-((3-bromo)-anilino)-6-(3-methylpyridin-2-yl)quinazolin-2-ylamine,
4-((3-bromo)-anilino)-6-(5-methylpyridin-2-yl)quinazolin-2-ylamine,
4-((3-bromo)-anilino)-6-(5-methylpyridin-3-yl)quinazolin-2-ylamine,
4-((3-bromo)-anilino)-6-(2-ethoxypyridin-5-yl)quinazolin-2-ylamine,
4-((3-bromo)-anilino)-6-(4-methylthien-2-yl)quinazolin-2-ylamine,
4-((3-bromo)-anilino)-6-(5-methylthien-2-yl)quinazolin-2-ylamine,
4-((3-bromo)-anilino)-6-(2-(2-morpholinoethylamino)-pyridin-5-yl)quinazolin-2-ylamine,
4-((3-bromo)-anilino)-6-(2-(2-morpholinoethyl)-1H-pyrazol-4-yl)quinazolin-2-ylamine,
4-((3-bromo)-anilino)-6-(2-(morpholin-1-yl)-pyridin-5-yl)quinazolin-2-ylamine,
4-((3-bromo)-anilino)-6-(1-(phenylsulfonyl)-1H-indol-3-yl)quinazolin-2-ylamine,
4-((3-bromo)-anilino)-6-(5-phenyl-2-thienyl)quinazolin-2-ylamine,
4-((3-bromo)-anilino)-6-(2-(piperazin-1-yl)-pyridin-5-yl)quinazolin-2-ylamine,
4-((3-bromo)-anilino)-6-(2-(piperazin-1-yl)-pyridin-4-yl)quinazolin-2-ylamine,
4-((3-bromo)-anilino)-6-(1-propyl-1H-pyrazol-4-yl)quinazolin-2-ylamine,
4-((3-bromo)-anilino)-6-(pyrazol-4-yl)quinazolin-2-ylamine,
4-((3-bromo)-anilino)-6-(pyridin-4-yl)quinazolin-2-ylamine,
4-((3-bromo)-anilino)-6-(4-phenoxathiinyl)quinazolin-2-ylamine,
4-((3-bromo)-anilino)-6-(quinolin-8-yl)quinazolin-2-ylamine,
4-((3-bromo)-anilino)-6-(quinolin-3-yl)quinazolin-2-ylamine,
4-((3-bromo)-anilino)-6-(2-(4-tert-butoxycarbonylpiperazinyl)-pyrid-4-yl)quinazolin-2-ylamine,
4-((3-bromo)-anilino)-6-(1-tert-butoxycarbonyl-1H-pyrazol-4-yl)quinazolin-2-ylamine,
4-((3-bromo)-anilino)-6-(1-tert-butoxycarbonyl-2-pyrrolyl)quinazolin-2-ylamine,
4-((3-bromo)-anilino)-6-(1-(tert-butoxycarbonyl)-5-bromo-1H-indol-2-yl)quinazolin-2-ylamine,
4-((3-bromo)-anilino)-6-(1-(tert-butoxycarbonyl)-1H-indol-5-yl)quinazolin-2-ylamine,
4-((3-bromo)-anilino)-6-(1-(tert-butoxycarbonyl)-5-methoxy-1H-indol-2-yl)quinazolin-2-ylamine,
4-((3-bromo)-anilino)-6-(1-thianthrenylthien-3-yl)quinazolin-2-ylamine, and
4-((3-bromo)-anilino)-6-(1,3,5-trimethyl-1H-pyrazol-4-yl)quinazolin-2-ylamine.

Examples 500 to 695

Synthesis of 2-amino-6-(4-fluorophenyl)-4-(N-cyclohexylamino)-quinazoline analogues The sequential experimental procedure of examples 6, 10, 13 and 24 is repeated, except that in the initial step 4-fluorophenylboronic acid is replaced with another aryl or heteroaryl boronic acid. In this way, the following quinazoline derivatives are obtained in similar yields:
4-(N-cyclohexylamino)-6-(4-(4'-allyloxycarbonylpiperazino)phenyl)quinazolin-2-ylamine,
4-(N-cyclohexylamino)-6-(3-aminocarbonylphenyl)quinazolin-2-ylamine,
4-(N-cyclohexylamino)-6-(4-aminocarbonylphenyl)quinazolin-2-ylamine,
4-(N-cyclohexylamino)-6-(2-amino-5-chlorophenyl)quinazolin-2-ylamine,
4-(N-cyclohexylamino)-6-(4-amino-3-ethoxyphenyl)quinazolin-2-ylamine,
4-(N-cyclohexylamino)-6-(2-amino-4-methylphenyl)quinazolin-2-ylamine,
4-(N-cyclohexylamino)-6-(2-amino-5-methylphenyl)quinazolin-2-ylamine,
4-(N-cyclohexylamino)-6-(4-amino-2-methyl phenyl)quinazolin-2-ylamine,
4-(N-cyclohexylamino)-6-(5-amino-2-methyl phenyl)quinazolin-2-ylamine,
4-(N-cyclohexylamino)-6-(4-amino-3-nitrophenyl)quinazolin-2-ylamine,
4-(N-cyclohexylamino)-6-(2-benzyloxyphenyl)quinazolin-2-ylamine,
4-(N-cyclohexylamino)-6-(3-benzyloxy-4-ethoxyphenyl)quinazolin-2-ylamine,
4-(N-cyclohexylamino)-6-(4-biphenyl)quinazolin-2-ylamine,
4-(N-cyclohexylamino)-6-(4-n-butyl phenyl)quinazolin-2-ylamine,
4-(N-cyclohexylamino)-6-(4-isobutylphenyl)quinazolin-2-ylamine,
4-(N-cyclohexylamino)-6-(4-carboxy-3-fluorophenyl)quinazolin-2-ylamine,
4-(N-cyclohexylamino)-6-(3-(3-carboxypropionylamino)phenyl)quinazolin-2-ylamine,
4-(N-cyclohexylamino)-6-(4-(3-carboxypropionylamino)phenyl)quinazolin-2-ylamine,
4-(N-cyclohexylamino)-6-(3-chloro-4-hydroxy-5-ethoxyphenyl)quinazolin-2-ylamine,
4-(N-cyclohexylamino)-6-(2-chloro-5-hydroxymethylphenyl)quinazolin-2-ylamine,
4-(N-cyclohexylamino)-6-(4-cyanoethoxyphenyl)quinazolin-2-ylamine,
4-(N-cyclohexylamino)-6-(3-cyanoethoxyphenyl)quinazolin-2-ylamine,
4-(N-cyclohexylamino)-6-(2-cyanoethoxyphenyl)quinazolin-2-ylamine,
4-(N-cyclohexylamino)-6-(4-cyanophenyl)quinazolin-2-ylamine,
4-(N-cyclohexylamino)-6-(3-cyanophenyl)quinazolin-2-ylamine,
4-(N-cyclohexylamino)-6-(2-cyanophenyl)quinazolin-2-ylamine,
4-(N-cyclohexylamino)-6-(3-(N-cyclopropylaminocarbonyl)phenyl)quinazolin-2-ylamine,
4-(N-cyclohexylamino)-6-(3-(N,N-diethylaminocarbonyl)phenyl)quinazolin-2-ylamine,
4-(N-cyclohexylamino)-6-(3-(N,N-dimethylamino)phenyl)quinazolin-2-ylamine,
4-(N-cyclohexylamino)-6-(2-(N,N-dimethylamino)phenyl)quinazolin-2-ylamine,
4-(N-cyclohexylamino)-6-(3-(N,N-dimethylaminocarbonyl)phenyl)quinazolin-2-ylamine,
4-(N-cyclohexylamino)-6-(3-[(N',N'-dimethylamino)ethylaminocarbonyl]phenyl)-quinazolin-2-ylamine,
4-(N-cyclohexylamino)-6-(4-[(N',N'-dimethylamino)ethylaminocarbonyl]phenyl)-quinazolin-2-ylamine,
4-(N-cyclohexylamino)-6-(3-[1,3]dioxolan-2-ylethoxyphenyl)quinazolin-2-ylamine, 4-(N-cyclohexylamino)-6-(3-(ethoxycarbonyl)ethoxyphenyl)quinazolin-2-ylamine,
4-(N-cyclohexylamino)-6-(4-(ethoxycarbonyl)ethoxyphenyl)quinazolin-2-ylamine,
4-(N-cyclohexylamino)-6-(4-ethoxycarbonylphenyl)quinazolin-2-ylamine,
4-(N-cyclohexylamino)-6-(3-ethoxycarbonylphenyl)quinazolin-2-ylamine,
4-(N-cyclohexylamino)-6-(2-ethoxycarbonylphenyl)quinazolin-2-ylamine,
4-(N-cyclohexylamino)-6-(4-(3-ethoxycarbonylpiperidino)carboxamidophenyl)quinazolin-2-ylamine,
4-(N-cyclohexylamino)-6-(4-formylaminophenyl)quinazolin-2-ylamine,
4-(N-cyclohexylamino)-6-(3-formylaminophenyl)quinazolin-2-ylamine,
4-(N-cyclohexylamino)-6-(2-formylaminophenyl)quinazolin-2-ylamine,
4-(N-cyclohexylamino)-6-(2-formyl-5-ethoxyphenyl)quinazolin-2-ylamine,
4-(N-cyclohexylamino)-6-(3-formyl-4-ethoxyphenyl)quinazolin-2-ylamine,
4-(N-cyclohexylamino)-6-(5-formyl-2-ethoxyphenyl)quinazolin-2-ylamine,
4-(N-cyclohexylamino)-6-(2-formyl-5-methylphenyl)quinazolin-2-ylamine,
4-(N-cyclohexylamino)-6-(4-formylphenyl)quinazolin-2-ylamine,
4-(N-cyclohexylamino)-6-(3-formylphenyl)quinazolin-2-ylamine,
4-(N-cyclohexylamino)-6-(2-formylphenyl)quinazolin-2-ylamine,
4-(N-cyclohexylamino)-6-(4-hydroxy-3,5-dimethylphenyl)quinazolin-2-ylamine,
4-(N-cyclohexylamino)-6-(3-(2-hydroxyethyl)-aminocarbonylphenyl)quinazolin-2-ylamine,
4-(N-cyclohexylamino)-6-(4-(2-hydroxyethyl)aminocarbonyl)phenyl)quinazolin-2-ylamine,
4-(N-cyclohexylamino)-6-(3-hydroxy-4-ethoxycarbonylphenyl)quinazolin-2-ylamine,
4-(N-cyclohexylamino)-6-(4-hydroxy-3-ethoxyphenyl)quinazolin-2-ylamine,
4-(N-cyclohexylamino)-6-(4-(hydroxymethyl)phenyl)quinazolin-2-ylamine,
4-(N-cyclohexylamino)-6-(3-(hydroxymethyl)phenyl)quinazolin-2-ylamine,
4-(N-cyclohexylamino)-6-(4-hydroxy-3-nitrophenyl)quinazolin-2-ylamine,
4-(N-cyclohexylamino)-6-(4-isopropoxyphenyl)quinazolin-2-ylamine,
4-(N-cyclohexylamino)-6-(4-(4-isopropylpiperazinyl)phenyl)quinazolin-2-ylamine,
4-(N-cyclohexylamino)-6-(4-isopropylphenyl)quinazolin-2-ylamine,
4-(N-cyclohexylamino)-6-(4-methanesulfonamidophenyl)quinazolin-2-ylamine,
4-(N-cyclohexylamino)-6-(3-methanesulfonamidophenyl)quinazolin-2-ylamine,
4-(N-cyclohexylamino)-6-(2-methanesulfonamido phenyl)quinazolin-2-ylamine,
4-(N-cyclohexylamino)-6-(4-ethoxycarbonylphenyl)quinazolin-2-ylamine,
4-(N-cyclohexylamino)-6-(3-ethoxycarbonylphenyl)quinazolin-2-ylamine,
4-(N-cyclohexylamino)-6-(2-ethoxycarbonylphenyl)quinazolin-2-ylamine,
4-(N-cyclohexylamino)-6-(3-ethoxy-4-ethoxycarbonylphenyl)quinazolin-2-ylamine,
4-(N-cyclohexylamino)-6-(2-ethoxy-5-methylphenyl)quinazolin-2-ylamine,
4-(N-cyclohexylamino)-6-(4-ethoxy-3-nitrophenyl)quinazolin-2-ylamine,
4-(N-cyclohexylamino)-6-(4-ethoxyphenyl)quinazolin-2-ylamine,
4-(N-cyclohexylamino)-6-(3-ethoxyphenyl)quinazolin-2-ylamine,
4-(N-cyclohexylamino)-6-(4-N-methylcarboxamidophenyl)quinazolin-2-ylamine,
4-(N-cyclohexylamino)-6-(4-(N-methylamino)phenyl)quinazolin-2-ylamine,
4-(N-cyclohexylamino)-6-(3-(4-methylpiperazine-1-carbonyl)phenyl)quinazolin-2-ylamine,
4-(N-cyclohexylamino)-6-(4-(4-methylpiperazine-1-carbonyl)phenyl)quinazolin-2-ylamine,
4-(N-cyclohexylamino)-6-(4-(methylthio)phenyl)quinazolin-2-ylamine,
4-(N-cyclohexylamino)-6-(3-(methylthio)phenyl)quinazolin-2-ylamine,
4-(N-cyclohexylamino)-6-(2-(methylthio)phenyl)quinazolin-2-ylamine,
4-(N-cyclohexylamino)-6-(4-(morpholinocarbonyl)phenyl)quinazolin-2-ylamine,
4-(N-cyclohexylamino)-6-(4-morpholinophenyl)quinazolin-2-ylamine,
4-(N-cyclohexylamino)-6-(2-(morpholinomethyl)phenyl)quinazolin-2-ylamine,
4-(N-cyclohexylamino)-6-(4-nitrophenyl)quinazolin-2-ylamine,
4-(N-cyclohexylamino)-6-(3-nitrophenyl)quinazolin-2-ylamine,
4-(N-cyclohexylamino)-6-(2-nitrophenyl)quinazolin-2-ylamine,
4-(N-cyclohexylamino)-6-(4-phenoxyphenyl)quinazolin-2-ylamine,
4-(N-cyclohexylamino)-6-(4-(N-phenylaminomethyl)phenyl)quinazolin-2-ylamine,
4-(N-cyclohexylamino)-6-(4-(phenylcarbonyl)phenyl)quinazolin-2-ylamine,
4-(N-cyclohexylamino)-6-(4-(piperazine-1-carbonyl)phenyl)quinazolin-2-ylamine,
4-(N-cyclohexylamino)-6-(4-piperazinylphenyl)quinazolin-2-ylamine,
4-(N-cyclohexylamino)-6-(4-succinamidophenyl)quinazolin-2-ylamine,
4-(N-cyclohexylamino)-6-(3-succinamidophenyl)quinazolin-2-ylamine,
4-(N-cyclohexylamino)-6-(sulfamoylphenyl)quinazolin-2-ylamine,
4-(N-cyclohexylamino)-6-(2-(toluene-4-sulfonamido)phenyl)quinazolin-2-ylamine,
4-(N-cyclohexylamino)-6-(4-(toluene-4-sulfonamido)phenyl)quinazolin-2-ylamine,
4-(N-cyclohexylamino)-6-(4-(tert-butoxycarbonylamino)-3-ethoxyphenyl)quinazolin-2-ylamine,
4-(N-cyclohexylamino)-6-(2-(tert-butoxycarbonyl)phenyl)quinazolin-2-ylamine,
4-(N-cyclohexylamino)-6-(3-(tert-butoxycarbonyl)phenyl)quinazolin-2-ylamine,
4-(N-cyclohexylamino)-6-(4-(tert-butoxycarbonyl)phenyl)quinazolin-2-ylamine,
4-(N-cyclohexylamino)-6-(2,3,4-trifluorophenyl)quinazolin-2-ylamine, 4-(N-cyclohexylamino)-6-(4-tert-butylphenyl)quinazolin-2-ylamine,
4-(N-cyclohexylamino)-6-(4-(tetrahydro-2H-pyran-2-yloxy)phenyl)quinazolin-2-ylamine,
4-(N-cyclohexylamino)-6-(4-(2-thienyl)phenyl)quinazolin-2-ylamine,
4-(N-cyclohexylamino)-6-(2,4,6-trimethylphenyl)quinazolin-2-ylamine,
4-(N-cyclohexylamino)-6-(3,4,5-trimethoxyphenyl) quinazolin-2-ylamine,
4-(N-cyclohexylamino)-6-(4-vinylphenyl)quinazolin-2-ylamine,
4-(N-cyclohexylamino)-6-(4-(2-hydroxyethoxyphenyl) quinazolin-2-ylamine,
4-(N-cyclohexylamino)-6-(6-benzyloxynaphth-2-yl) quinazolin-2-ylamine,
4-(N-cyclohexylamino)-6-(naphth-1-yl)quinazolin-2-ylamine,
4-(N-cyclohexylamino)-6-(naphth-2-yl)quinazolin-2-ylamine,
4-(N-cyclohexylamino)-6-(4'-benzoyl[1,1'-biphenyl]-4-yl) quinazolin-2-ylamine,
4-(N-cyclohexylamino)-6-(1-biphenylyl)quinazolin-2-ylamine,
4-(N-cyclohexylamino)-6-(oxoindan-5-yl)quinazolin-2-ylamine,
4-(N-cyclohexylamino)-6-(benzodioxolyl)quinazolin-2-ylamine,
4-(N-cyclohexylamino)-6-(2-acetamidopyridin-5-yl) quinazolin-2-ylamine,
4-(N-cyclohexylamino)-6-(2-aminopyridin-5-yl)quinazolin-2-ylamine,
4-(N-cyclohexylamino)-6-(2-aminopyrimidin-5-yl)quinazolin-2-ylamine,
4-(N-cyclohexylamino)-6-(1,4-benzodioxan-6-yl)quinazolin-2-ylamine,
4'-(N-cyclohexylamino)-6-(1-benzothien-3-yl)quinazolin-2-ylamine,
4-(N-cyclohexylamino)-6-(2-benzyloxypyridin-5-yl) quinazolin-2-ylamine,
4-(N-cyclohexylamino)-6-(1-benzyl-1H-pyrazol-4-yl) quinazolin-2-ylamine,
4-(N-cyclohexylamino)-6-(2-bromo-3-chloropyridin-4-yl) quinazolin-2-ylamine,
4-(N-cyclohexylamino)-6-(5-bromo-2,3-dihydrobenzo[b]furan-7-yl)quinazolin-2-ylamine,
4-(N-cyclohexylamino)-6-(2-bromo-3-methylpyridin-5-yl) quinazolin-2-ylamine,
4-(N-cyclohexylamino)-6-(2-bromopyridin-5-yl)quinazolin-2-ylamine,
4-(N-cyclohexylamino)-6-(3-bromopyridin-5-yl)quinazolin-2-ylamine,
4-(N-cyclohexylamino)-6-(5-bromothien-2-yl)quinazolin-2-ylamine,
4-(N-cyclohexylamino)-6-(2-chloro-6-isopropylpyridin-3-yl)quinazolin-2-ylamine,
4-(N-cyclohexylamino)-6-(2-chloro-3-methylpyridin-5-yl) quinazolin-2-ylamine,
4-(N-cyclohexylamino)-6-(2-[4-(4-chlorophenylsulfonyl) piperazin-1-yl]pyridin-5-yl)quinazolin-2-ylamine,
4-(N-cyclohexylamino)-6-(2-chloropyrid-4-yl)quinazolin-2-ylamine,
4-(N-cyclohexylamino)-6-(2-chloropyrid-5-yl)quinazolin-2-ylamine,
4-(N-cyclohexylamino)-6-(dibenzo[b,d]furan-4-yl)quinazolin-2-ylamine,
4-(N-cyclohexylamino)-6-(2-chloro-3-fluoropyridin-4-yl) quinazolin-2-ylamine,
4-(N-cyclohexylamino)-6-(dibenzo[b,d]thien-4-yl)quinazolin-2-ylamine,
4-(N-cyclohexylamino)-6-(3,4-dihydro-2H-1,5-benzodioxepin-7-yl)quinazolin-2-ylamine,
4-(N-cyclohexylamino)-6-(3,6-dihydro-2H-pyridine-1-tert-butoxycarbonyl)quinazolin-2-ylamine,
4-(N-cyclohexylamino)-6-(2,5-dibromopyridin-3-yl) quinazolin-2-ylamine,
4-(N-cyclohexylamino)-6-(2,6-dichloropyridin-3-yl) quinazolin-2-ylamine,
4-(N-cyclohexylamino)-6-(2,3-dihydro-1-benzofuran-5-yl) quinazolin-2-ylamine,
4-(N-cyclohexylamino)-6-(2,6-diethoxypyridin-5-yl) quinazolin-2-ylamine,
4-(N-cyclohexylamino)-6-(2,6-diethoxypyridin-3-yl) quinazolin-2-ylamine,
4-(N-cyclohexylamino)-6-(2,4-diethoxypyrimidin-5-yl) quinazolin-2-ylamine,
4-(N-cyclohexylamino)-6-(3,5-dimethylisoxazol-4-yl) quinazolin-2-ylamine,
4-(N-cyclohexylamino)-6-(2-(3-N,N-dimethylaminopropoxy)pyridin-5-yl)quinazolin-2-ylamine,
4-(N-cyclohexylamino)-6-(3,5-dimethylpyrazol-4-yl) quinazolin-2-ylamine,
4-(N-cyclohexylamino)-6-(1-[1,3]dioxolan-2-ylmethyl-1H-pyrazol-4-yl)quinazolin-2-ylamine,
4-(N-cyclohexylamino)-6-(2,4-dioxo-1,2,3,4-tetrahydro-5-pyrimidinyl)quinazolin-2-ylamine,
4-(N-cyclohexylamino)-6-(2,4-di(tert-butoxy)pyrimidin-5-yl)quinazolin-2-ylamine,
4-(N-cyclohexylamino)-6-(2-ethoxypyridin-3-yl)quinazolin-2-ylamine,
4-(N-cyclohexylamino)-6-(2-fluoro-3-methylpyridin-5-yl) quinazolin-2-ylamine,
4-(N-cyclohexylamino)-6-(2-fluoropyridin-5-yl)quinazolin-2-ylamine,
4-(N-cyclohexylamino)-6-(5-formyl-2-furyl)quinazolin-2-ylamine,
4-(N-cyclohexylamino)-6-(5-formylthien-2-yl)quinazolin-2-ylamine,
4-(N-cyclohexylamino)-6-(furan-2-yl)quinazolin-2-ylamine,
4-(N-cyclohexylamino)-6-(2-hydroxypyridin-5-yl)quinazolin-2-ylamine,
4-(N-cyclohexylamino)-6-(1-isobutyl-1H-pyrazol-4-yl) quinazolin-2-ylamine,
4-(N-cyclohexylamino)-6-(isoquinolin-4-yl)quinazolin-2-ylamine,
4-(N-cyclohexylamino)-6-(2-ethoxypyridin-3-yl)quinazolin-2-ylamine,
4-(N-cyclohexylamino)-6-(2-ethoxypyrimidin-5-yl) quinazolin-2-ylamine,
4-(N-cyclohexylamino)-6-(5-methyl-1-benzothien-2-yl) quinazolin-2-ylamine,
4-(N-cyclohexylamino)-6-(1-(3-methylbutyl)-1H-pyrazol-4-yl)quinazolin-2-ylamine,
4-(N-cyclohexylamino)-6-(5-methylfuran-2-yl)quinazolin-2-ylamine,
4-(N-cyclohexylamino)-6-(1-methylindol-5-yl)quinazolin-2-ylamine,
4-(N-cyclohexylamino)-6-(5-methyl-3-phenyl-4-isoxazolyl) quinazolin-2-ylamine,
4-(N-cyclohexylamino)-6-(5-(methylthio)thien-2-yl) quinazolin-2-ylamine, 4-(N-cyclohexylamino)-6-(2-(4-methylpiperazinyl)pyridin-4-yl)quinazolin-2-ylamine,
4-(N-cyclohexylamino)-6-(2-(4-methylpiperazinyl)pyridin-5-yl)quinazolin-2-ylamine,
4-(N-cyclohexylamino)-6-(1-methyl-1H-pyrazol-4-yl)quinazolin-2-ylamine,
4-(N-cyclohexylamino)-6-(3-methylpyridin-2-yl)quinazolin-2-ylamine,
4-(N-cyclohexylamino)-6-(5-methylpyridin-2-yl)quinazolin-2-ylamine,
4-(N-cyclohexylamino)-6-(5-methylpyridin-3-yl)quinazolin-2-ylamine,
4-(N-cyclohexylamino)-6-(2-ethoxypyridin-5-yl)quinazolin-2-ylamine,
4-(N-cyclohexylamino)-6-(4-methylthien-2-yl)quinazolin-2-ylamine,
4-(N-cyclohexylamino)-6-(5-methylthien-2-yl)quinazolin-2-ylamine,
4-(N-cyclohexylamino)-6-(2-(2-morpholinoethylamino)-pyridin-5-yl)quinazolin-2-ylamine,
4-(N-cyclohexylamino)-6-(2-(2-morpholinoethyl)-1H-pyrazol-4-yl)quinazolin-2-ylamine,
4-(N-cyclohexylamino)-6-(2-(morpholin-1-yl)-pyridin-5-yl)quinazolin-2-ylamine,
4-(N-cyclohexylamino)-6-(1-(phenylsulfonyl)-1H-indol-3-yl)quinazolin-2-ylamine,
4-(N-cyclohexylamino)-6-(5-phenyl-2-thienyl)quinazolin-2-ylamine,
4-(N-cyclohexylamino)-6-(2-(piperazin-1-yl)-pyridin-5-yl)quinazolin-2-ylamine,
4-(N-cyclohexylamino)-6-(2-(piperazin-1-yl)-pyridin-4-yl)quinazolin-2-ylamine,
4-(N-cyclohexylamino)-6-(1-propyl-1H-pyrazol-4-yl)quinazolin-2-ylamine,
4-(N-cyclohexylamino)-6-(pyrazol-4-yl)quinazolin-2-ylamine,
4-(N-cyclohexylamino)-6-(pyridin-4-yl)quinazolin-2-ylamine,
4-(N-cyclohexylamino)-6-(4-phenoxathiinyl)quinazolin-2-ylamine,
4-(N-cyclohexylamino)-6-(quinolin-8-yl)quinazolin-2-ylamine,
4-(N-cyclohexylamino)-6-(quinolin-3-yl)quinazolin-2-ylamine,
4-(N-cyclohexylamino)-6-(2-(4-tert-butoxycarbonylpiperazinyl)-pyrid-4-yl)quinazolin-2-ylamine,
4-(N-cyclohexylamino)-6-(1-tert-butoxycarbonyl-1H-pyrazol-4-yl)quinazolin-2-ylamine,
4-(N-cyclohexylamino)-6-(1-tert-butoxycarbonyl-2-pyrrolyl)quinazolin-2-ylamine,
4-(N-cyclohexylamino)-6-(1-(tert-butoxycarbonyl)-5-bromo-1H-indol-2-yl)quinazolin-2-ylamine,
4-(N-cyclohexylamino)-6-(1-(tert-butoxycarbonyl)-1H-indol-5-yl)quinazolin-2-ylamine,
4-(N-cyclohexylamino)-6-(1-(tert-butoxycarbonyl)-5-methoxy-1H-indol-2-yl)quinazolin-2-ylamine,
4-(N-cyclohexylamino)-6-(1-thianthrenylthien-3-yl)quinazolin-2-ylamine, and
4-(N-cyclohexylamino)-6-(1,3,5-trimethyl-1H-pyrazol-4-yl)quinazolin-2-ylamine.

Examples 700 to 895

Synthesis of 2-amino-6-(4-fluorophenyl)-4-(N-(4-methyl)piperazin-1-yl)-quinazoline analogues The sequential experimental procedure of examples 6, 10, 13 and 25 is repeated, except that in the initial step 4-fluorophenylboronic acid is replaced with another aryl or heteroaryl boronic acid. In this way, the following quinazoline derivatives are obtained in similar yields:

4-(N-(4-methyl)-piperazin-1-yl)-6-(4-(4'-allyloxycarbonylpiperazino)phenyl)quinazolin-2-ylamine,
4-(N-(4-methyl)-piperazin-1-yl)-6-(3-aminocarbonylphenyl)quinazolin-2-ylamine,
4-(N-(4-methyl)-piperazin-1-yl)-6-(4-aminocarbonylphenyl)quinazolin-2-ylamine,
4-(N-(4-methyl)-piperazin-1-yl)-6-(2-amino-5-chlorophenyl)quinazolin-2-ylamine,
4-(N-(4-methyl)-piperazin-1-yl)-6-(4-amino-3-ethoxyphenyl)quinazolin-2-ylamine,
4-(N-(4-methyl)-piperazin-1-yl)-6-(2-amino-4-methylphenyl)quinazolin-2-ylamine,
4-(N-(4-methyl)-piperazin-1-yl)-6-(2-amino-5-methylphenyl)quinazolin-2-ylamine,
4-(N-(4-methyl)-piperazin-1-yl)-6-(4-amino-2-methylphenyl)quinazolin-2-ylamine,
4-(N-(4-methyl)-piperazin-1-yl)-6-(5-amino-2-methylphenyl)quinazolin-2-ylamine,
4-(N-(4-methyl)-piperazin-1-yl)-6-(4-amino-3-nitrophenyl)quinazolin-2-ylamine,
4-(N-(4-methyl)-piperazin-1-yl)-6-(2-benzyloxyphenyl)quinazolin-2-ylamine,
4-(N-(4-methyl)-piperazin-1-yl)-6-(3-benzyloxy-4-ethoxyphenyl)quinazolin-2-ylamine,
4-(N-(4-methyl)-piperazin-1-yl)-6-(4-biphenyl)quinazolin-2-ylamine,
4-(N-(4-methyl)-piperazin-1-yl)-6-(4-n-butyl phenyl)quinazolin-2-ylamine,
4-(N-(4-methyl)-piperazin-1-yl)-6-(4-isobutylphenyl)quinazolin-2-ylamine,
4-(N-(4-methyl)-piperazin-1-yl)-6-(4-carboxy-3-fluorophenyl)quinazolin-2-ylamine,
4-(N-(4-methyl)-piperazin-1-yl)-6-(3-(3-carboxypropionylamino)phenyl)quinazolin-2-ylamine,
4-(N-(4-methyl)-piperazin-1-yl)-6-(4-(3-carboxypropionylamino)phenyl)quinazolin-2-ylamine,
4-(N-(4-methyl)-piperazin-1-yl)-6-(3-chloro-4-hydroxy-5-ethoxyphenyl)quinazolin-2-ylamine,
4-(N-(4-methyl)-piperazin-1-yl)-6-(2-chloro-5-hydroxymethylphenyl)quinazolin-2-ylamine,
4-(N-(4-methyl)-piperazin-1-yl)-6-(4-cyanoethoxyphenyl)quinazolin-2-ylamine,
4-(N-(4-methyl)-piperazin-1-yl)-6-(3-cyanoethoxyphenyl)quinazolin-2-ylamine,
4-(N-(4-methyl)-piperazin-1-yl)-6-(2-cyanoethoxyphenyl)quinazolin-2-ylamine,
4-(N-(4-methyl)-piperazin-1-yl)-6-(4-cyanophenyl)quinazolin-2-ylamine,
4-(N-(4-methyl)-piperazin-1-yl)-6-(3-cyanophenyl)quinazolin-2-ylamine,
4-(N-(4-methyl)-piperazin-1-yl)-6-(2-cyanophenyl)quinazolin-2-ylamine,
4-(N-(4-methyl)-piperazin-1-yl)-6-(3-(N-cyclopropylaminocarbonyl)phenyl)quinazolin-2-ylamine,
4-(N-(4-methyl)-piperazin-1-yl)-6-(3-(N,N-diethylaminocarbonyl)phenyl)quinazolin-2-ylamine,
4-(N-(4-methyl)-piperazin-1-yl)-6-(3-(N,N-dimethylamino)phenyl)quinazolin-2-ylamine,
4-(N-(4-methyl)-piperazin-1-yl)-6-(2-(N,N-dimethylamino)phenyl)quinazolin-2-ylamine,
4-(N-(4-methyl)-piperazin-1-yl)-6-(3-(N,N-dimethylaminocarbonyl)phenyl)quinazolin-2-ylamine, 4-(N-(4-methyl)-piperazin-1-yl)-6-(3-[(N',N'-dimethylamino)ethylaminocarbonyl]phenyl)-quinazolin-2-ylamine,
4-(N-(4-methyl)-piperazin-1-yl)-6-(4-[(N',N'-dimethylamino)ethylaminocarbonyl]phenyl)-quinazolin-2-ylamine,
4-(N-(4-methyl)-piperazin-1-yl)-6-(3-[1,3]dioxolan-2-ylethoxyphenyl)quinazolin-2-ylamine,
4-(N-(4-methyl)-piperazin-1-yl)-6-(3-(ethoxycarbonyl)ethoxyphenyl)quinazolin-2-ylamine,
4-(N-(4-methyl)-piperazin-1-yl)-6-(4-(ethoxycarbonyl)ethoxyphenyl)quinazolin-2-ylamine,
4-(N-(4-methyl)-piperazin-1-yl)-6-(4-ethoxycarbonylphenyl)quinazolin-2-ylamine,
4-(N-(4-methyl)-piperazin-1-yl)-6-(3-ethoxycarbonylphenyl)quinazolin-2-ylamine,
4-(N-(4-methyl)-piperazin-1-yl)-6-(2-ethoxycarbonylphenyl)quinazolin-2-ylamine,
4-(N-(4-methyl)-piperazin-1-yl)-6-(4-(3-ethoxycarbonylpiperidino)carboxamidophenyl)-quinazolin-2-ylamine,
4-(N-(4-methyl)-piperazin-1-yl)-6-(4-formylaminophenyl)quinazolin-2-ylamine,
4-(N-(4-methyl)-piperazin-1-yl)-6-(3-formylaminophenyl)quinazolin-2-ylamine,
4-(N-(4-methyl)-piperazin-1-yl)-6-(2-formylaminophenyl)quinazolin-2-ylamine,
4-(N-(4-methyl)-piperazin-1-yl)-6-(2-formyl-5-ethoxyphenyl)quinazolin-2-ylamine,
4-(N-(4-methyl)-piperazin-1-yl)-6-(3-formyl-4-ethoxyphenyl)quinazolin-2-ylamine,
4-(N-(4-methyl)-piperazin-1-yl)-6-(5-formyl-2-ethoxyphenyl)quinazolin-2-ylamine,
4-(N-(4-methyl)-piperazin-1-yl)-6-(2-formyl-5-methylphenyl)quinazolin-2-ylamine,
4-(N-(4-methyl)-piperazin-1-yl)-6-(4-formylphenyl)quinazolin-2-ylamine,
4-(N-(4-methyl)-piperazin-1-yl)-6-(3-formylphenyl)quinazolin-2-ylamine,
4-(N-(4-methyl)-piperazin-1-yl)-6-(2-formylphenyl)quinazolin-2-ylamine,
4-(N-(4-methyl)-piperazin-1-yl)-6-(4-hydroxy-3,5-dimethylphenyl)quinazolin-2-ylamine,
4-(N-(4-methyl)-piperazin-1-yl)-6-(3-(2-hydroxyethyl)aminocarbonylphenyl)quinazolin-2-ylamine,
4-(N-(4-methyl)-piperazin-1-yl)-6-(4-(2-hydroxyethyl)aminocarbonyl)phenyl)quinazolin-2-ylamine,
4-(N-(4-methyl)-piperazin-1-yl)-6-(3-hydroxy-4-ethoxycarbonylphenyl)quinazolin-2-ylamine,
4-(N-(4-methyl)-piperazin-1-yl)-6-(4-hydroxy-3-ethoxyphenyl)quinazolin-2-ylamine,
4-(N-(4-methyl)-piperazin-1-yl)-6-(4-(hydroxymethyl)phenyl)quinazolin-2-ylamine,
4-(N-(4-methyl)-piperazin-1-yl)-6-(3-(hydroxymethyl)phenyl)quinazolin-2-ylamine,
4-(N-(4-methyl)-piperazin-1-yl)-6-(4-hydroxy-3-nitrophenyl)quinazolin-2-ylamine,
4-(N-(4-methyl)-piperazin-1-yl)-6-(4-isopropoxyphenyl)quinazolin-2-ylamine,
4-(N-(4-methyl)-piperazin-1-yl)-6-(4-(4-isopropylpiperazinyl)phenyl)quinazolin-2-ylamine,
4-(N-(4-methyl)-piperazin-1-yl)-6-(4-isopropylphenyl)quinazolin-2-ylamine,
4-(N-(4-methyl)-piperazin-1-yl)-6-(4-methanesulfonamidophenyl)quinazolin-2-ylamine,
4-(N-(4-methyl)-piperazin-1-yl)-6-(3-methanesulfonamidophenyl)quinazolin-2-ylamine,
4-(N-(4-methyl)-piperazin-1-yl)-6-(2-methanesulfonamidophenyl)quinazolin-2-ylamine,
4-(N-(4-methyl)-piperazin-1-yl)-6-(4-ethoxycarbonylphenyl)quinazolin-2-ylamine,
4-(N-(4-methyl)-piperazin-1-yl)-6-(3-ethoxycarbonylphenyl)quinazolin-2-ylamine,
4-(N-(4-methyl)-piperazin-1-yl)-6-(2-ethoxycarbonylphenyl)quinazolin-2-ylamine,
4-(N-(4-methyl)-piperazin-1-yl)-6-(3-ethoxy-4-ethoxycarbonylphenyl)quinazolin-2-ylamine,
4-(N-(4-methyl)-piperazin-1-yl)-6-(2-ethoxy-5-methylphenyl)quinazolin-2-ylamine,
4-(N-(4-methyl)-piperazin-1-yl)-6-(4-ethoxy-3-nitrophenyl)quinazolin-2-ylamine,
4-(N-(4-methyl)-piperazin-1-yl)-6-(4-ethoxyphenyl)quinazolin-2-ylamine,
4-(N-(4-methyl)-piperazin-1-yl)-6-(3-ethoxyphenyl)quinazolin-2-ylamine,
4-(N-(4-methyl)-piperazin-1-yl)-6-(4-N-methylcarboxamidophenyl)quinazolin-2-ylamine,
4-(N-(4-methyl)-piperazin-1-yl)-6-(4-(N-methylamino)phenyl)quinazolin-2-ylamine,
4-(N-(4-methyl)-piperazin-1-yl)-6-(3-(4-methylpiperazine-1-carbonyl)phenyl)quinazolin-2-ylamine,
4-(N-(4-methyl)-piperazin-1-yl)-6-(4-(4-methylpiperazine-1-carbonyl)phenyl)quinazolin-2-ylamine,
4-(N-(4-methyl)-piperazin-1-yl)-6-(4-(methylthio)phenyl)quinazolin-2-ylamine,
4-(N-(4-methyl)-piperazin-1-yl)-6-(3-(methylthio)phenyl)quinazolin-2-ylamine,
4-(N-(4-methyl)-piperazin-1-yl)-6-(2-(methylthio)phenyl)quinazolin-2-ylamine,
4-(N-(4-methyl)-piperazin-1-yl)-6-(4-(morpholinocarbonyl)phenyl)quinazolin-2-ylamine,
4-(N-(4-methyl)-piperazin-1-yl)-6-(4-morpholinophenyl)quinazolin-2-ylamine,
4-(N-(4-methyl)-piperazin-1-yl)-6-(2-(morpholinomethyl)phenyl)quinazolin-2-ylamine,
4-(N-(4-methyl)-piperazin-1-yl)-6-(4-nitrophenyl)quinazolin-2-ylamine,
4-(N-(4-methyl)-piperazin-1-yl)-6-(3-nitrophenyl)quinazolin-2-ylamine,
4-(N-(4-methyl)-piperazin-1-yl)-6-(2-nitrophenyl)quinazolin-2-ylamine,
4-(N-(4-methyl)-piperazin-1-yl)-6-(4-phenoxyphenyl)quinazolin-2-ylamine,
4-(N-(4-methyl)-piperazin-1-yl)-6-(4-(N-phenylaminomethyl)phenyl)quinazolin-2-ylamine,
4-(N-(4-methyl)-piperazin-1-yl)-6-(4-(phenylcarbonyl)phenyl)quinazolin-2-ylamine,
4-(N-(4-methyl)-piperazin-1-yl)-6-(4-(piperazine-1-carbonyl)phenyl)quinazolin-2-ylamine,
4-(N-(4-methyl)-piperazin-1-yl)-6-(4-piperazinylphenyl)quinazolin-2-ylamine,
4-(N-(4-methyl)-piperazin-1-yl)-6-(4-succinamidophenyl)quinazolin-2-ylamine,
4-(N-(4-methyl)-piperazin-1-yl)-6-(3-succinamidophenyl)quinazolin-2-ylamine,
4-(N-(4-methyl)-piperazin-1-yl)-6-(sulfamoylphenyl)quinazolin-2-ylamine,
4-(N-(4-methyl)-piperazin-1-yl)-6-(2-(toluene-4-sulfonamido)phenyl)quinazolin-2-ylamine,
4-(N-(4-methyl)-piperazin-1-yl)-6-(4-(toluene-4-sulfonamido)phenyl)quinazolin-2-ylamine,
4-(N-(4-methyl)-piperazin-1-yl)-6-(4-(tert-butoxycarbonylamino)-3-ethoxyphenyl)quinazolin-2-ylamine, 4-(N-(4-methyl)-piperazin-1-yl)-6-(2-(tert-butoxycarbonyl)phenyl)quinazolin-2-ylamine,
4-(N-(4-methyl)-piperazin-1-yl)-6-(3-(tert-butoxycarbonyl)phenyl)quinazolin-2-ylamine,
4-(N-(4-methyl)-piperazin-1-yl)-6-(4-(tert-butoxycarbonyl)phenyl)quinazolin-2-ylamine,
4-(N-(4-methyl)-piperazin-1-yl)-6-(2,3,4-trifluorophenyl)quinazolin-2-ylamine,
4-(N-(4-methyl)-piperazin-1-yl)-6-(4-tert-butylphenyl)quinazolin-2-ylamine,
4-(N-(4-methyl)-piperazin-1-yl)-6-(4-(tetrahydro-2H-pyran-2-yloxy)phenyl)quinazolin-2-ylamine,
4-(N-(4-methyl)-piperazin-1-yl)-6-(4-(2-thienyl)phenyl)quinazolin-2-ylamine,
4-(N-(4-methyl)-piperazin-1-yl)-6-(2,4,6-trimethylphenyl)quinazolin-2-ylamine,
4-(N-(4-methyl)-piperazin-1-yl)-6-(3,4,5-trimethoxyphenyl)quinazolin-2-ylamine,
4-(N-(4-methyl)-piperazin-1-yl)-6-(4-vinylphenyl)quinazolin-2-ylamine,
4-(N-(4-methyl)-piperazin-1-yl)-6-(4-(2-hydroxyethoxyphenyl)quinazolin-2-ylamine,
4-(N-(4-methyl)-piperazin-1-yl)-6-(6-benzyloxynaphth-2-yl)quinazolin-2-ylamine,
4-(N-(4-methyl)-piperazin-1-yl)-6-(naphth-1-yl)quinazolin-2-ylamine,
4-(N-(4-methyl)-piperazin-1-yl)-6-(naphth-2-yl)quinazolin-2-ylamine,
4-(N-(4-methyl)-piperazin-1-yl)-6-(4'-benzoyl[1,1'-biphenyl]-4-yl)quinazolin-2-ylamine,
4-(N-(4-methyl)-piperazin-1-yl)-6-(1-biphenylyl)quinazolin-2-ylamine,
4-(N-(4-methyl)-piperazin-1-yl)-6-(oxoindan-5-yl)quinazolin-2-ylamine,
4-(N-(4-methyl)-piperazin-1-yl)-6-(benzodioxolyl)quinazolin-2-ylamine,
4-(N-(4-methyl)-piperazin-1-yl)-6-(2-acetamidopyridin-5-yl)quinazolin-2-ylamine,
4-(N-(4-methyl)-piperazin-1-yl)-6-(2-aminopyridin-5-yl)quinazolin-2-ylamine,
4-(N-(4-methyl)-piperazin-1-yl)-6-(2-aminopyrimidin-5-yl)quinazolin-2-ylamine,
4-(N-(4-methyl)-piperazin-1-yl)-6-(1,4-benzodioxan-6-yl)quinazolin-2-ylamine,
4-(N-(4-methyl)-piperazin-1-yl)-6-(1-benzothien-3-yl)quinazolin-2-ylamine,
4-(N-(4-methyl)-piperazin-1-yl)-6-(2-benzyloxypyridin-5-yl)quinazolin-2-ylamine,
4-(N-(4-methyl)-piperazin-1-yl)-6-(1-benzyl-1H-pyrazol-4-yl)quinazolin-2-ylamine,
4-(N-(4-methyl)-piperazin-1-yl)-6-(2-bromo-3-chloropyridin-4-yl)quinazolin-2-ylamine,
4-(N-(4-methyl)-piperazin-1-yl)-6-(5-bromo-2,3-dihydrobenzo[b]furan-7-yl)quinazolin-2-ylamine,
4-(N-(4-methyl)-piperazin-1-yl)-6-(2-bromo-3-methylpyridin-5-yl)quinazolin-2-ylamine,
4-(N-(4-methyl)-piperazin-1-yl)-6-(2-bromopyridin-5-yl)quinazolin-2-ylamine,
4-(N-(4-methyl)-piperazin-1-yl)-6-(3-bromopyridin-5-yl)quinazolin-2-ylamine,
4-(N-(4-methyl)-piperazin-1-yl)-6-(5-bromothien-2-yl)quinazolin-2-ylamine,
4-(N-(4-methyl)-piperazin-1-yl)-6-(2-chloro-6-isopropylpyridin-3-yl)quinazolin-2-ylamine,
4-(N-(4-methyl)-piperazin-1-yl)-6-(2-chloro-3-methylpyridin-5-yl)quinazolin-2-ylamine,
4-(N-(4-methyl)-piperazin-1-yl)-6-(2-[4-(4-chlorophenylsulfonyl)piperazin-1-yl]pyridin-5-yl)quinazolin-2-ylamine,
4-(N-(4-methyl)-piperazin-1-yl)-6-(2-chloropyrid-4-yl)quinazolin-2-ylamine,
4-(N-(4-methyl)-piperazin-1-yl)-6-(2-chloropyrid-5-yl)quinazolin-2-ylamine,
4-(N-(4-methyl)-piperazin-1-yl)-6-(dibenzo[b,d]furan-4-yl)quinazolin-2-ylamine,
4-(N-(4-methyl)-piperazin-1-yl)-6-(2-chloro-3-fluoropyridin-4-yl)quinazolin-2-ylamine,
4-(N-(4-methyl)-piperazin-1-yl)-6-(dibenzo[b,d]thien-4-yl)quinazolin-2-ylamine,
4-(N-(4-methyl)-piperazin-1-yl)-6-(3,4-dihydro-2H-1,5-benzodioxepin-7-yl)quinazolin-2-ylamine,
4-(N-(4-methyl)-piperazin-1-yl)-6-(3,6-dihydro-2H-pyridine-1-tertbutoxycarbonyl)quinazolin-2-ylamine,
4-(N-(4-methyl)-piperazin-1-yl)-6-(2,5-dibromopyridin-3-yl)quinazolin-2-ylamine,
4-(N-(4-methyl)-piperazin-1-yl)-6-(2,6-dichloropyridin-3-yl)quinazolin-2-ylamine,
4-(N-(4-methyl)-piperazin-1-yl)-6-(2,3-dihydro-1-benzofuran-5-yl)quinazolin-2-ylamine,
4-(N-(4-methyl)-piperazin-1-yl)-6-(2,6-diethoxypyridin-5-yl)quinazolin-2-ylamine,
4-(N-(4-methyl)-piperazin-1-yl)-6-(2,6-diethoxypyridin-3-yl)quinazolin-2-ylamine,
4-(N-(4-methyl)-piperazin-1-yl)-6-(2,4-diethoxypyrimidin-5-yl)quinazolin-2-ylamine,
4-(N-(4-methyl)-piperazin-1-yl)-6-(3,5-dimethylisoxazol-4-yl)quinazolin-2-ylamine,
4-(N-(4-methyl)-piperazin-1-yl)-6-(2-(3-N,N-dimethylaminopropoxy)pyridin-5-yl)quinazolin-2-ylamine,
4-(N-(4-methyl)-piperazin-1-yl)-6-(3,5-dimethylpyrazol-4-yl)quinazolin-2-ylamine,
4-(N-(4-methyl)-piperazin-1-yl)-6-(1-[1,3]dioxolan-2-ylmethyl-1H-pyrazol-4-yl)quinazolin-2-ylamine,
4-(N-(4-methyl)-piperazin-1-yl)-6-(2,4-dioxo-1,2,3,4-tetrahydro-5-pyrimidinyl)quinazolin-2-ylamine,
4-(N-(4-methyl)-piperazin-1-yl)-6-(2,4-di(tert-butoxy)pyrimidin-5-yl)quinazolin-2-ylamine,
4-(N-(4-methyl)-piperazin-1-yl)-6-(2-ethoxypyridin-3-yl)quinazolin-2-ylamine,
4-(N-(4-methyl)-piperazin-1-yl)-6-(2-fluoro-3-methylpyridin-5-yl)quinazolin-2-ylamine,
4-(N-(4-methyl)-piperazin-1-yl)-6-(2-fluoropyridin-5-yl)quinazolin-2-ylamine,
4-(N-(4-methyl)-piperazin-1-yl)-6-(5-formyl-2-furyl)quinazolin-2-ylamine,
4-(N-(4-methyl)-piperazin-1-yl)-6-(5-formylthien-2-yl)quinazolin-2-ylamine,
4-(N-(4-methyl)-piperazin-1-yl)-6-(furan-2-yl)quinazolin-2-ylamine,
4-(N-(4-methyl)-piperazin-1-yl)-6-(2-hydroxypyridin-5-yl)quinazolin-2-ylamine,
4-(N-(4-methyl)-piperazin-1-yl)-6-(1-isobutyl-1H-pyrazol-4-yl)quinazolin-2-ylamine,
4-(N-(4-methyl)-piperazin-1-yl)-6-(isoquinolin-4-yl)quinazolin-2-ylamine,
4-(N-(4-methyl)-piperazin-1-yl)-6-(2-ethoxypyridin-3-yl)quinazolin-2-ylamine,
4-(N-(4-methyl)-piperazin-1-yl)-6-(2-ethoxypyrimidin-5-yl)quinazolin-2-ylamine,
4-(N-(4-methyl)-piperazin-1-yl)-6-(5-methyl-1-benzothien-2-yl)quinazolin-2-ylamine,
4-(N-(4-methyl)-piperazin-1-yl)-6-(1-(3-methylbutyl)-1H-pyrazol-4-yl)quinazolin-2-ylamine, 4-(N-(4-methyl)-piperazin-1-yl)-6-(5-methylfuran-2-yl) quinazolin-2-ylamine,
4-(N-(4-methyl)-piperazin-1-yl)-6-(1-methylindol-5-yl) quinazolin-2-ylamine,
4-(N-(4-methyl)-piperazin-1-yl)-6-(5-methyl-3-phenyl-4-isoxazolyl)quinazolin-2-ylamine,
4-(N-(4-methyl)-piperazin-1-yl)-6-(5-(methylthio)thien-2-yl)quinazolin-2-ylamine,
4-(N-(4-methyl)-piperazin-1-yl)-6-(2-(4-methylpiperazinyl) pyridin-4-yl)quinazolin-2-ylamine,
4-(N-(4-methyl)-piperazin-1-yl)-6-(2-(4-methylpiperazinyl) pyridin-5-yl)quinazolin-2-ylamine,
4-(N-(4-methyl)-piperazin-1-yl)-6-(1-methyl-1H-pyrazol-4-yl)quinazolin-2-ylamine,
4-(N-(4-methyl)-piperazin-1-yl)-6-(3-methylpyridin-2-yl) quinazolin-2-ylamine,
4-(N-(4-methyl)-piperazin-1-yl)-6-(5-methylpyridin-2-yl) quinazolin-2-ylamine,
4-(N-(4-methyl)-piperazin-1-yl)-6-(5-methylpyridin-3-yl) quinazolin-2-ylamine,
4-(N-(4-methyl)-piperazin-1-yl)-6-(2-ethoxypyridin-5-yl) quinazolin-2-ylamine,
4-(N-(4-methyl)-piperazin-1-yl)-6-(4-methylthien-2-yl) quinazolin-2-ylamine,
4-(N-(4-methyl)-piperazin-1-yl)-6-(5-methylthien-2-yl) quinazolin-2-ylamine,
4-(N-(4-methyl)-piperazin-1-yl)-6-(2-(2-morpholinoethylamino)-pyridin-5-yl)quinazolin-2-ylamine,
4-(N-(4-methyl)-piperazin-1-yl)-6-(2-(2-morpholinoethyl)-1H-pyrazol-4-yl)quinazolin-2-ylamine,
4-(N-(4-methyl)-piperazin-1-yl)-6-(2-(morpholin-1-yl)-pyridin-5-yl)quinazolin-2-ylamine,
4-(N-(4-methyl)-piperazin-1-yl)-6-(1-(phenylsulfonyl)-1H-indol-3-yl)quinazolin-2-ylamine,
4-(N-(4-methyl)-piperazin-1-yl)-6-(5-phenyl-2-thienyl) quinazolin-2-ylamine,
4-(N-(4-methyl)-piperazin-1-yl)-6-(2-(piperazin-1-yl)-pyridin-5-yL)quinazolin-2-ylamine,
4-(N-(4-methyl)-piperazin-1-yl)-6-(2-(piperazin-1-yl)-pyridin-4-yl)quinazolin-2-ylamine,
4-(N-(4-methyl)-piperazin-1-yl)-6-(1-propyl-1H-pyrazol-4-yl)quinazolin-2-ylamine,
4-(N-(4-methyl)-piperazin-1-yl)-6-(pyrazol-4-yl)quinazolin-2-ylamine,
4-(N-(4-methyl)-piperazin-1-yl)-6-(pyridin-4-yl)quinazolin-2-ylamine,
4-(N-(4-methyl)-piperazin-1-yl)-6-(4-phenoxathiinyl) quinazolin-2-ylamine,
4-(N-(4-methyl)-piperazin-1-yl)-6-(quinolin-8-yl)quinazolin-2-ylamine,
4-(N-(4-methyl)-piperazin-1-yl)-6-(quinolin-3-yl)quinazolin-2-ylamine,
4-(N-(4-methyl)-piperazin-1-yl)-6-(2-(4-tert-butoxycarbonylpiperazinyl)-pyrid-4-yl)quinazolin-2-ylamine,
4-(N-(4-methyl)-piperazin-1-yl)-6-(1-tert-butoxycarbonyl-1H-pyrazol-4-yl)quinazolin-2-ylamine,
4-(N-(4-methyl)-piperazin-1-yl)-6-(1-tert-butoxycarbonyl-2-pyrrolyl)quinazolin-2-ylamine,
4-(N-(4-methyl)-piperazin-1-yl)-6-(1-(tert-butoxycarbonyl)-5-bromo-1H-indol-2-yl)quinazolin-2-ylamine,
4-(N-(4-methyl)-piperazin-1-yl)-6-(1-(tert-butoxycarbonyl)-1H-indol-5-yl)quinazolin-2-ylamine,
4-(N-(4-methyl)-piperazin-1-yl)-6-(1-(tert-butoxycarbonyl)-5-methoxy-1H-indol-2-yl)quinazolin-2-ylamine,
4-(N-(4-methyl)-piperazin-1-yl)-6-(1-thianthrenylthien-3-yl)quinazolin-2-ylamine, and
4-(N-(4-methyl)-piperazin-1-yl)-6-(1,3,5-trimethyl-1H-pyrazol-4-yl)quinazolin-2-ylamine.

Examples 900 to 1095

Synthesis of 6-(4-fluorophenyl)-4-(N-isopentylamino)quinazoline analogues

The sequential experimental procedure of examples 7, 36 and 42 is repeated, except that in the initial step 4-fluorophenylboronic acid is replaced with another aryl or heteroaryl boronic acid. In this way, the following quinazoline derivatives are obtained in similar yields:

4-(N-isopentylamino)-6-(4-(4'-allyloxycarbonylpiperazino) phenyl)quinazoline,
4-(N-isopentylamino)-6-(3-aminocarbonylphenyl)quinazoline,
4-(N-isopentylamino)-6-(4-aminocarbonylphenyl)quinazoline,
4-(N-isopentylamino)-6-(2-amino-5-chlorophenyl)quinazoline,
4-(N-isopentylamino)-6-(4-amino-3-ethoxyphenyl)quinazoline,
4-(N-isopentylamino)-6-(2-amino-4-methylphenyl) quinazoline,
4-(N-isopentylamino)-6-(2-amino-5-methylphenyl) quinazoline,
4-(N-isopentylamino)-6-(4-amino-2-methylphenyl) quinazoline,
4-(N-isopentylamino)-6-(5-amino-2-methylphenyl) quinazoline,
4-(N-isopentylamino)-6-(4-amino-3-nitrophenyl)quinazoline,
4-(N-isopentylamino)-6-(2-benzyloxyphenyl)quinazoline,
4-(N-isopentylamino)-6-(3-benzyloxy-4-ethoxyphenyl) quinazoline,
4-(N-isopentylamino)-6-(4-biphenyl)quinazoline,
4-(N-isopentylamino)-6-(4-n-butyl phenyl)quinazoline,
4-(N-isopentylamino)-6-(4-isobutylphenyl)quinazoline,
4-(N-isopentylamino)-6-(4-carboxy-3-fluorophenyl) quinazoline,
4-(N-isopentylamino)-6-(3-(3-carboxypropionylamino)phenyl)quinazoline,
4-(N-isopentylamino)-6-(4-(3-carboxypropionylamino)phenyl)quinazoline,
4-(N-isopentylamino)-6-(3-chloro-4-hydroxy-5-ethoxyphenyl)quinazoline,
4-(N-isopentylamino)-6-(2-chloro-5-hydroxymethylphenyl) quinazoline,
4-(N-isopentylamino)-6-(4-cyanoethoxyphenyl)quinazoline,
4-(N-isopentylamino)-6-(3-cyanoethoxyphenyl)quinazoline,
4-(N-isopentylamino)-6-(2-cyanoethoxyphenyl)quinazoline,
4-(N-isopentylamino)-6-(4-cyanophenyl)quinazoline,
4-(N-isopentylamino)-6-(3-cyanophenyl)quinazoline,
4-(N-isopentylamino)-6-(2-cyanophenyl)quinazoline,
4-(N-isopentylamino)-6-(3-(N-cyclopropylaminocarbonyl) phenyl)quinazoline,
4-(N-isopentylamino)-6-(3-(N,N-diethylaminocarbonyl) phenyl)quinazoline,
4-(N-isopentylamino)-6-(3-(N,N-dimethylamino)phenyl) quinazoline,
4-(N-isopentylamino)-6-(2-(N,N-dimethylamino)phenyl) quinazoline, 4-(N-isopentylamino)-6-(3-(N,N-dimethylaminocarbonyl)phenyl)quinazoline,
4-(N-isopentylamino)-6-(3-[(N',N'-dimethylamino)ethylaminocarbonyl]phenyl)quinazoline,
4-(N-isopentylamino)-6-(4-[(N',N'-dimethylamino)ethylaminocarbonyl]phenyl)quinazoline,
4-(N-isopentylamino)-6-(3-[1,3]dioxolan-2-ylethoxyphenyl)quinazoline,
4-(N-isopentylamino)-6-(3-(ethoxycarbonyl)ethoxyphenyl)quinazoline,
4-(N-isopentylamino)-6-(4-(ethoxycarbonyl)ethoxyphenyl)quinazoline,
4-(N-isopentylamino)-6-(4-ethoxycarbonylphenyl)quinazoline,
4-(N-isopentylamino)-6-(3-ethoxycarbonylphenyl)quinazoline,
4-(N-isopentylamino)-6-(2-ethoxycarbonylphenyl)quinazoline,
4-(N-isopentylamino)-6-(4-(3-ethoxycarbonylpiperidino)carboxamidophenyl)quinazoline,
4-(N-isopentylamino)-6-(4-formylaminophenyl)quinazoline,
4-(N-isopentylamino)-6-(3-formylaminophenyl)quinazoline,
4-(N-isopentylamino)-6-(2-formylaminophenyl)quinazoline,
4-(N-isopentylamino)-6-(2-formyl-5-ethoxyphenyl)quinazoline,
4-(N-isopentylamino)-6-(3-formyl-4-ethoxyphenyl)quinazoline,
4-(N-isopentylamino)-6-(5-formyl-2-ethoxyphenyl)quinazoline,
4-(N-isopentylamino)-6-(2-formyl-5-methylphenyl)quinazoline,
4-(N-isopentylamino)-6-(4-formylphenyl)quinazoline,
4-(N-isopentylamino)-6-(3-formylphenyl)quinazoline,
4-(N-isopentylamino)-6-(2-formylphenyl)quinazoline,
4-(N-isopentylamino)-6-(4-hydroxy-3,5-dimethylphenyl)quinazoline,
4-(N-isopentylamino)-6-(3-(2-hydroxyethyl)-aminocarbonylphenyl)quinazoline,
4-(N-isopentylamino)-6-(4-(2-hydroxyethyl)aminocarbonyl)phenyl)quinazoline,
4-(N-isopentylamino)-6-(3-hydroxy-4-ethoxycarbonylphenyl)quinazoline,
4-(N-isopentylamino)-6-(4-hydroxy-3-ethoxyphenyl)quinazoline,
4-(N-isopentylamino)-6-(4-(hydroxymethyl)phenyl)quinazoline,
4-(N-isopentylamino)-6-(3-(hydroxymethyl)phenyl)quinazoline,
4-(N-isopentylamino)-6-(4-hydroxy-3-nitrophenyl)quinazoline,
4-(N-isopentylamino)-6-(4-isopropoxyphenyl)quinazoline,
4-(N-isopentylamino)-6-(4-(4-isopropylpiperazinyl)phenyl)quinazoline,
4-(N-isopentylamino)-6-(4-isopropylphenyl)quinazoline,
4-(N-isopentylamino)-6-(4-methanesulfonamidophenyl)quinazoline,
4-(N-isopentylamino)-6-(3-methanesulfonamidophenyl)quinazoline,
4-(N-isopentylamino)-6-(2-methanesulfonamido phenyl)quinazoline,
4-(N-isopentylamino)-6-(4-ethoxycarbonylphenyl)quinazoline,
4-(N-isopentylamino)-6-(3-ethoxycarbonylphenyl)quinazoline,
4-(N-isopentylamino)-6-(2-ethoxycarbonylphenyl)quinazoline,
4-(N-isopentylamino)-6-(3-ethoxy-4-ethoxycarbonylphenyl)quinazoline,
4-(N-isopentylamino)-6-(2-ethoxy-5-methylphenyl)quinazoline,
4-(N-isopentylamino)-6-(4-ethoxy-3-nitrophenyl)quinazoline,
4-(N-isopentylamino)-6-(4-ethoxyphenyl)quinazoline,
4-(N-isopentylamino)-6-(3-ethoxyphenyl)quinazoline,
4-(N-isopentylamino)-6-(4-N-methylcarboxamidophenyl)quinazoline,
4-(N-isopentylamino)-6-(4-(N-methylamino)phenyl)quinazoline,
4-(N-isopentylamino)-6-(3-(4-methylpiperazine-1-carbonyl)phenyl)quinazoline,
4-(N-isopentylamino)-6-(4-(4-methylpiperazine-1-carbonyl)phenyl)quinazoline,
4-(N-isopentylamino)-6-(4-(methylthio)phenyl)quinazoline,
4-(N-isopentylamino)-6-(3-(methylthio)phenyl)quinazoline,
4-(N-isopentylamino)-6-(2-(methylthio)phenyl)quinazoline,
4-(N-isopentylamino)-6-(4-(morpholinocarbonyl)phenyl)quinazoline,
4-(N-isopentylamino)-6-(4-morpholinophenyl)quinazoline,
4-(N-isopentylamino)-6-(2-(morpholinomethyl)phenyl)quinazoline,
4-(N-isopentylamino)-6-(4-nitrophenyl)quinazoline,
4-(N-isopentylamino)-6-(3-nitrophenyl)quinazoline,
4-(N-isopentylamino)-6-(2-nitrophenyl)quinazoline,
4-(N-isopentylamino)-6-(4-phenoxyphenyl)quinazoline,
4-(N-isopentylamino)-6-(4-(N-phenylaminomethyl)phenyl)quinazoline,
4-(N-isopentylamino)-6-(4-(phenylcarbonyl)phenyl)quinazoline,
4-(N-isopentylamino)-6-(4-(piperazine-1-carbonyl)phenyl)quinazoline,
4-(N-isopentylamino)-6-(4-piperazinylphenyl)quinazoline,
4-(N-isopentylamino)-6-(4-succinamidophenyl)quinazoline,
4-(N-isopentylamino)-6-(3-succinamidophenyl)quinazoline,
4-(N-isopentylamino)-6-(sulfamoylphenyl)quinazoline,
4-(N-isopentylamino)-6-(2-(toluene-4-sulfonamido)phenyl)quinazoline,
4-(N-isopentylamino)-6-(4-(toluene-4-sulfonamido)phenyl)quinazoline,
4-(N-isopentylamino)-6-(4-(tert-butoxycarbonylamino)-3-ethoxyphenyl)quinazoline,
4-(N-isopentylamino)-6-(2-(tert-butoxycarbonyl)phenyl)quinazoline,
4-(N-isopentylamino)-6-(3-(tert-butoxycarbonyl)phenyl)quinazoline,
4-(N-isopentylamino)-6-(4-(tert-butoxycarbonyl)phenyl)quinazoline,
4-(N-isopentylamino)-6-(2,3,4-trifluorophenyl)quinazoline,
4-(N-isopentylamino)-6-(4-tert-butylphenyl)quinazoline,
4-(N-isopentylamino)-6-(4-(tetrahydro-2H-pyran-2-yloxy)phenyl)quinazoline,
4-(N-isopentylamino)-6-(4-(2-thienyl)phenyl)quinazoline,
4-(N-isopentylamino)-6-(2,4,6-trimethylphenyl)quinazoline,
4-(N-isopentylamino)-6-(3,4,5-trimethoxyphenyl)quinazoline,
4-(N-isopentylamino)-6-(4-vinylphenyl)quinazoline,
4-(N-isopentylamino)-6-(4-(2-hydroxyethoxyphenyl)quinazoline, 4-(N-isopentylamino)-6-(6-benzyloxynaphth-2-yl)quinazoline,
4-(N-isopentylamino)-6-(naphth-1-yl)quinazoline,
4-(N-isopentylamino)-6-(naphth-2-yl)quinazoline,
4-(N-isopentylamino)-6-(4'-benzoyl[1,1'-biphenyl]-4-yl)quinazoline,
4-(N-isopentylamino)-6-(1-biphenylyl)quinazoline,
4-(N-isopentylamino)-6-(oxoindan-5-yl)quinazoline,
4-(N-isopentylamino)-6-(benzodioxolyl)quinazoline,
4-(N-isopentylamino)-6-(2-acetamidopyridin-5-yl)quinazoline,
4-(N-isopentylamino)-6-(2-aminopyridin-5-yl)quinazoline,
4-(N-isopentylamino)-6-(2-aminopyrimidin-5-yl)quinazoline,
4-(N-isopentylamino)-6-(1,4-benzodioxan-6-yl)quinazoline,
4-(N-isopentylamino)-6-(1-benzothien-3-yl)quinazoline,
4-(N-isopentylamino)-6-(2-benzyloxypyridin-5-yl)quinazoline,
4-(N-isopentylamino)-6-(1-benzyl-1H-pyrazol-4-yl)quinazoline,
4-(N-isopentylamino)-6-(2-bromo-3-chloropyridin-4-yl)quinazoline,
4-(N-isopentylamino)-6-(5-bromo-2,3-dihydrobenzo[b]furan-7-yl)quinazoline,
4-(N-isopentylamino)-6-(2-bromo-3-methylpyridin-5-yl)quinazoline,
4-(N-isopentylamino)-6-(2-bromopyridin-5-yl)quinazoline,
4-(N-isopentylamino)-6-(3-bromopyridin-5-yl)quinazoline,
4-(N-isopentylamino)-6-(5-bromothien-2-yl)quinazoline,
4-(N-isopentylamino)-6-(2-chloro-6-isopropylpyridin-3-yl)quinazoline,
4-(N-isopentylamino)-6-(2-chloro-3-methylpyridin-5-yl)quinazoline,
4-(N-isopentylamino)-6-(2-[4-(4-chlorophenylsulfonyl)piperazin-1-yl]pyridin-5-yl)quinazoline,
4-(N-isopentylamino)-6-(2-chloropyrid-4-yl)quinazoline,
4-(N-isopentylamino)-6-(2-chloropyrid-5-yl)quinazoline,
4-(N-isopentylamino)-6-(dibenzo[b,d]furan-4-yl)quinazoline,
4-(N-isopentylamino)-6-(2-chloro-3-fluoropyridin-4-yl)quinazoline,
4-(N-isopentylamino)-6-(dibenzo[b,d]thien-4-yl)quinazoline,
4-(N-isopentylamino)-6-(3,4-dihydro-2H-1,5-benzodioxepin-7-yl)quinazoline,
4-(N-isopentylamino)-6-(3,6-dihydro-2H-pyridine-1-tertbutoxycarbonyl)quinazoline,
4-(N-isopentylamino)-6-(2,5-dibromopyridin-3-yl)quinazoline,
4-(N-isopentylamino)-6-(2,6-dichloropyridin-3-yl)quinazoline,
4-(N-isopentylamino)-6-(2,3-dihydro-1-benzofuran-5-yl)quinazoline,
4-(N-isopentylamino)-6-(2,6-diethoxypyridin-5-yl)quinazoline,
4-(N-isopentylamino)-6-(2,6-diethoxypyridin-3-yl)quinazoline,
4-(N-isopentylamino)-6-(2,4-diethoxypyrimidin-5-yl)quinazoline,
4-(N-isopentylamino)-6-(3,5-dimethylisoxazol-4-yl)quinazoline,
4-(N-isopentylamino)-6-(2-(3-N,N-dimethylaminopropoxy)pyridin-5-yl)quinazoline,
4-(N-isopentylamino)-6-(3,5-dimethylpyrazol-4-yl)quinazoline,
4-(N-isopentylamino)-6-(1-[1,3]dioxolan-2-ylmethyl-1H-pyrazol-4-yl)quinazoline,
4-(N-isopentylamino)-6-(2,4-dioxo-1,2,3,4-tetrahydro-5-pyrimidinyl)quinazoline,
4-(N-isopentylamino)-6-(2,4-di(tert-butoxy)pyrimidin-5-yl)quinazoline,
4-(N-isopentylamino)-6-(2-ethoxypyridin-3-yl)quinazoline,
4-(N-isopentylamino)-6-(2-fluoro-3-methylpyridin-5-yl)quinazoline,
4-(N-isopentylamino)-6-(2-fluoropyridin-5-yl)quinazoline,
4-(N-isopentylamino)-6-(5-formyl-2-furyl)quinazoline,
4-(N-isopentylamino)-6-(5-formylthien-2-yl)quinazoline,
4-(N-isopentylamino)-6-(furan-2-yl)quinazoline,
4-(N-isopentylamino)-6-(2-hydroxypyridin-5-yl)quinazoline,
4-(N-isopentylamino)-6-(1-isobutyl-1H-pyrazol-4-yl)quinazoline,
4-(N-isopentylamino)-6-(isoquinolin-4-yl)quinazoline,
4-(N-isopentylamino)-6-(2-ethoxypyridin-3-yl)quinazoline,
4-(N-isopentylamino)-6-(2-ethoxypyrimidin-5-yl)quinazoline,
4-(N-isopentylamino)-6-(5-methyl-1-benzothien-2-yl)quinazoline,
4-(N-isopentylamino)-6-(1-(3-methylbutyl)-1H-pyrazol-4-yl)quinazoline,
4-(N-isopentylamino)-6-(5-methylfuran-2-yl)quinazoline,
4-(N-isopentylamino)-6-(1-methylindol-5-yl)quinazoline,
4-(N-isopentylamino)-6-(5-methyl-3-phenyl-4-isoxazolyl)quinazoline,
4-(N-isopentylamino)-6-(5-(methylthio)thien-2-yl)quinazoline,
4-(N-isopentylamino)-6-(2-(4-methylpiperazinyl)pyridin-4-yl)quinazoline,
4-(N-isopentylamino)-6-(2-(4-methylpiperazinyl)pyridin-5-yl)quinazoline,
4-(N-isopentylamino)-6-(1-methyl-1H-pyrazol-4-yl)quinazoline,
4-(N-isopentylamino)-6-(3-methylpyridin-2-yl)quinazoline,
4-(N-isopentylamino)-6-(5-methylpyridin-2-yl)quinazoline,
4-(N-isopentylamino)-6-(5-methylpyridin-3-yl)quinazoline,
4-(N-isopentylamino)-6-(2-ethoxypyridin-5-yl)quinazoline,
4-(N-isopentylamino)-6-(4-methylthien-2-yl)quinazoline,
4-(N-isopentylamino)-6-(5-methylthien-2-yl)quinazoline,
4-(N-isopentylamino)-6-(2-(2-morpholinoethylamino)-pyridin-5-yl)quinazoline,
4-(N-isopentylamino)-6-(2-(2-morpholinoethyl)-1H-pyrazol-4-yl)quinazoline,
4-(N-isopentylamino)-6-(2-(morpholin-1-yl)-pyridin-5-yl)quinazoline,
4-(N-isopentylamino)-6-(1-(phenylsulfonyl)-1H-indol-3-yl)quinazoline,
4-(N-isopentylamino)-6-(5-phenyl-2-thienyl)quinazoline,
4-(N-isopentylamino)-6-(2-(piperazin-1-yl)-pyridin-5-yl)quinazoline,
4-(N-isopentylamino)-6-(2-(piperazin-1-yl)-pyridin-4-yl)quinazoline,
4-(N-isopentylamino)-6-(1-propyl-1H-pyrazol-4-yl)quinazoline,
4-(N-isopentylamino)-6-(pyrazol-4-yl)quinazoline,
4-(N-isopentylamino)-6-(pyridin-4-yl)quinazoline,
4-(N-isopentylamino)-6-(4-phenoxathiinyl)quinazoline,
4-(N-isopentylamino)-6-(quinolin-8-yl)quinazoline,
4-(N-isopentylamino)-6-(quinolin-3-yl)quinazoline,
4-(N-isopentylamino)-6-(2-(4-tert-butoxycarbonylpiperazinyl)-pyrid-4-yl)quinazoline,
4-(N-isopentylamino)-6-(1-tert-butoxycarbonyl-1H-pyrazol-4-yl)quinazoline, 4-(N-isopentylamino)-6-(1-tert-butoxycarbonyl-2-pyrrolyl)quinazoline,
4-(N-isopentylamino)-6-(1-(tert-butoxycarbonyl)-5-bromo-1H-indol-2-yl)quinazoline,
4-(N-isopentylamino)-6-(1-(tert-butoxycarbonyl)-1H-indol-5-yl)quinazoline,
4-(N-isopentylamino)-6-(1-(tert-butoxycarbonyl)-5-methoxy-1H-indol-2-yl)quinazoline,
4-(N-isopentylamino)-6-(1-thianthrenylthien-3-yl)quinazoline, and
4-(N-isopentylamino)-6-(1,3,5-trimethyl-1H-pyrazol-4-yl)quinazoline.

The invention claimed is:

1. A method for treating an infection due to a virus from the Flaviridae family by administering to a patient in need thereof an effective amount of a quinazoline derivative according to the structural formula (I)

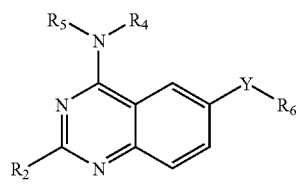

(I)

wherein,
$R_2$ is NR'R";
$R_4$ is selected from the group consisting of $C_{1-7}$ alkyl; $C_{2-7}$ alkenyl; $C_{3-10}$ cycloalkyl; $C_{3-10}$ cycloalkenyl; arylalkyl; heterocyclic-substituted $C_{1-7}$ alkyl and $C_{3-10}$ cycloalkyl-$C_{1-7}$ alkyl; and wherein said $R_4$ is optionally substituted with one or more $R_7$;
$R_5$ is hydrogen or $C_{1-7}$ alkyl; or $R_5$ and $R_4$, together with the nitrogen atom to which they are attached, form a 5 to 7-membered heterocyclic ring comprising a nitrogen atom and further optionally comprising at least one heteroatom independently selected from N, O and S, said ring being optionally substituted with one or more $R_7$;
Y is a single bond;
$R_6$ is selected from the group consisting of halogen; fused benzo-$C_{5-8}$ cycloalkyl optionally substituted with oxo; heteroaryl and aryl, wherein said heteroaryl or aryl is optionally substituted with one or more $R_8$;
each $R_7$ is independently selected from the group consisting of halogen; nitro; hydroxyl; sulfhydryl; hydroxylamino; cyano; amino; $C_{1-7}$ alkyl; halo $C_{1-7}$ alkyl; $C_{2-7}$ alkenyl; $C_{2-7}$ alkynyl; $C_{1-7}$ alkoxy; halo $C_{1-7}$ alkoxy; $C_{1-7}$ alkylthio; formyl; —CO—$NHR_9$; —CO—$NR_9R_9'$; —CS—$NHR_9$; —$NR_{12}$—CO—$NHR_{12}$; —$NR_{12}$—CS—$NHR_{12}$; —$SO_2NH_2$; —$NR_{12}$—$SO_2R_{11}$; —$NR_{12}$—$COR_{10}$; —$NR_{12}$—$CSR_{10}$; alkoxyamino; mercaptoamino; thioalkylamino; alkylamino; alkenylamino; alkynylamino; alkylsulfoxide; alkylsulfone; hydroxyalkylamino; mercaptoalkylamino; hydrazino; alkylhydrazino; $C_{3-10}$ cycloalkyl; aryl optionally substituted with arylcarbonyl, aryloxy, (O,O-dialkylphosphonyl)-alkyl; alkanoyl, alkoxy, hydroxy-$C_{1-7}$ alkoxy, hydroxy-$C_{1-7}$ alkyl, di-$C_{1-7}$ alkyl-amino $C_{1-7}$ alkyl, ω-carboxy-alkanoylamino, mono-($C_{3-7}$ cycloalkyl)aminocarbonyl, di-($C_{3-7}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy-$C_{1-7}$ alkyl)aminocarbonyl, formylamino, —$SO_2NH_2$, arylamino-$C_{1-7}$ alkyl, $C_{1-7}$ alkylsulfonyl, heterocyclyl-carbonyl, heterocyclyl-$C_{1-7}$ alkyl carboxylic acid or esters or thioesters or halides or anhydrides or amides thereof; and thiocarboxylic acid or esters or thioesters or halides or anhydrides or amides thereof;

each $R_9$ is independently selected from the group consisting of halogen; nitro; hydroxyl; sulfhydryl; hydroxylamino; cyano; amino; $C_{1-7}$ alkyl; halo $C_{1-7}$ alkyl; $C_{2-7}$ alkenyl; $C_{2-7}$ alkynyl; $C_{1-7}$ alkoxy; halo $C_{1-7}$ alkoxy; $C_{1-7}$ alkylthio; formyl; —CO—$NHR_9$; —CO—$NR_9R_9'$; —CS—$NHR_9$; —$NR_{12}$—CO—$NHR_{12}$; —$NR_{12}$—CS—$NHR_{12}$; $SO_2N$ $H_2$, $R_{12}$—$SO_2R_{11}$; $R_{12}$—$COR_{10}$, $R_{12}$—$CSR_{10}$, alkoxyamino; mercaptoamino; thioalkylamino; alkylamino; alkenylamino; alkynylamino; alkylsulfoxide; alkylsulfone; hydroxyalkylamino; mercaptoalkylamino; hydrazino; alkylhydrazino; $C_{3-10}$ cycloalkyl; aryl optionally substituted with arylcarbonyl, aryloxy, (O,O-dialkylphosphonyl)-alkyl; alkanoyl, alkoxy, hydroxy-$C_{1-7}$ alkoxy, hydroxy-$C_{1-7}$ alkyl, di-$C_{1-7}$ alkyl-amino $C_{1-7}$ alkyl, ω-carboxy-alkanoylamino, mono-($C_{3-7}$ cycloalkyl)aminocarbonyl, di-($C_{3-7}$ cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy-$C_{1-7}$ alkyl)aminocarbonyl, formylamino, —$SO_2NH_2$, arylamino-$C_{1-7}$ alkyl, $C_{1-7}$ alkylsulfonyl, heterocyclyl-carbonyl, heterocyclyl-$C_{1-7}$ alkyl or heterocyclyl, wherein said heterocyclyl is optionally substituted with $C_{3-7}$ alkenyloxycarbonyl, $C_{1-7}$ alkyl or $C_{1-7}$ alkyloxycarbonyl; carboxylic acid or esters or thioesters or halides or anhydrides or amides thereof; and thiocarboxylic acid or esters or thioesters or halides or anhydrides or amides thereof;

$R_9$ and $R_9'$ are each independently selected from the group consisting of hydrogen; $C_{3-10}$ cycloalkyl optionally substituted with one more substituents independently selected from the group consisting of cyano, halogen, hydroxy, amino, $C_{1-7}$ alkyl and $C_{1-7}$ alkoxy; $C_{1-7}$ alkoxy; halo $C_{1-7}$ alkoxy; $C_{1-7}$ alkyl optionally substituted with one or more substituents independently selected from the group consisting of amino, alkylamino, cyano, dialkylamino, and heterocyclyl optionally substituted with $C_{1-7}$ alkyl; halo $C_{1-7}$ alkyl; heterocyclyl optionally substituted with $C_{1-7}$ alkyl; aryl and aryl$C_{1-7}$ alkyl wherein the aryl moiety is optionally substituted with one or more halogen; or $R_9$ and $R_9'$ together with the nitrogen atom to which they are attached form a nitrogen-containing heterocyclyl group;

$R_{10}$ and $R_{11}$ are each independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, alkylamino, cyano, dialkylamino, halogen, and heterocyclyl; heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, $C_{1-7}$ alkylamino, cyano, dialkylamino, halogen and heterocyclyl;

$R_{12}$ is selected from the group consisting of hydrogen and $C_{1-7}$ alkyl, wherein said $C_{1-7}$ alkyl is optionally substituted with one or more substituents independently selected from the group consisting of cyano, halogen and hydroxy;

R' and R" are each independently selected from the group consisting of hydrogen and $C_{1-7}$ alkyl-carbonyl;

$R_{15}$ is selected from the group consisting of $C_{3-10}$ cycloalkyl, heteroaryl and aryl wherein said heteroaryl or aryl is optionally substituted with one or more substituents independently selected from the group consisting of halogen and $C_{1-7}$ alkyl and wherein said $C_{3-10}$ cycloalkyl is optionally substituted, at the carbon position adjacent to the nitrogen atom to which it is attached, with aryl or heteroaryl wherein said aryl is optionally substituted with halogen; and each $R_{16}$ is independently selected from the group consisting of halogen, hydroxy, amino, nitro, cyano, trifluoromethyl, trifluoromethoxy, $C_{1-7}$ alkyl, $C_{1-7}$ alkoxy, di-($C_{1-7}$ alkyl)amino, mono-($C_{1-7}$ alkyl)amino, carboxamido, —$SO_2NH_2$, carbamoyl, —$NR_{12}$—$SO_2R_{11}$ and phenoxy; provided that when $NR_4R_5$ is piperazinyl, said $NR_4R_5$ is either non-substituted or substituted with methyl or acetyl, and/or a pharmaceutically acceptable addition salt thereof and/or a stereo-isomer thereof and/or a mono- or a di-N-oxide thereof.

2. A method according to claim 1, wherein said virus belongs to a genus selected from the group consisting of Genus *Flavivirus*, Genus *Hepacivirus* and Genus *Pestivirus*.

3. A method according to claim 1, wherein said virus is hepatitis C virus.

4. A method according to claim 1, wherein Y is a bond, and $R_6$ is selected from the group consisting of 3,4-dimethoxyphenyl, 4-acetamidophenyl, 4-chlorophenyl and 4-fluorophenyl.

5. A method according to claim 1, wherein said at least one quinazoline derivative is administered together with one or more other antiviral drugs.

6. A method according to claim 5, wherein said other antiviral drug is selected from the group consisting of interferon alpha, ribavirin, NS3 protease inhibitors, and nucleoside- or non-nucleoside-based inhibitors of NS5B polymerase.

7. A method for treating an infection due to a virus from the Flaviridae family by administering to a patient in need thereof an effective amount of a quinazoline derivative selected from the group consisting of:

2-amino-6-(3,4-dimethoxyphenyl)-4-(N-morpholino)-quinazoline,
2-amino-6-(3,4-dimethoxyphenyl)-4-[N-(3-bromo)-anilino)]-quinazoline,
2-amino-6-(3,4-dimethoxyphenyl)-4-[N-(3-methylphenylcarbamoyl)-piperazin-1-yl]-quinazoline,
2-amino-6-(3,4-dimethoxyphenyl)-4-[N-(4-methylphenyl)piperazin-1-yl]-quinazoline,
2-amino-6-(3,4-dimethoxyphenyl)-4-(N-acetylpiperazino)-quinazoline,
2-amino-6-(3,4-dimethoxyphenyl)-4-(N-cyclohexylamino)-quinazoline,
2-amino-6-(3,4-dimethoxyphenyl)-4-(N-methylpiperazino)-quinazoline,
2-amino-6-(3,4-dimethoxyphenyl)-4-(N-piperidino)-quinazoline,
2-amino-6-(3,4-dimethoxyphenyl)-4-[N-(3-methyl)-anilino]-quinazoline,
2-amino-6-(3,4-dimethoxyphenyl)-4-hydrazino-quinazoline,
2-amino-6-(3,4-dimethoxyphenyl)-4-(N,N-dimethylamino)-quinazoline,
2-amino-6-(3,4-dimethoxyphenyl)-4-(N-butylamino)-quinazoline,
2-amino-6-(3,4-dimethoxyphenyl)-4-(N-cyclopentylamino)-quinazoline,
2-amino-6-(3,4-dimethoxyphenyl)-4-(N-cyclopropylamino)-quinazoline,
2-amino-6-(3,4-dimethoxyphenyl)-4-(N-isopentylamino)-quinazoline,
2-amino-6-(3,4-dimethoxyphenyl)-4-(N-propylamino)-quinazoline,
2-amino-6-(3,4-dimethoxyphenyl)-4-amino-quinazoline,
2-amino-6-(4-acetamidophenyl)-4-(N-morpholino)-quinazoline,
2-amino-6-(4-acetamidophenyl)-4-[N-(3-bromo)-anilino)]-quinazoline,
2-amino-6-(4-acetamidophenyl)-4-[N-(3-methylphenylcarbamoyl)-piperazin-1-yl]-quinazoline,
2-amino-6-(4-acetamidophenyl)-4-[N-(4-methylphenyl)piperazin-1-yl]-quinazoline,
2-amino-6-(4-acetamidophenyl)-4-(N-acetylpiperazino)-quinazoline,
2-amino-6-(4-acetamidophenyl)-4-(N-cyclohexylamino)-quinazoline,
2-amino-6-(4-acetamidophenyl)-4-(N-methylpiperazino)-quinazoline,
2-amino-6-(4-acetamidophenyl)-4-(N-piperidino)-quinazoline,
2-amino-6-(4-acetamidophenyl)-4-[N-(3-methyl)-anilino]-quinazoline,
2-amino-6-(4-acetamidophenyl)-4-hydrazino-quinazoline,
2-amino-6-(4-acetamidophenyl)-4-(N,N-dimethylamino)-quinazoline,
2-amino-6-(4-acetamidophenyl)-4-(N,N-dimethylamino)-quinazoline,
2-amino-6-(4-acetamidophenyl)-4-(N-butylamino)-quinazoline,
2-amino-6-(4-acetamidophenyl)-4-(N-cyclopentylamino)-quinazoline,
2-amino-6-(4-acetamidophenyl)-4-(N-cyclopropylamino)-quinazoline,
2-amino-6-(4-acetamidophenyl)-4-(N-isopentylamino)-quinazoline,
2-amino-6-(4-acetamidophenyl)-4-(N-propylamino)-quinazoline,
2-amino-6-(4-acetamidophenyl)-4-amino-quinazoline,
2-amino-6-(4-chlorophenyl)-4-(N-morpholino)-quinazoline,
2-amino-6-(4-chlorophenyl)-4-[N-(3-bromo)-anilino)]-quinazoline,
2-amino-6-(4-chlorophenyl)-4-[N-(3-methylphenylcarbamoyl)-piperazin-1-yl]-quinazoline,
2-amino-6-(4-chlorophenyl)-4-[N-(4-methylphenyl)piperazin-1-yl]-quinazoline,
2-amino-6-(4-chlorophenyl)-4-(N-acetylpiperazino)-quinazoline,
2-amino-6-(4-chlorophenyl)-4-(N-cyclohexylamino)-quinazoline,
2-amino-6-(4-chlorophenyl)-4-(N-methylpiperazino)-quinazoline, 2-amino-6-(4-chlorophenyl)-4-(N-piperidino)-quinazoline,
2-amino-6-(4-chlorophenyl)-4-[N-(3-methyl)-anilino]-quinazoline,
2-amino-6-(4-chlorophenyl)-4-hydrazino-quinazoline,
2-amino-6-(4-chlorophenyl)-4-(N,N-dimethylamino)-quinazoline,
2-amino-6-(4-chlorophenyl)-4-(N-butylamino)-quinazoline,
2-amino-6-(4-chlorophenyl)-4-(N-cyclopentylamino)-quinazoline,
2-amino-6-(4-chlorophenyl)-4-(N-cyclopropylamino)-quinazoline,
2-amino-6-(4-chlorophenyl)-4-(N-isopentylamino)-quinazoline,
2-amino-6-(4-chlorophenyl)-4-(N-propylamino)-quinazoline,
2-amino-6-(4-chlorophenyl)-4-amino-quinazoline,
2-amino-6-(4-fluorophenyl)-4-(N-morpholino)-quinazoline,
2-amino-6-(4-fluorophenyl)-4-[N-(3-bromo)-anilino)]-quinazoline,
2-amino-6-(4-fluorophenyl)-4-[N-(3-methylphenylcarbamoyl)-piperazin-1-yl]-quinazoline,
2-amino-6-(4-fluorophenyl)-4-[N-(4-methylphenyl)piperazin-1-yl]-quinazoline,
2-amino-6-(4-fluorophenyl)-4-(N-acetylpiperazino)-quinazoline,
2-amino-6-(4-fluorophenyl)-4-(N-cyclohexylamino)-quinazoline,
2-amino-6-(4-fluorophenyl)-4-(N-methylpiperazino)-quinazoline,
2-amino-6-(4-fluorophenyl)-4-(N-piperidino)-quinazoline,
2-amino-6-(4-fluorophenyl)-4-[N-(3-methyl)-anilino]-quinazoline,
2-amino-6-(4-fluorophenyl)-4-hydrazino-quinazoline,
2-amino-6-(4-fluorophenyl)-4-(N,N-dimethylamino)-quinazoline,
2-amino-6-(4-fluorophenyl)-4-(N,N-dimethylamino)-quinazoline,
2-amino-6-(4-fluorophenyl)-4-(N-butylamino)-quinazoline,
2-amino-6-(4-fluorophenyl)-4-(N-cyclopentylamino)-quinazoline,
2-amino-6-(4-fluorophenyl)-4-(N-cyclopropylamino)-quinazoline,
2-amino-6-(4-fluorophenyl)-4-(N-isopentylamino)-quinazoline,
2-amino-6-(4-fluorophenyl)-4-(N-propylamino)-quinazoline,
2-amino-6-(4-fluorophenyl)-4-amino-quinazoline,
2-amino-6-bromo-4-(N-morpholino)-quinazoline,
2-amino-6-bromo-4-[N-(3-bromo)-anilino)]-quinazoline,
2-amino-6-bromo-4-[N-(3-methylphenylcarbamoyl)-piperazin-1-yl]-quinazoline,
2-amino-6-bromo-4-[N-(4-methylphenyl)piperazin-1-yl]-quinazoline,
2-amino-6-bromo-4-(N-acetylpiperazino)-quinazoline,
2-amino-6-bromo-4-(N-cyclohexylamino)-quinazoline,
2-amino-6-bromo-4-(N-methylpiperazino)-quinazoline,
2-amino-6-bromo-4-(N-piperidino)-quinazoline,
2-amino-6-bromo-4-[N-(3-methyl)-anilino]-quinazoline,
2-amino-6-bromo-4-hydrazino-quinazoline,
2-amino-6-bromo-4-(N,N-dimethylamino)-quinazoline,
2-amino-6-bromo-4-(N,N-dimethylamino)-quinazoline,
2-amino-6-bromo-4-(N-butylamino)-quinazoline,
2-amino-6-bromo-4-(N-cyclopentylamino)-quinazoline,
2-amino-6-bromo-4-(N-cyclopropylamino)-quinazoline,
2-amino-6-bromo-4-(N-isopentylamino)-quinazoline,
2-amino-6-bromo-4-(N-propylamino)-quinazoline,
2-amino-6-bromo-4-amino-quinazoline,
2-acetamino-6-(3,4-dimethoxyphenyl)-4-(N-morpholino)-quinazoline,
2-acetamino-6-(3,4-dimethoxyphenyl)-4-[N-(3-bromo)-anilino)]-quinazoline,
2-acetamino-6-(3,4-dimethoxyphenyl)-4-[N-(3-methylphenylcarbamoyl)-piperazin-1-yl]-quinazoline,
2-acetamino-6-(3,4-dimethoxyphenyl)-4-[N-(4-methylphenyl)piperazin-1-yl]-quinazoline,
2-acetamino-6-(3,4-dimethoxyphenyl)-4-(N-acetylpiperazino)-quinazoline,
2-acetamino-6-(3,4-dimethoxyphenyl)-4-(N-cyclohexylamino)-quinazoline,
2-acetamino-6-(3,4-dimethoxyphenyl)-4-(N-methylpiperazino)-quinazoline,
2-acetamino-6-(3,4-dimethoxyphenyl)-4-(N-piperidino)-quinazoline,
2-acetamino-6-(3,4-dimethoxyphenyl)-4-[N-(3-methyl)-anilino]-quinazoline,
2-acetamino-6-(3,4-dimethoxyphenyl)-4-hydrazino-quinazoline,
2-acetamino-6-(3,4-dimethoxyphenyl)-4-(N,N-dimethylamino)-quinazoline,
2-acetamino-6-(3,4-dimethoxyphenyl)-4-(N,N-dimethylamino)-quinazoline,
2-acetamino-6-(3,4-dimethoxyphenyl)-4-(N-butylamino)-quinazoline,
2-acetamino-6-(3,4-dimethoxyphenyl)-4-(N-cyclopentylamino)-quinazoline,
2-acetamino-6-(3,4-dimethoxyphenyl)-4-(N-cyclopropylamino)-quinazoline,
2-acetamino-6-(3,4-dimethoxyphenyl)-4-(N-isopentylamino)-quinazoline,
2-acetamino-6-(3,4-dimethoxyphenyl)-4-(N-propylamino)-quinazoline,
2-acetamino-6-(3,4-dimethoxyphenyl)-4-amino-quinazoline,
2-acetamino-6-(4-acetamidophenyl)-4-(N-morpholino)-quinazoline,
2-acetamino-6-(4-acetamidophenyl)-4-[N-(3-bromo)-anilino)]-quinazoline,
2-acetamino-6-(4-acetamidophenyl)-4-[N-(3-methylphenylcarbamoyl)-piperazin-1-yl]-quinazoline,
2-acetamino-6-(4-acetamidophenyl)-4-[N-(4-methylphenyl)piperazin-1-yl]-quinazoline,
2-acetamino-6-(4-acetamidophenyl)-4-(N-acetylpiperazino)-quinazoline,
2-acetamino-6-(4-acetamidophenyl)-4-(N-cyclohexylamino)-quinazoline,
2-acetamino-6-(4-acetamidophenyl)-4-(N-methylpiperazino)-quinazoline,
2-acetamino-6-(4-acetamidophenyl)-4-(N-piperidino)-quinazoline,
2-acetamino-6-(4-acetamidophenyl)-4-[N-(3-methyl)-anilino]-quinazoline,
2-acetamino-6-(4-acetamidophenyl)-4-hydrazino-quinazoline,
2-acetamino-6-(4-acetamidophenyl)-4-(N,N-dimethylamino)-quinazoline,
2-acetamino-6-(4-acetamidophenyl)-4-(N,N-dimethylamino)-quinazoline,
2-acetamino-6-(4-acetamidophenyl)-4-(N-butylamino)-quinazoline, 2-acetamino-6-(4-acetamidophenyl)-4-(N-cyclopentylamino)-quinazoline,
2-acetamino-6-(4-acetamidophenyl)-4-(N-cyclopropylamino)-quinazoline,
2-acetamino-6-(4-acetamidophenyl)-4-(N-isopentylamino)-quinazoline,
2-acetamino-6-(4-acetamidophenyl)-4-(N-propylamino)-quinazoline,
2-acetamino-6-(4-acetamidophenyl)-4-amino-quinazoline,
2-acetamino-6-(4-chlorophenyl)-4-(N-morpholino)-quinazoline,
2-acetamino-6-(4-chlorophenyl)-4-[N-(3-bromo)-anilino)]-quinazoline,
2-acetamino-6-(4-chlorophenyl)-4-[N-(3-methylphenylcarbamoyl)-piperazin-1-yl]-quinazoline,
2-acetamino-6-(4-chlorophenyl)-4-[N-(4-methylphenyl)piperazin-1-yl]-quinazoline,
2-acetamino-6-(4-chlorophenyl)-4-(N-acetylpiperazino)-quinazoline,
2-acetamino-6-(4-chlorophenyl)-4-(N-cyclohexylamino)-quinazoline,
2-acetamino-6-(4-chlorophenyl)-4-(N-methylpiperazino)-quinazoline,
2-acetamino-6-(4-chlorophenyl)-4-(N-piperidino)-quinazoline,
2-acetamino-6-(4-chlorophenyl)-4-[N-(3-methyl)-anilino]-quinazoline,
2-acetamino-6-(4-chlorophenyl)-4-hydrazino-quinazoline,
2-acetamino-6-(4-chlorophenyl)-4-(N,N-dimethylamino)-quinazoline,
2-acetamino-6-(4-chlorophenyl)-4-(N,N-dimethylamino)-quinazoline,
2-acetamino-6-(4-chlorophenyl)-4-(N-butylamino)-quinazoline,
2-acetamino-6-(4-chlorophenyl)-4-(N-cyclopentylamino)-quinazoline,
2-acetamino-6-(4-chlorophenyl)-4-(N-cyclopropylamino)-quinazoline,
2-acetamino-6-(4-chlorophenyl)-4-(N-isopentylamino)-quinazoline,
2-acetamino-6-(4-chlorophenyl)-4-(N-propylamino)-quinazoline,
2-acetamino-6-(4-chlorophenyl)-4-amino-quinazoline,
2-acetamino-6-(4-fluorophenyl)-4-(N-morpholino)-quinazoline,
2-acetamino-6-(4-fluorophenyl)-4-[N-(3-bromo)-anilino)]-quinazoline,
2-acetamino-6-(4-fluorophenyl)-4-[N-(3-methylphenylcarbamoyl)-piperazin-1-yl]-quinazoline,
2-acetamino-6-(4-fluorophenyl)-4-[N-(4-methylphenyl)piperazin-1-yl]-quinazoline,
2-acetamino-6-(4-fluorophenyl)-4-(N-acetylpiperazino)-quinazoline,
2-acetamino-6-(4-fluorophenyl)-4-(N-cyclohexylamino)-quinazoline,
2-acetamino-6-(4-fluorophenyl)-4-(N-methylpiperazino)-quinazoline,
2-acetamino-6-(4-fluorophenyl)-4-(N-piperidino)-quinazoline,
2-acetamino-6-(4-fluorophenyl)-4-[N-(3-methyl)-anilino]-quinazoline,
2-acetamino-6-(4-fluorophenyl)-4-hydrazino-quinazoline,
2-acetamino-6-(4-fluorophenyl)-4-(N,N-dimethylamino)-quinazoline,
2-acetamino-6-(4-fluorophenyl)-4-(N-butylamino)-quinazoline,
2-acetamino-6-(4-fluorophenyl)-4-(N-cyclopentylamino)-quinazoline,
2-acetamino-6-(4-fluorophenyl)-4-(N-cyclopropylamino)-quinazoline,
2-acetamino-6-(4-fluorophenyl)-4-(N-isopentylamino)-quinazoline,
2-acetamino-6-(4-fluorophenyl)-4-(N-propylamino)-quinazoline,
2-acetamino-6-(4-fluorophenyl)-4-amino-quinazoline,
2-acetamino-6-bromo-4-(N-morpholino)-quinazoline,
2-acetamino-6-bromo-4-[N-(3-bromo)-anilino)]-quinazoline,
2-acetamino-6-bromo-4-[N-(3-methylphenylcarbamoyl)-piperazin-1-yl]-quinazoline,
2-acetamino-6-bromo-4-[N-(4-methylphenyl)piperazin-1-yl]-quinazoline,
2-acetamino-6-bromo-4-(N-acetylpiperazino)-quinazoline,
2-acetamino-6-bromo-4-(N-cyclohexylamino)-quinazoline,
2-acetamino-6-bromo-4-(N-methylpiperazino)-quinazoline,
2-acetamino-6-bromo-4-(N-piperidino)-quinazoline,
2-acetamino-6-bromo-4-[N-(3-methyl)-anilino]-quinazoline,
2-acetamino-6-bromo-4-hydrazino-quinazoline,
2-acetamino-6-bromo-4-(N,N-dimethylamino)-quinazoline,
2-acetamino-6-bromo-4-(N,N-dimethylamino)-quinazoline,
2-acetamino-6-bromo-4-(N-butylamino)-quinazoline,
2-acetamino-6-bromo-4-(N-cyclopentylamino)-quinazoline,
2-acetamino-6-bromo-4-(N-cyclopropylamino)-quinazoline,
2-acetamino-6-bromo-4-(N-isopentylamino)-quinazoline,
2-acetamino-6-bromo-4-(N-propylamino)-quinazoline,
2-acetamino-6-bromo-4-amino-quinazoline,
6-bromo-N4-(2-methoxy-ethyl)-quinazoline-2,4-diamine,
4-((3-bromo)-anilino)-6-(4-(4'-allyloxycarbonylpiperazino)phenyl)quinazolin-2-ylamine,
4-((3-bromo)-anilino)-6-(3-aminocarbonylphenyl)quinazolin-2-ylamine,
4-((3-bromo)-anilino)-6-(4-aminocarbonylphenyl)quinazolin-2-ylamine,
4-((3-bromo)-anilino)-6-(2-amino-5-chlorophenyl)quinazolin-2-ylamine,
4-((3-bromo)-anilino)-6-(4-amino-3-ethoxyphenyl)quinazolin-2-ylamine,
4-((3-bromo)-anilino)-6-(2-amino-4-methylphenyl)quinazolin-2-ylamine,
4-((3-bromo)-anilino)-6-(2-amino-5-methylphenyl)quinazolin-2-ylamine,
4-((3-bromo)-anilino)-6-(4-amino-2-methyl phenyl)quinazolin-2-ylamine,
4-((3-bromo)-anilino)-6-(5-amino-2-methyl phenyl)quinazolin-2-ylamine,
4-((3-bromo)-anilino)-6-(4-amino-3-nitrophenyl)quinazolin-2-ylamine,
4-((3-bromo)-anilino)-6-(2-benzyloxyphenyl)quinazolin-2-ylamine,
4-((3-bromo)-anilino)-6-(3-benzyloxy-4-ethoxyphenyl)quinazolin-2-ylamine, 4-((3-bromo)-anilino)-6-(4-biphenyl)quinazolin-2-ylamine,
4-((3-bromo)-anilino)-6-(4-n-butyl phenyl)quinazolin-2-ylamine,
4-((3-bromo)-anilino)-6-(4-isobutylphenyl)quinazolin-2-ylamine,
4-((3-bromo)-anilino)-6-(4-carboxy-3-fluorophenyl)quinazolin-2-ylamine,
4-((3-bromo)-anilino)-6-(3-(3-carboxypropionylamino)phenyl)quinazolin-2-ylamine,
4-((3-bromo)-anilino)-6-(4-(3-carboxypropionylamino)phenyl)quinazolin-2-ylamine,
4-((3-bromo)-anilino)-6-(3-chloro-4-hydroxy-5-ethoxyphenyl)quinazolin-2-ylamine,
4-((3-bromo)-anilino)-6-(2-chloro-5-hydroxymethylphenyl)quinazolin-2-ylamine,
4-((3-bromo)-anilino)-6-(4-cyanoethoxyphenyl)quinazolin-2-ylamine,
4-((3-bromo)-anilino)-6-(3-cyanoethoxyphenyl)quinazolin-2-ylamine,
4-((3-bromo)-anilino)-6-(2-cyanoethoxyphenyl)quinazolin-2-ylamine,
4-((3-bromo)-anilino)-6-(4-cyanophenyl)quinazolin-2-ylamine,
4-((3-bromo)-anilino)-6-(3-cyanophenyl)quinazolin-2-ylamine,
4-((3-bromo)-anilino)-6-(2-cyanophenyl)quinazolin-2-ylamine,
4-((3-bromo)-anilino)-6-(3-(N-cyclopropylaminocarbonyl)phenyl)quinazolin-2-ylamine,
4-((3-bromo)-anilino)-6-(3-(N,N-diethylaminocarbonyl)phenyl)quinazolin-2-ylamine,
4-((3-bromo)-anilino)-6-(3-(N,N-dimethylamino)phenyl)quinazolin-2-ylamine,
4-((3-bromo)-anilino)-6-(2-(N,N-dimethylamino)phenyl)quinazolin-2-ylamine,
4-((3-bromo)-anilino)-6-(3-(N,N-dimethylaminocarbonyl)phenyl)quinazolin-2-ylamine,
4-((3-bromo)-anilino)-6-(3-[(N',N'-dimethylamino)ethylaminocarbonyl]phenyl)-quinazolin-2-ylamine,
4-((3-bromo)-anilino)-6-(4-[(N',N'-dimethylamino)ethylaminocarbonyl]phenyl)-quinazolin-2-ylamine,
4-((3-bromo)-anilino)-6-(3-[1,3]dioxolan-2-ylethoxyphenyl)quinazolin-2-ylamine,
4-((3-bromo)-anilino)-6-(3-(ethoxycarbonyl)ethoxyphenyl)quinazolin-2-ylamine,
4-((3-bromo)-anilino)-6-(4-(ethoxycarbonyl)ethoxyphenyl)quinazolin-2-ylamine,
4-((3-bromo)-anilino)-6-(4-ethoxycarbonylphenyl)quinazolin-2-ylamine,
4-((3-bromo)-anilino)-6-(3-ethoxycarbonylphenyl)quinazolin-2-ylamine,
4-((3-bromo)-anilino)-6-(2-ethoxycarbonylphenyl)quinazolin-2-ylamine,
4-((3-bromo)-anilino)-6-(4-(3-ethoxycarbonylpiperidino)carboxamidophenyl)-quinazolin-2-ylamine,
4-((3-bromo)-anilino)-6-(4-formylaminophenyl)quinazolin-2-ylamine,
4-((3-bromo)-anilino)-6-(3-formylaminophenyl)quinazolin-2-ylamine,
4-((3-bromo)-anilino)-6-(2-formylaminophenyl)quinazolin-2-ylamine,
4-((3-bromo)-anilino)-6-(2-formyl-5-ethoxyphenyl)quinazolin-2-ylamine,
4-((3-bromo)-anilino)-6-(3-formyl-4-ethoxyphenyl)quinazolin-2-ylamine,
4-((3-bromo)-anilino)-6-(5-formyl-2-ethoxyphenyl)quinazolin-2-ylamine,
4-((3-bromo)-anilino)-6-(2-formyl-5-methylphenyl)quinazolin-2-ylamine,
4-((3-bromo)-anilino)-6-(4-formylphenyl)quinazolin-2-ylamine,
4-((3-bromo)-anilino)-6-(3-formylphenyl)quinazolin-2-ylamine,
4-((3-bromo)-anilino)-6-(2-formylphenyl)quinazolin-2-ylamine,
4-((3-bromo)-anilino)-6-(4-hydroxy-3,5-dimethylphenyl)quinazolin-2-ylamine,
4-((3-bromo)-anilino)-6-(3-(2-hydroxyethyl)-aminocarbonylphenyl)quinazolin-2-ylamine,
4-((3-bromo)-anilino)-6-(4-(2-hydroxyethyl)aminocarbonyl)phenyl)quinazolin-2-ylamine,
4-((3-bromo)-anilino)-6-(3-hydroxy-4-ethoxycarbonylphenyl)quinazolin-2-ylamine,
4-((3-bromo)-anilino)-6-(4-hydroxy-3-ethoxyphenyl)quinazolin-2-ylamine,
4-((3-bromo)-anilino)-6-(4-(hydroxymethyl)phenyl)quinazolin-2-ylamine,
4-((3-bromo)-anilino)-6-(3-(hydroxymethyl)phenyl)quinazolin-2-ylamine,
4-((3-bromo)-anilino)-6-(4-hydroxy-3-nitrophenyl)quinazolin-2-ylamine,
4-((3-bromo)-anilino)-6-(4-isopropoxyphenyl)quinazolin-2-ylamine,
4-((3-bromo)-anilino)-6-(4-(4-isopropylpiperazinyl)phenyl)quinazolin-2-ylamine,
4-((3-bromo)-anilino)-6-(4-isopropylphenyl)quinazolin-2-ylamine,
4-((3-bromo)-anilino)-6-(4-methanesulfonamidophenyl)quinazolin-2-ylamine,
4-((3-bromo)-anilino)-6-(3-methanesulfonamidophenyl)quinazolin-2-ylamine,
4-((3-bromo)-anilino)-6-(2-methanesulfonamido phenyl)quinazolin-2-ylamine,
4-((3-bromo)-anilino)-6-(4-ethoxycarbonylphenyl)quinazolin-2-ylamine,
4-((3-bromo)-anilino)-6-(3-ethoxycarbonylphenyl)quinazolin-2-ylamine,
4-((3-bromo)-anilino)-6-(2-ethoxycarbonylphenyl)quinazolin-2-ylamine,
4-((3-bromo)-anilino)-6-(3-ethoxy-4-ethoxycarbonylphenyl)quinazolin-2-ylamine,
4-((3-bromo)-anilino)-6-(2-ethoxy-5-methylphenyl)quinazolin-2-ylamine,
4-((3-bromo)-anilino)-6-(4-ethoxy-3-nitrophenyl)quinazolin-2-ylamine,
4-((3-bromo)-anilino)-6-(4-ethoxyphenyl)quinazolin-2-ylamine,
4-((3-bromo)-anilino)-6-(3-ethoxyphenyl)quinazolin-2-ylamine,
4-((3-bromo)-anilino)-6-(4-N-methylcarboxamidophenyl)quinazolin-2-ylamine,
4-((3-bromo)-anilino)-6-(4-(N-methylamino)phenyl)quinazolin-2-ylamine,
4-((3-bromo)-anilino)-6-(3-(4-methylpiperazine-1-carbonyl)phenyl)quinazolin-2-ylamine,
4-((3-bromo)-anilino)-6-(4-(4-methylpiperazine-1-carbonyl)phenyl)quinazolin-2-ylamine,
4-((3-bromo)-anilino)-6-(4-(methylthio)phenyl)quinazolin-2-ylamine,
4-((3-bromo)-anilino)-6-(3-(methylthio)phenyl)quinazolin-2-ylamine, 4-((3-bromo)-anilino)-6-(2-(methylthio)phenyl)quinazolin-2-ylamine,
4-((3-bromo)-anilino)-6-(4-(morpholinocarbonyl)phenyl)quinazolin-2-ylamine,
4-((3-bromo)-anilino)-6-(4-morpholinophenyl)quinazolin-2-ylamine,
4-((3-bromo)-anilino)-6-(2-(morpholinomethyl)phenyl)quinazolin-2-ylamine,
4-((3-bromo)-anilino)-6-(4-nitrophenyl)quinazolin-2-ylamine,
4-((3-bromo)-anilino)-6-(3-nitrophenyl)quinazolin-2-ylamine,
4-((3-bromo)-anilino)-6-(2-nitrophenyl)quinazolin-2-ylamine,
4-((3-bromo)-anilino)-6-(4-phenoxyphenyl)quinazolin-2-ylamine,
4-((3-bromo)-anilino)-6-(4-(N-phenylaminomethyl)phenyl)quinazolin-2-ylamine,
4-((3-bromo)-anilino)-6-(4-(phenylcarbonyl)phenyl)quinazolin-2-ylamine,
4-((3-bromo)-anilino)-6-(4-(piperazine-1-carbonyl)phenyl)quinazolin-2-ylamine,
4-((3-bromo)-anilino)-6-(4-piperazinylphenyl)quinazolin-2-ylamine,
4-((3-bromo)-anilino)-6-(4-succinamidophenyl)quinazolin-2-ylamine,
4-((3-bromo)-anilino)-6-(3-succinamidophenyl)quinazolin-2-ylamine,
4-((3-bromo)-anilino)-6-(sulfamoylphenyl)quinazolin-2-ylamine,
4-((3-bromo)-anilino)-6-(2-(toluene-4-sulfonamido)phenyl)quinazolin-2-ylamine,
4-((3-bromo)-anilino)-6-(4-(toluene-4-sulfonamido)phenyl)quinazolin-2-ylamine,
4-((3-bromo)-anilino)-6-(4-(tert-butoxycarbonylamino)-3-ethoxyphenyl)quinazolin-2-ylamine,
4-((3-bromo)-anilino)-6-(2-(tert-butoxycarbonyl)phenyl)quinazolin-2-ylamine,
4-((3-bromo)-anilino)-6-(3-(tert-butoxycarbonyl)phenyl)quinazolin-2-ylamine,
4-((3-bromo)-anilino)-6-(4-(tert-butoxycarbonyl)phenyl)quinazolin-2-ylamine,
4-((3-bromo)-anilino)-6-(2,3,4-trifluorophenyl)quinazolin-2-ylamine,
4-((3-bromo)-anilino)-6-(4-tert-butylphenyl)quinazolin-2-ylamine,
4-((3-bromo)-anilino)-6-(4-(tetrahydro-2H-pyran-2-yloxy)phenyl)quinazolin-2-ylamine,
4-((3-bromo)-anilino)-6-(4-(2-thienyl)phenyl)quinazolin-2-ylamine,
4-((3-bromo)-anilino)-6-(2,4,6-trimethylphenyl)quinazolin-2-ylamine,
4-((3-bromo)-anilino)-6-(3,4,5-trimethoxyphenyl)quinazolin-2-ylamine,
4-((3-bromo)-anilino)-6-(4-vinylphenyl)quinazolin-2-ylamine,
4-((3-bromo)-anilino)-6-(4-(2-hydroxyethoxyphenyl)quinazolin-2-ylamine,
4-((3-bromo)-anilino)-6-(6-benzyloxynaphth-2-yl)quinazolin-2-ylamine,
4-((3-bromo)-anilino)-6-(naphth-1-yl)quinazolin-2-ylamine,
4-((3-bromo)-anilino)-6-(naphth-2-yl)quinazolin-2-ylamine,
4-((3-bromo)-anilino)-6-(4'-benzoyl[1,1'-biphenyl]-4-yl)quinazolin-2-ylamine,
4-((3-bromo)-anilino)-6-(1-biphenylyl)quinazolin-2-ylamine,
4-((3-bromo)-anilino)-6-(oxoindan-5-yl)quinazolin-2-ylamine,
4-((3-bromo)-anilino)-6-(benzodioxolyl)quinazolin-2-ylamine,
4-((3-bromo)-anilino)-6-(2-acetamidopyridin-5-yl)quinazolin-2-ylamine,
4-((3-bromo)-anilino)-6-(2-aminopyridin-5-yl)quinazolin-2-ylamine,
4-((3-bromo)-anilino)-6-(2-aminopyrimidin-5-yl)quinazolin-2-ylamine,
4-((3-bromo)-anilino)-6-(1,4-benzodioxan-6-yl)quinazolin-2-ylamine,
4-((3-bromo)-anilino)-6-(1-benzothien-3-yl)quinazolin-2-ylamine,
4-((3-bromo)-anilino)-6-(2-benzyloxypyridin-5-yl)quinazolin-2-ylamine,
4-((3-bromo)-anilino)-6-(1-benzyl-1H-pyrazol-4-yl)quinazolin-2-ylamine,
4-((3-bromo)-anilino)-6-(2-bromo-3-chloropyridin-4-yl)quinazolin-2-ylamine,
4-((3-bromo)-anilino)-6-(5-bromo-2,3-dihydrobenzo[b]furan-7-yl)quinazolin-2-ylamine,
4-((3-bromo)-anilino)-6-(2-bromo-3-methylpyridin-5-yl)quinazolin-2-ylamine,
4-((3-bromo)-anilino)-6-(2-bromopyridin-5-yl)quinazolin-2-ylamine,
4-((3-bromo)-anilino)-6-(3-bromopyridin-5-yl)quinazolin-2-ylamine,
4-((3-bromo)-anilino)-6-(5-bromothien-2-yl)quinazolin-2-ylamine,
4-((3-bromo)-anilino)-6-(2-chloro-6-isopropylpyridin-3-yl)quinazolin-2-ylamine,
4-((3-bromo)-anilino)-6-(2-chloro-3-methylpyridin-5-yl)quinazolin-2-ylamine,
4-((3-bromo)-anilino)-6-(2-[4-(4-chlorophenylsulfonyl)piperazin-1-yl]pyridin-5-yl)quinazolin-2-ylamine,
4-((3-bromo)-anilino)-6-(2-chloropyrid-4-yl)quinazolin-2-ylamine,
4-((3-bromo)-anilino)-6-(2-chloropyrid-5-yl)quinazolin-2-ylamine,
4-((3-bromo)-anilino)-6-(dibenzo[b,d]furan-4-yl)quinazolin-2-ylamine,
4-((3-bromo)-anilino)-6-(2-chloro-3-fluoropyridin-4-yl)quinazolin-2-ylamine,
4-((3-bromo)-anilino)-6-(dibenzo[b,d]thien-4-yl)quinazolin-2-ylamine,
4-((3-bromo)-anilino)-6-(3,4-dihydro-2H-1,5-benzodioxepin-7-yl)quinazolin-2-ylamine,
4-((3-bromo)-anilino)-6-(3,6-dihydro-2H-pyridine-1-tert-butoxycarbonyl)quinazolin-2-ylamine,
4-((3-bromo)-anilino)-6-(2,5-dibromopyridin-3-yl)quinazolin-2-ylamine,
4-((3-bromo)-anilino)-6-(2,6-dichloropyridin-3-yl)quinazolin-2-ylamine,
4-((3-bromo)-anilino)-6-(2,3-dihydro-1-benzofuran-5-yl)quinazolin-2-ylamine,
4-((3-bromo)-anilino)-6-(2,6-diethoxypyridin-5-yl)quinazolin-2-ylamine,
4-((3-bromo)-anilino)-6-(2,6-diethoxypyridin-3-yl)quinazolin-2-ylamine,
4-((3-bromo)-anilino)-6-(2,4-diethoxypyrimidin-5-yl)quinazolin-2-ylamine,
4-((3-bromo)-anilino)-6-(3,5-dimethylisoxazol-4-yl)quinazolin-2-ylamine, 4-((3-bromo)-anilino)-6-(2-(3-N,N-dimethylaminopropoxy)pyridin-5-yl)quinazolin-2-ylamine,
4-((3-bromo)-anilino)-6-(3,5-dimethylpyrazol-4-yl)quinazolin-2-ylamine,
4-((3-bromo)-anilino)-6-(1-[1,3]dioxolan-2-ylmethyl-1H-pyrazol-4-yl)quinazolin-2-ylamine,
4-((3-bromo)-anilino)-6-(2,4-dioxo-1,2,3,4-tetrahydro-5-pyrimidinyl)quinazolin-2-ylamine,
4-((3-bromo)-anilino)-6-(2,4-di(tert-butoxy)pyrimidin-5-yl)quinazolin-2-ylamine,
4-((3-bromo)-anilino)-6-(2-ethoxypyridin-3-yl)quinazolin-2-ylamine,
4-((3-bromo)-anilino)-6-(2-fluoro-3-methylpyridin-5-yl)quinazolin-2-ylamine,
4-((3-bromo)-anilino)-6-(2-fluoropyridin-5-yl)quinazolin-2-ylamine,
4-((3-bromo)-anilino)-6-(5-formyl-2-furyl)quinazolin-2-ylamine,
4-((3-bromo)-anilino)-6-(5-formylthien-2-yl)quinazolin-2-ylamine,
4-((3-bromo)-anilino)-6-(furan-2-yl)quinazolin-2-ylamine,
4-((3-bromo)-anilino)-6-(2-hydroxypyridin-5-yl)quinazolin-2-ylamine,
4-((3-bromo)-anilino)-6-(1-isobutyl-1H-pyrazol-4-yl)quinazolin-2-ylamine,
4-((3-bromo)-anilino)-6-(isoquinolin-4-yl)quinazolin-2-ylamine,
4-((3-bromo)-anilino)-6-(2-ethoxypyridin-3-yl)quinazolin-2-ylamine,
4-((3-bromo)-anilino)-6-(2-ethoxypyrimidin-5-yl)quinazolin-2-ylamine,
4-((3-bromo)-anilino)-6-(5-methyl-1-benzothien-2-yl)quinazolin-2-ylamine,
4-((3-bromo)-anilino)-6-(1-(3-methylbutyl)-1H-pyrazol-4-yl)quinazolin-2-ylamine,
4-((3-bromo)-anilino)-6-(5-methylfuran-2-yl)quinazolin-2-ylamine,
4-((3-bromo)-anilino)-6-(1-methylindol-5-yl)quinazolin-2-ylamine,
4-((3-bromo)-anilino)-6-(5-methyl-3-phenyl-4-isoxazolyl)quinazolin-2-ylamine,
4-((3-bromo)-anilino)-6-(5-(methylthio)thien-2-yl)quinazolin-2-ylamine,
4-((3-bromo)-anilino)-6-(2-(4-methylpiperazinyl)pyridin-4-yl)quinazolin-2-ylamine,
4-((3-bromo)-anilino)-6-(2-(4-methylpiperazinyl)pyridin-5-yl)quinazolin-2-ylamine,
4-((3-bromo)-anilino)-6-(1-methyl-1H-pyrazol-4-yl)quinazolin-2-ylamine,
4-((3-bromo)-anilino)-6-(3-methylpyridin-2-yl)quinazolin-2-ylamine,
4-((3-bromo)-anilino)-6-(5-methylpyridin-2-yl)quinazolin-2-ylamine,
4-((3-bromo)-anilino)-6-(5-methylpyridin-3-yl)quinazolin-2-ylamine,
4-((3-bromo)-anilino)-6-(2-ethoxypyridin-5-yl)quinazolin-2-ylamine,
4-((3-bromo)-anilino)-6-(4-methylthien-2-yl)quinazolin-2-ylamine,
4-((3-bromo)-anilino)-6-(5-methylthien-2-yl)quinazolin-2-ylamine,
4-((3-bromo)-anilino)-6-(2-(2-morpholinoethylamino)-pyridin-5-yl)quinazolin-2-ylamine,
4-((3-bromo)-anilino)-6-(2-(2-morpholinoethyl)-1H-pyrazol-4-yl)quinazolin-2-ylamine,
4-((3-bromo)-anilino)-6-(2-(morpholin-1-yl)-pyridin-5-yl)quinazolin-2-ylamine,
4-((3-bromo)-anilino)-6-(1-(phenylsulfonyl)-1H-indol-3-yl)quinazolin-2-ylamine,
4-((3-bromo)-anilino)-6-(5-phenyl-2-thienyl)quinazolin-2-ylamine,
4-((3-bromo)-anilino)-6-(2-(piperazin-1-yl)-pyridin-5-yl)quinazolin-2-ylamine,
4-((3-bromo)-anilino)-6-(2-(piperazin-1-yl)-pyridin-4-yl)quinazolin-2-ylamine,
4-((3-bromo)-anilino)-6-(1-propyl-1H-pyrazol-4-yl)quinazolin-2-ylamine,
4-((3-bromo)-anilino)-6-(pyrazol-4-yl)quinazolin-2-ylamine,
4-((3-bromo)-anilino)-6-(pyridin-4-yl)quinazolin-2-ylamine,
4-((3-bromo)-anilino)-6-(4-phenoxathiinyl)quinazolin-2-ylamine,
4-((3-bromo)-anilino)-6-(quinolin-8-yl)quinazolin-2-ylamine,
4-((3-bromo)-anilino)-6-(quinolin-3-yl)quinazolin-2-ylamine,
4-((3-bromo)-anilino)-6-(2-(4-tert-butoxycarbonylpiperazinyl)-pyrid-4-yl)quinazolin-2-ylamine,
4-((3-bromo)-anilino)-6-(1-tert-butoxycarbonyl-1H-pyrazol-4-yl)quinazolin-2-ylamine,
4-((3-bromo)-anilino)-6-(1-tert-butoxycarbonyl-2-pyrrolyl)quinazolin-2-ylamine,
4-((3-bromo)-anilino)-6-(1-(tert-butoxycarbonyl)-5-bromo-1H-indol-2-yl)quinazolin-2-ylamine,
4-((3-bromo)-anilino)-6-(1-(tert-butoxycarbonyl)-1H-indol-5-yl)quinazolin-2-ylamine,
4-((3-bromo)-anilino)-6-(1-(tert-butoxycarbonyl)-5-methoxy-1H-indol-2-yl)quinazolin-2-ylamine,
4-((3-bromo)-anilino)-6-(1-thianthrenylthien-3-yl)quinazolin-2-ylamine,
4-((3-bromo)-anilino)-6-(1,3,5-trimethyl-1H-pyrazol-4-yl)quinazolin-2-ylamine,
4-hydrazino-6-(4-(4'-allyloxycarbonylpiperazino)phenyl)quinazolin-2-ylamine,
4-hydrazino-6-(3-aminocarbonylphenyl)quinazolin-2-ylamine,
4-hydrazino-6-(4-aminocarbonylphenyl)quinazolin-2-ylamine,
4-hydrazino-6-(2-amino-5-chlorophenyl)quinazolin-2-ylamine,
4-hydrazino-6-(4-amino-3-ethoxyphenyl)quinazolin-2-ylamine,
4-hydrazino-6-(2-amino-4-methylphenyl)quinazolin-2-ylamine,
4-hydrazino-6-(2-amino-5-methylphenyl)quinazolin-2-ylamine,
4-hydrazino-6-(4-amino-2-methyl phenyl)quinazolin-2-ylamine,
4-hydrazino-6-(5-amino-2-methyl phenyl)quinazolin-2-ylamine,
4-hydrazino-6-(4-amino-3-nitrophenyl)quinazolin-2-ylamine,
4-hydrazino-6-(2-benzyloxyphenyl)quinazolin-2-ylamine,
4-hydrazino-6-(3-benzyloxy-4-ethoxyphenyl)quinazolin-2-ylamine,
4-hydrazino-6-(4-biphenyl)quinazolin-2-ylamine,
4-hydrazino-6-(4-n-butyl phenyl)quinazolin-2-ylamine,
4-hydrazino-6-(4-isobutylphenyl)quinazolin-2-ylamine,
4-hydrazino-6-(4-carboxy-3-fluorophenyl)quinazolin-2-ylamine, 4-hydrazino-6-(3-(3-carboxypropionylamino)phenyl) quinazolin-2-ylamine,
4-hydrazino-6-(4-(3-carboxypropionylamino)phenyl) quinazolin-2-ylamine,
4-hydrazino-6-(3-chloro-4-hydroxy-5-ethoxyphenyl) quinazolin-2-ylamine,
4-hydrazino-6-(2-chloro-5-hydroxymethylphenyl) quinazolin-2-ylamine,
4-hydrazino-6-(4-cyanoethoxyphenyl)quinazolin-2-ylamine,
4-hydrazino-6-(3-cyanoethoxyphenyl)quinazolin-2-ylamine,
4-hydrazino-6-(2-cyanoethoxyphenyl)quinazolin-2-ylamine,
4-hydrazino-6-(4-cyanophenyl)quinazolin-2-ylamine,
4-hydrazino-6-(3-cyanophenyl)quinazolin-2-ylamine,
4-hydrazino-6-(2-cyanophenyl)quinazolin-2-ylamine,
4-hydrazino-6-(3-(N-cyclopropylaminocarbonyl)phenyl) quinazolin-2-ylamine,
4-hydrazino-6-(3-(N,N-diethylaminocarbonyl)phenyl) quinazolin-2-ylamine,
4-hydrazino-6-(3-(N,N-dimethylamino)phenyl)quinazolin-2-ylamine,
4-hydrazino-6-(2-(N,N-dimethylamino)phenyl)quinazolin-2-ylamine,
4-hydrazino-6-(3-(N,N-dimethylaminocarbonyl)phenyl) quinazolin-2-ylamine,
4-hydrazino-6-(3-[(N',N'-dimethylamino)ethylaminocarbonyl]phenyl)-quinazolin-2-ylamine,
4-hydrazino-6-(4-[(N',N'-dimethylamino)ethylaminocarbonyl]phenyl)-quinazolin-2-ylamine,
4-hydrazino-6-(3-[1,3]dioxolan-2-ylethoxyphenyl) quinazolin-2-ylamine,
4-hydrazino-6-(3-(ethoxycarbonyl)ethoxyphenyl) quinazolin-2-ylamine,
4-hydrazino-6-(4-(ethoxycarbonyl)ethoxyphenyl) quinazolin-2-ylamine,
4-hydrazino-6-(4-ethoxycarbonylphenyl)quinazolin-2-ylamine,
4-hydrazino-6-(3-ethoxycarbonylphenyl)quinazolin-2-ylamine,
4-hydrazino-6-(2-ethoxycarbonylphenyl)quinazolin-2-ylamine,
4-hydrazino-6-(4-(3-ethoxycarbonylpiperidino)carboxamidophenyl)-quinazolin-2-ylamine,
4-hydrazino-6-(4-formylaminophenyl)quinazolin-2-ylamine,
4-hydrazino-6-(3-formylaminophenyl)quinazolin-2-ylamine,
4-hydrazino-6-(2-formylaminophenyl)quinazolin-2-ylamine,
4-hydrazino-6-(2-formyl-5-ethoxyphenyl)quinazolin-2-ylamine,
4-hydrazino-6-(3-formyl-4-ethoxyphenyl)quinazolin-2-ylamine,
4-hydrazino-6-(5-formyl-2-ethoxyphenyl)quinazolin-2-ylamine,
4-hydrazino-6-(2-formyl-5-methylphenyl)quinazolin-2-ylamine,
4-hydrazino-6-(4-formylphenyl)quinazolin-2-ylamine,
4-hydrazino-6-(3-formylphenyl)quinazolin-2-ylamine,
4-hydrazino-6-(2-formylphenyl)quinazolin-2-ylamine,
4-hydrazino-6-(4-hydroxy-3,5-dimethylphenyl)quinazolin-2-ylamine,
4-hydrazino-6-(3-(2-hydroxyethyl)-aminocarbonylphenyl)quinazolin-2-ylamine,
4-hydrazino-6-(4-(2-hydroxyethyl)aminocarbonylphenyl)quinazolin-2-ylamine,
4-hydrazino-6-(3-hydroxy-4-ethoxycarbonylphenyl) quinazolin-2-ylamine,
4-hydrazino-6-(4-hydroxy-3-ethoxyphenyl)quinazolin-2-ylamine,
4-hydrazino-6-(4-(hydroxymethyl)phenyl)quinazolin-2-ylamine,
4-hydrazino-6-(3-(hydroxymethyl)phenyl)quinazolin-2-ylamine,
4-hydrazino-6-(4-hydroxy-3-nitrophenyl)quinazolin-2-ylamine,
4-hydrazino-6-(4-isopropoxyphenyl)quinazolin-2-ylamine,
4-hydrazino-6-(4-(4-isopropylpiperazinyl)phenyl) quinazolin-2-ylamine,
4-hydrazino-6-(4-isopropylphenyl)quinazolin-2-ylamine,
4-hydrazino-6-(4-methanesulfonamidophenyl)quinazolin-2-ylamine,
4-hydrazino-6-(3-methanesulfonamidophenyl)quinazolin-2-ylamine,
4-hydrazino-6-(2-methanesulfonamido phenyl)quinazolin-2-ylamine,
4-hydrazino-6-(4-ethoxycarbonylphenyl)quinazolin-2-ylamine,
4-hydrazino-6-(3-ethoxycarbonylphenyl)quinazolin-2-ylamine,
4-hydrazino-6-(2-ethoxycarbonylphenyl)quinazolin-2-ylamine,
4-hydrazino-6-(3-ethoxy-4-ethoxycarbonylphenyl) quinazolin-2-ylamine,
4-hydrazino-6-(2-ethoxy-5-methylphenyl)quinazolin-2-ylamine,
4-hydrazino-6-(4-ethoxy-3-nitrophenyl)quinazolin-2-ylamine,
4-hydrazino-6-(4-ethoxyphenyl)quinazolin-2-ylamine,
4-hydrazino-6-(3-ethoxyphenyl)quinazolin-2-ylamine,
4-hydrazino-6-(4-N-methylcarboxamidophenyl)quinazolin-2-ylamine,
4-hydrazino-6-(4-(N-methylamino)phenyl)quinazolin-2-ylamine,
4-hydrazino-6-(3-(4-methylpiperazine-1-carbonyl)phenyl)quinazolin-2-ylamine,
4-hydrazino-6-(4-(4-methylpiperazine-1-carbonyl)phenyl)quinazolin-2-ylamine,
4-hydrazino-6-(4-(methylthio)phenyl)quinazolin-2-ylamine,
4-hydrazino-6-(3-(methylthio)phenyl)quinazolin-2-ylamine,
4-hydrazino-6-(2-(methylthio)phenyl)quinazolin-2-ylamine,
4-hydrazino-6-(4-(morpholinocarbonyl)phenyl)quinazolin-2-ylamine,
4-hydrazino-6-(4-morpholinophenyl)quinazolin-2-ylamine,
4-hydrazino-6-(2-(morpholinomethyl)phenyl)quinazolin-2-ylamine,
4-hydrazino-6-(4-nitrophenyl)quinazolin-2-ylamine,
4-hydrazino-6-(3-nitrophenyl)quinazolin-2-ylamine,
4-hydrazino-6-(2-nitrophenyl)quinazolin-2-ylamine,
4-hydrazino-6-(4-phenoxyphenyl)quinazolin-2-ylamine,
4-hydrazino-6-(4-(N-phenylaminomethyl)phenyl) quinazolin-2-ylamine,
4-hydrazino-6-(4-(phenylcarbonyl)phenyl)quinazolin-2-ylamine,
4-hydrazino-6-(4-(piperazine-1-carbonyl)phenyl) quinazolin-2-ylamine, 4-hydrazino-6-(4-piperazinylphenyl)quinazolin-2-ylamine,
4-hydrazino-6-(4-succinamidophenyl)quinazolin-2-ylamine,
4-hydrazino-6-(3-succinamidophenyl)quinazolin-2-ylamine,
4-hydrazino-6-(sulfamoylphenyl)quinazolin-2-ylamine,
4-hydrazino-6-(2-(toluene-4-sulfonamido)phenyl)quinazolin-2-ylamine,
4-hydrazino-6-(4-(toluene-4-sulfonamido)phenyl)quinazolin-2-ylamine,
4-hydrazino-6-(4-(tert-butoxycarbonylamino)-3-ethoxyphenyl)quinazolin-2-ylamine,
4-hydrazino-6-(2-(tert-butoxycarbonyl)phenyl)quinazolin-2-ylamine,
4-hydrazino-6-(3-(tert-butoxycarbonyl)phenyl)quinazolin-2-ylamine,
4-hydrazino-6-(4-(tert-butoxycarbonyl)phenyl)quinazolin-2-ylamine,
4-hydrazino-6-(2,3,4-trifluorophenyl)quinazolin-2-ylamine,
4-hydrazino-6-(4-tert-butylphenyl)quinazolin-2-ylamine,
4-hydrazino-6-(4-(tetrahydro-2H-pyran-2-yloxy)phenyl)quinazolin-2-ylamine,
4-hydrazino-6-(4-(2-thienyl)phenyl)quinazolin-2-ylamine,
4-hydrazino-6-(2,4,6-trimethylphenyl)quinazolin-2-ylamine,
4-hydrazino-6-(3,4,5-trimethoxyphenyl)quinazolin-2-ylamine,
4-hydrazino-6-(4-vinylphenyl)quinazolin-2-ylamine,
4-hydrazino-6-(4-(2-hydroxyhydrazino)phenyl)quinazolin-2-ylamine,
4-hydrazino-6-(6-benzyloxynaphth-2-yl)quinazolin-2-ylamine,
4-hydrazino-6-(naphth-1-yl)quinazolin-2-ylamine,
4-hydrazino-6-(naphth-2-yl)quinazolin-2-ylamine,
4-hydrazino-6-(4'-benzoyl[1,1'-biphenyl]-4-yl)quinazolin-2-ylamine,
4-hydrazino-6-(1-biphenylyl)quinazolin-2-ylamine,
4-hydrazino-6-(oxoindan-5-yl)quinazolin-2-ylamine,
4-hydrazino-6-(benzodioxolyl)quinazolin-2-ylamine,
4-hydrazino-6-(2-acetamidopyridin-5-yl)quinazolin-2-ylamine,
4-hydrazino-6-(2-aminopyridin-5-yl)quinazolin-2-ylamine,
4-hydrazino-6-(2-aminopyrimidin-5-yl)quinazolin-2-ylamine,
4-hydrazino-6-(1,4-benzodioxan-6-yl)quinazolin-2-ylamine,
4-hydrazino-6-(1-benzothien-3-yl)quinazolin-2-ylamine,
4-hydrazino-6-(2-benzyloxypyridin-5-yl)quinazolin-2-ylamine,
4-hydrazino-6-(1-benzyl-1H-pyrazol-4-yl)quinazolin-2-ylamine,
4-hydrazino-6-(2-bromo-3-chloropyridin-4-yl)quinazolin-2-ylamine,
4-hydrazino-6-(5-bromo-2,3-dihydrobenzo[b]furan-7-yl)quinazolin-2-ylamine,
4-hydrazino-6-(2-bromo-3-methylpyridin-5-yl)quinazolin-2-ylamine,
4-hydrazino-6-(2-bromopyridin-5-yl)quinazolin-2-ylamine,
4-hydrazino-6-(3-bromopyridin-5-yl)quinazolin-2-ylamine,
4-hydrazino-6-(5-bromothien-2-yl)quinazolin-2-ylamine,
4-hydrazino-6-(2-chloro-6-isopropylpyridin-3-yl)quinazolin-2-ylamine,
4-hydrazino-6-(2-chloro-3-methylpyridin-5-yl)quinazolin-2-ylamine,
4-hydrazino-6-(2-[4-(4-chlorophenylsulfonyl)piperazin-1-yl]pyridin-5-yl)quinazolin-2-ylamine,
4-hydrazino-6-(2-chloropyrid-4-yl)quinazolin-2-ylamine,
4-hydrazino-6-(2-chloropyrid-5-yl)quinazolin-2-ylamine,
4-hydrazino-6-(dibenzo[b,d]furan-4-yl)quinazolin-2-ylamine,
4-hydrazino-6-(2-chloro-3-fluoropyridin-4-yl)quinazolin-2-ylamine,
4-hydrazino-6-(dibenzo[b,d]thien-4-yl)quinazolin-2-ylamine,
4-hydrazino-6-(3,4-dihydro-2H-1,5-benzodioxepin-7-yl)quinazolin-2-ylamine,
4-hydrazino-6-(3,6-dihydro-2H-pyridine-1-tert-butoxycarbonyl)quinazolin-2-ylamine,
4-hydrazino-6-(2,5-dibromopyridin-3-yl)quinazolin-2-ylamine,
4-hydrazino-6-(2,6-dichloropyridin-3-yl)quinazolin-2-ylamine,
4-hydrazino-6-(2,3-dihydro-1-benzofuran-5-yl)quinazolin-2-ylamine,
4-hydrazino-6-(2,6-diethoxypyridin-5-yl)quinazolin-2-ylamine,
4-hydrazino-6-(2,6-diethoxypyridin-3-yl)quinazolin-2-ylamine,
4-hydrazino-6-(2,4-diethoxypyrimidin-5-yl)quinazolin-2-ylamine,
4-hydrazino-6-(3,5-dimethylisoxazol-4-yl)quinazolin-2-ylamine,
4-hydrazino-6-(2-(3-N,N-dimethylaminopropoxy)pyridin-5-yl)quinazolin-2-ylamine,
4-hydrazino-6-(3,5-dimethylpyrazol-4-yl)quinazolin-2-ylamine,
4-hydrazino-6-(1-[1,3]dioxolan-2-ylmethyl-1H-pyrazol-4-yl)quinazolin-2-ylamine,
4-hydrazino-6-(2,4-dioxo-1,2,3,4-tetrahydro-5-pyrimidinyl)quinazolin-2-ylamine,
4-hydrazino-6-(2,4-di(tert-butoxy)pyrimidin-5-yl)quinazolin-2-ylamine,
4-hydrazino-6-(2-hydrazinopyridin-3-yl)quinazolin-2-ylamine,
4-hydrazino-6-(2-fluoro-3-methylpyridin-5-yl)quinazolin-2-ylamine,
4-hydrazino-6-(2-fluoropyridin-5-yl)quinazolin-2-ylamine,
4-hydrazino-6-(5-formyl-2-furyl)quinazolin-2-ylamine,
4-hydrazino-6-(5-formylthien-2-yl)quinazolin-2-ylamine,
4-hydrazino-6-(furan-2-yl)quinazolin-2-ylamine,
4-hydrazino-6-(2-hydroxypyridin-5-yl)quinazolin-2-ylamine,
4-hydrazino-6-(1-isobutyl-1H-pyrazol-4-yl)quinazolin-2-ylamine,
4-hydrazino-6-(isoquinolin-4-yl)quinazolin-2-ylamine,
4-hydrazino-6-(2-ethoxypyridin-3-yl)quinazolin-2-ylamine,
4-hydrazino-6-(2-ethoxypyrimidin-5-yl)quinazolin-2-ylamine,
4-hydrazino-6-(5-methyl-1-benzothien-2-yl)quinazolin-2-ylamine,
4-hydrazino-6-(1-(3-methylbutyl)-1H-pyrazol-4-yl)quinazolin-2-ylamine,
4-hydrazino-6-(5-methylfuran-2-yl)quinazolin-2-ylamine, 4-hydrazino-6-(1-methylindol-5-yl)quinazolin-2-ylamine,
4-hydrazino-6-(5-methyl-3-phenyl-4-isoxazolyl)quinazolin-2-ylamine,
4-hydrazino-6-(5-(methylthio)thien-2-yl)quinazolin-2-ylamine,
4-hydrazino-6-(2-(4-methylpiperazinyl)pyridin-4-yl)quinazolin-2-ylamine,
4-hydrazino-6-(2-(4-methylpiperazinyl)pyridin-5-yl)quinazolin-2-ylamine,
4-hydrazino-6-(1-methyl-1H-pyrazol-4-yl)quinazolin-2-ylamine,
4-hydrazino-6-(3-methylpyridin-2-yl)quinazolin-2-ylamine,
4-hydrazino-6-(5-methylpyridin-2-yl)quinazolin-2-ylamine,
4-hydrazino-6-(5-methylpyridin-3-yl)quinazolin-2-ylamine,
4-hydrazino-6-(2-ethoxypyridin-5-yl)quinazolin-2-ylamine,
4-hydrazino-6-(4-methylthien-2-yl)quinazolin-2-ylamine,
4-hydrazino-6-(5-methylthien-2-yl)quinazolin-2-ylamine,
4-hydrazino-6-(2-(2-morpholinoethylamino)-pyridin-5-yl)quinazolin-2-ylamine,
4-hydrazino-6-(2-(2-morpholinoethyl)-1H-pyrazol-4-yl)quinazolin-2-ylamine,
4-hydrazino-6-(2-(morpholin-1-yl)-pyridin-5-yl)quinazolin-2-ylamine,
4-hydrazino-6-(1-(phenylsulfonyl)-1H-indol-3-yl)quinazolin-2-ylamine,
4-hydrazino-6-(5-phenyl-2-thienyl)quinazolin-2-ylamine,
4-hydrazino-6-(2-(piperazin-1-yl)-pyridin-5-yl)quinazolin-2-ylamine,
4-hydrazino-6-(2-(piperazin-1-yl)-pyridin-4-yl)quinazolin-2-ylamine,
4-hydrazino-6-(1-propyl-1H-pyrazol-4-yl)quinazolin-2-ylamine,
4-hydrazino-6-(pyrazol-4-yl)quinazolin-2-ylamine,
4-hydrazino-6-(pyridin-4-yl)quinazolin-2-ylamine,
4-hydrazino-6-(4-phenoxathiinyl)quinazolin-2-ylamine,
4-hydrazino-6-(quinolin-8-yl)quinazolin-2-ylamine,
4-hydrazino-6-(quinolin-3-yl)quinazolin-2-ylamine,
4-hydrazino-6-(2-(4-tert-butoxycarbonylpiperazinyl)-pyrid-4-yl)quinazolin-2-ylamine,
4-hydrazino-6-(1-tert-butoxycarbonyl-1H-pyrazol-4-yl)quinazolin-2-ylamine,
4-hydrazino-6-(1-tert-butoxycarbonyl-2-pyrrolyl)quinazolin-2-ylamine,
4-hydrazino-6-(1-(tert-butoxycarbonyl)-5-bromo-1H-indol-2-yl)quinazolin-2-ylamine,
4-hydrazino-6-(1-(tert-butoxycarbonyl)-1H-indol-5-yl)quinazolin-2-ylamine,
4-hydrazino-6-(1-(tert-butoxycarbonyl)-5-methoxy-1H-indol-2-yl)quinazolin-2-ylamine,
4-hydrazino-6-(1-thianthrenylthien-3-yl)quinazolin-2-ylamine,
4-hydrazino-6-(1,3,5-trimethyl-1H-pyrazol-4-yl)quinazolin-2-ylamine,
4-(N-cyclohexylamino)-6-(4-(4'-allyloxycarbonylpiperazino)phenyl)quinazolin-2-ylamine,
4-(N-cyclohexylamino)-6-(3-aminocarbonylphenyl)quinazolin-2-ylamine,
4-(N-cyclohexylamino)-6-(4-aminocarbonylphenyl)quinazolin-2-ylamine,
4-(N-cyclohexylamino)-6-(2-amino-5-chlorophenyl)quinazolin-2-ylamine,
4-(N-cyclohexylamino)-6-(4-amino-3-ethoxyphenyl)quinazolin-2-ylamine,
4-(N-cyclohexylamino)-6-(2-amino-4-methylphenyl)quinazolin-2-ylamine,
4-(N-cyclohexylamino)-6-(2-amino-5-methylphenyl)quinazolin-2-ylamine,
4-(N-cyclohexylamino)-6-(4-amino-2-methyl phenyl)quinazolin-2-ylamine,
4-(N-cyclohexylamino)-6-(5-amino-2-methyl phenyl)quinazolin-2-ylamine,
4-(N-cyclohexylamino)-6-(4-amino-3-nitrophenyl)quinazolin-2-ylamine,
4-(N-cyclohexylamino)-6-(2-benzyloxyphenyl)quinazolin-2-ylamine,
4-(N-cyclohexylamino)-6-(3-benzyloxy-4-ethoxyphenyl)quinazolin-2-ylamine,
4-(N-cyclohexylamino)-6-(4-biphenyl)quinazolin-2-ylamine,
4-(N-cyclohexylamino)-6-(4-n-butyl phenyl)quinazolin-2-ylamine,
4-(N-cyclohexylamino)-6-(4-isobutylphenyl)quinazolin-2-ylamine,
4-(N-cyclohexylamino)-6-(4-carboxy-3-fluorophenyl)quinazolin-2-ylamine,
4-(N-cyclohexylamino)-6-(3-(3-carboxypropionylamino)phenyl)quinazolin-2-ylamine,
4-(N-cyclohexylamino)-6-(4-(3-carboxypropionylamino)phenyl)quinazolin-2-ylamine,
4-(N-cyclohexylamino)-6-(3-chloro-4-hydroxy-5-ethoxyphenyl)quinazolin-2-ylamine,
4-(N-cyclohexylamino)-6-(2-chloro-5-hydroxymethylphenyl)quinazolin-2-ylamine,
4-(N-cyclohexylamino)-6-(4-cyanoethoxyphenyl)quinazolin-2-ylamine,
4-(N-cyclohexylamino)-6-(3-cyanoethoxyphenyl)quinazolin-2-ylamine,
4-(N-cyclohexylamino)-6-(2-cyanoethoxyphenyl)quinazolin-2-ylamine,
4-(N-cyclohexylamino)-6-(4-cyanophenyl)quinazolin-2-ylamine,
4-(N-cyclohexylamino)-6-(3-cyanophenyl)quinazolin-2-ylamine,
4-(N-cyclohexylamino)-6-(2-cyanophenyl)quinazolin-2-ylamine,
4-(N-cyclohexylamino)-6-(3-(N-cyclopropylaminocarbonyl)phenyl)quinazolin-2-ylamine,
4-(N-cyclohexylamino)-6-(3-(N,N-diethylaminocarbonyl)phenyl)quinazolin-2-ylamine,
4-(N-cyclohexylamino)-6-(3-(N,N-dimethylamino)phenyl)quinazolin-2-ylamine,
4-(N-cyclohexylamino)-6-(2-(N,N-dimethylamino)phenyl)quinazolin-2-ylamine,
4-(N-cyclohexylamino)-6-(3-(N,N-dimethylaminocarbonyl)phenyl)quinazolin-2-ylamine,
4-(N-cyclohexylamino)-6-(3-[(N',N'-dimethylamino)ethylaminocarbonyl]phenyl)-quinazolin-2-ylamine,
4-(N-cyclohexylamino)-6-(4-[(N',N'-dimethylamino)ethylaminocarbonyl]phenyl)-quinazolin-2-ylamine,
4-(N-cyclohexylamino)-6-(3-[1,3]dioxolan-2-ylethoxyphenyl)quinazolin-2-ylamine,
4-(N-cyclohexylamino)-6-(3-(ethoxycarbonyl)ethoxyphenyl)quinazolin-2-ylamine,
4-(N-cyclohexylamino)-6-(4-(ethoxycarbonyl)ethoxyphenyl)quinazolin-2-ylamine, 4-(N-cyclohexylamino)-6-(4-ethoxycarbonylphenyl)quinazolin-2-ylamine,
4-(N-cyclohexylamino)-6-(3-ethoxycarbonylphenyl)quinazolin-2-ylamine,
4-(N-cyclohexylamino)-6-(2-ethoxycarbonylphenyl)quinazolin-2-ylamine,
4-(N-cyclohexylamino)-6-(4-(3-ethoxycarbonylpiperidino)carboxamidophenyh-quinazolin-2-ylamine,
4-(N-cyclohexylamino)-6-(4-formylaminophenyl)quinazolin-2-ylamine,
4-(N-cyclohexylamino)-6-(3-formylaminophenyl)quinazolin-2-ylamine,
4-(N-cyclohexylamino)-6-(2-formylaminophenyl)quinazolin-2-ylamine,
4-(N-cyclohexylamino)-6-(2-formyl-5-ethoxyphenyl)quinazolin-2-ylamine,
4-(N-cyclohexylamino)-6-(3-formyl-4-ethoxyphenyl)quinazolin-2-ylamine,
4-(N-cyclohexylamino)-6-(5-formyl-2-ethoxyphenyl)quinazolin-2-ylamine,
4-(N-cyclohexylamino)-6-(2-formyl-5-methylphenyl)quinazolin-2-ylamine,
4-(N-cyclohexylamino)-6-(4-formylphenyl)quinazolin-2-ylamine,
4-(N-cyclohexylamino)-6-(3-formylphenyl)quinazolin-2-ylamine,
4-(N-cyclohexylamino)-6-(2-formylphenyl)quinazolin-2-ylamine,
4-(N-cyclohexylamino)-6-(4-hydroxy-3,5-dimethylphenyl)quinazolin-2-ylamine,
4-(N-cyclohexylamino)-6-(3-(2-hydroxyethyl)-aminocarbonylphenyl)quinazolin-2-ylamine,
4-(N-cyclohexylamino)-6-(4-(2-hydroxyethyl)aminocarbonyl)phenyl)quinazolin-2-ylamine,
4-(N-cyclohexylamino)-6-(3-hydroxy-4-ethoxycarbonylphenyl)quinazolin-2-ylamine,
4-(N-cyclohexylamino)-6-(4-hydroxy-3-ethoxyphenyl)quinazolin-2-ylamine,
4-(N-cyclohexylamino)-6-(4-(hydroxymethyl)phenyl)quinazolin-2-ylamine,
4-(N-cyclohexylamino)-6-(3-(hydroxymethyl)phenyl)quinazolin-2-ylamine,
4-(N-cyclohexylamino)-6-(4-hydroxy-3-nitrophenyl)quinazolin-2-ylamine,
4-(N-cyclohexylamino)-6-(4-isopropoxyphenyl)quinazolin-2-ylamine,
4-(N-cyclohexylamino)-6-(4-(4-isopropylpiperazinyl)phenyl)quinazolin-2-ylamine,
4-(N-cyclohexylamino)-6-(4-isopropylphenyl)quinazolin-2-ylamine,
4-(N-cyclohexylamino)-6-(4-methanesulfonamidophenyl)quinazolin-2-ylamine,
4-(N-cyclohexylamino)-6-(3-methanesulfonamidophenyl)quinazolin-2-ylamine,
4-(N-cyclohexylamino)-6-(2-methanesulfonamido phenyl)quinazolin-2-ylamine,
4-(N-cyclohexylamino)-6-(4-ethoxycarbonylphenyl)quinazolin-2-ylamine,
4-(N-cyclohexylamino)-6-(3-ethoxycarbonylphenyl)quinazolin-2-ylamine,
4-(N-cyclohexylamino)-6-(2-ethoxycarbonylphenyl)quinazolin-2-ylamine,
4-(N-cyclohexylamino)-6-(3-ethoxy-4-ethoxycarbonylphenyl)quinazolin-2-ylamine,
4-(N-cyclohexylamino)-6-(2-ethoxy-5-methylphenyl)quinazolin-2-ylamine,
4-(N-cyclohexylamino)-6-(4-ethoxy-3-nitrophenyl)quinazolin-2-ylamine,
4-(N-cyclohexylamino)-6-(4-ethoxyphenyl)quinazolin-2-ylamine,
4-(N-cyclohexylamino)-6-(3-ethoxyphenyl)quinazolin-2-ylamine,
4-(N-cyclohexylamino)-6-(4-N-methylcarboxamidophenyl)quinazolin-2-ylamine,
4-(N-cyclohexylamino)-6-(4-(N-methylamino)phenyl)quinazolin-2-ylamine,
4-(N-cyclohexylamino)-6-(3-(4-methylpiperazine-1-carbonyl)phenyl)quinazolin-2-ylamine,
4-(N-cyclohexylamino)-6-(4-(4-methylpiperazine-1-carbonyl)phenyl)quinazolin-2-ylamine,
4-(N-cyclohexylamino)-6-(4-(methylthio)phenyl)quinazolin-2-ylamine,
4-(N-cyclohexylamino)-6-(3-(methylthio)phenyl)quinazolin-2-ylamine,
4-(N-cyclohexylamino)-6-(2-(methylthio)phenyl)quinazolin-2-ylamine,
4-(N-cyclohexylamino)-6-(4-(morpholinocarbonyl)phenyl)quinazolin-2-ylamine,
4-(N-cyclohexylamino)-6-(4-morpholinophenyl)quinazolin-2-ylamine,
4-(N-cyclohexylamino)-6-(2-(morpholinomethyl)phenyl)quinazolin-2-ylamine,
4-(N-cyclohexylamino)-6-(4-nitrophenyl)quinazolin-2-ylamine,
4-(N-cyclohexylamino)-6-(3-nitrophenyl)quinazolin-2-ylamine,
4-(N-cyclohexylamino)-6-(2-nitrophenyl)quinazolin-2-ylamine,
4-(N-cyclohexylamino)-6-(4-phenoxyphenyl)quinazolin-2-ylamine,
4-(N-cyclohexylamino)-6-(4-(N-phenylaminomethyl)phenyl)quinazolin-2-ylamine,
4-(N-cyclohexylamino)-6-(4-(phenylcarbonyl)phenyl)quinazolin-2-ylamine,
4-(N-cyclohexylamino)-6-(4-(piperazine-1-carbonyl)phenyl)quinazolin-2-ylamine,
4-(N-cyclohexylamino)-6-(4-piperazinylphenyl)quinazolin-2-ylamine,
4-(N-cyclohexylamino)-6-(4-succinamidophenyl)quinazolin-2-ylamine,
4-(N-cyclohexylamino)-6-(3-succinamidophenyl)quinazolin-2-ylamine,
4-(N-cyclohexylamino)-6-(sulfamoylphenyl)quinazolin-2-ylamine,
4-(N-cyclohexylamino)-6-(2-(toluene-4-sulfonamido)phenyl)quinazolin-2-ylamine,
4-(N-cyclohexylamino)-6-(4-(toluene-4-sulfonamido)phenyl)quinazolin-2-ylamine,
4-(N-cyclohexylamino)-6-(4-(tert-butoxycarbonylamino)-3-ethoxyphenyl)quinazolin-2-ylamine,
4-(N-cyclohexylamino)-6-(2-(tert-butoxycarbonyl)phenyl)quinazolin-2-ylamine,
4-(N-cyclohexylamino)-6-(3-(tert-butoxycarbonyl)phenyl)quinazolin-2-ylamine,
4-(N-cyclohexylamino)-6-(4-(tert-butoxycarbonyl)phenyl)quinazolin-2-ylamine,
4-(N-cyclohexylamino)-6-(2,3,4-trifluorophenyl)quinazolin-2-ylamine,
4-(N-cyclohexylamino)-6-(4-tert-butylphenyl)quinazolin-2-ylamine,
4-(N-cyclohexylamino)-6-(4-(tetrahydro-2H-pyran-2-yloxy)phenyl)quinazolin-2-ylamine, 4-(N-cyclohexylamino)-6-(4-(2-thienyl)phenyl)quinazolin-2-ylamine,
4-(N-cyclohexylamino)-6-(2,4,6-trimethylphenyl)quinazolin-2-ylamine,
4-(N-cyclohexylamino)-6-(3,4,5-trimethoxyphenyl)quinazolin-2-ylamine,
4-(N-cyclohexylamino)-6-(4-vinylphenyl)quinazolin-2-ylamine,
4-(N-cyclohexylamino)-6-(4-(2-hydroxyethoxyphenyl)quinazolin-2-ylamine,
4-(N-cyclohexylamino)-6-(6-benzyloxynaphth-2-yl)quinazolin-2-ylamine,
4-(N-cyclohexylamino)-6-(naphth-1-yl)quinazolin-2-ylamine,
4-(N-cyclohexylamino)-6-(naphth-2-yl)quinazolin-2-ylamine,
4-(N-cyclohexylamino)-6-(4'-benzoyl[1,1'-biphenyl]-4-yl)quinazolin-2-ylamine,
4-(N-cyclohexylamino)-6-(1-biphenylyl)quinazolin-2-ylamine,
4-(N-cyclohexylamino)-6-(oxoindan-5-yl)quinazolin-2-ylamine,
4-(N-cyclohexylamino)-6-(benzodioxolyl)quinazolin-2-ylamine,
4-(N-cyclohexylamino)-6-(2-acetamidopyridin-5-yl)quinazolin-2-ylamine,
4-(N-cyclohexylamino)-6-(2-aminopyridin-5-yl)quinazolin-2-ylamine,
4-(N-cyclohexylamino)-6-(2-aminopyrimidin-5-yl)quinazolin-2-ylamine,
4-(N-cyclohexylamino)-6-(1,4-benzodioxan-6-yl)quinazolin-2-ylamine,
4-(N-cyclohexylamino)-6-(1-benzothien-3-yl)quinazolin-2-ylamine,
4-(N-cyclohexylamino)-6-(2-benzyloxypyridin-5-yl)quinazolin-2-ylamine,
4-(N-cyclohexylamino)-6-(1-benzyl-1H-pyrazol-4-yl)quinazolin-2-ylamine,
4-(N-cyclohexylamino)-6-(2-bromo-3-chloropyridin-4-yl)quinazolin-2-ylamine,
4-(N-cyclohexylamino)-6-(5-bromo-2,3-dihydrobenzo[b]furan-7-yl)quinazolin-2-ylamine,
4-(N-cyclohexylamino)-6-(2-bromo-3-methylpyridin-5-yl)quinazolin-2-ylamine,
4-(N-cyclohexylamino)-6-(2-bromopyridin-5-yl)quinazolin-2-ylamine,
4-(N-cyclohexylamino)-6-(3-bromopyridin-5-yl)quinazolin-2-ylamine,
4-(N-cyclohexylamino)-6-(5-bromothien-2-yl)quinazolin-2-ylamine,
4-(N-cyclohexylamino)-6-(2-chloro-6-isopropylpyridin-3-yl)quinazolin-2-ylamine,
4-(N-cyclohexylamino)-6-(2-chloro-3-methylpyridin-5-yl)quinazolin-2-ylamine,
4-(N-cyclohexylamino)-6-(2-[4-(4-chlorophenylsulfonyhpiperazin-1-yl]pyridin-5-yl)quinazolin-2-ylamine,
4-(N-cyclohexylamino)-6-(2-chloropyrid-4-yl)quinazolin-2-ylamine,
4-(N-cyclohexylamino)-6-(2-chloropyrid-5-yl)quinazolin-2-ylamine,
4-(N-cyclohexylamino)-6-(dibenzo[b,d]furan-4-yl)quinazolin-2-ylamine,
4-(N-cyclohexylamino)-6-(2-chloro-3-fluoropyridin-4-yl)quinazolin-2-ylamine,
4-(N-cyclohexylamino)-6-(dibenzo[b,d]thien-4-yl)quinazolin-2-ylamine,
4-(N-cyclohexylamino)-6-(3,4-dihydro-2H-1,5-benzodioxepin-7-yl)quinazolin-2-ylamine,
4-(N-cyclohexylamino)-6-(3,6-dihydro-2H-pyridine-1-tert-butoxycarbonyl)quinazolin-2-ylamine,
4-(N-cyclohexylamino)-6-(2,5-dibromopyridin-3-yl)quinazolin-2-ylamine,
4-(N-cyclohexylamino)-6-(2,6-dichloropyridin-3-yl)quinazolin-2-ylamine,
4-(N-cyclohexylamino)-6-(2,3-dihydro-1-benzofuran-5-yl)quinazolin-2-ylamine,
4-(N-cyclohexylamino)-6-(2,6-diethoxypyridin-5-yl)quinazolin-2-ylamine,
4-(N-cyclohexylamino)-6-(2,6-diethoxypyridin-3-yl)quinazolin-2-ylamine,
4-(N-cyclohexylamino)-6-(2,4-diethoxypyrimidin-5-yl)quinazolin-2-ylamine,
4-(N-cyclohexylamino)-6-(3,5-dimethylisoxazol-4-yl)quinazolin-2-ylamine,
4-(N-cyclohexylamino)-6-(2-(3-N,N-dimethylaminopropoxy)pyridin-5-yl)quinazolin-2-ylamine,
4-(N-cyclohexylamino)-6-(3,5-dimethylpyrazol-4-yl)quinazolin-2-ylamine,
4-(N-cyclohexylamino)-6-(1-[1,3]dioxolan-2-ylmethyl-1H-pyrazol-4-yl)quinazolin-2-ylamine,
4-(N-cyclohexylamino)-6-(2,4-dioxo-1,2,3,4-tetrahydro-5-pyrimidinyl)quinazolin-2-ylamine,
4-(N-cyclohexylamino)-6-(2,4-di(tert-butoxy)pyrimidin-5-yl)quinazolin-2-ylamine,
4-(N-cyclohexylamino)-6-(2-ethoxypyridin-3-yl)quinazolin-2-ylamine,
4-(N-cyclohexylamino)-6-(2-fluoro-3-methylpyridin-5-yl)quinazolin-2-ylamine,
4-(N-cyclohexylamino)-6-(2-fluoropyridin-5-yl)quinazolin-2-ylamine,
4-(N-cyclohexylamino)-6-(5-formyl-2-furyl)quinazolin-2-ylamine,
4-(N-cyclohexylamino)-6-(5-formylthien-2-yl)quinazolin-2-ylamine,
4-(N-cyclohexylamino)-6-(furan-2-yl)quinazolin-2-ylamine,
4-(N-cyclohexylamino)-6-(2-hydroxypyridin-5-yl)quinazolin-2-ylamine,
4-(N-cyclohexylamino)-6-(1-isobutyl-1H-pyrazol-4-yl)quinazolin-2-ylamine,
4-(N-cyclohexylamino)-6-(isoquinolin-4-yl)quinazolin-2-ylamine,
4-(N-cyclohexylamino)-6-(2-ethoxypyridin-3-yl)quinazolin-2-ylamine,
4-(N-cyclohexylamino)-6-(2-ethoxypyrimidin-5-yl)quinazolin-2-ylamine,
4-(N-cyclohexylamino)-6-(5-methyl-1-benzothien-2-yl)quinazolin-2-ylamine,
4-(N-cyclohexylamino)-6-(1-(3-methylbutyl)-1H-pyrazol-4-yl)quinazolin-2-ylamine,
4-(N-cyclohexylamino)-6-(5-methylfuran-2-yl)quinazolin-2-ylamine,
4-(N-cyclohexylamino)-6-(1-methylindol-5-yl)quinazolin-2-ylamine,
4-(N-cyclohexylamino)-6-(5-methyl-3-phenyl-4-isoxazolyl)quinazolin-2-ylamine,
4-(N-cyclohexylamino)-6-(5-(methylthio)thien-2-yl)quinazolin-2-ylamine,
4-(N-cyclohexylamino)-6-(2-(4-methylpiperazinyl)pyridin-4-yl)quinazolin-2-ylamine,
4-(N-cyclohexylamino)-6-(2-(4-methylpiperazinyl)pyridin-5-yl)quinazolin-2-ylamine, 4-(N-cyclohexylamino)-6-(1-methyl-1H-pyrazol-4-yl)quinazolin-2-ylamine,
4-(N-cyclohexylamino)-6-(3-methylpyridin-2-yl)quinazolin-2-ylamine,
4-(N-cyclohexylamino)-6-(5-methylpyridin-2-yl)quinazolin-2-ylamine,
4-(N-cyclohexylamino)-6-(5-methylpyridin-3-yl)quinazolin-2-ylamine,
4-(N-cyclohexylamino)-6-(2-ethoxypyridin-5-yl)quinazolin-2-ylamine,
4-(N-cyclohexylamino)-6-(4-methylthien-2-yl)quinazolin-2-ylamine,
4-(N-cyclohexylamino)-6-(5-methylthien-2-yl)quinazolin-2-ylamine,
4-(N-cyclohexylamino)-6-(2-(2-morpholinoethylamino)-pyridin-5-yl)quinazolin-2-ylamine,
4-(N-cyclohexylamino)-6-(2-(2-morpholinoethyl)-1H-pyrazol-4-yl)quinazolin-2-ylamine,
4-(N-cyclohexylamino)-6-(2-(morpholin-1-yl)-pyridin-5-yl)quinazolin-2-ylamine,
4-(N-cyclohexylamino)-6-(1-(phenylsulfonyl)-1H-indol-3-yl)quinazolin-2-ylamine,
4-(N-cyclohexylamino)-6-(5-phenyl-2-thienyl)quinazolin-2-ylamine,
4-(N-cyclohexylamino)-6-(2-(piperazin-1-yl)-pyridin-5-yl)quinazolin-2-ylamine,
4-(N-cyclohexylamino)-6-(2-(piperazin-1-yl)-pyridin-4-yl)quinazolin-2-ylamine,
4-(N-cyclohexylamino)-6-(1-propyl-1H-pyrazol-4-yl)quinazolin-2-ylamine,
4-(N-cyclohexylamino)-6-(pyrazol-4-yl)quinazolin-2-ylamine,
4-(N-cyclohexylamino)-6-(pyridin-4-yl)quinazolin-2-ylamine,
4-(N-cyclohexylamino)-6-(4-phenoxathiinyl)quinazolin-2-ylamine,
4-(N-cyclohexylamino)-6-(quinolin-8-yl)quinazolin-2-ylamine,
4-(N-cyclohexylamino)-6-(quinolin-3-yl)quinazolin-2-ylamine,
4-(N-cyclohexylamino)-6-(2-(4-tert-butoxycarbonylpiperazinyl)-pyrid-4-yl)quinazolin-2-ylamine,
4-(N-cyclohexylamino)-6-(1-tert-butoxycarbonyl-1H-pyrazol-4-yl)quinazolin-2-ylamine,
4-(N-cyclohexylamino)-6-(1-tert-butoxycarbonyl-2-pyrrolyl)quinazolin-2-ylamine,
4-(N-cyclohexylamino)-6-(1-(tert-butoxycarbonyl)-5-bromo-1H-indol-2-yl)quinazolin-2-ylamine,
4-(N-cyclohexylamino)-6-(1-(tert-butoxycarbonyl)-1H-indol-5-yl)quinazolin-2-ylamine,
4-(N-cyclohexylamino)-6-(1-(tert-butoxycarbonyl)-5-methoxy-1H-indol-2-yl)quinazolin-2-ylamine,
4-(N-cyclohexylamino)-6-(1-thianthrenylthien-3-yl)quinazolin-2-ylamine,
4-(N-cyclohexylamino)-6-(1,3,5-trimethyl-1H-pyrazol-4-yl)quinazolin-2-ylamine,
4-(N-(4-methyl)-piperazin-1-yl)-6-(4-(4'-allyloxycarbonylpiperazino)phenyl)quinazolin-2-ylamine,
4-(N-(4-methyl)-piperazin-1-yl)-6-(3-aminocarbonylphenyl)quinazolin-2-ylamine,
4-(N-(4-methyl)-piperazin-1-yl)-6-(4-aminocarbonylphenyl)quinazolin-2-ylamine,
4-(N-(4-methyl)-piperazin-1-yl)-6-(2-amino-5-chlorophenyl)quinazolin-2-ylamine,
4-(N-(4-methyl)-piperazin-1-yl)-6-(4-amino-3-ethoxyphenyl)quinazolin-2-ylamine,
4-(N-(4-methyl)-piperazin-1-yl)-6-(2-amino-4-methylphenyl)quinazolin-2-ylamine,
4-(N-(4-methyl)-piperazin-1-yl)-6-(2-amino-5-methylphenyl)quinazolin-2-ylamine,
4-(N-(4-methyl)-piperazin-1-yl)-6-(4-amino-2-methylphenyl)quinazolin-2-ylamine,
4-(N-(4-methyl)-piperazin-1-yl)-6-(5-amino-2-methylphenyl)quinazolin-2-ylamine,
4-(N-(4-methyl)-piperazin-1-yl)-6-(4-amino-3-nitrophenyl)quinazolin-2-ylamine,
4-(N-(4-methyl)-piperazin-1-yl)-6-(2-benzyloxyphenyl)quinazolin-2-ylamine,
4-(N-(4-methyl)-piperazin-1-yl)-6-(3-benzyloxy-4-ethoxyphenyl)quinazolin-2-ylamine,
4-(N-(4-methyl)-piperazin-1-yl)-6-(4-biphenyl)quinazolin-2-ylamine,
4-(N-(4-methyl)-piperazin-1-yl)-6-(4-n-butyl phenyl)quinazolin-2-ylamine,
4-(N-(4-methyl)-piperazin-1-yl)-6-(4-isobutylphenyl)quinazolin-2-ylamine,
4-(N-(4-methyl)-piperazin-1-yl)-6-(4-carboxy-3-fluorophenyl)quinazolin-2-ylamine,
4-(N-(4-methyl)-piperazin-1-yl)-6-(3-(3-carboxypropionylamino)phenyl)quinazolin-2-ylamine,
4-(N-(4-methyl)-piperazin-1-yl)-6-(4-(3-carboxypropionylamino)phenyl)quinazolin-2-ylamine,
4-(N-(4-methyl)-piperazin-1-yl)-6-(3-chloro-4-hydroxy-5-ethoxyphenyl)quinazolin-2-ylamine,
4-(N-(4-methyl)-piperazin-1-yl)-6-(2-chloro-5-hydroxymethylphenyl)quinazolin-2-ylamine,
4-(N-(4-methyl)-piperazin-1-yl)-6-(4-cyanoethoxyphenyl)quinazolin-2-ylamine,
4-(N-(4-methyl)-piperazin-1-yl)-6-(3-cyanoethoxyphenyl)quinazolin-2-ylamine,
4-(N-(4-methyl)-piperazin-1-yl)-6-(2-cyanoethoxyphenyl)quinazolin-2-ylamine,
4-(N-(4-methyl)-piperazin-1-yl)-6-(4-cyanophenyl)quinazolin-2-ylamine,
4-(N-(4-methyl)-piperazin-1-yl)-6-(3-cyanophenyl)quinazolin-2-ylamine,
4-(N-(4-methyl)-piperazin-1-yl)-6-(2-cyanophenyl)quinazolin-2-ylamine,
4-(N-(4-methyl)-piperazin-1-yl)-6-(3-(N-cyclopropylaminocarbonyl)phenyl)quinazolin-2-ylamine,
4-(N-(4-methyl)-piperazin-1-yl)-6-(3-(N,N-diethylaminocarbonyl)phenyl)quinazolin-2-ylamine,
4-(N-(4-methyl)-piperazin-1-yl)-6-(3-(N,N-dimethylamino)phenyl)quinazolin-2-ylamine,
4-(N-(4-methyl)-piperazin-1-yl)-6-(2-(N,N-dimethylamino)phenyl)quinazolin-2-ylamine,
4-(N-(4-methyl)-piperazin-1-yl)-6-(3-(N,N-dimethylaminocarbonyl)phenyl)quinazolin-2-ylamine,
4-(N-(4-methyl)-piperazin-1-yl)-6-(3-[(N',N'-dimethylamino)ethylaminocarbonyl]phenyl)-quinazolin-2-ylamine,
4-(N-(4-methyl)-piperazin-1-yl)-6-(4-[(N',N'-dimethylamino)ethylaminocarbonyl]phenyl)-quinazolin-2-ylamine,
4-(N-(4-methyl)-piperazin-1-yl)-6-(3-[1,3]dioxolan-2-ylethoxyphenyl)quinazolin-2-ylamine,
4-(N-(4-methyl)-piperazin-1-yl)-6-(3-(ethoxycarbonyl)ethoxyphenyl)quinazolin-2-ylamine,
4-(N-(4-methyl)-piperazin-1-yl)-6-(4-(ethoxycarbonyl)ethoxyphenyl)quinazolin-2-ylamine,
4-(N-(4-methyl)-piperazin-1-yl)-6-(4-ethoxycarbonylphenyl)quinazolin-2-ylamine, 4-(N-(4-methyl)-piperazin-1-yl)-6-(3-ethoxycarbonylphenyl)quinazolin-2-ylamine,
4-(N-(4-methyl)-piperazin-1-yl)-6-(2-ethoxycarbonylphenyl)quinazolin-2-ylamine,
4-(N-(4-methyl)-piperazin-1-yl)-6-(4-(3-ethoxycarbonylpipericlino)carboxamidophenyl)-quinazolin-2-ylamine,
4-(N-(4-methyl)-piperazin-1-yl)-6-(4-formylaminophenyl)quinazolin-2-ylamine,
4-(N-(4-methyl)-piperazin-1-yl)-6-(3-formylaminophenyl)quinazolin-2-ylamine,
4-(N-(4-methyl)-piperazin-1-yl)-6-(2-formylaminophenyl)quinazolin-2-ylamine,
4-(N-(4-methyl)-piperazin-1-yl)-6-(2-formyl-5-ethoxyphenyl)quinazolin-2-ylamine,
4-(N-(4-methyl)-piperazin-1-yl)-6-(3-formyl-4-ethoxyphenyl)quinazolin-2-ylamine,
4-(N-(4-methyl)-piperazin-1-yl)-6-(5-formyl-2-ethoxyphenyl)quinazolin-2-ylamine,
4-(N-(4-methyl)-piperazin-1-yl)-6-(2-formyl-5-methylphenyl)quinazolin-2-ylamine,
4-(N-(4-methyl)-piperazin-1-yl)-6-(4-formylphenyl)quinazolin-2-ylamine,
4-(N-(4-methyl)-piperazin-1-yl)-6-(3-formylphenyl)quinazolin-2-ylamine,
4-(N-(4-methyl)-piperazin-1-yl)-6-(2-formylphenyl)quinazolin-2-ylamine,
4-(N-(4-methyl)-piperazin-1-yl)-6-(4-hydroxy-3,5-dimethylphenyl)quinazolin-2-ylamine,
4-(N-(4-methyl)-piperazin-1-yl)-6-(3-(2-hydroxyethyl)-aminocarbonylphenyl)quinazolin-2-ylamine,
4-(N-(4-methyl)-piperazin-1-yl)-6-(4-(2-hydroxyethyl)aminocarbonyl)phenyl)quinazolin-2-ylamine,
4-(N-(4-methyl)-piperazin-1-yl)-6-(3-hydroxy-4-ethoxycarbonylphenyl)quinazolin-2-ylamine,
4-(N-(4-methyl)-piperazin-1-yl)-6-(4-hydroxy-3-ethoxyphenyl)quinazolin-2-ylamine,
4-(N-(4-methyl)-piperazin-1-yl)-6-(4-(hydroxymethyl)phenyl)quinazolin-2-ylamine,
4-(N-(4-methyl)-piperazin-1-yl)-6-(3-(hydroxymethyl)phenyl)quinazolin-2-ylamine,
4-(N-(4-methyl)-piperazin-1-yl)-6-(4-hydroxy-3-nitrophenyl)quinazolin-2-ylamine,
4-(N-(4-methyl)-piperazin-1-yl)-6-(4-isopropoxyphenyl)quinazolin-2-ylamine,
4-(N-(4-methyl)-piperazin-1-yl)-6-(4-(4-isopropylpiperazinyl)phenyl)quinazolin-2-ylamine,
4-(N-(4-methyl)-piperazin-1-yl)-6-(4-isopropylphenyl)quinazolin-2-ylamine,
4-(N-(4-methyl)-piperazin-1-yl)-6-(4-methanesulfonamidophenyl)quinazolin-2-ylamine,
4-(N-(4-methyl)-piperazin-1-yl)-6-(3-methanesulfonamidophenyl)quinazolin-2-ylamine,
4-(N-(4-methyl)-piperazin-1-yl)-6-(2-methanesulfonamido phenyl)quinazolin-2-ylamine,
4-(N-(4-methyl)-piperazin-1-yl)-6-(4-ethoxycarbonylphenyl)quinazolin-2-ylamine,
4-(N-(4-methyl)-piperazin-1-yl)-6-(3-ethoxycarbonylphenyl)quinazolin-2-ylamine,
4-(N-(4-methyl)-piperazin-1-yl)-6-(2-ethoxycarbonylphenyl)quinazolin-2-ylamine,
4-(N-(4-methyl)-piperazin-1-yl)-6-(3-ethoxy-4-ethoxycarbonylphenyl)quinazolin-2-ylamine,
4-(N-(4-methyl)-piperazin-1-yl)-6-(2-ethoxy-5-methylphenyl)quinazolin-2-ylamine,
4-(N-(4-methyl)-piperazin-1-yl)-6-(4-ethoxy-3-nitrophenyl)quinazolin-2-ylamine,
4-(N-(4-methyl)-piperazin-1-yl)-6-(4-ethoxyphenyl)quinazolin-2-ylamine,
4-(N-(4-methyl)-piperazin-1-yl)-6-(3-ethoxyphenyl)quinazolin-2-ylamine,
4-(N-(4-methyl)-piperazin-1-yl)-6-(4-N-methylcarboxamidophenyl)quinazolin-2-ylamine,
4-(N-(4-methyl)-piperazin-1-yl)-6-(4-(N-methylamino)phenyl)quinazolin-2-ylamine,
4-(N-(4-methyl)-piperazin-1-yl)-6-(3-(4-methylpiperazine-1-carbonyl)phenyl)quinazolin-2-ylamine,
4-(N-(4-methyl)-piperazin-1-yl)-6-(4-(4-methylpiperazine-1-carbonyl)phenyl)quinazolin-2-ylamine,
4-(N-(4-methyl)-piperazin-1-yl)-6-(4-(methylthio)phenyl)quinazolin-2-ylamine,
4-(N-(4-methyl)-piperazin-1-yl)-6-(3-(methylthio)phenyl)quinazolin-2-ylamine,
4-(N-(4-methyl)-piperazin-1-yl)-6-(2-(methylthio)phenyl)quinazolin-2-ylamine,
4-(N-(4-methyl)-piperazin-1-yl)-6-(4-(morpholinocarbonyl)phenyl)quinazolin-2-ylamine,
4-(N-(4-methyl)-piperazin-1-yl)-6-(4-morpholinophenyl)quinazolin-2-ylamine,
4-(N-(4-methyl)-piperazin-1-yl)-6-(2-(morpholinomethyl)phenyl)quinazolin-2-ylamine,
4-(N-(4-methyl)-piperazin-1-yl)-6-(4-nitrophenyl)quinazolin-2-ylamine,
4-(N-(4-methyl)-piperazin-1-yl)-6-(3-nitrophenyl)quinazolin-2-ylamine,
4-(N-(4-methyl)-piperazin-1-yl)-6-(2-nitrophenyl)quinazolin-2-ylamine,
4-(N-(4-methyl)-piperazin-1-yl)-6-(4-phenoxyphenyl)quinazolin-2-ylamine,
4-(N-(4-methyl)-piperazin-1-yl)-6-(4-(N-phenylaminomethyl)phenyl)quinazolin-2-ylamine,
4-(N-(4-methyl)-piperazin-1-yl)-6-(4-(phenylcarbonyl)phenyl)quinazolin-2-ylamine,
4-(N-(4-methyl)-piperazin-1-yl)-6-(4-(piperazine-1-carbonyl)phenyl)quinazolin-2-ylamine,
4-(N-(4-methyl)-piperazin-1-yl)-6-(4-piperazinylphenyl)quinazolin-2-ylamine,
4-(N-(4-methyl)-piperazin-1-yl)-6-(4-succinamidophenyl)quinazolin-2-ylamine,
4-(N-(4-methyl)-piperazin-1-yl)-6-(3-succinamidophenyl)quinazolin-2-ylamine,
4-(N-(4-methyl)-piperazin-1-yl)-6-(sulfamoylphenyl)quinazolin-2-ylamine,
4-(N-(4-methyl)-piperazin-1-yl)-6-(2-(toluene-4-sulfonamido)phenyl)quinazolin-2-ylamine,
4-(N-(4-methyl)-piperazin-1-yl)-6-(4-(toluene-4-sulfonamido)phenyl)quinazolin-2-ylamine,
4-(N-(4-methyl)-piperazin-1-yl)-6-(4-(tert-butoxycarbonylamino)-3-ethoxyphenyl)quinazolin-2-ylamine,
4-(N-(4-methyl)-piperazin-1-yl)-6-(2-(tert-butoxycarbonyl)phenyl)quinazolin-2-ylamine,
4-(N-(4-methyl)-piperazin-1-yl)-6-(3-(tert-butoxycarbonyl)phenyl)quinazolin-2-ylamine,
4-(N-(4-methyl)-piperazin-1-yl)-6-(4-(tert-butoxycarbonyl)phenyl)quinazolin-2-ylamine,
4-(N-(4-methyl)-piperazin-1-yl)-6-(2,3,4-trifluorophenyl)quinazolin-2-ylamine,
4-(N-(4-methyl)-piperazin-1-yl)-6-(4-tert-butylphenyl)quinazolin-2-ylamine,
4-(N-(4-methyl)-piperazin-1-yl)-6-(4-(tetrahydro-2H-pyran-2-yloxy)phenyl)quinazolin-2-ylamine,
4-(N-(4-methyl)-piperazin-1-yl)-6-(4-(2-thienyl)phenyl)quinazolin-2-ylamine, 4-(N-(4-methyl)-piperazin-1-yl)-6-(2,4,6-trimethylphenyl)quinazolin-2-ylamine,
4-(N-(4-methyl)-piperazin-1-yl)-6-(3,4,5-trimethoxyphenyl)quinazolin-2-ylamine,
4-(N-(4-methyl)-piperazin-1-yl)-6-(4-vinylphenyl)quinazolin-2-ylamine,
4-(N-(4-methyl)-piperazin-1-yl)-6-(4-(2-hydroxyethoxyphenyl)quinazolin-2-ylamine,
4-(N-(4-methyl)-piperazin-1-yl)-6-(6-benzyloxynaphth-2-yl)quinazolin-2-ylamine,
4-(N-(4-methyl)-piperazin-1-yl)-6-(naphth-1-yl)quinazolin-2-ylamine,
4-(N-(4-methyl)-piperazin-1-yl)-6-(naphth-2-yl)quinazolin-2-ylamine,
4-(N-(4-methyl)-piperazin-1-yl)-6-(4'-benzoyl[1,1'-biphenyl]-4-yl)quinazolin-2-ylamine,
4-(N-(4-methyl)-piperazin-1-yl)-6-(1-biphenylyl)quinazolin-2-ylamine,
4-(N-(4-methyl)-piperazin-1-yl)-6-(oxoindan-5-yl)quinazolin-2-ylamine,
4-(N-(4-methyl)-piperazin-1-yl)-6-(benzodioxolyl)quinazolin-2-ylamine,
4-(N-(4-methyl)-piperazin-1-yl)-6-(2-acetamidopyridin-5-yl)quinazolin-2-ylamine,
4-(N-(4-methyl)-piperazin-1-yl)-6-(2-aminopyridin-5-yl)quinazolin-2-ylamine,
4-(N-(4-methyl)-piperazin-1-yl)-6-(2-aminopyrimidin-5-yl)quinazolin-2-ylamine,
4-(N-(4-methyl)-piperazin-1-yl)-6-(1,4-benzodioxan-6-yl)quinazolin-2-ylamine,
4-(N-(4-methyl)-piperazin-1-yl)-6-(1-benzothien-3-yl)quinazolin-2-ylamine,
4-(N-(4-methyl)-piperazin-1-yl)-6-(2-benzyloxypyridin-5-yl)quinazolin-2-ylamine,
4-(N-(4-methyl)-piperazin-1-yl)-6-(1-benzyl-1H-pyrazol-4-yl)quinazolin-2-ylamine,
4-(N-(4-methyl)-piperazin-1-yl)-6-(2-bromo-3-chloropyridin-4-yl)quinazolin-2-ylamine,
4-(N-(4-methyl)-piperazin-1-yl)-6-(5-bromo-2,3-dihydrobenzo[b]furan-7-yl)quinazolin-2-ylamine,
4-(N-(4-methyl)-piperazin-1-yl)-6-(2-bromo-3-methylpyridin-5-yl)quinazolin-2-ylamine,
4-(N-(4-methyl)-piperazin-1-yl)-6-(2-bromopyridin-5-yl)quinazolin-2-ylamine,
4-(N-(4-methyl)-piperazin-1-yl)-6-(3-bromopyridin-5-yl)quinazolin-2-ylamine,
4-(N-(4-methyl)-piperazin-1-yl)-6-(5-bromothien-2-yl)quinazolin-2-ylamine,
4-(N-(4-methyl)-piperazin-1-yl)-6-(2-chloro-6-isopropylpyridin-3-yl)quinazolin-2-ylamine,
4-(N-(4-methyl)-piperazin-1-yl)-6-(2-chloro-3-methylpyridin-5-yl)quinazolin-2-ylamine,
4-(N-(4-methyl)-piperazin-1-yl)-6-(2-[4-(4-chlorophenylsulfonyl)piperazin-1-yl]pyridin-5-yl)quinazolin-2-ylamine,
4-(N-(4-methyl)-piperazin-1-yl)-6-(2-chloropyrid-4-yl)quinazolin-2-ylamine,
4-(N-(4-methyl)-piperazin-1-yl)-6-(2-chloropyrid-5-yl)quinazolin-2-ylamine,
4-(N-(4-methyl)-piperazin-1-yl)-6-(dibenzo[b,d]furan-4-yl)quinazolin-2-ylamine,
4-(N-(4-methyl)-piperazin-1-yl)-6-(2-chloro-3-fluoropyridin-4-yl)quinazolin-2-ylamine,
4-(N-(4-methyl)-piperazin-1-yl)-6-(dibenzo[b,d]thien-4-yl)quinazolin-2-ylamine,
4-(N-(4-methyl)-piperazin-1-yl)-6-(3,4-dihydro-2H-1,5-benzodioxepin-7-yl)quinazolin-2-ylamine,
4-(N-(4-methyl)-piperazin-1-yl)-6-(3,6-dihydro-2H-pyridine-1-tert-butoxycarbonyl)quinazolin-2-ylamine,
4-(N-(4-methyl)-piperazin-1-yl)-6-(2,5-dibromopyridin-3-yl)quinazolin-2-ylamine,
4-(N-(4-methyl)-piperazin-1-yl)-6-(2,6-dichloropyridin-3-yl)quinazolin-2-ylamine,
4-(N-(4-methyl)-piperazin-1-yl)-6-(2,3-dihydro-1-benzofuran-5-yl)quinazolin-2-ylamine,
4-(N-(4-methyl)-piperazin-1-yl)-6-(2,6-diethoxypyridin-5-yl)quinazolin-2-ylamine,
4-(N-(4-methyl)-piperazin-1-yl)-6-(2,6-diethoxypyridin-3-yl)quinazolin-2-ylamine,
4-(N-(4-methyl)-piperazin-1-yl)-6-(2,4-diethoxypyrimidin-5-yl)quinazolin-2-ylamine,
4-(N-(4-methyl)-piperazin-1-yl)-6-(3,5-dimethylisoxazol-4-yl)quinazolin-2-ylamine,
4-(N-(4-methyl)-piperazin-1-yl)-6-(2-(3-N,N-dimethylaminopropoxy)pyridin-5-yl)quinazolin-2-ylam ine,
4-(N-(4-methyl)-piperazin-1-yl)-6-(3,5-dimethylpyrazol-4-yl)quinazolin-2-ylamine,
4-(N-(4-methyl)-piperazin-1-yl)-6-(1-[1,3]dioxolan-2-ylmethyl-1H-pyrazol-4-yl)quinazolin-2-ylamine,
4-(N-(4-methyl)-piperazin-1-yl)-6-(2,4-dioxo-1,2,3,4-tetrahydro-5-pyrimidinyl)quinazolin-2-ylamine,
4-(N-(4-methyl)-piperazin-1-yl)-6-(2,4-di(tert-butoxy)pyrimidin-5-yl)quinazolin-2-ylamine,
4-(N-(4-methyl)-piperazin-1-yl)-6-(2-ethoxypyridin-3-yl)quinazolin-2-ylamine,
4-(N-(4-methyl)-piperazin-1-yl)-6-(2-fluoro-3-methylpyridin-5-yl)quinazolin-2-ylamine,
4-(N-(4-methyl)-piperazin-1-yl)-6-(2-fluoropyridin-5-yl)quinazolin-2-ylamine,
4-(N-(4-methyl)-piperazin-1-yl)-6-(5-formyl-2-furyl)quinazolin-2-ylamine,
4-(N-(4-methyl)-piperazin-1-yl)-6-(5-formylthien-2-yl)quinazolin-2-ylamine,
4-(N-(4-methyl)-piperazin-1-yl)-6-(furan-2-yl)quinazolin-2-ylamine,
4-(N-(4-methyl)-piperazin-1-yl)-6-(2-hydroxypyridin-5-yl)quinazolin-2-ylamine,
4-(N-(4-methyl)-piperazin-1-yl)-6-(1-isobutyl-1H-pyrazol-4-yl)quinazolin-2-ylamine,
4-(N-(4-methyl)-piperazin-1-yl)-6-(isoquinolin-4-yl)quinazolin-2-ylamine,
4-(N-(4-methyl)-piperazin-1-yl)-6-(2-ethoxypyridin-3-yl)quinazolin-2-ylamine,
4-(N-(4-methyl)-piperazin-1-yl)-6-(2-ethoxypyrimidin-5-yl)quinazolin-2-ylamine,
4-(N-(4-methyl)-piperazin-1-yl)-6-(5-methyl-1-benzothien-2-yl)quinazolin-2-ylamine,
4-(N-(4-methyl)-piperazin-1-yl)-6-(1-(3-methylbutyl)-1H-pyrazol-4-yl)quinazolin-2-ylamine,
4-(N-(4-methyl)-piperazin-1-yl)-6-(5-methylfuran-2-yl)quinazolin-2-ylamine,
4-(N-(4-methyl)-piperazin-1-yl)-6-(1-methylindol-5-yl)quinazolin-2-ylamine,
4-(N-(4-methyl)-piperazin-1-yl)-6-(5-methyl-3-phenyl-4-isoxazolyl)quinazolin-2-ylamine,
4-(N-(4-methyl)-piperazin-1-yl)-6-(5-(methylthio)thien-2-yl)quinazolin-2-ylamine,
4-(N-(4-methyl)-piperazin-1-yl)-6-(2-(4-methylpiperazinyl)pyridin-4-yl)quinazolin-2-ylamine,
4-(N-(4-methyl)-piperazin-1-yl)-6-(2-(4-methylpiperazinyl)pyridin-5-yl)quinazolin-2-ylamine,
4-(N-(4-methyl)-piperazin-1-yl)-6-(1-methyl-1H-pyrazol-4-yl)quinazolin-2-ylamine, 4-(N-(4-methyl)-piperazin-1-yl)-6-(3-methylpyridin-2-yl)quinazolin-2-ylamine,
4-(N-(4-methyl)-piperazin-1-yl)-6-(5-methylpyridin-2-yl)quinazolin-2-ylamine,
4-(N-(4-methyl)-piperazin-1-yl)-6-(5-methylpyridin-3-yl)quinazolin-2-ylamine,
4-(N-(4-methyl)-piperazin-1-yl)-6-(2-ethoxypyridin-5-yl)quinazolin-2-ylamine,
4-(N-(4-methyl)-piperazin-1-yl)-6-(4-methylthien-2-yl)quinazolin-2-ylamine,
4-(N-(4-methyl)-piperazin-1-yl)-6-(5-methylthien-2-yl)quinazolin-2-ylamine,
4-(N-(4-methyl)-piperazin-1-yl)-6-(2-(2-morpholinoethylamino)-pyridin-5-yl)quinazolin-2-ylamine,
4-(N-(4-methyl)-piperazin-1-yl)-6-(2-(2-morpholinoethyl)-1H-pyrazol-4-yl)quinazolin-2-ylamine,
4-(N-(4-methyl)-piperazin-1-yl)-6-(2-(morpholin-1-yl)-pyridin-5-yl)quinazolin-2-ylamine,
4-(N-(4-methyl)-piperazin-1-yl)-6-(1-(phenylsulfonyl)-1H-indol-3-yl)quinazolin-2-ylamine,
4-(N-(4-methyl)-piperazin-1-yl)-6-(5-phenyl-2-thienyl)quinazolin-2-ylamine,
4-(N-(4-methyl)-piperazin-1-yl)-6-(2-(piperazin-1-yl)-pyridin-5-yl)quinazolin-2-ylamine,
4-(N-(4-methyl)-piperazin-1-yl)-6-(2-(piperazin-1-yl)-pyridin-4-yl)quinazolin-2-ylamine,
4-(N-(4-methyl)-piperazin-1-yl)-6-(1-propyl-1H-pyrazol-4-yl)quinazolin-2-ylamine,
4-(N-(4-methyl)-piperazin-1-yl)-6-(pyrazol-4-yl)quinazolin-2-ylamine,
4-(N-(4-methyl)-piperazin-1-yl)-6-(pyridin-4-yl)quinazolin-2-ylamine,
4-(N-(4-methyl)-piperazin-1-yl)-6-(4-phenoxathiinyl)quinazolin-2-ylamine,
4-(N-(4-methyl)-piperazin-1-yl)-6-(quinolin-8-yl)quinazolin-2-ylamine,
4-(N-(4-methyl)-piperazin-1-yl)-6-(quinolin-3-yl)quinazolin-2-ylamine,
4-(N-(4-methyl)-piperazin-1-yl)-6-(2-(4-tert-butoxycarbonylpiperazinyl)-pyrid-4-yl)quinazolin-2-ylamine,
4-(N-(4-methyl)-piperazin-1-yl)-6-(1-tert-butoxycarbonyl-1H-pyrazol-4-yl)quinazolin-2-ylamine,
4-(N-(4-methyl)-piperazin-1-yl)-6-(1-tert-butoxycarbonyl-2-pyrrolyl)quinazolin-2-ylamine,
4-(N-(4-methyl)-piperazin-1-yl)-6-(1-(tert-butoxycarbonyl)-5-bromo-1H-indol-2-yl)quinazolin-2-ylamine,
4-(N-(4-methyl)-piperazin-1-yl)-6-(1-(tert-butoxycarbonyl)-1H-indol-5-yl)quinazolin-2-ylamine,
4-(N-(4-methyl)-piperazin-1-yl)-6-(1-(tert-butoxycarbonyl)-5-methoxy-1H-indol-2-yl)quinazolin-2-ylamine,
4-(N-(4-methyl)-piperazin-1-yl)-6-(1-thianthrenylthien-3-yl)quinazolin-2-ylamine,
4-(N-(4-methyl)-piperazin-1-yl)-6-(1,3,5-trimethyl-1H-pyrazol-4-yl)quinazolin-2-ylamine,
and/or a pharmaceutically acceptable addition salt thereof and/or a stereo-isomer thereof and/or a mono- or a di-N-oxide thereof.

8. The method of claim 1, wherein $R_2$ is $NH_2$.

* * * * *

UNITED STATES PATENT AND TRADEMARK OFFICE
CERTIFICATE OF CORRECTION

PATENT NO. : 9,259,426 B2  
APPLICATION NO. : 12/374433  
DATED : February 16, 2016  
INVENTOR(S) : Ling-Jie Gao et al.

Page 1 of 1

It is certified that error appears in the above-identified patent and that said Letters Patent is hereby corrected as shown below:

Claims

Column 99, Claim 1, Line 15, replace "Flaviridae" with --Flaviviridae--.

Column 100, Claim 1, Line 6, replace "$R_9$" with --$R_8$--;

Lines 12-13, replace "$SO_2N\ H_2$, $R_{12}$-$SO_2R_{11}$; $R_{12}$-$COR_{10}$, $R_{12}$-$CSR_{10}$," with --$SO_2NH_2$; $NR_{12}$-$SO_2R_{11}$; -$NR_{12}$-$COR_{10}$; $R_{12}$-$CSR_{10}$;--;

Line 20, replace "alkoxy" with --halo-$C_{1-7}$alkoxy--;

Line 49, replace "attached form a" with --attached to form a--.

Column 101, Claim 7, Line 49, replace "Flaviridae" with --Flaviviridae--.

Column 121, Claim 7, Lines 56-57, replace "sulfonyhpiperazin" with --sulfonyl)piperazin--.

Column 128, Claim 7, Line 19, replace "ylam ine" with --ylamine--.

Signed and Sealed this  
Twenty-eighth Day of June, 2016

Michelle K. Lee  
*Director of the United States Patent and Trademark Office*